(12) United States Patent
Barr et al.

(10) Patent No.: US 9,486,448 B2
(45) Date of Patent: Nov. 8, 2016

(54) PYRROLIDINE DERIVED BETA 3 ADRENERGIC RECEPTOR AGONISTS

(71) Applicants: Kenneth Jay Barr, Boston, MA (US); Mark E. Scott, Edmonton, CA (US); Christopher F. Thompson, Arlington, MA (US); Neville Anthony, Northborough, MA (US); Carolyn Michele Cammarano, Newton, MA (US); Raman Kumar Bakshi, Edison, NJ (US); Subhendu Kumar Mohanty, Bangalore (IN); Chandra Sekhar Korapala, Bangalore (IN); Prashant R. Latthe, Bangalore (IN); Vyjayanthi N. Kambam, Bangalore (IN); Sujit Kumar Sarkar, Bangalore (IN); Jayanth Thiruvellore Thatai, Bangalore (IN)

(72) Inventors: Kenneth Jay Barr, Boston, MA (US); Mark E. Scott, Edmonton, CA (US); Christopher F. Thompson, Arlington, MA (US); Neville Anthony, Northborough, MA (US); Carolyn Michele Cammarano, Newton, MA (US); Raman Kumar Bakshi, Edison, NJ (US); Subhendu Kumar Mohanty, Bangalore (IN); Chandra Sekhar Korapala, Bangalore (IN); Prashant R. Latthe, Bangalore (IN); Vyjayanthi N. Kambam, Bangalore (IN); Sujit Kumar Sarkar, Bangalore (IN); Jayanth Thiruvellore Thatai, Bangalore (IN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/026,267

(22) PCT Filed: Sep. 29, 2014

(86) PCT No.: PCT/US2014/057950
§ 371 (c)(1),
(2) Date: Mar. 31, 2016

(87) PCT Pub. No.: WO2015/050798
PCT Pub. Date: Apr. 9, 2015

(65) Prior Publication Data
US 2016/0235727 A1 Aug. 18, 2016

Related U.S. Application Data

(60) Provisional application No. 61/886,267, filed on Oct. 3, 2013.

(51) Int. Cl.

| | | |
|---|---|---|
| C07C 53/06 | (2006.01) |
| C07C 53/18 | (2006.01) |
| C07D 401/06 | (2006.01) |
| C07D 401/14 | (2006.01) |
| C07D 413/14 | (2006.01) |
| C07D 471/04 | (2006.01) |
| A61K 31/444 | (2006.01) |
| A61K 31/4439 | (2006.01) |
| A61K 31/497 | (2006.01) |
| A61K 31/501 | (2006.01) |
| C07D 495/04 | (2006.01) |
| A61K 31/519 | (2006.01) |
| A61K 31/517 | (2006.01) |

(52) U.S. Cl.
CPC ......... *A61K 31/4439* (2013.01); *A61K 31/444* (2013.01); *A61K 31/497* (2013.01); *A61K 31/501* (2013.01); *A61K 31/517* (2013.01); *A61K 31/519* (2013.01); *C07C 53/06* (2013.01); *C07C 53/18* (2013.01); *C07D 401/06* (2013.01); *C07D 401/14* (2013.01); *C07D 413/14* (2013.01); *C07D 471/04* (2013.01); *C07D 495/04* (2013.01); *C07B 2200/07* (2013.01)

(58) Field of Classification Search
None
See application file for complete search history.

(56) References Cited

U.S. PATENT DOCUMENTS

2012/0225886 A1   9/2012   Edmondson et al.

*Primary Examiner* — Yevegeny Valenrod
(74) *Attorney, Agent, or Firm* — Patricia A. Shatynski; Catherine D. Fitch

(57) ABSTRACT

The present invention provides compounds of Formula (I), pharmaceutical compositions thereof, and method of using the same in the treatment or prevention of diseases mediated by the activation of β3-adrenoceptor.

14 Claims, No Drawings

PYRROLIDINE DERIVED BETA 3 ADRENERGIC RECEPTOR AGONISTS

CROSS REFERENCE TO RELATED APPLICATIONS

This application is a U.S. National Phase application under 35 U.S.C. §371 of PCT Application No. PCT/US2014/057950, filed Sep. 29, 2014 which claims priority under 35 U.S.C. §119(e) from U.S. Provisional Application Ser. No. 61/886,267, filed on Oct. 3, 2013.

BACKGROUND OF THE INVENTION

The function of the lower urinary tract is to store and periodically release urine. This requires the orchestration of storage and micturition reflexes which involve a variety of afferent and efferent neural pathways, leading to modulation of central and peripheral neuroeffector mechanisms, and resultant coordinated regulation of sympathetic and parasympathetic components of the autonomic nervous system as well as somatic motor pathways. These proximally regulate the contractile state of bladder (detrusor) and urethral smooth muscle, and urethral sphincter striated muscle.

β Adrenergic receptors (βAR) are present in detrusor smooth muscle of various species, including human, rat, guinea pig, rabbit, ferret, dog, cat, pig and non-human primate. However, pharmacological studies indicate there are marked species differences in the receptor subtypes mediating relaxation of the isolated detrusor; β1AR predominate in cats and guinea pig, β2AR predominate in rabbit, and β3AR contribute or predominate in dog, rat, ferret, pig, cynomolgus and human detrusor. Expression of βAR subtypes in the human and rat detrusor has been examined by a variety of techniques, and the presence of β3AR was confirmed using in situ hybridization and/or reverse transcription-polymerase chain reaction (RT-PCR). Real time quantitative PCR analyses of β1AR, β2AR and β3AR mRNAs in bladder tissue from patients undergoing radical cystectomy revealed a preponderance of β3AR mRNA (97%, cf 1.5% for β1AR mRNA and 1.4% for β2AR mRNA). Moreover, β3AR mRNA expression was equivalent in control and obstructed human bladders. These data suggest that bladder outlet obstruction does not result in downregulation of β3AR, or in alteration of β3AR-mediated detrusor relaxation. β3AR responsiveness also has been compared in bladder strips obtained during cystectomy or enterocystoplasty from patients judged to have normal bladder function, and from patients with detrusor hyporeflexia or hyperreflexia. No differences in the extent or potency of β3AR agonist mediated relaxation were observed, consistent with the concept that the β3AR activation is an effective way of relaxing the detrusor in normal and pathogenic states.

Functional evidence in support of an important role for the β3AR in urine storage emanates from studies in vivo. Following intravenous administration to rats, the rodent selective β3AR agonist CL316243 reduces bladder pressure and in cystomeric studies increases bladder capacity leading to prolongation of micturition interval without increasing residual urine volume.

Overactive bladder is characterized by the symptoms of urinary urgency, with or without urgency urinary incontinence, usually associated with frequency and nocturia. The prevalence of OAB in the United States and Europe has been estimated at 16 to 17% in both women and men over the age of 18 years. Overactive bladder is most often classified as idiopathic, but can also be secondary to neurological condition, bladder outlet obstruction, and other causes. From a pathophysiologic perspective, the overactive bladder symptom complex, especially when associated with urge incontinence, is suggestive of detrusor overactivity. Urgency with or without incontinence has been shown to negatively impact both social and medical well-being, and represents a significant burden in terms of annual direct and indirect healthcare expenditures. Importantly, current medical therapy for urgency (with or without incontinence) is suboptimal, as many patients either do not demonstrate an adequate response to current treatments, and/or are unable to tolerate current treatments (for example, dry mouth associated with anticholinergic therapy). Therefore, there is need for new, well-tolerated therapies that effectively treat urinary frequency, urgency and incontinence, either as monotherapy or in combination with available therapies. Agents that relax bladder smooth muscle, such as β3AR agonists, are expected to be effective for treating such urinary disorders.

International patent application filed on Aug. 17, 2010 and published as WO 2011/025774, discloses β3AR agonists of the following generic formula:

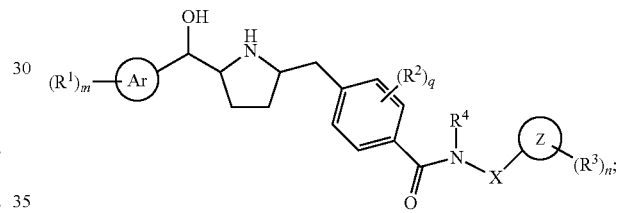

where Ar is phenyl or pyridyl, and Z is a single or fused ring system.

SUMMARY OF THE INVENTION

The present invention relates to novel β3AR agonists of Formula I,

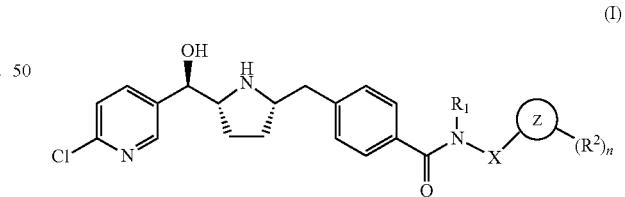

pharmaceutical compositions containing them, as well as methods for the treatment or prophylaxis of disorders mediated through the β3AR using such novel compounds.

DESCRIPTION OF THE INVENTION

Described herein are compounds of structural Formula I, or a stereoisomer, or a pharmaceutically acceptable salt thereof, or a pharmaceutically acceptable salt of the stereoisomer thereof:

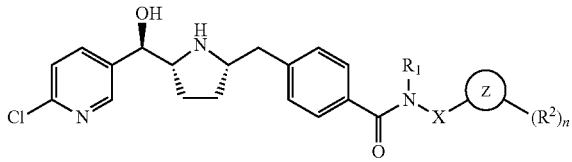

(I)

wherein: n is 0, 1, 2, 3, or 4;
X is selected from:
  (1) a bond, and
  (2) $C_1$-$C_6$ alkanediyl optionally substituted with 1 to 5 groups independently selected from:
    (a) halogen,
    (b) —OR$^a$,
    (c) aryl, and
    (d) heteroaryl;
Z is selected from:
  (1) a bond,
  (2) 5 to 6-membered heterocyclic ring with from 1 to 4 heteroatoms selected from oxygen, sulfur and nitrogen,
  (3) benzene ring fused to a $C_5$-$C_{10}$ carbocyclic ring,
  (4) 5 or 6-membered heterocyclic ring with from 1 to 4 heteroatoms selected from oxygen, sulfur and nitrogen fused to a $C_5$-$C_{10}$ carbocyclic ring, and
  (5) 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen;
$R^1$ is selected from:
  (1) $C_1$-$C_6$ alkyl,
  (2) —($C_{1-10}$ alkyl)OH,
  (3) —($C_{1-10}$ alkyl)oxy($C_{1-10}$ alkyl),
  (4) hydroxy, and
  (5) —O($C_{1-10}$alkyl);
each occurrence of $R^2$ is independently selected from:
  (1) $C_1$-$C_6$ alkyl optionally substituted with 1 to 5 halogen atoms,
  (2) $C_3$-$C_6$ cycloalkyl, optionally substituted with 1 to 5 halogen atoms,
  (3) oxo,
  (4) halogen,
  (5) cyano,
  (6) —OH,
  (7) —$C_0$-$C_6$ alkyloxy$C_1$-$C_6$ alkyl,
  (8) —$CO_2R^a$,
  (9) —(C=O) $C_1$-$C_6$ alkyl,
  (10) 5 to 6-membered heterocyclic ring with from 1 to 4 heteroatoms selected from oxygen, sulfur and nitrogen,
wherein the $C_1$-$C_6$ alkyl, $C_3$-$C_6$ cycloalkyl, —$C_0$-$C_6$ alkyloxy$C_1$-$C_6$ alkyl, and —(C=O) $C_1$-$C_6$ alkyl groups of $R^2$ are optionally substituted with 0, 1, 2, or 3 $R^3$ substituents selected from:
  (1) $C_1$-$C_6$ alkyl optionally substituted with 1 to 5 halogens,
  (2) halogen,
  (3) —OH, and
  (4) —$CO_2H$;
each occurrence of $R^a$ is independently selected from:
  (1) hydrogen,
  (2) $C_3$-$C_6$ cycloalkyl;
  (3) $C_1$-$C_6$ alkyl optionally substituted with 1 to 5 groups independently selected from:
    (a) halogen,
    (b) hydroxy,
    (c) —CO($C_1$-$C_6$ alkyl),
    (d) —$CO_2$($C_1$-$C_6$ alkyl), and
    (e) —$CO_2H$, and
provided that when n is 1, X is —$CH_2$—, $R^1$ is —$CH_3$, and $R^2$ is —$CH_3$ or F, then Z is other than pyridinyl, pyrazolyl, or [1,2,4]triazolo[4,3-a]pyridinyl.

The present invention discloses unexpected and surprising properties associated with the inclusion of a 2-chloropyridine aryl pharmacophore in nearly every instance increases the potency of the β3AR agonists versus other aryl pharmacophore substituent choices. The compounds of the present invention exhibit a poency increase when compared to other aryl pharmacophore substituent choices.

Representative compounds of the instant invention include, but are not limited to the following compounds and their pharmaceutically acceptable salts and stereoisomers thereof:

4-(((2S,5R)-5-((R)-(4-chlorophenyl)(hydroxy)methyl)pyrrolidin-2-yl)methyl)-N-(2-methoxyethyl)-N-methylbenzamide;

4-(((2S,5R)-5-((R)-(6-chloropyridin-3-yl)(hydroxy)methyl)pyrrolidin-2-yl)methyl)-N-(2-methoxypropyl)-N-methylbenzamide;

4-(((2S,5R)-5-((R)-(6-chloropyridin-3-yl)(hydroxy)methyl)pyrrolidin-2-yl)methyl)-N-(2-methoxy-2-(6-oxo-1,6-dihydropyridin-2-yl)ethyl)-N-methylbenzamide;

4-(((2S,5R)-5-((R)-(6-chloropyridin-3-yl)(hydroxy)methyl)pyrrolidin-2-yl)methyl)-N-methyl-N-(1-(5-methyl-1H-pyrazol-3-yl)propyl)benzamide;

4-(((2S,5R)-5-((R)-(6-chloropyridin-3-yl)(hydroxy)methyl)pyrrolidin-2-yl)methyl)-N-methyl-N-(1-(5-methyl-1H-pyrazol-3-yl)-2-phenylethyl)benzamide;

4-(((2S,5R)-5-((R)-(6-chloropyridin-3-yl)(hydroxy)methyl)pyrrolidin-2-yl)methyl)-N-((5-isopropyl-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-((5-cyclopropyl-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-((5-(methoxymethyl)-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-methyl-N-((5-(trifluoromethyl)-1H-pyrazol-3-yl)methyl)benzamide;

4-(((2S,5R)-5-((R)-(6-chloropyridin-3-yl)(hydroxy)methyl)pyrrolidin-2-yl)methyl)-N-((5-ethoxy-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-((5-ethyl-4-methyl-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-methyl-N-((1,4,5,6-tetrahydrocyclopenta[c]pyrazol-3-yl)methyl)benzamide;

4-(((2S,5R)-5-((R)-(6-chloropyridin-3-yl)(hydroxy)methyl)pyrrolidin-2-yl)methyl)-N-methyl-N-((4,5,6,7-tetrahydro-1H-indazol-3-yl)methyl)benzamide;

4-(((2S,5R)-5-((R)-(6-chloropyridin-3-yl)(hydroxy)methyl)pyrrolidin-2-yl)methyl)-N-((4-hydroxy-5-methyl-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-((4-methoxy-5-methyl-1H-pyrazol-3-yl)methyl)-N-methylbenzamide;

N-((4-chloro-5-methyl-1H-pyrazol-3-yl)methyl)-4-(((2S,5R)-5-((R)-(6-chloropyridin-3-yl)(hydroxy)methyl)pyrrolidin-2-yl)methyl)-N-methylbenzamide;

4-(((2S,5R)-5-((R)-(6-chloropyridin-3-yl)(hydroxy)methyl)pyrrolidin-2-yl)methyl)-N-methyl-N—((R)-1-(4-methyl-5-oxo-4,5-dihydro-1,3,4-oxadiazol-2-yl)ethyl)benzamide;

4-(((2S,5R)-5-((R)-(6-chloropyridin-3-yl)(hydroxy)methyl)pyrrolidin-2-yl)methyl)-N-methyl-N—((R)-2-methyl-1-(4-methyl-5-oxo-4,5-dihydro-1,3,4-oxadiazol-2-yl)propyl) benzamide;

4-(((2S,5R)-5-((R)-(6-chloropyridin-3-yl)(hydroxy)methyl)pyrrolidin-2-yl)methyl)-N-methyl-N-((6-oxo-1,6-dihydropyridin-2-yl)methyl)benzamide;

4-(((2S,5R)-5-((R)-(6-chloropyridin-3-yl)(hydroxy)methyl)pyrrolidin-2-yl)methyl)-N-methyl-N-(pyridin-3-ylmethyl)benzamide, 4-(((2S,5R)-5-((R)-(6-chloropyridin-3-yl)(hydroxy)methyl)pyrrolidin-2-yl)methyl)-N-ethyl-N-(pyridin-3-ylmethyl)benzamide;

4-(((2S,5R)-5-((R)-(6-chloropyridin-3-yl)(hydroxy)methyl)pyrrolidin-2-yl)methyl)-N-methyl-N-(1-(pyridin-3-yl)ethyl)benzamide;

4-(((2S,5R)-5-((R)-(6-chloropyridin-3-yl)(hydroxy)methyl)pyrrolidin-2-yl)methyl)-N-(6,7-dihydro-5H-cyclopenta[b]pyridin-5-yl)-N-methylbenzamide;

4-(((2S,5R)-5-((R)-(6-chloropyridin-3-yl)(hydroxy)methyl)pyrrolidin-2-yl)methyl)-N-((2-methoxypyridin-3-yl)methyl)-N-methylbenzamide;

4-(((2S,5R)-5-((R)-(6-chloropyridin-3-yl)(hydroxy)methyl)pyrrolidin-2-yl)methyl)-N-((2-fluoropyridin-3-yl)methyl)-N-methylbenzamide;

4-(((2S,5R)-5-((R)-(6-chloropyridin-3-yl)(hydroxy)methyl)pyrrolidin-2-yl)methyl)-N-((2-fluoropyridin-3-yl)methyl)-N-(2-hydroxyethyl)benzamide;

4-(((2S,5R)-5-((R)-(6-chloropyridin-3-yl)(hydroxy)methyl)pyrrolidin-2-yl)methyl)-N-methyl-N-((6-oxo-1,6-dihydropyridin-3-yl)methyl)benzamide, 4-(((2S,5R)-5-((R)-(6-chloropyridin-3-yl)(hydroxy)methyl)pyrrolidin-2-yl)methyl)-N-((6-methoxypyridin-3-yl)methyl)-N-methylbenzamide, 4-(((2S,5R)-5-((R)-(6-chloropyridin-3-yl)(hydroxy)methyl)pyrrolidin-2-yl)methyl)-N-((6-chloropyridin-3-yl)methyl)-N-methylbenzamide, (((2S,5R)-5-((R)-(6-chloropyridin-3-yl)(hydroxy)methyl)pyrrolidin-2-yl)methyl)-N-((5-(1-hydroxyethyl)pyridin-3-yl)methyl)-N-methylbenzamide;

4-(((2S,5R)-5-((R)-(6-chloropyridin-3-yl)(hydroxy)methyl)pyrrolidin-2-yl)methyl)-N-((5-(2-hydroxypropan-2-yl)pyridin-3-yl)methyl)-N-methylbenzamide;

5-((4-(((2S,5R)-5-((R)-(6-chloropyridin-3-yl)(hydroxy)methyl)pyrrolidin-2-yl)methyl)-N-methylbenzamido)methyl)nicotinic acid;

Methyl 5-((4-(((2S,5R)-5-((R)-(6-chloropyridin-3-yl)(hydroxy)methyl)pyrrolidin-2-yl) methyl)-N-methylbenzamido)methyl)nicotinate;

4-(((2S,5R)-5-((R)-(6-chloropyridin-3-yl)(hydroxy)methyl)pyrrolidin-2-yl)methyl)-N-((5-cyanopyridin-3-yl)methyl)-N-methylbenzamide;

4-(((2S,5R)-5-((R)-(6-chloropyridin-3-yl)(hydroxy)methyl)pyrrolidin-2-yl)methyl)-N-methyl-N-((5-(5-methyl-1,3,4-oxadiazol-2-yl)pyridin-3-yl)methyl)benzamide;

N-((5-(1H-tetrazol-5-yl)pyridin-3-yl)methyl)-4-(((2S,5R)-5-((R)-(6-chloropyridin-3-yl)(hydroxy)methyl)pyrrolidin-2-yl)methyl)-N-methylbenzamide;

4-(((2S,5R)-5-((R)-(6-chloropyridin-3-yl)(hydroxy)methyl)pyrrolidin-2-yl)methyl)-N-((6-fluoro-5-methylpyridin-3-yl)methyl)-N-methylbenzamide;

4-(((2S,5R)-5-((R)-(6-chloropyridin-3-yl)(hydroxy)methyl)pyrrolidin-2-yl)methyl)-N-methyl-N-(pyrazin-2-ylmethyl)benzamide;

4-(((2S,5R)-5-((R)-(6-chloropyridin-3-yl)(hydroxy)methyl)pyrrolidin-2-yl)methyl)-N-methyl-N-(1-(pyrazin-2-yl)ethyl)benzamide;

4-(((2S,5R)-5-((R)-(6-chloropyridin-3-yl)(hydroxy)methyl)pyrrolidin-2-yl)methyl)-N-methyl-N-(pyridazin-4-ylmethyl)benzamide;

4-(((2S,5R)-5-((R)-(6-chloropyridin-3-yl)(hydroxy)methyl)pyrrolidin-2-yl)methyl)-N-methyl-N-((4-oxo-3,4-dihydrothieno[3,2-d]pyrimidin-2-yl)methyl)benzamide; and 4-(((2S,5R)-5-((R)-(6-chloropyridin-3-yl)(hydroxy)methyl)pyrrolidin-2-yl)methyl)-N-methyl-N-((3-methyl-4-oxo-3,4-dihydroquinazolin-2-yl)methyl)benzamide.

As used herein, the term "alkyl" means both branched- and straight-chain saturated aliphatic hydrocarbon groups having the specified number of carbon atoms. For example, $C_1$-$C_6$ alkyl includes, but is not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tert-butyl (t-Bu), isopentyl, sec-pentyl, tert-pentyl, isohexyl and the like.

The term "cycloalkyl" means a monocyclic saturated carbocyclic ring, having the specified number of carbon atoms, e.g., 3, 4, 5 or 6 carbon atoms. Non-limiting examples of $C_3$-$C_6$ cycloalkyl include cyclopropyl, cyclobutyl, cyclopentyl and cyclohexyl.

The term "alkanediyl" means a straight or branched divalent hydrocarbon radical having the specified number of carbon atoms. Non-limiting examples of $C_1$-$C_4$ "alkanediyl" include, but are not limited to, methylene (—$CH_2$—), ethylene (—$CH_2CH_2$—), 1,1-ethanediyl (—CH($CH_3$)—), 1,2-propanediyl (—CH($CH_3$)$CH_2$—), 2-methyl-1,1-propanediyl (—CH[C($CH_3$)$_2$]—), 1,4-butanediyl (—$CH_2CH_2CH_2CH_2$—), 2,3-butanediyl (—CH($CH_3$)CH($CH_3$)—, and the like. Example of a halogen substituted alkanediyl is —C($CH_3$)(F)—.

The term "optionally substituted" means "unsubstituted or substituted," and therefore, the generic structural Formulas described herein encompass compounds containing the specified optional substituent as well as compounds that do not contain the optional substituent. Each variable is independently defined each time it occurs within the generic structural formula definitions.

The terms "halo" or "halogen" are meant to include fluoro, chloro, bromo and iodo, unless otherwise noted.

The terms "carbocycle" or "carbocyclic" refer to saturated, partially unsaturated and aromatic rings having only ring carbon atoms. For examples, $C_1$-$C_4$ carbocyclic ring include, but are not limited to, cyclopentyl, cyclohexyl, cycloheptyl, cyclooctyl, cyclopentenyl, cyclohexenyl, cyclohexadienyl, and phenyl.

The term "aryl" refers to an aromatic carbocycle.

The terms "heterocycle" or "heterocyclic" refer to saturated, partially unsaturated and aromatic rings having at least one ring heteroatom and at least one ring carbon atom; the heterocycle may be attached to the rest of the molecule via a ring carbon atom or a ring hetero atom, for example, a ring nitrogen atom. The terms "heteroaryl" or "heteroaromatic" refer to an aromatic heterocycle. For example, within the definition for Z, the term "a 5- or 6-membered heterocyclic ring with from 1 to 4 heteroatoms selected from oxygen, sulfur and nitrogen" includes, but is not limited to, pyrrolyl, thienyl, furanyl, imidazolyl, pyrazolyl, oxazolyl, isoxazolyl, thiazolyl, isothiazolyl, triazolyl, tetrazolyl, oxadiazolyl, dihydro-oxadiazolyl, thiadiazolyl, pyrrolidinyl, tetrahydrofuranyl, pyridinyl, dihydropyridinyl, tetrahydropyridinyl, pyrimidinyl, dihydropyrimidinyl, tetrahydropyrimidinyl, pyrazinyl, dihydropyrazinyl, tetrahydropyrazinyl, pyridazinyl, dihydropyridazinyl, tetrahydropyridazinyl, piperidinyl, piperazinyl, morpholinyl, pyranyl, dihydropyranyl, tetrahydropyranyl, and the like.

Within the definition for Z, the term "a benzene ring fused to a $C_5$-$C_{10}$ carbocyclic ring" includes, but is not limited to, naphthyl, dihydronaphthyl, tetrahydronaphthyl, indanyl, indenyl, benzocycloheptene, tetrahydrobenzocyloheptene, and the like. In one embodiment, a benzene ring is fused to a $C_5$-$C_6$ carbocyclic ring. Such fused ring may be attached to the rest of the molecule via a carbon atom on either ring.

Within the definition for Z, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" includes, but is not limited to, naphthyridinyl, dihydronaphthyridinyl, tetrahydronaphthyridinyl, imidazopyridinyl, pteridinyl, purinyl, quinolizinyl, indolizinyl, tetrahydroquinolizinyl, and tetrahydroindolizinyl. In one embodiment, Z is selected from:

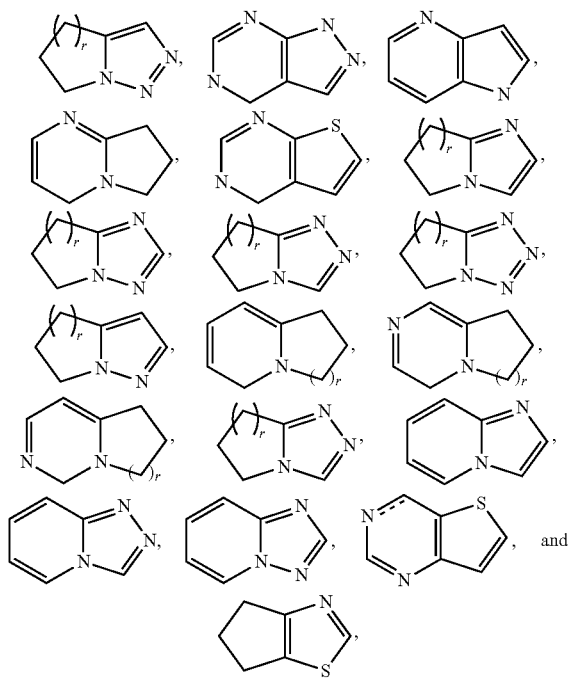

wherein r is 1 or 2. Such fused ring may be attached to the rest of the molecule via a carbon atom or a nitrogen atom on either ring.

To avoid any doubt, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" as used herein includes compounds having only one nitrogen as the sole heteroatom when the nitrogen is located at the bridgehead.

Within the definition for Z, the term "a 5- or 6-membered heterocyclic ring with from 1 to 4 heteroatoms selected from oxygen, sulfur and nitrogen fused to a $C_5$-$C_{10}$ carbocyclic ring" includes, but is not limited to, indolyl, isoindolyl, benzofuranyl, benzothienyl, benzimidazolyl, benzotriazolyl, benzoxazolyl, benzisoxazolyl, benzthiazolyl, benzisothiazolyl, quinolinyl, isoquinolinyl, quinoxalinyl, quinazolinyl, cinnolinyl, indazolyl, tetrahydroquinolinyl, tetrahydroindazolyl, dihydroindazolyl, chromenyl, chromanyl benztriazolyl,

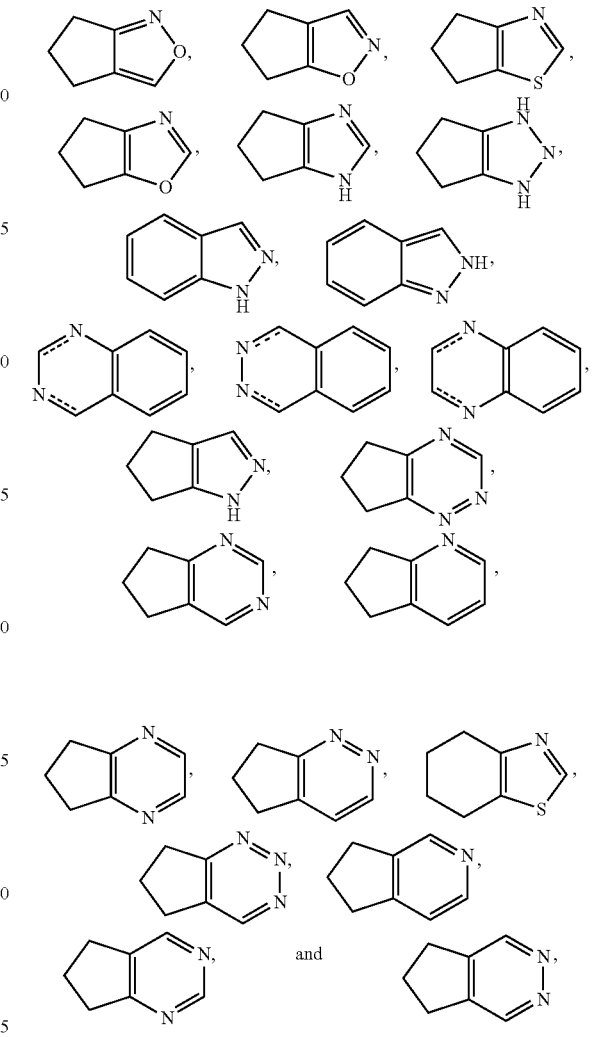

where the dash bond "===" means a single or double bond while conforming to the valency rule for the ring atoms. Such fused ring may be attached to the rest of the molecule via a carbon atom on either ring or a nitrogen atom on the heterocyclic ring.

For the term $(R^2)_n$, as well as other similar notations, when n is 0, then $R^2$ is hydrogen; when n is greater than 1, then each occurrence of $R^2$ is independently selected from other occurrences of $R^2$. For example, when n is 2, the two $R^2$ substituents can be the same or different.

In one embodiment of compounds of Formula I, n is 0, 1, 2, 3 or 4. In another embodiment, n is 0, 1, 2 or 3. In another embodiment, n is 0, 1, or 2. In yet another embodiment, n is 0, 1 or 3. In a variant of this embodiment, n is 0.

In one embodiment, X is a bond or $C_1$-$C_6$ alkanediyl optionally substituted with 1 to three groups selected from halogen, —$OR^a$, aryl and heteroaryl. In another embodiment, X is a bond or $C_1$-$C_6$ alkanediyl optionally substituted with 1 to three groups selected from —$OR^a$ and aryl. In a variant of this embodiment, X is a bond or $C_1$-$C_6$ alkanediyl optionally substituted with 1 to three groups selected from —OCH₃, and phenyl. In yet another embodiment, X is a bond.

In one embodiment, X is $C_1$-$C_4$ alkanediyl. In another embodiment, X is selected from —CH₂—, —CH₂CH₂—, —CH(CH₃)—, —CH(CH(CH₃)₂)—, —CH₂CHCH₃—, —CH(CH₂CH₃)—, CH₂CHCH₃—, —CH₂CH(CH₃)₂—. or —CH(CH₃)CH₂— and X is optionally substituted with one to three groups selected from —$OR^a$, and aryl. In one variant of this embodiment, X is optionally substituted with one to three groups selected from —OCH₃, —OCHCH₃, —OCH(CH₃)₂, and phenyl.

In one embodiment of the invention, Z is selected from:
(1) a bond,
(2) 5 to 6-membered heterocyclic ring with from 1 to 4 heteroatoms selected from oxygen, sulfur and nitrogen,
(3) 5 or 6-membered heterocyclic ring with from 1 to 4 heteroatoms selected from oxygen, sulfur and nitrogen fused to a $C_5$-$C_6$ carbocyclic ring, and
(4) 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen.

In yet another embodiment, Z is selected from thiazolyl, oxazolyl, pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, pyridinyl, dihydropyridinyl, dihydropyridazinyl, pyrrolidinyl, imidazolyl, pyrazolyl, 2,3-dihydro-1,3,4-oxadiazolyl, oxadiazolyl, dihydro-oxadiazolyl, 4,5-dihydro-1,3,4-oxadiazolyl, 1,2,4-oxadiazolyl, 1,2,5-oxadiazolyl,

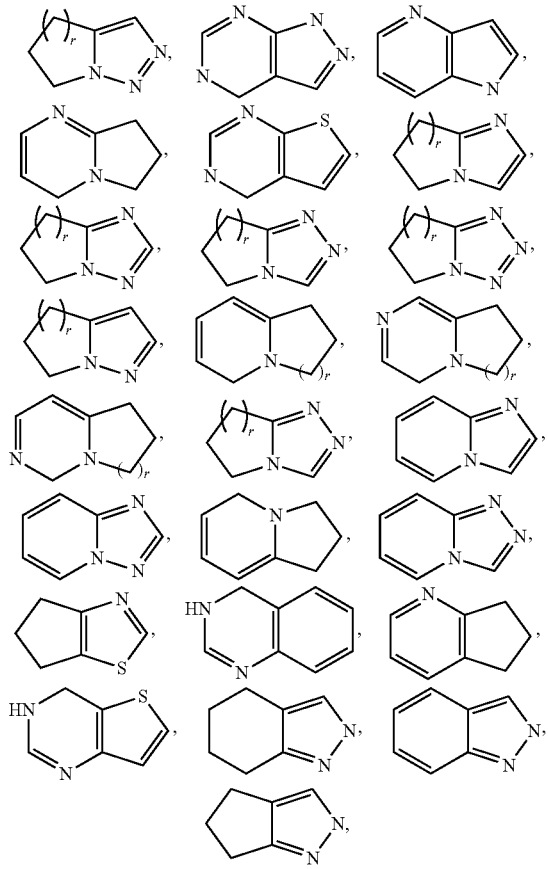

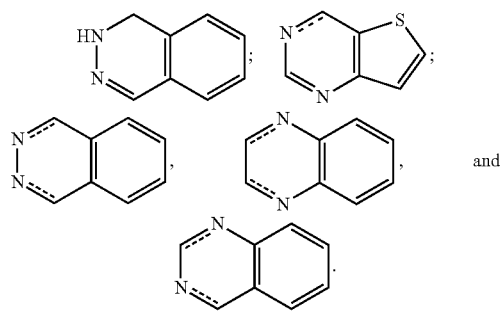

It should be pointed out that the heterocyle is attached to the rest of the molecue vaia any available valence on the hetrocyclic ring.

In yet another embodiment, Z is selected from: dihydropyrazinyl, pyrazolyl,

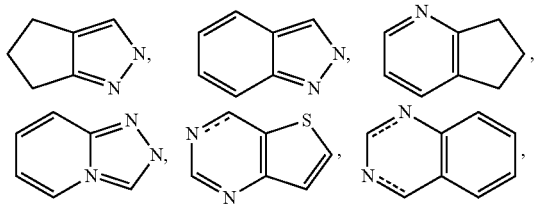

dihydro-oxadiazolyl, 4,5-dihydro-1,3,4-oxadiazolyl, dihydropyridinyl, pyridinyl, pyrazinyl, and pyridazinyl.

In one embodiment, $R^1$ is selected from: $C_1$-$C_6$ alkyl, —($C_{1-10}$ alkyl)OH, —($C_{1-10}$ alkyl)oxy($C_{1-10}$ alkyl), hydroxy, and —O($C_{1-10}$alkyl).

In another embodiment, $R^1$ is selected from: $C_1$-$C_4$ alkyl, —($C_{1-4}$alkyl)OH, —($C_{1-4}$ alkyl)oxy($C_{1-4}$alkyl), hydroxy, and —O($C_{1-4}$alkyl). In a variant of this embodiment, $R^1$ is selected from: methyl, ethyl, —CH₂—CH₂OH.

In one embodiment of the invention, $R^2$ is independently selected from:
(1) $C_1$-$C_6$ alkyl optionally substituted with 1 to 5 halogen atoms,
(2) $C_3$-$C_6$ cycloalkyl, optionally substituted with 1 to 5 halogen atoms,
(3) oxo,
(4) halogen,
(5) cyano,
(6) —OH,
(7) —$C_0$-$C_6$ alkyl oxy $C_1$-$C_6$ alkyl,
(8) —$CO_2R^a$,
(9) —(C═O) $C_1$-$C_6$ alkyl,
(10) 5 to 6-membered heterocyclic ring with from 1 to 4 heteroatoms selected from oxygen, sulfur and nitrogen, wherein the $C_1$-$C_6$ alkyl, $C_3$-$C_6$ cycloalkyl, —$C_0$-$C_6$ alkyloxy$C_1$-$C_6$ alkyl, and —(C═O) $C_1$-$C_6$ alkyl groups of $R^2$ are optionally substituted with 0, 1, 2, or 3 $R^3$ substituents selected from:
(1) $C_1$-$C_4$ alkyl optionally substituted with 1 to 5 halogens,
(2) halogen,
(3) —OH, and
(4) —$CO_2H$.

In one embodiment, $R^2$ is independently selected from: methyl, ethyl, propyl, isopropyl, butyl, pentyl, trifluoromethyl, trifluoroethyl, cyclopropyl, cyclobutyl; cyclopentyl, cyclohexyl, oxo; Cl, F, cyano, —OH, methoxymethyl, methoxyethyl, ethoxy, hydroxyisopropyl, hydroxyethyl, hydroxypropyl,
—CO₂H, —CO₂C₁-C₄ alkyl, oxadiazolyl, 1,3,4-oxadiazolyl, tetrazolyl, pyridinyl, pyrrolidinyl, pyrazinyl, methylcarbonyl, ethylcarbonyl, propylcarbonyl; wherein $R^2$ is optionally substituted with 0, 1, 2, or 3 $R^3$ substituents selected from: methyl, ethyl, propyl, butyl, trifluoromethyl, trifluoroethyl, Cl, F, —OH, and —CO₂H.

In one embodiment of the invention each occurrence of $R^a$ is independently selected from:
(1) hydrogen, $C_1$-$C_6$ alkyl, optionally substituted with 1 to 5 groups independently selected from: halogen, and hydroxy; and
(2) $C_3$-$C_6$ cycloalkyl.

In another embodiment of the invention, each occurrence of $R^a$ is independently selected from: hydrogen, and $C_1$-$C_6$ alkyl.

In another embodiment, each occurrence of $R^a$ is independently hydrogen or $C_1$-$C_4$ alkyl. In another embodiment, each occurrence of $R^a$ is independently hydrogen or methyl.

In another embodiment of the invention is a compound or a pharmaceutically acceptable salt thereof, or a stereoisomer thereof, or a pharmaceutically acceptable salt of the stereoisomer thereof, selected from:

4-(((2S,5R)-5-((R)-(6-chloropyridin-3-yl)(hydroxy)methyl) pyrrolidin-2-yl)methyl)-N-(2-methoxy-2-(6-oxo-1,6-dihydropyridin-2-yl)ethyl)-N-methylbenzamide;
4-(((2S,5R)-5-((R)-(6-chloropyridin-3-yl)(hydroxy)methyl) pyrrolidin-2-yl)methyl)-N-methyl-N-((1,4,5,6-tetrahydrocyclopenta[c]pyrazol-3-yl)methyl)benzamide;
4-(((2S,5R)-5-((R)-(6-chloropyridin-3-yl)(hydroxy)methyl) pyrrolidin-2-yl)methyl)-N-methyl-N-((4,5,6,7-tetrahydro-1H-indazol-3-yl)methyl)benzamide;
4-(((2S,5R)-5-((R)-(6-chloropyridin-3-yl)(hydroxy)methyl) pyrrolidin-2-yl)methyl)-N-methyl-N-((6-oxo-1,6-dihydropyridin-2-yl)methyl)benzamide;
4-(((2S,5R)-5-((R)-(6-chloropyridin-3-yl)(hydroxy)methyl) pyrrolidin-2-yl)methyl)-N-methyl-N-(pyridin-3-ylmethyl)benzamide;
4-(((2S,5R)-5-((R)-(6-chloropyridin-3-yl)(hydroxy)methyl) pyrrolidin-2-yl)methyl)-N-ethyl-N-(pyridin-3-ylmethyl) benzamide;
4-(((2S,5R)-5-((R)-(6-chloropyridin-3-yl)(hydroxy)methyl) pyrrolidin-2-yl)methyl)-N-methyl-N-(1-(pyridin-3-yl) ethyl)benzamide;
4-(((2S,5R)-5-((R)-(6-chloropyridin-3-yl)(hydroxy)methyl) pyrrolidin-2-yl)methyl)-N-(6,7-dihydro-5H-cyclopenta [b]pyridin-5-yl)-N-methylbenzamide;
4-(((2S,5R)-5-((R)-(6-chloropyridin-3-yl)(hydroxy)methyl) pyrrolidin-2-yl)methyl)-N-((2-methoxypyridin-3-yl) methyl)-N-methylbenzamide;
4-(((2S,5R)-5-((R)-(6-chloropyridin-3-yl)(hydroxy)methyl) pyrrolidin-2-yl)methyl)-N-((2-fluoropyridin-3-yl) methyl)-N-methylbenzamide;
4-(((2S,5R)-5-((R)-(6-chloropyridin-3-yl)(hydroxy)methyl) pyrrolidin-2-yl)methyl)-N-((2-fluoropyridin-3-yl) methyl)-N-(2-hydroxyethyl)benzamide;
4-(((2S,5R)-5-((R)-(6-chloropyridin-3-yl)(hydroxy)methyl) pyrrolidin-2-yl)methyl)-N-methyl-N-((6-oxo-1,6-dihydropyridin-3-yl)methyl)benzamide;
4-(((2S,5R)-5-((R)-(6-chloropyridin-3-yl)(hydroxy)methyl) pyrrolidin-2-yl)methyl)-N-((6-methoxypyridin-3-yl) methyl)-N-methylbenzamide;
4-(((2S,5R)-5-((R)-(6-chloropyridin-3-yl)(hydroxy)methyl) pyrrolidin-2-yl)methyl)-N-((6-chloropyridin-3-yl) methyl)-N-methylbenzamide;
(((2S,5R)-5-((R)-(6-chloropyridin-3-yl)(hydroxy)methyl) pyrrolidin-2-yl)methyl)-N-((5-(1-hydroxyethyl)pyridin-3-yl)methyl)-N-methylbenzamide;
4-(((2S,5R)-5-((R)-(6-chloropyridin-3-yl)(hydroxy)methyl) pyrrolidin-2-yl)methyl)-N-((5-(2-hydroxypropan-2-yl) pyridin-3-yl)methyl)-N-methylbenzamide;
5-((4-(((2S,5R)-5-((R)-(6-chloropyridin-3-yl)(hydroxy) methyl)pyrrolidin-2-yl)methyl)-N-methylbenzamido) methyl)nicotinic acid;
Methyl 5-((4-(((2S,5R)-5-((R)-(6-chloropyridin-3-yl)(hydroxy)methyl)pyrrolidin-2-yl) methyl)-N-methylbenzamido)methyl)nicotinate;
4-(((2S,5R)-5-((R)-(6-chloropyridin-3-yl)(hydroxy)methyl) pyrrolidin-2-yl)methyl)-N-((5-cyanopyridin-3-yl) methyl)-N-methylbenzamide;
4-(((2S,5R)-5-((R)-(6-chloropyridin-3-yl)(hydroxy)methyl) pyrrolidin-2-yl)methyl)-N-methyl-N-((5-(5-methyl-1,3, 4-oxadiazol-2-yl)pyridin-3-yl)methyl)benzamide;
N-((5-(1H-tetrazol-5-yl)pyridin-3-yl)methyl)-4-(((2S,5R)-5-((R)-(6-chloropyridin-3-yl)(hydroxy)methyl)pyrrolidin-2-yl)methyl)-N-methylbenzamide;
4-(((2S,5R)-5-((R)-(6-chloropyridin-3-yl)(hydroxy)methyl) pyrrolidin-2-yl)methyl)-N-((5-fluoropyridin-3-yl) methyl)-N-methylbenzamide;
4-(((2S,5R)-5-((R)-(6-chloropyridin-3-yl)(hydroxy)methyl) pyrrolidin-2-yl)methyl)-N-((6-fluoro-5-methylpyridin-3-yl)methyl)-N-methylbenzamide;
4-(((2S,5R)-5-((R)-(6-chloropyridin-3-yl)(hydroxy)methyl) pyrrolidin-2-yl)methyl)-N-methyl-N-(pyrazin-2-ylmethyl)benzamide;
4-(((2S,5R)-5-((R)-(6-chloropyridin-3-yl)(hydroxy)methyl) pyrrolidin-2-yl)methyl)-N-methyl-N-(1-(pyrazin-2-yl) ethyl)benzamide;
4-(((2S,5R)-5-((R)-(6-chloropyridin-3-yl)(hydroxy)methyl) pyrrolidin-2-yl)methyl)-N-methyl-N-(pyridazin-4-ylmethyl)benzamide;
4-(((2S,5R)-5-((R)-(6-chloropyridin-3-yl)(hydroxy)methyl) pyrrolidin-2-yl)methyl)-N-methyl-N-((3-methyl-[1,2,4] triazolo[4,3-a]pyridin-6-yl)methyl)benzamide;
4-(((2S,5R)-5-((R)-(6-chloropyridin-3-yl)(hydroxy)methyl) pyrrolidin-2-yl)methyl)-N-methyl-N-((4-oxo-3,4-dihydrothieno[3,2-d]pyrimidin-2-yl)methyl)benzamide; and
4-(((2S,5R)-5-((R)-(6-chloropyridin-3-yl)(hydroxy)methyl) pyrrolidin-2-yl)methyl)-N-methyl-N-((3-methyl-4-oxo-3, 4-dihydroquinazolin-2-yl)methyl)benzamide.

In one embodiment of the invention is a compound or a pharmaceutically acceptable salt thereof, or a stereoisomer thereof, or a pharmaceutically acceptable salt of the stereoisomer thereof, selected from:
4-(((2S,5R)-5-((R)-(6-chloropyridin-3-yl)(hydroxy)methyl) pyrrolidin-2-yl)methyl)-N-methyl-N-((5-methyl-1H-pyrazol-3-yl)methyl)benzamide;
4-(((2S,5R)-5-((R)-(6-chloropyridin-3-yl)(hydroxy)methyl) pyrrolidin-2-yl)methyl)-N-methyl-N-(1-(5-methyl-1H-pyrazol-3-yl)propyl)benzamide;
4-(((2S,5R)-5-((R)-(6-chloropyridin-3-yl)(hydroxy)methyl) pyrrolidin-2-yl)methyl)-N-methyl-N-(1-(5-methyl-1H-pyrazol-3-yl)-2-phenylethyl)benzamide;
4-(((2S,5R)-5-((R)-(6-chloropyridin-3-yl)(hydroxy)methyl) pyrrolidin-2-yl)methyl)-N-((5-isopropyl-1H-pyrazol-3-yl)methyl)-N-methylbenzamide;
4-(((2S,5R)-5-((R)-(6-chloropyridin-3-yl)(hydroxy)methyl) pyrrolidin-2-yl)methyl)-N-((5-cyclopropyl-1H-pyrazol-3-yl)methyl)-N-methylbenzamide;
4-(((2S,5R)-5-((R)-(6-chloropyridin-3-yl)(hydroxy)methyl) pyrrolidin-2-yl)methyl)-N-((5-(methoxymethyl)-1H-pyrazol-3-yl)methyl)-N-methylbenzamide;

4-(((2S,5R)-5-((R)-(6-chloropyridin-3-yl)(hydroxy)methyl) pyrrolidin-2-yl)methyl)-N-methyl-N-((5-(trifluoromethyl)-1H-pyrazol-3-yl)methyl)benzamide;
4-(((2S,5R)-5-((R)-(6-chloropyridin-3-yl)(hydroxy)methyl) pyrrolidin-2-yl)methyl)-N-((5-ethoxy-1H-pyrazol-3-yl) methyl)-N-methylbenzamide;
4-(((2S,5R)-5-((R)-(6-chloropyridin-3-yl)(hydroxy)methyl) pyrrolidin-2-yl)methyl)-N-((5-ethyl-4-methyl-1H-pyrazol-3-yl)methyl)-N-methylbenzamide;
4-(((2S,5R)-5-((R)-(6-chloropyridin-3-yl)(hydroxy)methyl) pyrrolidin-2-yl)methyl)-N-((4-hydroxy-5-methyl-1H-pyrazol-3-yl)methyl)-N-methylbenzamide;
4-(((2S,5R)-5-((R)-(6-chloropyridin-3-yl)(hydroxy)methyl) pyrrolidin-2-yl)methyl)-N-((4-methoxy-5-methyl-1H-pyrazol-3-yl)methyl)-N-methylbenzamide; and
N-((4-chloro-5-methyl-1H-pyrazol-3-yl)methyl)-4-(((2S, 5R)-5-((R)-(6-chloropyridin-3-yl)(hydroxy)methyl)pyrrolidin-2-yl)methyl)-N-methylbenzamide.

In a variant of this embodiment, the invention is the compound or a pharmaceutically acceptable salt thereof, or a stereoisomer thereof, or a pharmaceutically acceptable salt of the stereoisomer thereof, which is 4-(((2S,5R)-5-((R)-(6-chloropyridin-3-yl)(hydroxy)methyl) pyrrolidin-2-yl) methyl)-N-methyl-N-((5-methyl-1H-pyrazol-3-yl)methyl) benzamide.

In one embodiment of the invention is the compound or a pharmaceutically acceptable salt thereof, or a stereoisomer thereof, or a pharmaceutically acceptable salt of the stereoisomer thereof, which is 4-(((2S,5R)-5-((R)-(6-chloropyridin-3-yl)(hydroxy)methyl)pyrrolidin-2-yl)methyl)-N-methyl-N-(1-(5-methyl-1H-pyrazol-3-yl)propyl)benzamide.

In one embodiment of the invention is the compound or a pharmaceutically acceptable salt thereof, or a stereoisomer thereof, or a pharmaceutically acceptable salt of the stereoisomer thereof, which is 4-(((2S,5R)-5-((R)-(6-chloropyridin-3-yl)(hydroxy)methyl)pyrrolidin-2-yl)methyl)-N-methyl-N-(1-(5-methyl-1H-pyrazol-3-yl)-2-phenylethyl) benzamide.

In one embodiment of the invention is the compound or a pharmaceutically acceptable salt thereof, or a stereoisomer thereof, or a pharmaceutically acceptable salt of the stereoisomer thereof, which is 4-(((2S,5R)-5-((R)-(6-chloropyridin-3-yl)(hydroxy)methyl)pyrrolidin-2-yl)methyl)-N-((5-isopropyl-1H-pyrazol-3-yl)methyl)-N-methylbenzamide.

In one embodiment of the invention is the compound or a pharmaceutically acceptable salt thereof, or a stereoisomer thereof, or a pharmaceutically acceptable salt of the stereoisomer thereof, which is 4-(((2S,5R)-5-((R)-(6-chloropyridin-3-yl)(hydroxy)methyl)pyrrolidin-2-yl)methyl)-N-((5-cyclopropyl-1H-pyrazol-3-yl)methyl)-N-methylbenzamide.

In one embodiment of the invention is the compound or a pharmaceutically acceptable salt thereof, or a stereoisomer thereof, or a pharmaceutically acceptable salt of the stereoisomer thereof, which is 4-(((2S,5R)-5-((R)-(6-chloropyridin-3-yl)(hydroxy)methyl)pyrrolidin-2-yl)methyl)-N-((5-(methoxymethyl)-1H-pyrazol-3-yl)methyl)-N-methylbenzamide.

In one embodiment of the invention is the compound or a pharmaceutically acceptable salt thereof, or a stereoisomer thereof, or a pharmaceutically acceptable salt of the stereoisomer thereof, which is 4-(((2S,5R)-5-((R)-(6-chloropyridin-3-yl)(hydroxy)methyl)pyrrolidin-2-yl)methyl)-N-methyl-N-((5-(trifluoromethyl)-1H-pyrazol-3-yl)methyl) benzamide.

In one embodiment of the invention is the compound or a pharmaceutically acceptable salt thereof, or a stereoisomer thereof, or a pharmaceutically acceptable salt of the stereoisomer thereof, which is 4-(((2S,5R)-5-((R)-(6-chloropyridin-3-yl)(hydroxy)methyl)pyrrolidin-2-yl)methyl)-N-((5-ethoxy-1H-pyrazol-3-yl)methyl)-N-methylbenzamide.

In one embodiment of the invention is the compound or a pharmaceutically acceptable salt thereof, or a stereoisomer thereof, or a pharmaceutically acceptable salt of the stereoisomer thereof, which is 4-(((2S,5R)-5-((R)-(6-chloropyridin-3-yl)(hydroxy)methyl)pyrrolidin-2-yl)methyl)-N-((5-ethyl-4-methyl-1H-pyrazol-3-yl)methyl)-N-methylbenzamide.

In one embodiment of the invention is the compound or a pharmaceutically acceptable salt thereof, or a stereoisomer thereof, or a pharmaceutically acceptable salt of the stereoisomer thereof, which is 4-(((2S,5R)-5-((R)-(6-chloropyridin-3-yl)(hydroxy)methyl)pyrrolidin-2-yl)methyl)-N-((4-hydroxy-5-methyl-1H-pyrazol-3-yl)methyl)-N-methylbenzamide.

In one embodiment of the invention is the compound or a pharmaceutically acceptable salt thereof, or a stereoisomer thereof, or a pharmaceutically acceptable salt of the stereoisomer thereof, which is 4-(((2S,5R)-5-((R)-(6-chloropyridin-3-yl)(hydroxy)methyl)pyrrolidin-2-yl)methyl)-N-((4-methoxy-5-methyl-1H-pyrazol-3-yl)methyl)-N-methylbenzamide.

In one embodiment of the invention is the compound or a pharmaceutically acceptable salt thereof, or a stereoisomer thereof, or a pharmaceutically acceptable salt of the stereoisomer thereof, which is N-((4-chloro-5-methyl-1H-pyrazol-3-yl)methyl)-4-(((2S,5R)-5-((R)-(6-chloropyridin-3-yl)(hydroxy)methyl)pyrrolidin-2-yl)methyl)-N-methylbenzamide.

In one embodiment, the compounds disclosed herein have Formula I, or an N-oxide thereof, or a pharmaceutically acceptable salt thereof, or a stereoisomer thereof, or a pharmaceutically acceptable salt of the stereoisomer thereof:

In one embodiment, compounds described herein have the specified stereo configuration at the indicated chiral center:

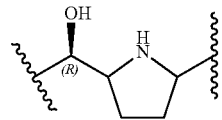

In another embodiment, compounds described herein have the specified stereoconfiguration at the indicated chiral centers, with the chiral center marked with an asterisk being R or S:

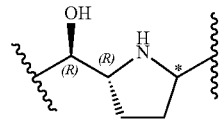

In one subset, the configuration at the chiral center marked with an asterisk is S.

In one embodiment, compounds described herein are as described in the Examples below.

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound described herein may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to, water, ethanol, and acetic acid. When the solvent is water, the solvate is known as hydrate; hydrates include, but are not limited to, hemi-, mono, sesqui-, di- and trihydrates.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound described herein or with a compound which may not be a compound described herein, but which converts to a compound described herein in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are potent agonists of the β3-adrenoceptor, and as such are useful in treating or preventing diseases, disorders or conditions mediated by the activation of β3-adrenoceptor. Thus one aspect of the present invention provides a method for the treatment, control or prevention of such diseases, disorders, or conditions in a mammal which comprises administering to such mammal a therapeutically effective amount of a compound described herein. The term "mammal" includes human and non-human animals such as dogs and cats and the like. The diseases, disorders or conditions for which compounds of the present invention are useful in treating or preventing include, but are not limited to, (1) overactive bladder, (2) urinary incontinence, (3) urge urinary incontinence, (4) urinary urgency, (5) diabetes mellitus, (6) hyperglycemia, (7) obesity, (8) hyperlipidemia, (9) hypertriglyceridemia, (10) hypercholesterolemia, (11) atherosclerosis of coronary, cerebrovascular and peripheral arteries, (12) gastrointestinal disorders including peptid ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (13) neurogenic inflammation of airways, including cough, asthma, (14) depression, (15) prostate diseases such as benign prostate hyperplasia, (16) irritable bowel syndrome and other disorders needing decreased gut motility, (17) diabetic retinopathy, (18) preterm labor, and (19)-elevated intraocular pressure and glaucoma.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds described herein are administered orally.

The effective dosage of active ingredient employed may vary depending on the particular compound employed, the mode of administration, the condition being treated and the severity of the condition being treated. Such dosage may be ascertained readily by a person skilled in the art.

When treating overactive bladder (OAB) in conjunction with other anti-OAB agents, or alone, generally satisfactory results are obtained when the compounds of the present invention are administered at a daily dosage of from 0.01 mg to about 100 mg per kg of animal body weight, preferably given in a single dose or in divided doses two to six times a day, or in sustained release form. In the case of a 70 kg adult human, the total daily dose will generally be from about 0.7 mg to about 3500 mg, or more specifically, from about 0.7 mg to about 2000 mg. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 0.01 mg to about 100 mg per kg of animal body weight, preferably given in a single dose or in divided doses two to six times a day, or in sustained release form. In the case of a 70 kg adult human, the total daily dose will generally be from about 0.7 mg to about 3500 mg. This dosage regimen may be adjusted to provide the optimal therapeutic response.

When treating diabetes mellitus and/or hyperglycemia, as well as other diseases or disorders for which compounds described herein are useful, generally satisfactory results are obtained when the compounds of the present invention are administered at a daily dosage of from about 0.001 mg to about 100 mg per kg of animal body weight, preferably given in a single dose or in divided doses two to six times a day, or in sustained release form. In the case of a 70 kg adult human, the total daily dose will generally be from about 0.07 mg to about 350 mg. This dosage regimen may be adjusted to provide the optimal therapeutic response.

In one embodiment, a compound of the present invention is used in the manufacture of a medicament for the treatment of a disease or disorder mediated by the activation of β3-adrenoceptor.

In one embodiment, a compound of the present invention is used in the manufacture of a medicament for the prevention of a disease or disorder mediated by the activation of β3-adrenoceptor.

Another aspect of the present invention provides pharmaceutical compositions which comprises a compound described herein and a pharmaceutically acceptable carrier. The pharmaceutical compositions of the present invention comprise a compound described herein as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, intravesical, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds described herein can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. Compounds described herein may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Compounds described herein may be used in combination with other drugs that are used in the treatment/prevention/suppression or amelioration of the diseases or conditions for which compounds described herein are useful. Such other drugs may be administered, by a route and in an amount commonly used therefor, contemporaneously or sequentially with a compound described herein. When a compound described herein is used contemporaneously with one or more other drugs, a pharmaceutical unit dosage form containing such other drugs in addition to the compound described herein is preferred. Accordingly, the pharmaceutical compositions of the present invention include those that also contain one or more other active ingredients, in addition to a compound described herein. Examples of other active ingredients that may be combined with a compound described herein, either administered separately or in the same pharmaceutical compositions, include, but are not limited to:

(a) overactive bladder medicines including (i) muscarinic receptor antagonists (e.g. tolterodine, mirabegron, oxybutynin including S-oxybutynin, hyoscyamine, propantheline, propiverine, trospium including trospium chloride, solifenacin, darifenacin, imidafenacin, fesoterodine, temiverine, SVT-40776, 202405 by GlaxoSmithKline, TD6301, RBX9841, DDP200, PLD179, and other anticholinergics. See, for example, U.S. Pat. No. 5,382,600; U.S. Pat. No. 3,176,019; U.S. Pat. No. 3,480,626; U.S. Pat. No. 4,564,621; U.S. Pat. No. 5,096,890; U.S. Pat. No. 6,017,927; U.S. Pat. No. 6,174,896; U.S. Pat. No. 5,036,098; U.S. Pat. No. 5,932,607; U.S. Pat. No. 6,713,464; U.S. Pat. No. 6,858,650; and DD 106643. See also, U.S. Pat. No. 6,103,747; U.S. Pat. No. 6,630,162; U.S. Pat. No. 6,770,295; U.S. Pat. No. 6,911,217; U.S. Pat. No. 5,164,190; U.S. Pat. No. 5,601,839; U.S. Pat. No. 5,834,010; U.S. Pat. No. 6,743,441; WO2002000652; WO200400414853. As will be appreciated by those of skill in the art, these drugs may be administered orally or topically in standard or extended release forms, such as extended release tolterodine, extended relesase oxybutynin and transdermal oxybutynin), (ii) NK-1 or NK-2 antagonists (e.g. aprepitant, cizolirtine, compounds disclosed in WO2005/073191, WO2005/032464, and other reported NK-1 antagonists), (iii) alpha adrenergic receptor antagonists (e.g. alfuzosin, doxazosin, prazosin, tamsulosin, terazosin, and others), (iv) potassium channel openers (e.g. cromakalim, pinacidil, and others), (v) vanilloids and other afferent-nerve modulators—agonists and antagonists (e.g. capsaicin, resiniferatoxin, and others), (vi) dopamine D1 receptor agonists (e.g. pergolinde), (vii) serotonergic and/or norepinephrine reuptake inhibitors (e.g. duloxetine), (viii) neuromuscular junction inhibition of acetylcholine release (e.g. botulinum toxin), (ix) calcium channel blockers (e.g. diltiazem, nifedipine, verapamil, and others), (x) inhibitors of prostaglandin synthesis (e.g. flurbiprofen), (xi) gamma aminobutyric acid receptor antagonists (e.g. baclofen), (xii) vaginal estrogen preparations (xiii) selective norepinephrine reuptake inhibitors, (xiv) 5-HT2C agonists, (xv) voltage gated sodium channel blocker, (xvi) P2X purinergic receptor antagonists (e.g. P2X1 or P2X3 antagonists), (xvii) PAR2 inhibitors, (xviii) phosphodiesterase inhibitors (e.g. PDE1, PDE4, and PDE5 inhibitors); and (xix) ATP sensitive potassium channel openers.

(b) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(c) insulin or insulin mimetics;

(d) sulfonylureas such as tolbutamide and glipizide;

(e) α-glucosidase inhibitors (such as acarbose), (f) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor a agonists such as fenofibric acid derivatives (gemfibrozil, clofibrat, fenofibrate and benzafibrate), (iv) inhibitors of cholesterol absorption for example beta-sitosterol and ezetimibe, and (acyl CoA:cholesterol acyltransferase) inhibitors for example melinamide, (v) probucol, (vi) vitamin E, and (vii) thyromimetics;

(g) PPARδ agonists such as those disclosed in WO97/28149;

(h) antiobesity compounds such as fenfluramine, dexfenfluramine, phentermine, sibutramine, orlistat, and other β$_3$ adrenergic receptor agonists;

(i) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(j) PPARα agonists such as described in WO 97/36579 by Glaxo;

(k) PPARγ antagonists as described in WO97/10813; and (l) serotonin reuptake inhibitors such as fluoxetine and sertraline.

In one embodiment, a compound of the present invention and a second active agent as described above are used in the manufacture of a medicament for the treatment or prevention of a disease or disorder mediated by the activation of β3-adrenoceptor.

The compounds of disclosed herein can be prepared according to the procedures of the following Schemes and Examples using appropriate materials, and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electronspray ion-mass spectroscopy.

A variety of chromatographic techniques may be employed in the preparation of the compounds. These techniques include, but are not limited to: High Performance Liquid Chromatography (HPLC) including normal phase, reversed phase, and chiral phase HPLC; Medium Pressure Liquid Chromatography (MPLC), Super Critical Fluid Chromatography; preparative Thin Layer Chromatography (prep TLC); flash chromatography with silica gel or reversed-phase silica gel; ion-exchange chromatography; and radial chromatography. Unless otherwise noted, solvent quantities used in the chromatographic examples are given on a volume to volume ratio or percentage. For example 50% ethyl acetate in petroleum either means 50% by volume and 100 ml of THF:Water (1:1) solution means 50 mL of THF and 50 mL of water.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT and HOAT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. MOZ and BOC are commonly used protecting groups in organic synthesis, and their removal conditions are known to those skilled in the art. For example, MOZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of MOZ groups can also be achieved by treatment with a solution of trifluoroacetic acid, hydrochloric acid or hydrogen chloride gas, in a solvent such as dichloromethane, methanol, or ethyl acetate. Removal of BOC protecting groups is carried out with a strong acid, such as trifluoroacetic acid, hydrochloric acid, or hydrogen chloride gas, in a solvent such as dichloromethane, methanol, or ethyl acetate.

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated:

All reactions were stirred (mechanically, stir bar/stir plate, or shaken) and conducted under an inert atmosphere of nitrogen or argon unless specifically stated otherwise.

All starting materials used to prepare the intermediates and final compounds described herein were obtained from commercial vendors, and were used as is upon receipt.

All temperatures are degrees Celsius (° C.) unless otherwise noted. Ambient temperature is 15-25° C.

Most compounds were purified by reverse-phase preparative HPLC, MPLC on silica gel, recrystallization and/or swish (suspension in a solvent followed by filtration of the solid). Automated flash chromatography was conducted using a Biotage Isolera system.

Asymmetric analysis and purification was performed using chiral HPLC employing CHIRALPAK columns (Chiral Technologies, Inc.).

The course of the reactions was followed by thin layer chromatography (TLC) and/or LCMS and/or NMR and reaction times are given for illustration only.

All end products were analyzed by NMR and LCMS. Intermediates were analyzed by NMR and/or TLC and/or LCMS.

Throughout the application, the following terms have the indicated meanings unless noted otherwise:

| Term | Meaning |
| --- | --- |
| Ac | Acyl ($CH_3C(O)$-) |
| AcOH | Acetic Acid |
| Aq. | Aqueous |
| Bn | Benzyl |
| BOC (Boc) | t-Butyloxycarbonyl |
| $BOC_2O$ | Di-tert-butyl_dicarbonate |
| BOP | Benzotriazol-1-yloxytris(dimethylamino)phosphonium hexafluorophosphate |
| ° C. | Degree Celsius |
| Calc. or calc' d | Calculated |
| Celite | Celite ™ diatomaceous earth |
| CDI | 1,1'-Carbonyldiimidazole |
| DBU | 1,8-Diazabicycloundec-7-ene |
| DCC | Dicyclohexylcarbodiimide |
| DCM | Dichloromethane |
| DEANB | Borane-N,N-diethylaniline complex |
| DIEA | N,N-diisopropyl-ethylamine |
| DIPEA | N,N-diisopropyl-ethylamine |
| DMAP | 4-Dimethylaminopyridine |
| DMP | Dimethyl phosphoramide |
| DMSO | N,N-dimethylsulfoxide |
| DMF | N,N-dimethylformamide |
| DPPA | Diphenylphosphoryl azide |
| EDC | 1-Ethyl-3-(3-dimethylaminopropyl) carbodiimide |
| EDCHCl | 1-Ethyl-3-(3-dimethylaminopropyl) carbodiimide hydrochloride |
| Eq. or equiv. | Equivalent(s) |
| ES-MS and ESI-MS | Electron spray ion-mass spectroscopy |
| Et | Ethyl |
| EtOAc | Ethyl acetate |
| EtOH | Ethanol |
| g | Gram(s) |
| h or hr | Hour(s) |
| HATU | O-(7-azabenzotriazol-1-yl)-N, N, N', N'-tetramethyluronium hexafluorophosphate |
| HCl | Hydrogen chloride |
| HOAc | Acetic acid |
| HOAT | 1-Hydroxy-7-azabenzotriazole |
| HOBT or HOBt | 1-Hydroxybenzotriazole |
| HPLC | High performance liquid chromatography |
| IPA | Isopropyl alcohol |
| kg | Kilogram(s) |
| LC/MS or LC-MASS or LCMS | Liquid chromatography mass spectrum |
| L | Liter(s) |
| LAH | Lithium aluminum hydride |
| LDA | Lithium diisopropylamide |
| LiOH | Lithium hydroxide |
| LiHMDS | Lithium bis(trimethylsilyl)amide |
| $LiALH_4$ | Lithium aluminum hydride |
| M | Molar(s) |
| $M-CO_2$ | Calculated mass of parent molecule following the loss of $CO_2$ |
| MM-ESI + APCI | Electrospray ionization (ESI) and atmospheric pressure chemical ionization (APCI) multimode (also commonly abbreviated as MM: ESI/APCI or MM: ESI-APCI) |
| Me | Methyl |
| MeCBS | Methyl Oxazaborolidine |
| MeOH | Methanol |
| MF | Molecular formula |
| min | Minute(s) |
| mg | Milligram(s) |
| mL | Milliliter(s) |

| Term | Meaning |
| --- | --- |
| mmol | Millimole(s) |
| MOZ (Moz) | p-Methoxybenzyloxycarbonyl |
| MP | Melting point |
| MS | Mass spectrum |
| M-$^t$Bu | Calculated mass of parent molecule following the loss of a tertiary-butyl group |
| NaBH(OAc)$_3$ | Sodium triacetoxyaluminum hydride |
| NaH | Sodium hydride |
| NCS | N-chlorosuccinimide |
| nM | Nanomolar |
| OTf | Trifluoromethanesulfonyl |
| 10% Pd/C | Palladium, 10 weight percent on activated carbon |
| Pd(PPh$_3$)$_4$ | Tetrakis(triphenylphosphine)palladium(0) |
| Pd$_2$(dba)$_3$ | Tris(dibenzylideneacetone)dipalladium(0) |
| Pd(ddpf)Cl$_2$ | 1,1'-Bis(diphenylphosphino)ferrocene-palladium(II)dichloride dichloromethane |
| Ph | Phenyl |
| Prep. | Preparative |
| PS-NaCNBH$_3$ | Polymer-supported cyanoborohydride |
| Ref. | Reference |
| R$_f$ | Rate of flow |
| r.t. or rt or RT | RT |
| Sat. | Saturated |
| SFC | Supercritical fluid chromatography |
| SCF CO$_2$ S | Super critical fluid carbon dioxide |
| TBAF | Tetrabutylammonium fluoride |
| TBAI | Tetrabutylammonium iodide |
| TBDMSCl | Tert-butyl dimethylsilyl chloride |
| TBDPS | Tert-butyl diphenylsilyl |
| TBS, TBDMS | Tert-butyl dimethylsilyl |
| TBSO | Tert-butyl dimethylsiloxy |
| TEA or Et$_3$N | Triethylamine |
| Tf | Triflate or trifluoromethanesulfonate |
| TFA | Trifluoroacetic acid |
| THF | Tetrahydrofuran |
| Ti(O$^i$Pr) | Titanium tetraisopropoxide |
| TLC | Thin-layer chromatography |
| TMS | Trimethylsilyl |
| TMSOK | Potassium trimethylsilanolate |
| XanthPHOS | 4,5-Bis(diphenylphosphino)-9,9-dimethylxanthene |

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT and HOAT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. MOZ and BOC are commonly used protecting groups in organic synthesis, and their removal conditions are known to those skilled in the art. For example, MOZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of MOZ groups can also be achieved by treatment with a solution of trifluoroacetic acid, hydrochloric acid or hydrogen chloride gas, in a solvent such as dichloromethane, methanol, or ethyl acetate. Removal of BOC protecting groups is carried out with a strong acid, such as trifluoroacetic acid, hydrochloric acid, or hydrogen chloride gas, in a solvent such as dichloromethane, methanol, or ethyl acetate.

Reaction Schemes below illustrate the methods employed in the synthesis of the compounds described herein. All substituents are as defined above unless indicated otherwise.

The synthesis of the novel compounds described herein may be accomplished by one or more of several similar routes. The Examples further illustrate details for the preparation of the compounds described herein. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless noted otherwise. Mass spectra (MS) were measured by electron-spray ion-mass spectroscopy.

General Reaction Schemes

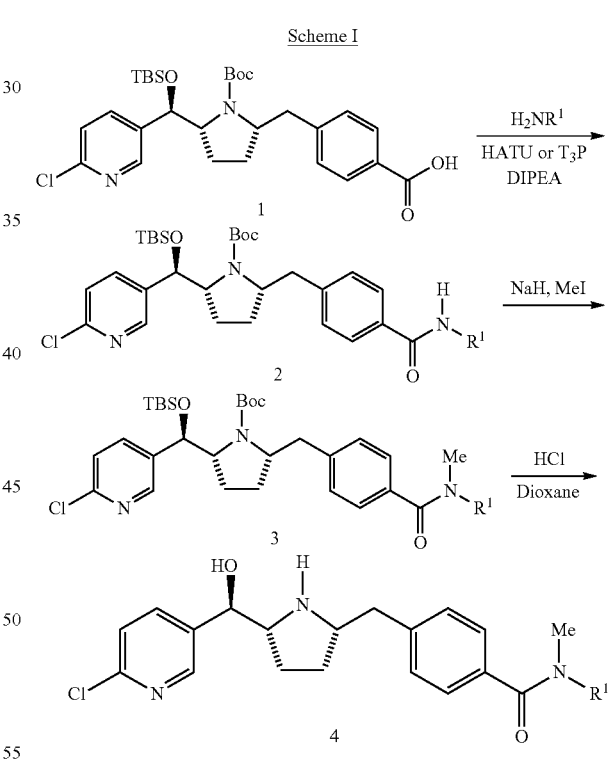

In Scheme I, a stirred cold solution of 4-(((2S,5R)-1-(tert-butoxycarbonyl)-5-((R)-((tert-butyldimethylsilyl)oxy)(6-chloropyridin-3-yl)methyl)pyrrolidin-2-yl)methyl)benzoic acid (1) in an inert solvent such as DMF is treated slowly with a 2-fold excess of a suitable coupling reagent such as HATU and in some cases some portion of a co-coupling reagent such as HOAT, in addition to a suitably basic tertiary amine such as DIPEA. Next, a primary amine is added, after which the reaction mixture may be permitted to warm to room temperature and continue stirring until most of the starting acid and/or amine are consumed. The reaction mixture is then concentrated under reduced pressure, and the resultant residue is taken up in a suitable solvent such as DCM. The resulting solution is washed successively with saturated NaHCO$_3$ and brine, dried over anhydrous Na$_2$SO$_4$, and concentrated to dryness. The crude product is purified by flash column chromatography or a suitable alternative to afford doubly protected intermediate 2.

Next, a stirred cold solution of 2 in an inert solvent such as THF is treated with a slight excess of NaH, followed by a 2-fold excess of MeI. After continued stirring at low temperature, the reaction mixture is quenched by the addition of saturated NH$_4$Cl and extracted with ethyl acetate. The organic fraction is dried over anhydrous Na$_2$SO$_4$, and concentrated to dryness. The crude product is purified by flash column chromatography or a suitable alternative to afford doubly protected intermediate 3.

Finally, a solution of intermediate 3 in an inert solvent such as dioxane is treated with a solution of HCl in dioxane. Once the double-deprotection is complete, the reaction mixture is concentrated to dryness and the crude product is purified by flash column chromatography or a suitable alternative to afford the final example 4.

Next, a solution of intermediate 3 in an inert solvent such as dioxane is treated with a solution of HCl in dioxane. Once the double-deprotection is complete, the reaction mixture is concentrated to dryness and the crude product is purified by flash column chromatography or a suitable alternative to afford the final example 4.

Scheme II

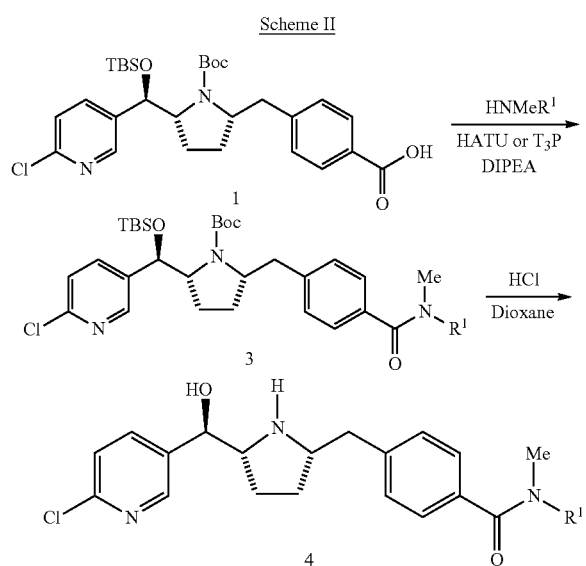

In Scheme II, a stirred cold solution of 4-(((2S,5R)-1-(tert-butoxycarbonyl)-5-((R)-((tert-butyldimethylsilyl)oxy)(6-chloropyridin-3-yl)methyl)pyrrolidin-2-yl)methyl)benzoic acid (1) in an inert solvent such as DMF is treated slowly with a 2-fold excess of a suitable coupling reagent such as HATU and in some cases some portion of a co-coupling reagent such as HOAT, in addition to a suitably basic tertiary amine such as DIPEA. Next, an N-methylated secondary amine is added, after which the reaction mixture may be permitted to warm to room temperature and continue stirring until most of the starting acid and/or amine are consumed. The reaction mixture is then concentrated under reduced pressure, and the resultant residue is taken up in a suitable solvent such as DCM. The resulting solution is washed successively with saturated NaHCO$_3$ and brine, dried over anhydrous Na$_2$SO$_4$, and concentrated to dryness. The crude product is purified by flash column chromatography or a suitable alternative to afford doubly protected intermediate 3.

Scheme III

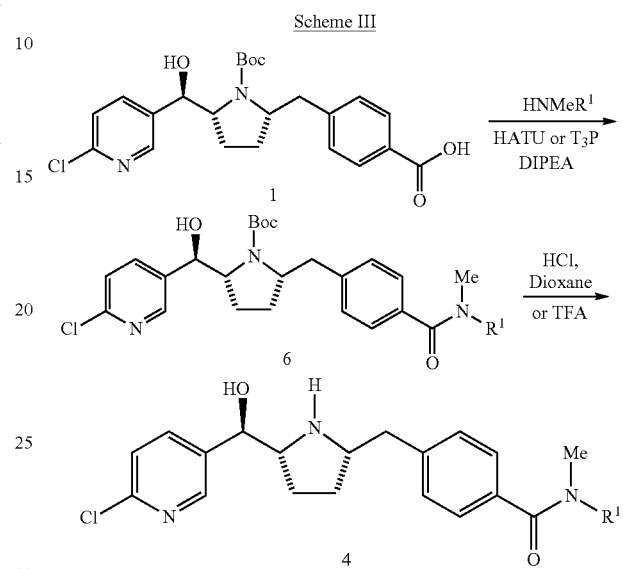

In Scheme III, a stirred cold solution of 4-(((2S,5R)-1-(tert-butoxycarbonyl)-5-((R)-(6-chloropyridin-3-yl)(hydroxy)methyl)pyrrolidin-2-yl)methyl)benzoic acid (5) in an inert solvent such as DMF is treated slowly with a 2-fold excess of a suitable coupling reagent such as HATU and in some cases some portion of a co-coupling reagent such as HOAT, in addition to a suitably basic tertiary amine such as DIPEA. Next, an N-methylated secondary amine is added, after which the reaction mixture may be permitted to warm to room temperature and continue stirring until most of the starting acid and/or amine are consumed. The reaction mixture is then concentrated under reduced pressure, and the resultant residue is taken up in a suitable solvent such as DCM. The resulting solution is washed successively with saturated NaHCO$_3$ and brine, dried over anhydrous Na$_2$SO$_4$, and concentrated to dryness. The crude product is purified by flash column chromatography or a suitable alternative to afford doubly protected intermediate 6.

Next, a solution of intermediate 6 in an inert solvent such as dioxane is treated with a solution of HCl in dioxane. Once the double-deprotection is complete, the reaction mixture is concentrated to dryness and the crude product is purified by flash column chromatography or a suitable alternative to afford the final compound 4.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Core Acids A-S

Core Acids A-S were used as intermediates in the synthesis of the compounds of the present invention and the comparative compounds disclosed in this application. The independent syntheses for Core Acids I, J, L, N and O were not required, as final products employing the pharmacophore functionality within were obtained directly from alternative advanced-stage intermediates. The preparations of these final products are provided below.

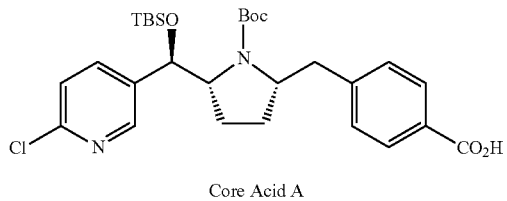

Core Acid A

The preparation of 4-(((2S,5R)-1-(tert-butoxycarbonyl)-5-((R)-((tert-butyldimethylsilyl) oxy)(6-chloropyridin-3-yl)methyl)pyrrolidin-2-yl)methyl)benzoic acid (A) is disclosed in the international patent application published as WO2011/025690 to Edmondson, S. D., et al.

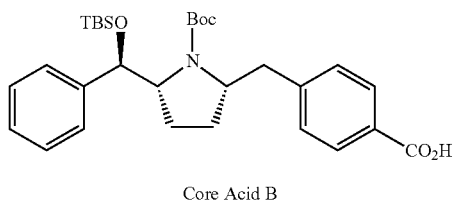

Core Acid B

The preparation of 4-(((2S,5R)-1-(tert-butoxycarbonyl)-5-((R)-((tert-butyldimethylsilyl) oxy)(phenyl)methyl)pyrrolidin-2-yl)methyl)benzoic acid (B) was previously reported in the international patent application published as WO2011/025690 to Edmondson, S. D., et al.

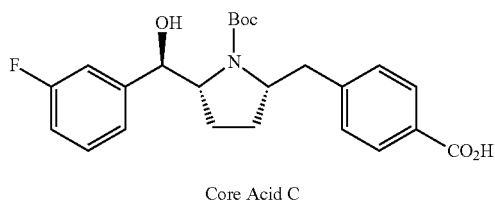

Core Acid C

The preparation of 4-(((2S,5R)-1-(tert-butoxycarbonyl)-5-((R)-(3-fluorophenyl)(hydroxy) methyl)pyrrolidin-2-yl)methyl)benzoic acid © proceeded similarly to the method for Core Acid D.

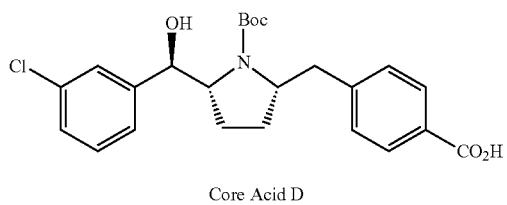

Core Acid D

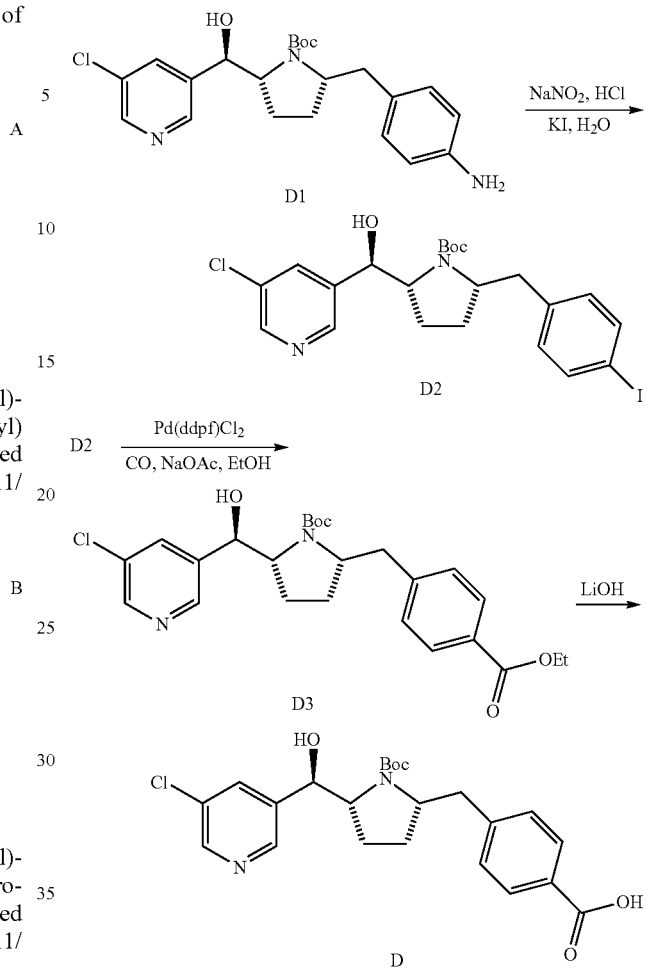

Step A (2R,5S)-tert-butyl 2-((R)-(3-chlorophenyl)(hydroxy)methyl)-5-(4-iodobenzyl)pyrrolidine-1-carboxylate (D2)

Aniline derivative (2S,5R)-tert-butyl 2-(4-aminobenzyl)-5-((R)-(3-chlorophenyl) (hydroxy) methyl)pyrrolidine-1-carboxylate (D1) (for synthesis, see international patent application to Berger, R., et al., published as WO 2011/135054) (8.8 g, 21 mmol) was taken in conc. HCl (5 mL) and cooled to −15° C. To this cooled solution, sodium nitrite (1.8 g, 27 mmol) was added in portions (internal temperature was maintained at 0° C.) and was stirred for 1 h at the same temperature. This cold reaction mixture was added to a solution of potassium iodide (17.4 g, 105 mmol) in acetonitrile (20 mL) at −15° C. through cannula and stirred at the same temperature for 20 min. The reaction mixture was allowed to attain room temperature was stirred for 3 h. The reaction mixture was neutralized with aqueous NaOH (10%, 12 mL) solution and extracted with ethyl acetate. The organic layer was separated and washed with water and brine successively, dried over anhydrous $Na_2SO_4$ and concentrated under reduced pressure. The residue was purified by column chromatography using 50% ethyl acetate in petroleum ether (v/v) to yield D2. The crude compound was taken to the next step without further purification.

Step B (2R,5S)-tert-butyl 2-((R)-(3-chlorophenyl)(hydroxy)methyl)-5-(4-(ethoxycarbonyl)benzyl)pyrrolidine-1-carboxylate (D3)

To a solution of D2 (9.2 g, 17 mmol) in ethanol (200 mL) sodium acetate (4.18 g, 51 mmol) and Pd(dppf)Cl$_2$ (1.46 g, 2 mmol) were added and the reaction mixture was heated to reflux overnight under the atmosphere of carbon monoxide (balder pressure). The reaction mixture was passed through a celite bed and concentrated under reduced pressure. The crude mass was purified by column chromatography using 12% ethyl acetate in petroleum ether (v/v) to afford D3 (4.5 g over two steps).

$^1$H NMR (300 MHz, DMSO-d$_6$): δ 7.82 (d, J=8.13 Hz, 2H), 7.47-7.27 (m, 5H), 7.17-7.06 (m, 2H), 5.75-5.64 (m, 1H), 5.25-5.12 (m, 1H), 4.25 (q, J=7.17 Hz, 2H), 4.10-3.94 (m, 2H), 3.89-3.72 (m, 1H), 1.89-1.67 (m, 2H), 1.36-1.29 (m, 4H), 1.43 (s, 9H), 1.27 (t, J=7.08 Hz, 3H). Molecular Formula: C$_{26}$H$_{32}$ClNO$_5$; LC-MS purity: 45.2%; Expected: 473.2; Observed: 374 (M-Boc).

Step C 4-(((2S,5R)-1-(tert-butoxycarbonyl)-5-((R)-(3-chlorophenyl)(hydroxy)methyl) pyrrolidin-2-yl)methyl)benzoic acid (D)

To a solution of D3 (4.2 g, 8.8 mmol) in THF:water (1:1, 40 mL) and methanol (10 mL) lithium hydroxide (1.5 g, 26 mmol) was added and the reaction mixture was stirred at room temperature for 2 h. The reaction mixture was neutralized with citric acid and was extracted with ethyl acetate. The organic layer was dried over Na$_2$SO$_4$ and concentrated under reduced pressure. The crude mass was purified by automated flash chromatography using 50% ethyl acetate in petroleum ether (v/v) to yield D (3.4 g).

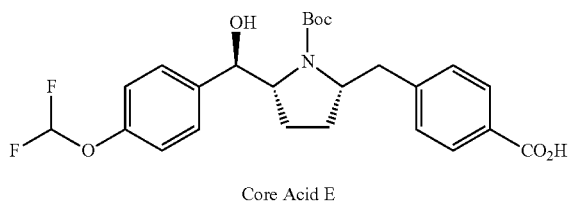

Core Acid E

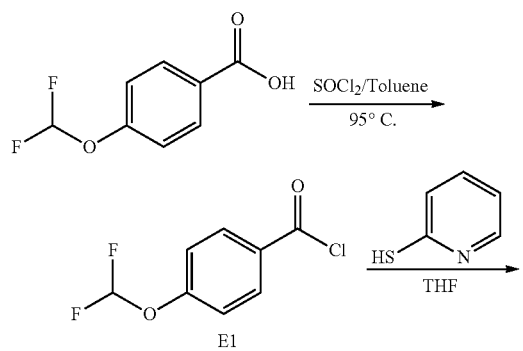

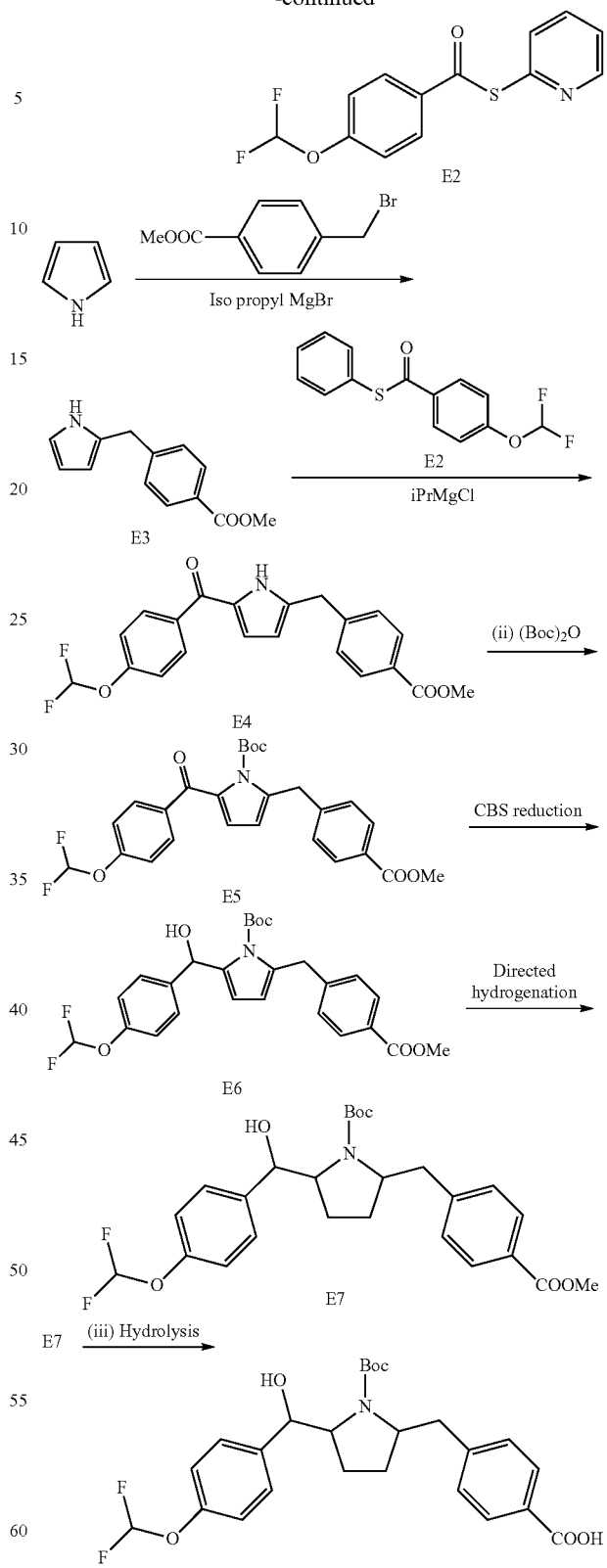

Step A 4-(difluoromethoxy)benzoyl chloride (E1)

To a stirred solution of 4-(difluoromethoxy)benzoic acid (5 g, 26.57 mmol) in dry toluene (50 mL) was added thionyl chloride (2.9 mL, 39.86 mmol) at 0° C. and heated at 95° C. for 3 h. The solvents were removed under reduced pressure and the residue was co-evaporated with toluene to obtain 4-(difluoromethoxy) benzoyl chloride E1 which was taken to next step without further purification.

Step B S-pyridin-2-yl 4-(difluoromethoxy)benzothioate (E2)

A solution of 2-mercaptopyridine (2.7 g, 24.2 mmol) in THF (10 mL) was treated slowly with E1 (5 g, 24.2 mmol) in THF (10 mL). The resulting slurry was stirred for 30 min. The reaction was quenched with 10% $NaHCO_3$ solution and diluted with ethyl acetate. The layers were separated and the aqueous layer was extracted with ethyl acetate. The combined organic extract was washed with brine, dried over anhydrous $Na_2SO_4$ and concentrated to give a solid, which was washed with hexanes to afford E2 (3.7 g, quantitative).

$^1$H NMR (300 MHz, $CD_3OD$): δ 8.61 (d, J=0.75 Hz, 1H), 8.07 (dd, J=2.01 and 6.87 Hz, 2H), 7.98-7.92 (m, 1H), 7.77 (dd, J=0.87 and 7.86 Hz, 2H), 7.52-7.48 (m, 1H), 7.29 (d, J=8.85 Hz, 2H). Molecular Formula: $C_{13}H_9F_2NO_2S$; LC-MS purity: 86.5%; Expected: 281.3; Observed: 281.8 (M+1).

Step C Methyl 4-((1H-pyrrol-2-yl)methyl)benzoate (E3)

Pyrrole (2.9 g, 43.66 mmol) was dissolved in a solution of THF:DCM (1:1, 100 mL) and cooled to 0° C. Isopropyl magnesium bromide (25 mL, 110.4 mmol, 1.7 M in THF) was added drop wise and stirred for 1 h at room temperature. The solution was cooled again to 0° C. and Methyl 4-(bromomethyl)benzoate (10 g, 43.66 mmol) was added and stirred at room temperature for 12 h. The reaction was quenched with $NH_4Cl$ and diluted with ethyl acetate. The layers were separated and the aqueous layer was extracted with ethyl acetate. The combined organic extracts was washed with brine, dried over anhydrous $Na_2SO_4$ and filtered. The filtrate was concentrated and the residue was purified by column chromatography using 15% ethyl acetate in petroleum ether (v/v) to afford compound E3 (5.8 g) as a white solid. Molecular Formula: $C_{13}H_{13}NO_2$; LCMS purity: 91%; Expected: 215.3; Observed: 216.2 (M+1).

Step D Methyl 4-((5-(4-(difluoromethoxy)benzoyl)-1H-pyrrol-2-yl)methyl)benzoate (E4)

A solution of isopropyl magnesium chloride (34 mL, 68.18 mmol, 2 M in THF) was added slowly to a solution of E3 (5.8 g, 26.95 mmol) in THF (30 mL) under nitrogen at −78° C. The resulting mixture was then warmed to −30° C. A solution of E2 (7.7 g, 26.95 mmol) in THF (30 mL) was then added to this cooled reaction mixture. The reaction mixture was allowed to stir at room temperature for 14 h. The reaction was quenched by the addition of saturated aqueous $NH_4Cl$ solution. The mixture was extracted with ethyl acetate. The organic layer was washed with water and brine, dried over anhydrous $Na_2SO_4$ and filtered. The filtrate was concentrated. The residue was purified by column chromatography using 15% ethyl acetate in petroleum ether (v/v) to afford E4 (4.6 g) as a white solid.

$^1$H NMR (400 MHz, $CD_3OD$): δ 7.96 (dd, J=1.88 and 6.56 Hz, 2H), 7.88 (dd, J=2.08 and 6.72 Hz, 2H), 7.38 (d, J=8.52 Hz, 2H), 7.25 (dd, J=6.88 and 8.8 Hz, 2H), 7.15-6.80 (t, J=69.24 Hz, 1H), 6.79 (d, J=1.92 Hz, 1H), 6.06 (d, J=3.84 Hz, 1H), 4.25 (s, 2H), 4.11 (s, 2H), 3.91 (s, 3H). Molecular Formula: $C_{21}H_{17}F_2NO_4$; LCMS purity: 73.8%; Expected: 385.4; Observed: 385.8 (M+1).

Step E Tert-butyl 2-(4-(difluoromethoxy)benzoyl)-5-(4-(methoxycarbonyl)benzyl)-1H-pyrrole-1-carboxylate (E5)

To a solution of compound E4 (4.6 g, 11.94 mmol) in THF (50 mL) di-tert-butyl dicarbonate (2.86 mL, 13.14 mmol) was added at room temperature with stirring. To this stirred solution catalytic amount of DMAP (150 mg) was added and the reaction mixture was heated to 80° C. for 3 h. The solvents were removed under reduced pressure and the residue was dissolved in $CH_2Cl_2$, successively washed with water and brine, dried over anhydrous $Na_2SO_4$ and filtered through a celite bed. The solvent was removed under reduced pressure and the crude mass was purified by column chromatography using 8% ethyl acetate in petroleum ether (v/v) to afford compound E5 (4.1 g) as a white solid.

$^1$H NMR (400 MHz, $CD_3OD$): δ 7.97-7.94 (m, 4H), 7.29-7.27 (m, 4H), 7.0 (t, J=73.32 Hz, 1H), 6.68 (d, J=3.68 Hz, 1H), 6.13 (d, J=3.68 Hz, 1H), 4.31 (s, 2H), 3.89 (s, 3H), 1.26 (s, 9H). Molecular Formula: $C_{26}H_{25}F_2NO_6$; LC-MS purity: 80.6%; Expected: 485.5; Observed: 485.8 (M+1).

Step F Tert-butyl 2-((4-(difluoromethoxy)phenyl)(hydroxy)methyl)-5-(4-(methoxycarbonyl)benzyl)-1H-pyrrole-1-carboxylate (E6)

To a dried round bottomed flask freshly distilled anhydrous toluene (4 mL) was added followed by To a dried round bottomed flask freshly distilled anhydrous toluene (4 mL) was added followed by (R)-MeCBS (1M in toluene, 0.86 mL, 0.827 mmol) and DEANB (0.76 mL, 4.92 mmol) was added via syringe and the reaction mixture was stirred for 10 min at room temperature. To a dried round bottomed flask freshly distilled anhydrous toluene (4 mL) was added followed by (R)-MeCBS (1M in toluene, 0.86 mL, 0.827 mmol) and DEANB (0.76 mL, 4.92 mmol) was added via syringe and the reaction mixture was stirred for 10 min at room temperature. -MeCBS (1M in toluene, 0.86 mL, 0.827 mmol) and DEANB (0.76 mL, 4.92 mmol) was added via syringe and the reaction mixture was stirred for 10 min at room temperature. To this stirred solution was added compound E5 (2.0 g, 4.12 mmol) in toluene (2 mL) over a period of 10 min and the resultant mixture was stirred at room temperature for 2 h. The reaction was carefully quenched with MeOH. The solvents were removed under reduced pressure and the crude mass was purified by column chromatography using 12% ethyl acetate in petroleum ether (v/v) to afford E6 (1.5 g) as white solid.

Analysis by analytical chiral HPLC (Hexane(60) Ethanol (40), 25° C., 1.0 mL/min) showed 87% ee versus a racemic reference.

$^1$H NMR (400 MHz, $CD_3OD$): δ 7.92 (d, J=8.32 Hz, 2H), 7.32 (d, J=8.56 Hz, 2H), 7.17 (d, J=8.28 Hz, 2H), 7.11 (d, J=8.52 Hz, 2H), 6.80 (t, J=74.16 Hz, 1H), 6.16 (s, 1H), 5.95 (dd, J=3.32 and 7.16 Hz, 2H), 4.25 (s, 2H), 3.88 (s, 3H), 1.23 (s, 9H).

Step G Tert-butyl 2-((4-(difluoromethoxy)phenyl)(hydroxy)methyl)-5-(4-(methoxycarbonyl)benzyl) pyrrolidine-1-carboxylate (E7)

A solution of compound E6 (1.5 g, 3.08 mmol) in dry methanol (20 mL) was degassed with argon and 5% Pt/C (400 mg, 30% by wt) was added. The reaction mixture was stirred under bladder pressure (1 Kg) for 18 h. The reaction mixture was filtered through a celite bed followed by a short pass through column. The solvent was removed under reduced pressure and the residue was purified by column chromatography using 25% ethyl acetate in petroleum ether (v/v) to afford compound E7 (500 mg) as white solid.

Molecular Formula: $C_{26}H_{31}F_2NO_6$; LC-MS purity: 99.2%; Expected: 491.5; Observed: 392 (M+1-Boc).

Step H 4-(((2S,5R)-1-(tert-butoxycarbonyl)-5-((R)-(4-(difluoromethoxy) phenyl)(hydroxy)methyl)pyrrolidin-2-yl)methyl)benzoic acid (E)

Compound E was prepared following similar procedure as for the preparation of acid A. Molecular Formula: $C_{25}H_{29}F_2NO_6$; LCMS purity: 98.5%; Expected: 477.5; Observed: 378.2 (M+1-Boc).

The preparation of 4-(((2S,5R)-1-(tert-butoxycarbonyl)-5-((R)-((tert-butyldimethylsilyl) oxy)(4-fluorophenyl)methyl)pyrrolidin-2-yl)methyl)benzoic acid (F) proceeded similarly to the method for Core Acid D.

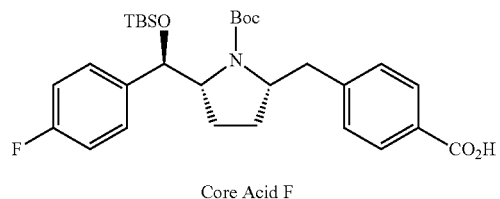

Core Acid F

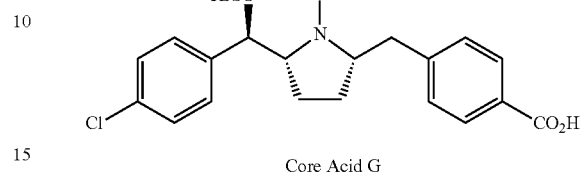

Core Acid G

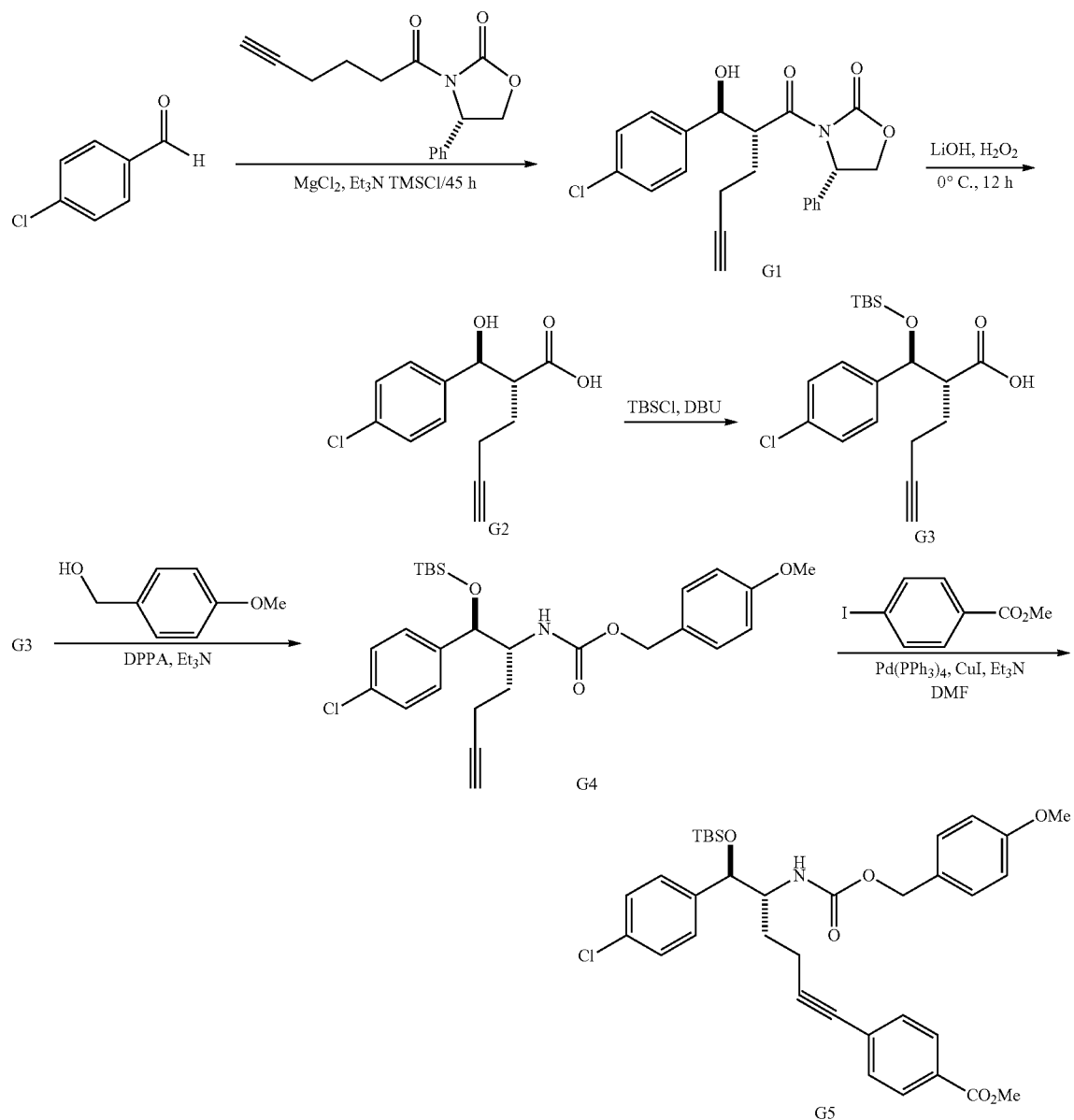

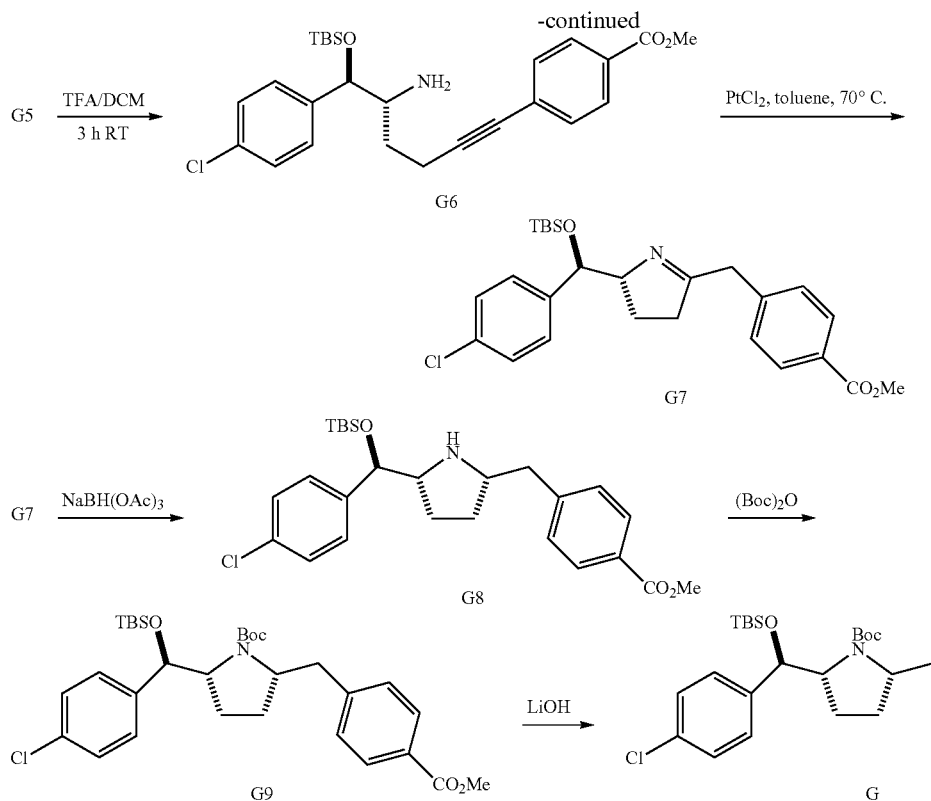

Step A (S)-3-((R)-2-((S)-(4-chlorophenyl)(hydroxy)methyl)hex-5-ynoyl)-4-phenyloxazolidin-2-one (G1)

To a stirred solution of (S)-3-(hex-5-ynoyl)-4-phenyloxazolidin-2-one (16 g, 62.6 mmol) in ethyl acetate (100 mL) were added MgCl$_2$ (1.35 g, 14.23 mmol), TEA (19.8 mL, 142.27 mmol), 4-Chloro benzaldehyde (10 g, 71.13 mmol) and TMS-Cl (13.9 mL, 108.84 mmol). The resulting mixture was stirred at room temperature for 48 h under Argon. The reaction mixture was filtered and filtrate was evaporated to dryness. The residue was dissolved in MeOH (100 mL) and TFA (2.5 mL) was added; and the mixture was then stirred for 4 h at room temperature. The solvent was removed under reduced pressure and the residue was purified by column chromatography using 15% ethyl acetate in petroleum ether (v/v) to afford G1 (18 g).

Molecular Formula: $C_{22}H_{20}ClNO_4$; LC-MS purity: 87.5%; Expected: 397.8; Observed: 398.2 (M+1).

Step B (R)-2-((S)-(4-chlorophenyl)(hydroxy)methyl)hex-5-ynoic acid (G2)

Compound G1 (18 g, 45.24 mmol) was dissolved in a mixture of THF (275 mL) and water (25 mL) at 0° C. and 30% H$_2$O$_2$ (19.8 mL) was added slowly followed by aq. LiOH (2.8 g, 67.87 mmol). The reaction mixture was then stirred overnight at room temperature. The reaction mixture was cooled to 0° C. and was quenched with saturated Na$_2$SO$_3$ solution. The reaction mixture was allowed to attain room temperature and THF was removed under reduced pressure. The aqueous phase was cooled to 0° C., adjusted to pH~5 with 1N HCl and extracted with ethyl acetate. The organic layer was washed with brine, dried over anhydrous Na$_2$SO$_4$, filtered and evaporated to obtain G2 (10 g).

Molecular Formula: $C_{13}H_{13}ClO_3$; LC-MS purity: 83.4%; Expected: 252.7; Observed: 253.2 (M+1).

Step C (R)-2-((S)-((tert-butyldimethylsilyl)oxy)(4-chlorophenyl)methyl)hex-5-ynoic acid (G3)

TBSCl (9.1 g, 59.76 mmol) was added to a stirred mixture of G2 (10 g, 39.84 mmol) and DBU (17.9 ml, 119.52 mmol) in acetonitrile (150 mL), and the mixture was stirred overnight at room temperature. The reaction mixture was concentrated to dryness under reduced pressure. The residue was dissolved in dichloromethane (300 mL) and water (200 mL) was added to it and the pH was adjusted to 3 with 2N HCl and the organic layer was separated. The organic layer was washed with brine, dried over anhydrous Na$_2$SO$_4$, filtered and the solvent was evaporated under reduced pressure. Resulting solid was washed with n-hexane and dried to afford G3 (10 g) as white solids.

Molecular Formula: $C_{19}H_{27}ClO_3Si$; LC-MS purity: 80%; Expected: 366.95; Observed: 365 (M−2).

Step D 4-methoxybenzyl ((1R,2R)-1-((tert-butyldimethylsilyl)oxy)-1-(4-chlorophenyl)hex-5-yn-2-yl)carbamate (G4)

To a stirred solution of G3 (10 g, 27.25 mmol) in toluene (100 mL) was added TEA (7.5 mL, 54.5 mmol) followed by the addition of DPPA (6 mL, 27.25 mmol). The resulting solution was stirred at ambient temperature for 1 h and p-methoxy benzyl alcohol (9.4 mL, 68.13 mmol) was added. The reaction mixture was heated to 80° C. for 16 h. The reaction mixture was cooled to room temperature and solvents were evaporated. The crude product was purified by column chromatography using 15% ethyl acetate in petroleum ether (v/v) to afford G4 (10 g) as yellow foam.

$^1$H NMR (300 MHz, CDCl$_3$): δ 7.26-7.17 (m, 6H), 6.91-6.88 (m, 2H), 5.32 (s, 2H), 5.04-4.93 (m, 2H), 3.83 (s, 3H), 2.28-2.25 (m, 1H), 1.97-1.87 (m, 2H), 1.40-1.32 (m, 2H), 0.98 (s, 9H), 0.11 (s, 3H), −0.06 (s, 3H). Molecular Formula: $C_{19}H_{27}ClO_3Si$; LC-MS purity: 92.6%; Expected: 502.1; Observed: 458.2 (M-CO$_2$).

Step E Methyl 4-((5R,6R)-6-((tert-butyldimethylsilyl)oxy)-6-(4-chlorophenyl)-5-((((4-methoxybenzyl)oxy)carbonyl)amino)hex-1-yn-1-yl)benzoate (G5)

Methyl 4-iodo benzoate (6 g, 21.91 mmol), G4 (10.0 g, 19.92 mmol) and TEA (8.3 mL, 59.76 mmol) were suspended in DMF (80 mL) and nitrogen was bubbled through the reaction mixture for 15 min. Then Pd(dppf)CH$_2$Cl$_2$ adduct (650 mg, 0.79 mmol) and CuI (303 mg, 1.59 mmol) were added and the resulting solution was stirred overnight at room temperature. The reaction was slowly quenched with water and extracted with ethyl acetate. The combined extracts was washed with water and brine, dried over anhydrous Na$_2$SO$_4$, filtered and evaporated under reduced pressure. The crude product was purified by column chromatography using 10% ethyl acetate in petroleum ether (v/v) to yield G5 (11 g).

$^1$H NMR (300 MHz, CDCl$_3$): δ 7.96-7.90 (m, 2H), 7.45-7.42 (m, 2H), 7.26-7.17 (m, 5H), 6.98-6.87 (m, 3H), 5.30 (s, 2H), 5.03-4.91 (m, 2H), 3.92 (s, 3H), 3.78 (s, 3H), 2.54-2.50 (m, 2H), 2.05-1.93 (m, 2H), 1.64-1.61 (m, 1H), 0.98 (s, 9H), 0.10 (s, 3H), −0.07 (s, 3H). Molecular Formula: $C_{19}H_{27}ClO_3Si$; LC-MS purity: 99.3%; Expected: 636.3; Observed: 592.2 (M-CO$_2$).

Step F Methyl 4-((5R,6R)-5-amino-6-((tert-butyldimethylsilyl)oxy)-6-(4-chlorophenyl)hex-1-yn-1-yl)benzoate (G6)

To a stirred solution of G5 (11 g, 17.29 mmol) in CH$_2$Cl$_2$ (110 mL) was added TFA (6.6 mL, 86.44 mmol) and the resulting mixture was stirred for 1 h at room temperature. All volatiles were evaporated under reduced pressure and the residue was diluted with water and basified using NaHCO$_3$ solution, extracted with dichloromethane (100 mL). The organic layer was washed with water and brine, dried over anhydrous Na$_2$SO$_4$ and evaporated to dryness to afford G6 (8 g, quantitative) as light brown gum.

Molecular Formula: $C_{26}H_{34}ClNO_3Si$; LC-MS purity: 38.85%; Expected: 472.1; Observed: 472 (M).

Step G Methyl 4-(((R)-2-((R)-((tert-butyldimethylsilyl)oxy)(4-chlorophenyl)methyl)-3,4-dihydro-2H-pyrrol-5-yl)methyl)benzoate (G7)

A stirred solution of G6 (8 g, 16.95 mmol) in toluene (80 mL) was degassed by bubbling Argon and PtCl$_2$ (450 mg, 1.69 mmol) was added. The resulting mixture was heated at 80° C. for 3 h under Argon. The reaction mixture was concentrated under reduced pressure to afford G7 (8 g, quantitative) which was used in the next step without further purification.

Step H Methyl 4-(((2S,5R)-5-((R)-((tert-butyldimethylsilyl)oxy)(4-chlorophenyl)methyl)pyrrolidin-2-yl)methyl)benzoate (G8)

To a stirred solution of compound G7 (8 g, 16.95 mmol) in anhydrous dichloromethane (80 mL) was added NaBH(OAc)$_3$ (10.7 g, 50.12 mmol) at 0° C. The resulting mixture was allowed to gradually warm to room temperature overnight. The homogeneous mixture was filtered through celite and the celite bed was washed with dichloromethane. The filtrate was washed with saturated NaHCO$_3$ solution. The organic layer was dried over anhydrous Na$_2$SO$_4$, filtered, and evaporated under reduced pressure to afford G8 (8 g, quantitative) which was used in the next step without purification.

Molecular Formula: $C_{26}H_{36}ClNO_3Si$; Expected: 474.11; Observed: 474 (M).

Step I (2R,5S)-tert-butyl 2-((R)-((tert-butyldimethylsilyl)oxy)(4-chlorophenyl)methyl)-5-(4-(methoxycarbonyl)benzyl)pyrrolidine-1-carboxylate (G9)

To a stirred solution of G8 (8.0 g, 16.87 mmol) in Dichloromethane (80 mL) was added DIEA (5.9 mL, 33.75 mmol) followed by slow addition of Boc anhydride (4.04 mL, 18.56 mmol). The resulting reaction mixture was stirred at ambient temperature for 16 h, and solvents were evaporated under reduced pressure. The crude mixture was purified by column chromatography using 5% ethyl acetate in petroleum ether (v/v) to provide G9 (2.5 g) as colorless foam.

Molecular Formula: $C_{31}H_{44}ClNO_5Si$; Expected: 574.2; Observed: 474 (M-Boc).

Step J 4-(((2S,5R)-1-(tert-butoxycarbonyl)-5-((R)-((tert-butyldimethylsilyl)oxy)(4-chlorophenyl)methyl)pyrrolidin-2-yl)methyl)benzoic acid (G)

Compound G was prepared following similar procedure as for the preparation of acid A.

Molecular Formula: $C_{26}H_{36}ClNO_3Si$; LCMS purity: 90.6%; Expected: 560.2; Observed: 460 (M-Boc).

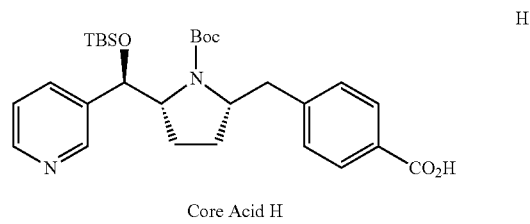 [SMILES: CC(C)(C)OC(=O)N1[C@H](Cc2ccc(C(=O)O)cc2)CC[C@@H]1[C@H](O[Si](C)(C)C(C)(C)C)c1ccccc1]

Core Acid H

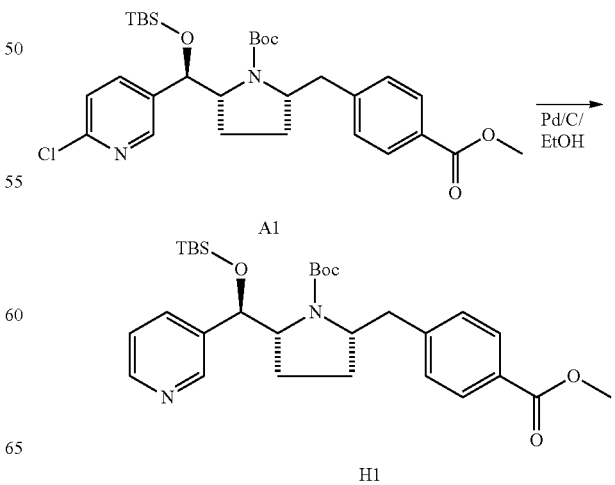

-continued

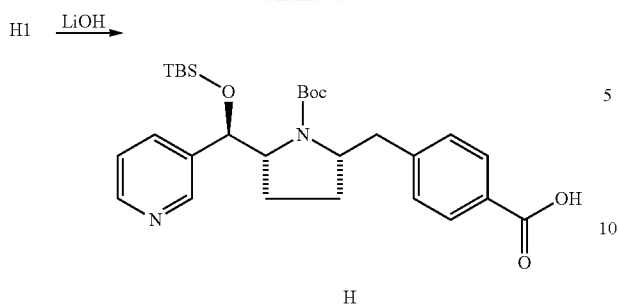

H

Step A (2R,5S)-tert-butyl 2-((R)-((tert-butyldimethylsilyl)oxy)(pyridin-3-yl)methyl)-5-(4-(methoxycarbonyl)benzyl)pyrrolidine-1-carboxylate (H1)

To a stirred solution of (2R,5S)-tert-butyl 2-((R)-((tert-butyldimethylsilyl)oxy)(6-chloropyridin-3-yl)methyl)-5-(4-(methoxycarbonyl)benzyl)pyrrolidine-1-carboxylate (A1) (1 g, 1.74 mmol) in ethanol (25 mL) was added 10% Pd/C (200 mg) and the reaction mixture was degassed. The reaction mixture stirred under balloon pressure (1 atm) till the completion of the reaction and the reaction mixture was filtered through a pad of celite. The filtrate was concentrated under reduced pressure and the residue was purified over silica gel using 50% ethyl acetate in petroleum ether to yield H1 (400 mg).

Molecular Formula: $C_{30}H_{44}N_2O_5Si$; LCMS purity: 72%; Expected: 540.3; Observed: 541 (M+1).

Step B 4-(((2S,5R)-1-(tert-butoxycarbonyl)-5-((R)-((tert-butyldimethylsilyl) oxy)(pyridin-3-yl)methyl) pyrrolidin-2-yl)methyl)benzoic acid (H)

Compound H was prepared from H1 following similar procedure as for the preparation of Core Acid A. Molecular Formula: $C_{29}H_{42}N_2O_5Si$; LCMS purity: 96.8%; Expected: 526.3; Observed: 527.4 (M+1).

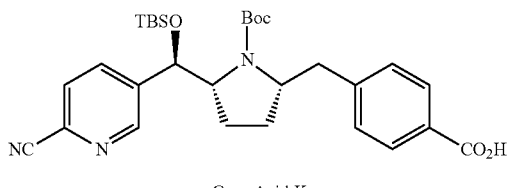

Core Acid K

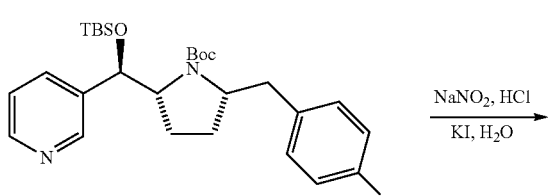

K1

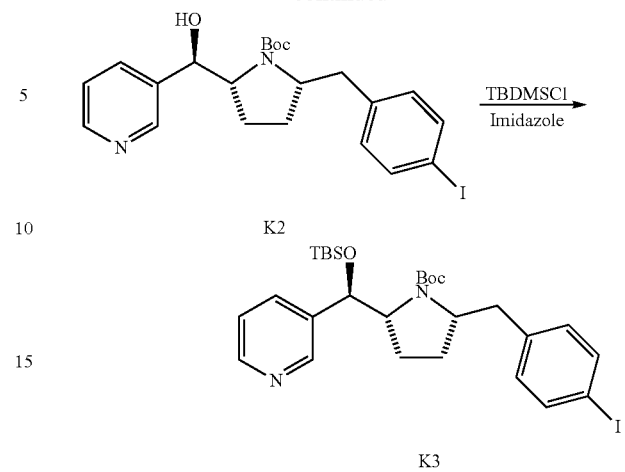

K2

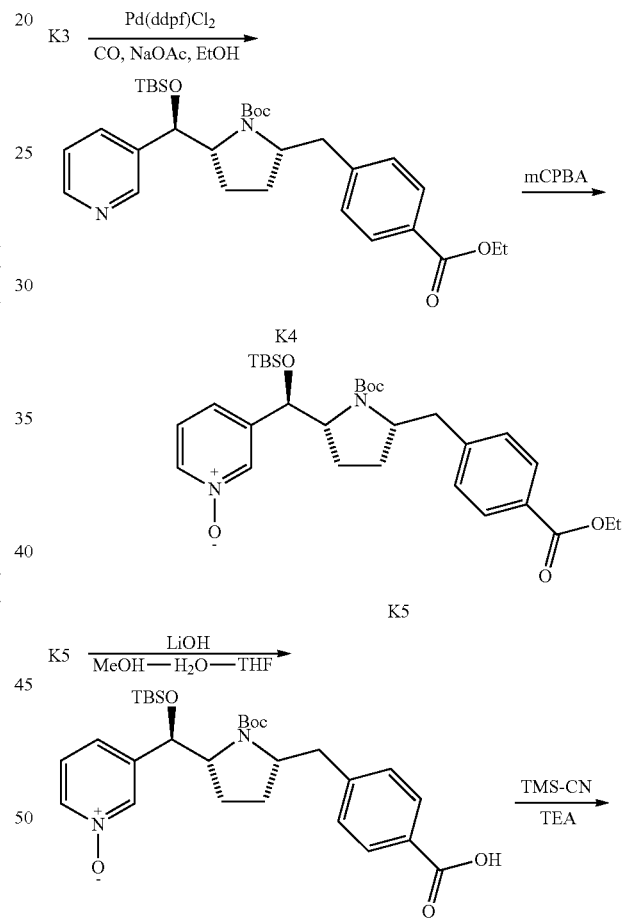

K

Step A (2R,5S)-tert-butyl 2-((R)-hydroxy(pyridin-3-yl)methyl)-5-(4-iodobenzyl) pyrrolidine-1-carboxylate (K2)

Aniline derivative (2S,5R)-tert-butyl 2-(4-aminobenzyl)-5-((R)-((tert-butyldimethylsilyl) oxy)(pyridin-3-yl)methyl) pyrrolidine-1-carboxylate (K1)) (for synthesis, see international patent application to Berger, R., et al., published as WO 2011/135054) (25 g, 50.3 mmol) was taken in conc. HCl (12 mL) and cooled to −15° C. Sodium nitrite (4.4 g, 65.3 mmol) was added in portions (internal temperature maintained at 0° C.) and stirred for 1 h at the same temperature. This cold reaction mixture was added to a solution of potassium iodide (41.7 g, 65.3 mmol) in acetonitrile (20 mL) at −15° C. through a cannula and stirred at the same temperature for 20 min. The reaction mixture was stirred at room temperature for 3 h. The reaction mixture was neutralized with aqueous NaOH solution (10%, 12 mL) and extracted with ethyl acetate. The organic layer was separated and washed with water and brine successively, dried over anhydrous $Na_2SO_4$ and concentrated under reduced pressure. The crude product was purified by column chromatography using 50% ethyl acetate in petroleum ether (v/v) to yield K2 (20 g). The compound was taken to the next step without further purification.

Step B (2R,5S)-tert-butyl 2-((R)-((tert-butyldimethylsilyl)oxy)(pyridin-3-yl)methyl)-5-(4-iodobenzyl) pyrrolidine-1-carboxylate (K3)

To a solution of K2 (20 g, 33.6 mmol) in DMF (200 mL) TBDMS-Cl (15.1 g, 101 mmol) and Imidazole (5.7 g, 84 mmol) were added and stirred at room temperature for overnight. The solvent was removed under reduced pressure and the crude mass was dissolved in ethyl acetate, washed with water and brine successively, dried over anhydrous $Na_2SO_4$ and concentrated under reduced pressure. The residue was purified by column chromatography using 10% ethyl acetate in petroleum ether (v/v) to yield K3 (20 g).

$^1$H NMR (300 MHz, DMSO-$d_6$): δ 8.48 (s, 1H), 8.42 (s, 1H), 7.67 (d, J=8.22 Hz, 1H), 7.63-7.61 (m, 2H), 7.56 (d, J=8.16 Hz, 1H), 6.71 (d, J=8.19 Hz, 2H), 4.09-4.06 (m, 1H), 3.32-3.18 (m, 2H), 1.44 (s, 9H), 1.24 (m, 3H), 0.99 (s, 9H), 0.02 (s, 3H), −0.02 (s, 3H). Molecular Formula: $C_{28}H_{41}IN_2O_3Si$; LC-MS purity: 94%; Expected: 608.2; Observed: 609.2 (M+1).

Step C (2R,5S)-tert-butyl 2-((R)-((tert-butyldimethylsilyl)oxy)(pyridin-3-yl)methyl)-5-(4-(ethoxycarbonyl)benzyl)pyrrolidine-1-carboxylate (K4)

To a solution of K3 (20 g, 32.8 mmol) in ethanol (200 mL) sodium acetate (8 g, 98.6 mmol) and Pd(dppf)Cl$_2$ (4 g, 4.93 mmol) were added and the reaction mixture was heated to reflux under the atmosphere of carbon monoxide (bladder pressure). The reaction mixture was passed through a celite bed and concentrated under reduced pressure. The crude mass was purified by column chromatography using 30% ethyl acetate in petroleum ether (v/v) to yield K4 (14.8 g).

$^1$H NMR (400 MHz, DMSO-$d_6$): δ 8.51 (s, 1H), 8.44 (s, 1H), 7.81 (d, J=8.04 Hz, 2H), 7.69 (d, J=8.16 Hz, 1H), 7.44 (s, 1H), 7.05 (d, J=7.96 Hz, 2H), 5.45-5.28 (m, 1H), 4.27 (q, J=6.80 Hz, 2H), 4.15-4.10 (m, 1H), 3.81-3.72 (m, 1H), 1.85-1.81 (m, 3H), 1.46 (s, 9H), 1.43-1.41 (m, 2H), 1.28 (t, J=6.80 Hz, 3H), 1.15-1.1 (m, 2H), 0.85 (s, 10H), 0.02 (s, 3H), −0.02 (s, 3H). Molecular Formula: $C_{31}H_{46}N_2O_5Si$; LC-MS purity: 96.9%; Expected: 554.3; Observed: 555.2 (M+1).

Step D 3-((R)-((2R,5S)-1-(tert-butoxycarbonyl)-5-(4-(ethoxycarbonyl)benzyl) pyrrolidin-2-yl)((tert-butyldimethylsilyl)oxy)methyl)pyridine 1-oxide (K5)

To a cold solution of K4 (3 g, 5.4 mmol) in dichloroethane (20 mL) m-CPBA (2.7 g, 21.6 mmol) was added and the reaction mixture was refluxed for 2 h at 80° C. The reaction was quenched with saturated NaHCO$_3$ solution and extracted with ethyl acetate. The organic layer was washed successively with water and brine, dried over anhydrous Na$_2$SO$_4$ and concentrated under reduced pressure. The crude mass was purified by column chromatography using 70% ethyl acetate in petroleum ether (v/v) to yield K5 (1.8 g).

$^1$H NMR (400 MHz, DMSO-$d_6$): δ 8.18 (s, 1H), 8.01 (s, 1H), 7.86 (d, J=8.08 Hz, 2H), 7.45 (s, 1H), 7.24 (d, J=7.64 Hz, 1H), 7.18 (d, J=7.96 Hz, 2H), 5.2-5.1 (m, 2H), 4.28 (q, J=7.04 Hz, 2H), 4.12-4.01 (m, 1H), 3.9-3.85 (m, 2H), 1.85-1.71 (m, 3H), 1.67-6.1 (m, 2H), 1.49 (t, J=7.05 Hz, 3H), 1.42 (s, 9H), 0.9 (s, 9H), 0.02 (s, 3H), −0.02 (s, 3H). Molecular Formula: $C_{31}H_{46}N_2O_6Si$; LC-MS purity: 94%; Expected: 570.3; Observed: 571.4 (M+1).

Step E 3-((R)-((2R,5S)-1-(tert-butoxycarbonyl)-5-(4-carboxybenzyl)pyrrolidin-2-yl)((tert-butyldimethylsilyl)oxy)methyl)pyridine 1-oxide (K6)

The compound K6 was prepared from K5 following the similar procedure for the synthesis of D from D3.

$^1$H NMR (300 MHz, DMSO-$d_6$): δ 8.2 (s, 1H), 8.02 (s, 1H), 7.82 (d, J=7.86 Hz, 2H), 7.43-7.41 (m, 1H), 7.25-7.23 (m, 1H), 7.13 (d, J=8.16 Hz, 2H), 5.2-5.1 (m, 1H), 4.07-4.01 (m, 1H), 3.82-3.79 (m, 2H), 1.98-1.8 (m, 2H), 1.44-1.43 (m, 1H), 1.42 (s, 9H), 0.08 (s, 9H), 0.1 (s, 3H), −0.02 (s, 3H). Molecular Formula: $C_{29}H_{42}N_2O_6Si$; LC-MS purity: 91%; Expected: 542.3; Observed: 543.2 (M+1).

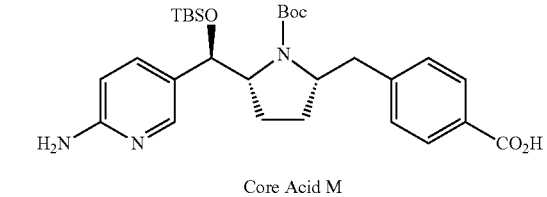

Core Acid M

The preparation of 4-(((2S,5R)-5-((R)-(6-aminopyridin-3-yl)((tert-butyldimethylsilyl)oxy) methyl)-1-(tert-butoxycarbonyl)pyrrolidin-2-yl)methyl)benzoic acid (M) proceeded similarly to the method for B, as previously reported i in the international patent application published as WO2011/025690 to Edmondson, S. D., et al.

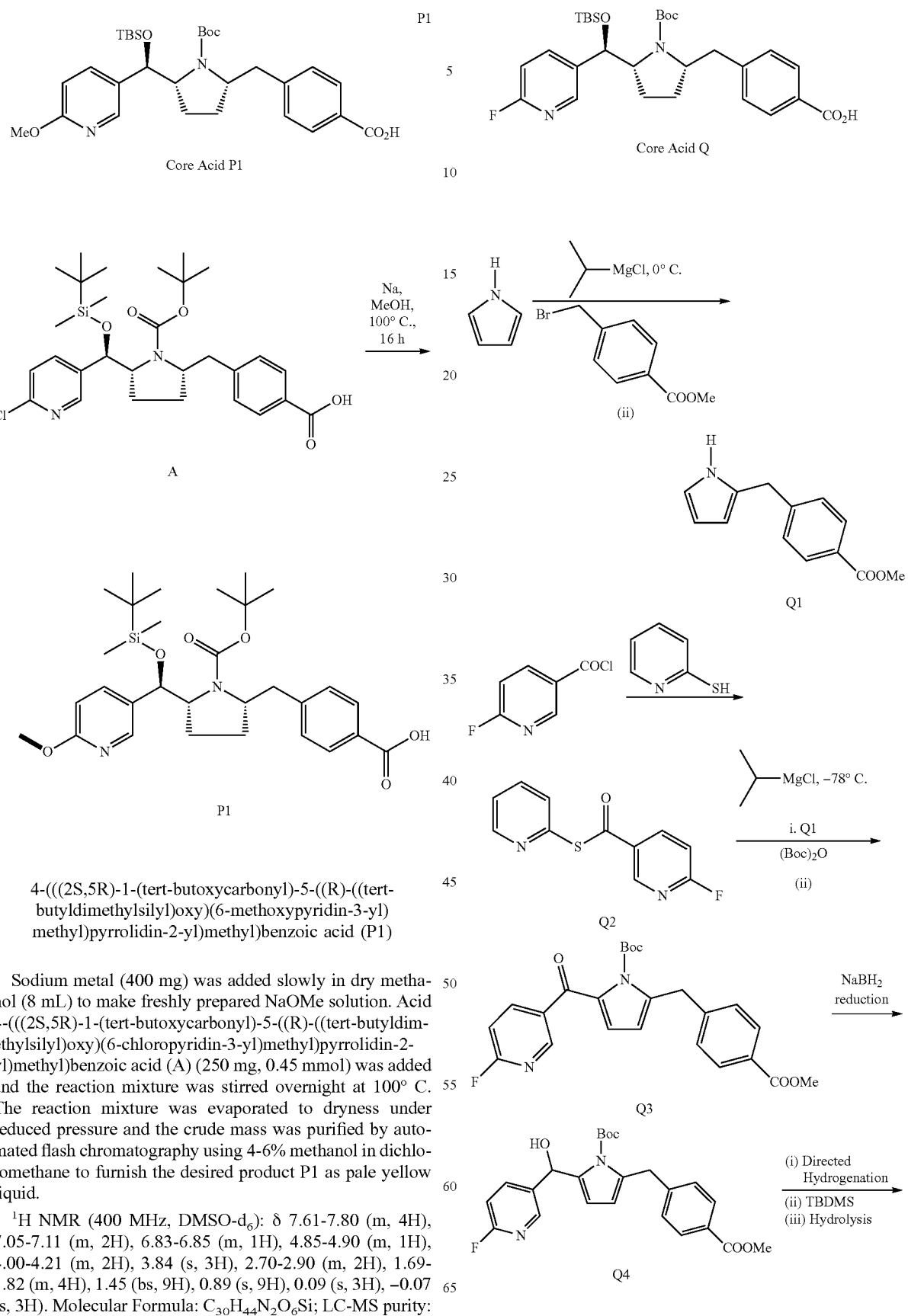

4-(((2S,5R)-1-(tert-butoxycarbonyl)-5-((R)-((tert-butyldimethylsilyl)oxy)(6-methoxypyridin-3-yl)methyl)pyrrolidin-2-yl)methyl)benzoic acid (P1)

Sodium metal (400 mg) was added slowly in dry methanol (8 mL) to make freshly prepared NaOMe solution. Acid 4-(((2S,5R)-1-(tert-butoxycarbonyl)-5-((R)-((tert-butyldimethylsilyl)oxy)(6-chloropyridin-3-yl)methyl)pyrrolidin-2-yl)methyl)benzoic acid (A) (250 mg, 0.45 mmol) was added and the reaction mixture was stirred overnight at 100° C. The reaction mixture was evaporated to dryness under reduced pressure and the crude mass was purified by automated flash chromatography using 4-6% methanol in dichloromethane to furnish the desired product P1 as pale yellow liquid.

$^1$H NMR (400 MHz, DMSO-$d_6$): δ 7.61-7.80 (m, 4H), 7.05-7.11 (m, 2H), 6.83-6.85 (m, 1H), 4.85-4.90 (m, 1H), 4.00-4.21 (m, 2H), 3.84 (s, 3H), 2.70-2.90 (m, 2H), 1.69-1.82 (m, 4H), 1.45 (bs, 9H), 0.89 (s, 9H), 0.09 (s, 3H), −0.07 (s, 3H). Molecular Formula: $C_{30}H_{44}N_2O_6Si$; LC-MS purity: 79.6%; Expected: 556.2; Observed: 557.2 (M+1).

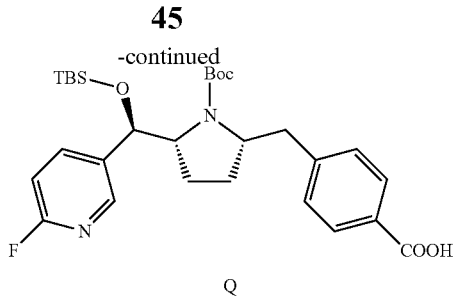

Q

Step A Tert-butyl 2-(4-(methoxycarbonyl)benzyl)-1H-pyrrole-1-carboxylate (Q1)

To a cooled (0° C.) solution of Pyrrole (3.5 g, 0.052 mol) in THF:CH$_2$Cl$_2$ (1:1, 150 mL) was added isopropyl magnesium chloride (2M solution in THF, 21.8 mL) drop wise and stirred for 1 h at room temperature. The solution was then cooled again to 0° C. and methyl 4-(bromomethyl)benzoate (10 g, 0.044 mol) was added and stirred for 12 h at room temperature. After the disappearance of the methyl 4-(bromomethyl)benzoate the reaction was cooled and quenched with saturated NH$_4$Cl solution. The solvents were removed under reduced pressure and the residue was dissolved in ethyl acetate and washed with water. The aqueous layer was extracted with ethyl acetate (3×50 mL) and the combined organic layers was washed with brine and dried over anhydrous Na$_2$SO$_4$. The solvent was removed under reduced pressure and the crude mass was purified by column chromatography using hexane-ethyl acetate to obtain compound Q1.

$^1$H NMR (300 MHz, DMSO-d$_6$): δ 3.82 (s, 3H), 3.94 (s, 2H), 6.61 (m, 1H), 5.90 (m, 1H), 5.77 (m, 1H), 7.34 (d, J=8.24 Hz, 1H), 7.87 (d, J=8.24 Hz, 1H), 10.6 (s, NH).

Step B S-pyridin-2-yl 6-fluoropyridine-3-carbothioate (Q2)

A solution of 2-mercaptopyridine (5.7 g, 0.0512 mol) in THF (50 mL) was treated slowly with 6-fluoronicotinoyl chloride (10.0 g, 0.0512 mol) in THF (150 mL). The resulting slurry was stirred for 1 h at room temperature. The reaction mixture was quenched with 10% NaHCO$_3$ solution (50 mL) and diluted with ethyl acetate (100 mL). The layers were separated and the aqueous layer was extracted with ethyl acetate (2×50 mL). The combined organic extract was washed with brine (100 mL), dried over anhydrous Na$_2$SO$_4$ and filtered. The filtrate was evaporated to dryness under reduced pressure to give a solid, which was washed with hexanes (20 mL) to afford Q2.

$^1$H NMR (300 MHz, DMSO-d$_6$): δ 8.65 (s, 1H), 8.56 (d, J=3.00 Hz, 1H), 8.53 (t, J=3.00 Hz, 1H), 7.98 (t, J=9.00 Hz, 1H), 7.78 (d, J=6.00 Hz, 1H), 7.52 (d, J=3.00 Hz, 1H), 7.43 (d, J=9.00 Hz, 2H). Molecular Formula: C$_{11}$H$_7$FN$_2$OS; LCMS; Expected: 234.2; Observed: 235.2 (M+1).

Step C Tert-butyl 2-(6-fluoronicotinoyl)-5-(4-(methoxycarbonyl)benzyl)-1H-pyrrole-1-carboxylate (Q3)

A solution of isopropyl magnesium chloride (19.18 mL, 0.0383 mol, 2 M in THF) was added slowly to a solution of Q1 (8.2 g, 0.0383 mol) in THF (70 mL) under nitrogen at −78° C. The resulting mixture was then warmed to −30° C. A solution of Mukaiyama reagent (2-Chloro-1-methylpyridinium iodide) Q2 (9 g, 0.0383 mol) in THF (30 mL) was added to this cooled reaction mixture. The solution was allowed to attain room temperature and stirred at room temperature for 14 h. The reaction was quenched by the addition of saturated aqueous NH$_4$Cl solution. The mixture was extracted with ethyl acetate. The organic layer was washed with water and brine, dried over anhydrous Na$_2$SO$_4$, filtered and concentrated under reduced pressure. The resulting mass was purified by column chromatography to afford the intermediate (5.7 g).

The above purified product (5.7 g, 0.0168 mol) was dissolved in THF (60 mL) and di-tert-butyl dicarbonate (7.3 g, 0.0336 mol) added under stirring. To this stirred solution was added catalytic amount of DMAP (0.1 g) and the reaction mixture was further stirred for 3 h. The solvent was removed under reduced pressure and the residue was dissolved in CH$_2$Cl$_2$, successively washed with water and brine, and dried over anhydrous Na$_2$SO$_4$. The solvent was removed under reduced pressure and the residue was purified by column chromatography using hexane-ethyl acetate to obtain compound Q3 (6.3 g).

$^1$H NMR (300 MHz, CDCl$_3$): δ 8.78 (s, 1H), 8.31-8.34 (m, 1H), 8.00 (d, J=9.00 Hz, 2H), 7.27 (d, J=6.00 Hz, 2H), 7.04-7.08 (m, 1H), 6.63 (d, J=6.00 Hz, 1H), 5.96 (d, J=3.00 Hz, 1H), 4.27 (s, 2H), 3.92 (s, 3H), 1.35 (s, 9H). Molecular Formula: C$_{24}$H$_{23}$FN$_2$O$_5$; LC-MS; Expected: 438.4; Observed: 339.2 (M+1-Boc).

Step D Tert-butyl 2-((6-fluoropyridin-3-yl)(hydroxy)methyl)-5-(4-(methoxy carbonyl)benzyl)-1H-pyrrole-1-carboxylate (Q4)

To a stirred solution of compound Q3 (2 g, 0.0045 mol) in dry methanol (20 ml) was added NaBH$_4$ (0.69 g, 0.0182 mol) in portions and stirred till the starting material was fully consumed. The reaction was quenched by the addition of saturated aqueous NH$_4$Cl solution. The mixture was extracted with ethyl acetate. The organic layers were washed with water and brine, dried over anhydrous Na$_2$SO$_4$ and filtered. The filtrate was evaporated under reduced pressure to dryness and the residue was purified by column chromatography. The still crude product was analyzed by chiral HPLC [Chiralpak ADH (250×4.6) mm 5µ, EtOH:Hexane (95:5), 0.8 mL/min], followed by purification by SFC using Chiralpak ADH (250×4.6 mm 5µ), solvent: EtOH, to furnish compound Q4 (1.3 g).

$^1$H NMR (400 MHz, CDCl$_3$): δ 8.17 (s, 1H), 7.98 (d, J=8.00 Hz, 2H), 7.88 (t, J=8.00 Hz, 1H), 7.13 (d, J=8.00 Hz, 2H), 6.95-6.92 (m, 1H), 6.00 (s, 1H), 5.84 (d, J=3.32 Hz, 1H), 5.79 (d, J=4.00 Hz, 1H), 4.67 (s, 1H), 4.21 (s, 2H), 3.92 (s, 3H), 1.30 (s, 9H). Molecular Formula: C$_{24}$H$_{25}$FN$_2$O$_5$; LC-MS; Expected: 440.5; Observed: 324 (M+1-Boc-O).

Step E 4-(((2S,5R)-1-(tert-butoxycarbonyl)-5-((R)-((tert-butyldimethylsilyl)oxy)(6-fluoropyridin-3-yl)methyl)pyrrolidin-2-yl)methyl)benzoic acid (Q)

A solution of the compound Q4 (0.69 g) in EtOAc (15 mL) was degassed by bubbling argon and 5% Pt/C (0.24 g, 40% by wt) was added. The reaction mixture was stirred under bladder pressure (1 Kg) for 36 h at room temperature. The reaction mixture was filtered on a celite bed followed by a short pass through column. The solvent was removed under reduced pressure to yield (0.5 g) the reduced compound. Analysis by chiral HPLC [Chiralpak ADH (250×4.6) mm 5µ, EtOH:Hexane (95:5), 0.8 mL/min], followed by purification by SFC (using Chiralpak ADH (250×4.6 mm 5μ), solvent: EtOH), afforded the title compound. Molecular Formula: C$_{24}$H$_{29}$FN$_2$O$_5$; LC-MS; Expected: 444.49; Observed: 445.2 (M+1).

To the solution of the required SFC purified isomer (0.23 g, 0.000516 mol) in DMF (5 mL) TBDMSCl (0.31 g, 0.002 mol) and imidazole (0.13 g, 0.002 mol) were added and the reaction mixture was stirred at room temperature for 12 h. Water (20 mL) was added to the reaction mixture and extracted with ethyl acetate (2×10 mL). The organic layer was washed with brine, dried over anhydrous Na$_2$SO$_4$, filtered and evaporated to dryness under reduced pressure. The residue was purified by column chromatography using hexane-ethyl acetate to provide TBS protected compound (0.23 g).

To a stirred solution of TBS protected compound in THF:H$_2$O (3 ml) was added LiOH.H$_2$O (0.02 g, 0.000537 mol). The resulting mixture was stirred at room temperature for 4 h. The aqueous layer was acidified with 1.5 N HCl to adjust pH~6 and extracted with ethyl acetate. The organic layer was washed with water and brine, dried over anhydrous Na$_2$SO$_4$, filtered and concentrated under reduced pressure to obtain compound Q.

$^1$H NMR (300 MHz, DMSO-d$_6$): δ 7.67-7.69 (m, 1H), 7.26-7.37 (m, 5H), 6.70-6.77 (m, 2H), 5.21-5.53 (m, 1H), 4.12 (t, J=6.00 Hz, 2H), 4.02-4.04 (m, 1H), 1.46 (s, 9H), 0.87 (s, 9H), 0.04 (s, 3H), −0.10 (s, 3H). Molecular Formula: C$_{29}$H$_{49}$FN$_2$O$_5$Si; LC-MS; Expected: 544.7; Observed: 445.2 (M+1-Boc).

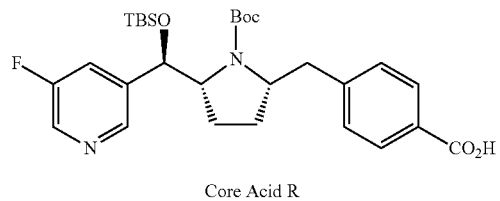 [SMILES: CC(C)(C)OC(=O)N1[C@H](Cc2ccc(C(=O)O)cc2)CC[C@@H]1[C@H](O[Si](C)(C)C(C)(C)C)c1cncc(F)c1]

Core Acid R

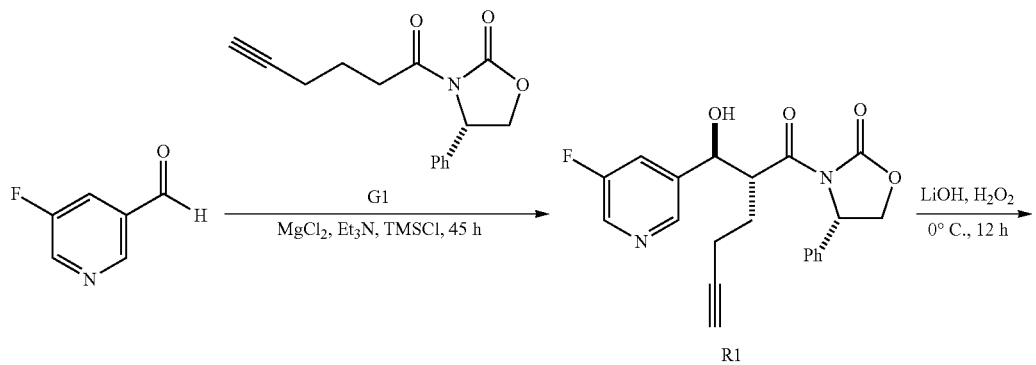

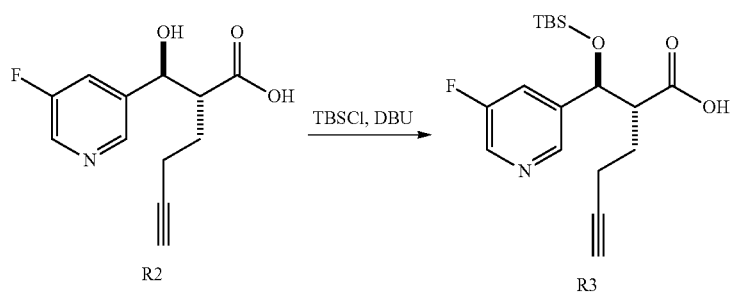

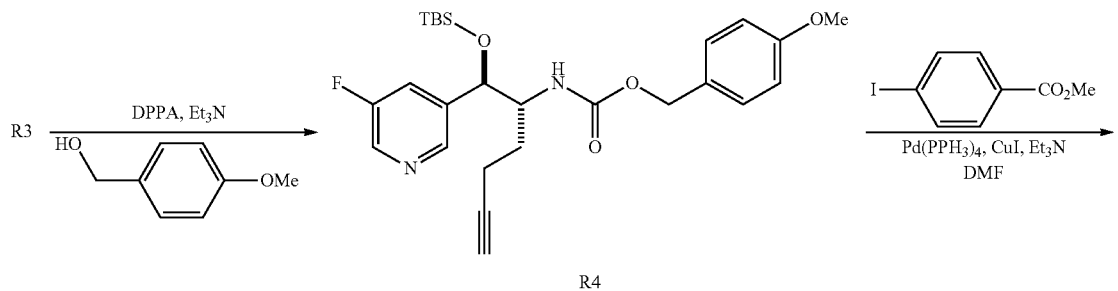

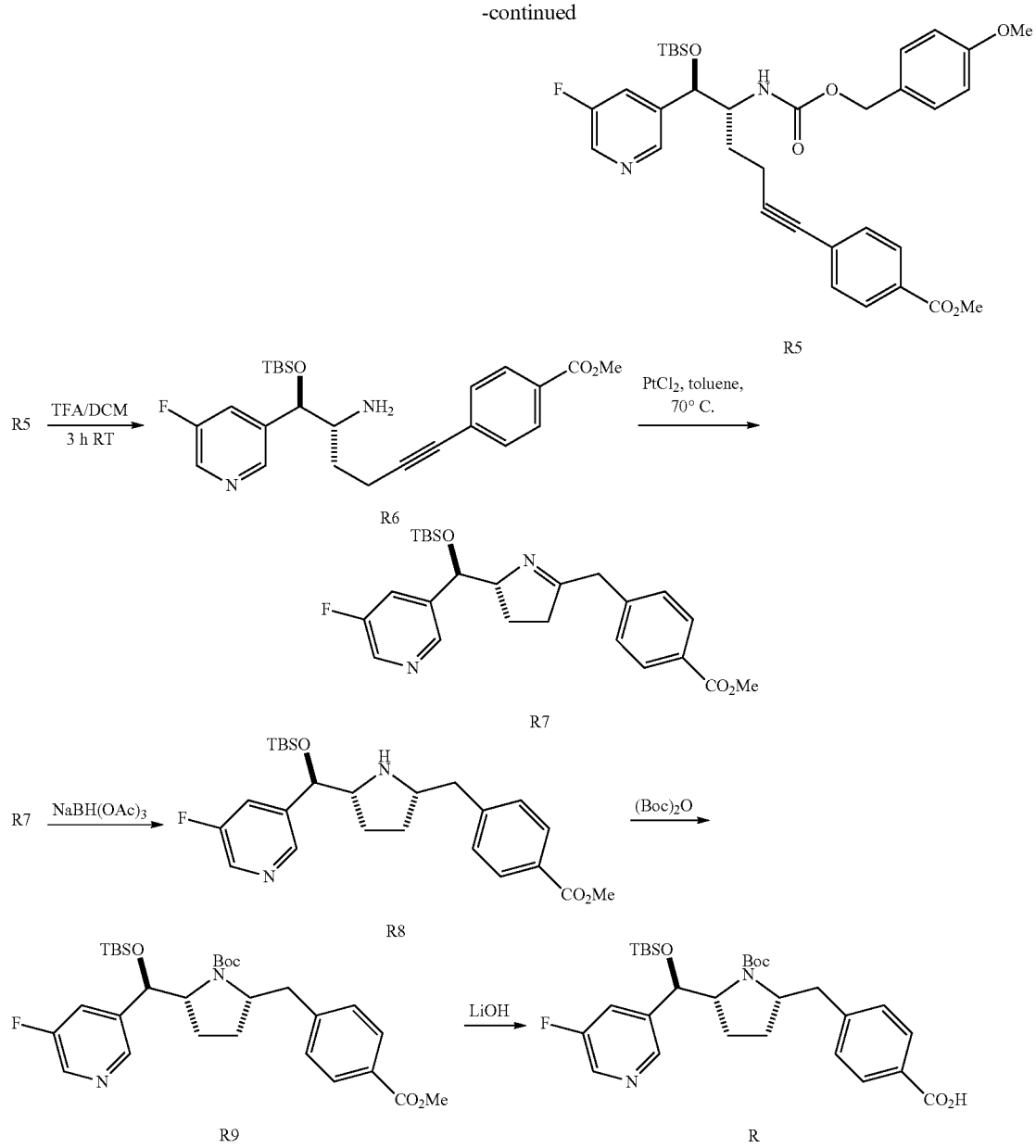
Preparation 4-(((2S,5R)-1-(tert-butoxycarbonyl)-5-((R)-((tert-butyldimethylsilyl)oxy)(5-fluoropyridin-3-yl)methyl)pyrrolidin-2-yl)methyl)benzoic acid (R). The compound R was prepared in the same manner as in preparation of G.
Molecular Formula: $C_{29}H_{41}FN_2O_5Si$; LCMS purity: 87%; Expected: 544.7; Observed: 545.2 (M+1).
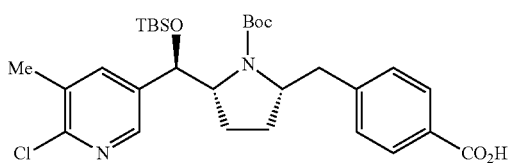
Core Acid S
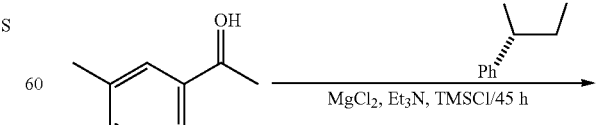

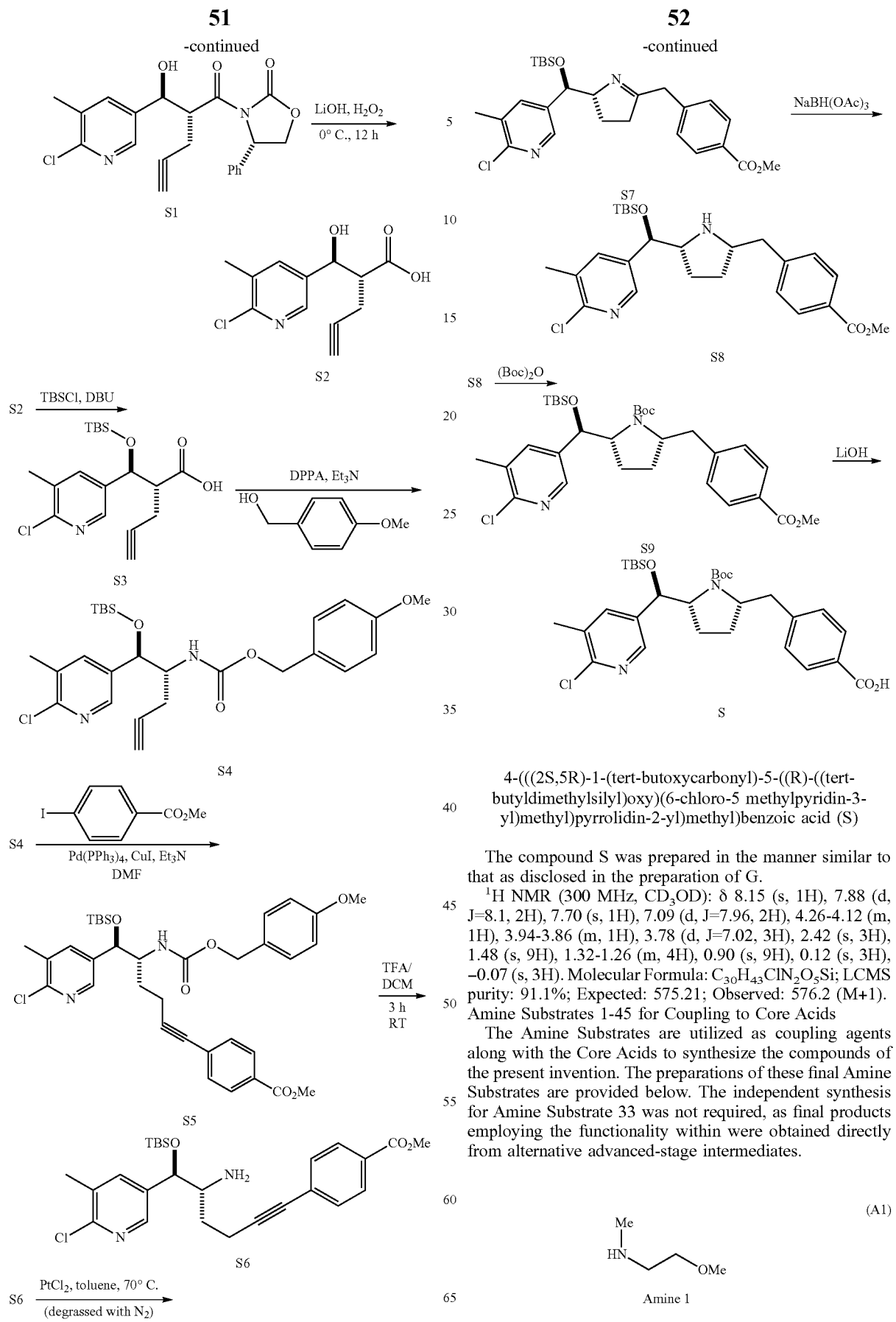

4-(((2S,5R)-1-(tert-butoxycarbonyl)-5-((R)-((tert-butyldimethylsilyl)oxy)(6-chloro-5 methylpyridin-3-yl)methyl)pyrrolidin-2-yl)methyl)benzoic acid (S)

The compound S was prepared in the manner similar to that as disclosed in the preparation of G.

$^1$H NMR (300 MHz, CD$_3$OD): δ 8.15 (s, 1H), 7.88 (d, J=8.1, 2H), 7.70 (s, 1H), 7.09 (d, J=7.96, 2H), 4.26-4.12 (m, 1H), 3.94-3.86 (m, 1H), 3.78 (d, J=7.02, 3H), 2.42 (s, 3H), 1.48 (s, 9H), 1.32-1.26 (m, 4H), 0.90 (s, 9H), 0.12 (s, 3H), −0.07 (s, 3H). Molecular Formula: C$_{30}$H$_{43}$ClN$_2$O$_5$Si; LCMS purity: 91.1%; Expected: 575.21; Observed: 576.2 (M+1).

Amine Substrates 1-45 for Coupling to Core Acids

The Amine Substrates are utilized as coupling agents along with the Core Acids to synthesize the compounds of the present invention. The preparations of these final Amine Substrates are provided below. The independent synthesis for Amine Substrate 33 was not required, as final products employing the functionality within were obtained directly from alternative advanced-stage intermediates.

Amine 2-methoxy-N-methylethanamine (A1) was procured from Fluorochem Ltd., United Kingdom.

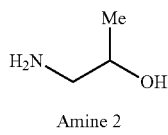

Amine 2

Amine 1-aminopropan-2-ol (A2) was procured from Sigma-Aldrich, St. Louis, Mo., USA.

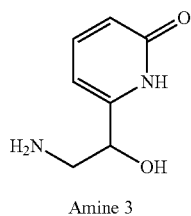

Amine 3

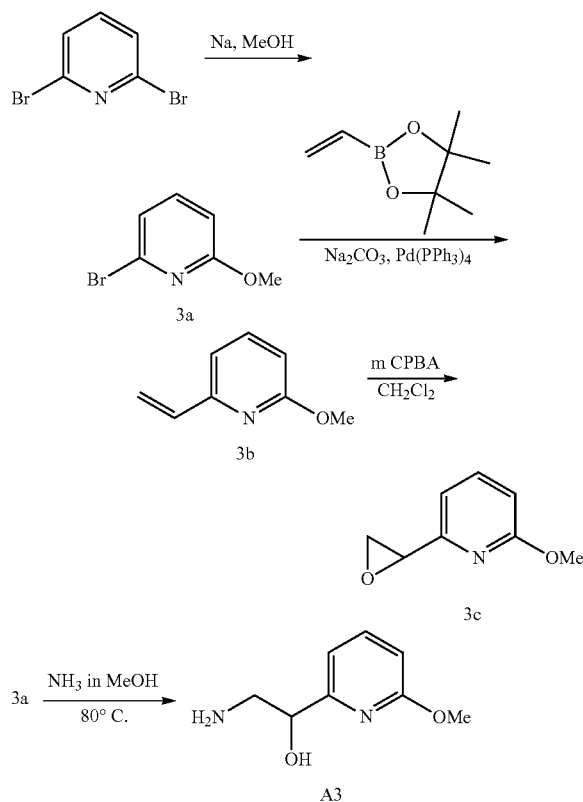

Step A 2-bromo-6-methoxypyridine (3a)

To a solution of sodium metal (1.5 g, 62 mmol) in methanol (200 mL) stirred at room temperature for 10 min was added 2,6-dibromopyridine (10 g, 46 mmol). The resulting solution was stirred at room temperature for 3 h. The reaction mixture was quenched with dilute HCl and then extracted with dichloromethane. The combined organic layer was washed with water, brine successively, dried over anhydrous $Na_2SO_4$, filtered and concentrated under reduced pressure. The resulting crude product was purified by column by eluting with 5% ethyl acetate in petroleum ether (v/v) to afford 2-bromo-6-methoxypyridine (7 g).

MM-ESI+APCI [M+H]$^+$ m/z 187.8.

Step B 2-methoxy-6-vinylpyridine (3b)

To a solution of 2-bromo-6-methoxypyridine (5 g, 20.8 mmol) in 1,4 dioxane (100 mL) was added sodium carbonate (6.63 g 62 mmol) in water (50 mL) and 4,4,5,5-tetramethyl-2-vinyl-1,3,2-dioxaborolane (4.8 g, 31 mmol). The mixture was degasified under nitrogen for 10 min and tetrakis(triphenylphosphine)palladium(0) (140 mg, 2.08 mmol) was then added. The reaction mass was heated at 80° C. for overnight. The reaction mass was diluted with ethyl acetate, washed with water, brine solution and dried over anhydrous $Na_2SO_4$ filtered and concentrated under reduced pressure, the resulting crude product was purified by column by eluting with 10% ethyl acetate in petroleum ether (v/v) to afford 2-methoxy-6-vinylpyridine (1.5 g) as liquid.

MM-ESI+APCI [M+H]$^+$ m/z 136.2.

Step C 2-methoxy-6-(oxiran-2-yl)pyridine (3c)

To a solution of 2-methoxy-6-vinylpyridine (3 g, 22 mmol) in dichloromethane (100 mL) was added meta chloroperbenzoic acid (4.1 g, 26 mmol). The reaction mixture was stirred at room temperature for 5 h. The reaction mixture was passed through a pad of celite and the filtrate was washed with aqueous sodium bicarbonate, brine and water successively and dried anhydrous $Na_2SO_4$ filtered and concentrated under reduced pressure, the resulting crude product was purified by column by eluting with 20% ethyl acetate in petroleum ether (v/v) to afford 2-methoxy-6-(oxiran-2-yl)pyridine (2 g) as liquid.

$^1$H NMR (CDCl$_3$, 400 MHz): δ 7.55 (dd, J=8.1, 7.3 Hz, 1H), 6.86 (d, J=7.2 Hz, 1H), 6.68-6.66 (m, 1H), 3.94 (s, 3H), 3.9-3.89 (m, 1H), 3.14 (dd, J=6 Hz, 4 Hz, 1H), 3.03 (dd, J=6 Hz, 2.5 Hz, 1H). MM-ESI+APCI [M+H]$^+$ 152.

Step D 2-amino-1-(6-methoxypyridin-2-yl)ethan-1-ol (A3)

2-methoxy-6-(oxiran-2-yl)pyridine (1 g, 6.6 mmol) methanolic ammonia (10 mL) was heated at 50° C. for 3 h and the reaction mixture was cooled to room temperature and concentrated. The resulting crude product was purified by column by eluting with 2% methanol in dichloromethane to give 2-amino-1-(6-methoxypyridin-2-yl)ethan-1-ol (3).

$^1$H NMR (MeOD, 400 MHz): δδ 7.67-7.6 (m, 1H), 7.08-7 (m, 1H), 6.66 (d, J=8.2 Hz, 1H), 4.61-0.59 (m, 1H), 3.91 (s, 3H), 3.24-3.21 (m, 1H), 3.07-3.02 (m, 1H).

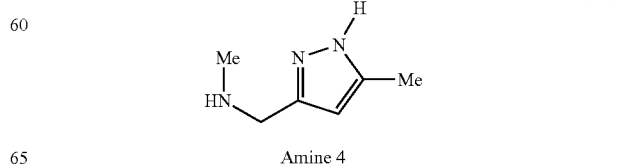

Amine 4

Amine N-methyl-1-(5-methyl-1H-pyrazol-3-yl)methanamine (A4) was procured from Oakwood Products, Inc., West Columbia, S.C., USA.

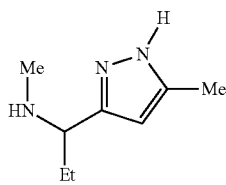

Amine 5

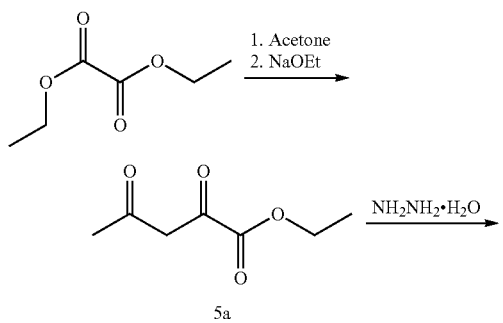

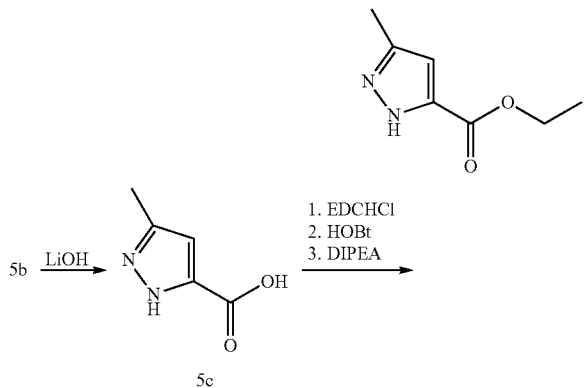

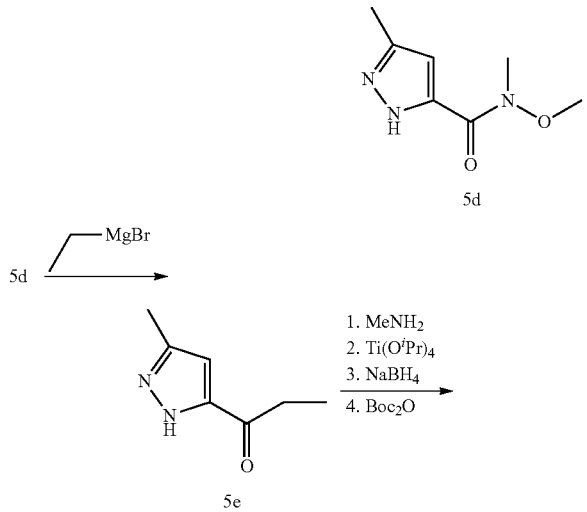

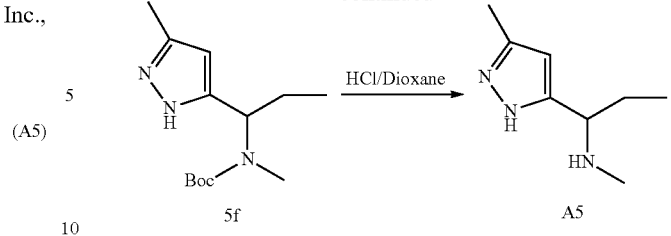

Step A Ethyl 2,4-dioxopentanoate (5a)

Sodium metal (8.6 g, 376.6 mmol) was added to ethanol (200 mL) at 0° C. and the mixture was stirred vigorously with mechanical stirrer. Diethyl oxalate (50 g, 342.4 mmol) in acetone (19.86 g, 342.4 mmol) was added to the reaction mixture at 0° C. when a pale yellow solid started separating out. The reaction mixture was stirred for 1 h. The solids were filtered off, suspended in ice and cooled sulfuric acid (14 mL) was added to the mixture. The mixture was stirred for 1 h. The product was then extracted with dichloromethane (2×200 mL) and the combined organic layer was evaporated to dryness to yield the product 5a (33 g).
$^1$H NMR (300 MHz, CDCl$_3$): δ 6.35 (s, 1H), 4.32 (q, J=7.10 Hz, 2H), 2.24 (s, 3H), 1.36 (t, J=7.10 Hz, 3H).

Step B Ethyl 3-methyl-1H-pyrazole-5-carboxylate (5b)

To a stirred solution of 5a (33 g, 208.8 mmol) in ethanol (500 mL) at 0° C., hydrazine hydrate (12.5 g, 250.6 mmol) was added and the reaction mixture was stirred for 30 min. The volatiles were removed under reduced pressure and the crude material thus obtained was suspended in water and the product was extracted with ethyl acetate. The combined organic layer was evaporated to dryness to yield 5b (25 g).
$^1$H NMR (300 MHz, CDCl$_3$): δ 12.56 (s, 1H), 6.57 (s, 1H), 4.36 (q, J=7.10 Hz, 2H), 2.36 (s, 3H), 1.35 (t, J=7.10 Hz, 3H). Molecular Formula: C$_7$H$_{10}$N$_2$O$_2$; LCMS purity: 99.6%; Expected: 154.1; Observed: 155 (M+1).

Step C 3-methyl-1H-pyrazole-5-carboxylic acid (5c)

To a stirred solution of 5b (28 g, 181.8 mmol) in THF (560 mL) was added LiOH (10.04 g, 454.5 mmol) dissolved in water (453 mL). The reaction mixture was heated at 100° C. for 1 h. After the completion, the reaction mixture was cooled to room temperature. The volatiles were removed under reduced pressure and the crude mass was acidified with citric acid solution. The product was extracted with ethyl acetate and the organic layer was concentrated under reduced pressure to yield 5c (20 g).
$^1$H NMR (300 MHz, DMSO-d$_6$): δ 6.45 (d, J=0.7 Hz, 1H), 2.23 (s, 3H). Molecular Formula: C$_5$H$_6$N$_2$O$_2$; LCMS purity: 98.1%; Expected: 126; Observed: 127 (M+1).

Step D N-methoxy-N,3-dimethyl-1H-pyrazole-5-carboxamide (5d)

To a stirred solution of 5c (1 g, 7.936 mmol) in DMF (20 mL) N-methoxy-N-methyl amine hydrochloride (0.928 g, 9.523 mmol), EDC.HCl (1.825 g, 9.523 mmol), DIPEA (3.5 mL, 19.046 mmol) and HOBt (1.071 g, 7.926 mmol) were added and the reaction mixture was allowed to stir overnight at room temperature. The volatiles were removed under reduced pressure and the crude mass was taken in water. The product was extracted with ethyl acetate, washed with water and brine, dried over anhydrous $Na_2SO_4$ and concentrated under reduced pressure which was purified over silica gel using 40% ethyl acetate in petroleum ether to yield 5d (750 mg).

$^1$H NMR (400 MHz, DMSO-$d_6$): δ 12.72 (s, 1H), 6.42 (s, 1H), 3.71 (s, 3H), 3.31 (s, 3H), 2.25 (s, 3H). Molecular Formula: $C_7H_{11}N_3O_2$; LCMS purity: 92.8%; Expected: 169.1; Observed: 170 (M+1).

Step E 1-(3-methyl-1H-pyrazol-5-yl)propan-1-one (5e)

To a stirred solution of 5d (1.8 g, 11.6 mmol) in THF (30 mL) at −10° C. ethylmagnesium bromide (34.8 mL, 34.8 mmol, 1 M soln in THF) was added drop wise. The reaction mixture was stirred at room temperature for 3 h. The reaction was quenched with saturated $NH_4Cl$ solution. The reaction mass was filtered through a pad of celite. The celite pad was washed with EtOAc:THF (1:1) and the filtrate was evaporated to dryness. The crude mass was purified by column using ethyl acetate (50%) in hexane (v/v) to furnish 5e (0.8 g).

$^1$H NMR (400 MHz, DMSO-$d_6$): δ 13.08 (s, 1H), 6.48-6.41 (m, 1H), 2.94-2.88 (m, 2H), 2.25 (s, 3H), 1.05 (t, J=7.6 Hz, 3H). Molecular Formula: $C_7H_{10}N_2O$; LCMS purity: 80%; Expected: 138.1; Observed: 139.2 (M+1).

Step F Tert-butyl methyl(1-(3-methyl-1H-pyrazol-5-yl)propyl)carbamate (5f)

To a solution of the 5e (0.8 g, 5.79 mmol) in THF (15 mL) were added methyl amine (3.4 mL, 6.9 mmol, 2M in THF) and titanium isopropoxide (2.46 g, 8.68 mmol). The reaction mixture was stirred overnight at room temperature. The volatiles were removed under reduced pressure and the crude mass was dissolved in methanol (20 mL) and was cooled to 0° C. To the cooled solution was added $NaBH_4$ (0.44 g, 11.5 mmol). The reaction mixture was stirred for 3 h. Water was added to the reaction mixture and was filtered. The filtrate was concentrated under reduced pressure. The residue was dissolved in THF and triethylamine (4.7 ml, 2.89 mmol) was added followed by ditertiarybutyl dicarbonate (1.89 g, 8.68 mmol). The reaction mixture was stirred overnight at room temperature. The reaction mixture was diluted with water and the product was extracted with ethyl acetate. The organic layer was concentrated under reduced pressure and the residue was purified over silica gel using 50% ethyl acetate in hexane (v/v) to yield 5f (0.45 g)

Molecular Formula: $C_{13}H_{23}N_3O_2$; LCMS purity: 88.7%; Expected: 253.2; Observed: 507 (2M+1).

Step G N-methyl-1-(5-methyl-1H-pyrazol-3-yl)propan-1-amine (A5)

To the solution of compound 5f (200 mg, 0.790 mmol) in 1, 4-Dioxane (10 mL) at 0° C. was added HCl in Dioxane (5 mL). The reaction mixture was warmed to RT and stirred for 3 h. Reaction mixture was concentrated under reduced pressure and the crude thus obtained was taken for next step without further purification.

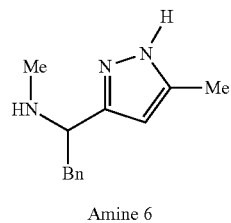

Amine 6

N-methyl-1-(5-methyl-1H-pyrazol-3-yl)-2-phenylethanamine (A6) was synthesized in a similar manner as is described for preparation A5.

Molecular Formula: $C_{13}H_{17}N_3$; LCMS purity: 94.1%; Expected: 215.1; Observed: 216 (M+1).

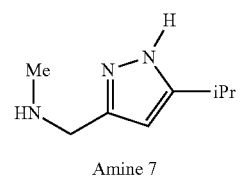

Amine 7

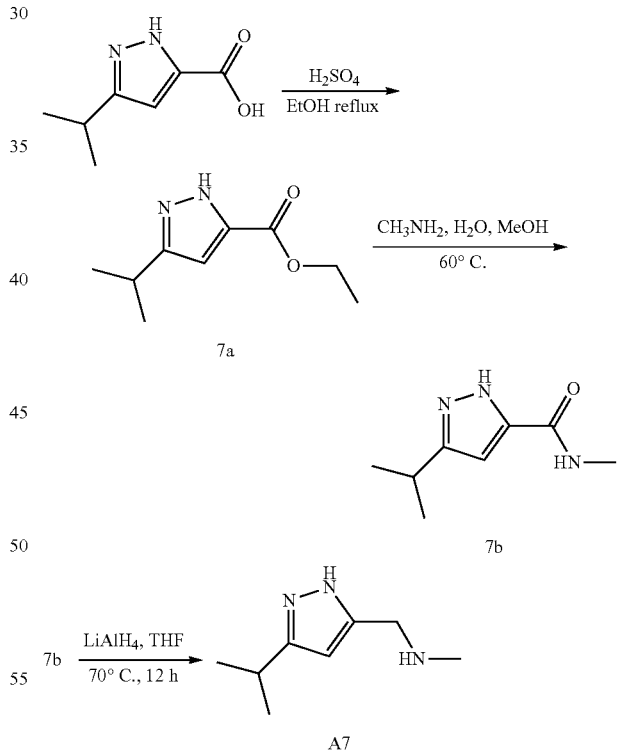

Step A Ethyl 3-isopropyl-1H-pyrazole-5-carboxylate (7a)

To a solution of 3-isopropyl-1H-pyrazole-5-carboxylic acid (2.5 g, 16.2 mmol) [commercially available from Alfa Aesar, Ward Hill, Mass., USA] in MeOH (25 mL) was added conc. sulfuric acid (1 mL) and refluxed for 12 h. The reaction mixture was cooled and the solvent was removed under reduced pressure. The crude mass was purified by flash column chromatography using 1:9 MeOH in CHCl₃ to yield compound 7a (2.6 g).

¹H NMR (400 MHz, CDCl₃): δ 6.64 (s, 1H), 4.39 (q, J=8.00 Hz, 2H), 3.06-3.01 (m, 1H), 1.39 (t, J=8.00 Hz, 3H), 1.31 (d, J=8.00 Hz, 6H). Molecular Formula: C₉H₁₄N₂O₂; LCMS purity: 96%; Expected: 182.1; Observed: 183 (M+1).

Step B
3-isopropyl-N-methyl-1H-pyrazole-5-carboxamide (7b)

To a solution of 7a (2 g, 10.9 mmol) in MeOH (10 mL) was added 40% methylamine in water (30 mL). The resulting solution was stirred at 60° C. for 12 h. The reaction mixture was cooled and solvent was removed under reduced pressure and the crude mass was purified by flash column chromatography using 1:4 MeOH in CHCl₃ to yield compound 7b (1.8 g, quantitative).

¹H NMR (400 MHz, DMSO-d₆): δ 12.90 (bs, 1H), 8.00 (bs, 1H), 6.36 (s, 1H), 2.94-2.88 (m, 1H), 2.70 (s, 1H), 1.19 (d, J=8.00 Hz, 6H). Molecular Formula: C₈H₁₃N₃O; LCMS purity: 97%; Expected: 167.1; Observed: 168 (M+1).

Step C 1-(5-isopropyl-1H-pyrazol-3-yl)-N-methyl-methanamine (A7)

To a suspension of lithium aluminum hydride (0.86 g, 22.7 mmol) in THF (10 mL) was added a solution of 7b (1.9 g, 11.3 mmol) in THF (10 mL) at 0° C. The reaction mixture was heated at 80° C. for 12 h. The reaction mixture was cooled to 0° C. and quenched with cold water followed by 10% NaOH solution. The quenched reaction mixture was diluted with 1:1 methanol-chloroform (30 mL) and filtered through a celite pad. The filtrate was concentrated to dryness and was dissolved in THF (10 mL). To the solution was added 15% solution of oxalic acid in THF until the precipitation was complete. The white precipitate was filtered and dried to yield A7 (oxalate salt) as white solid.

¹H NMR (400 MHz, DMSO-d₆): δ 9.22 (s, 2H), 6.12 (s, 1H), 4.02 (s, 2H), 2.97-2.90 (m, 1H), 2.53 (s, 3H), 1.20 (d, J=8.00 Hz, 6H). Molecular Formula: C₈H₁₅N₃; LCMS purity: 99%; Expected: 153.2; Observed: 154.2 (M+1).

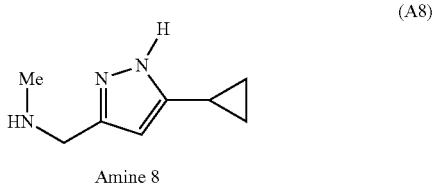 [SMILES: CNCc1cc(C2CC2)[nH]n1]

Amine 8

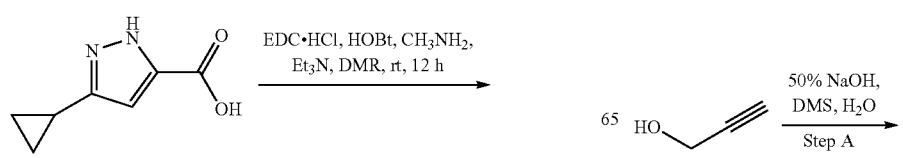

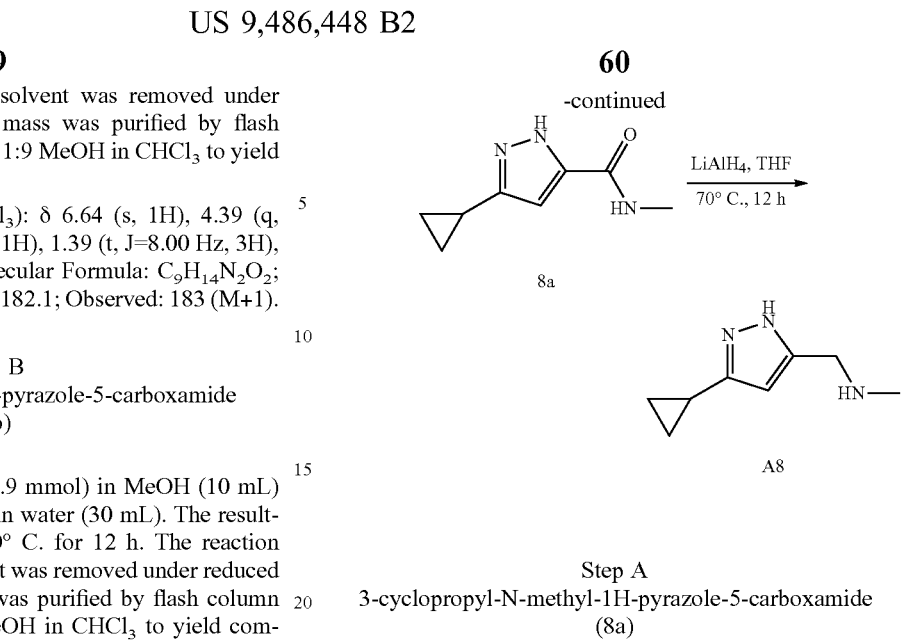

Step A
3-cyclopropyl-N-methyl-1H-pyrazole-5-carboxamide (8a)

To a solution of 3-cyclopropyl-1H-pyrazole-5-carboxylic acid (0.5 g, 3.29 mmol) [commercially available from Matrix Scientific, Columbia, S.C., USA] and methylamine (4.9 mL, 9.87 mmol, 2M solution in THF) in DMF (10 mL) was added HOBt (0.1 g, 0.82 mmol), EDC.HCl (1.3 g, 6.57 mmol) followed by the addition of triethylamine (2.3 mL, 16.4 mmol). The reaction mixture was stirred at room temperature for 12 h. The reaction mixture was diluted with dichloromethane and washed with brine (2×), dried over anhydrous MgSO₄, filtered and evaporated to dryness under reduced pressure. The crude mass was purified by flash column chromatography using 1:9 MeOH—CHCl₃ to yield 8a (0.4 g).

Molecular Formula: C₈H₁₁N₃O; LC-MS purity: 97%; Expected: 165.1; Observed: 166.2 (M+1).

Step B 1-(5-cyclopropyl-1H-pyrazol-3-yl)-N-methylmethanamine (A8)

Compound A8 was prepared from 8a following similar procedure as for the synthesis of 7 from 7b.

¹H NMR (400 MHz, CD₃OD): δ 5.92 (s, 1H), 3.65 (s, 2H), 2.35 (s, 3H), 1.91-1.85 (m, 1H), 0.96-0.93 (m, 2H), 0.71-0.68 (m, 2H). Molecular Formula: C₈H₁₃N₃; LC-MS purity: 96%; Expected: 151.2; Observed: 152.2 (M+1).

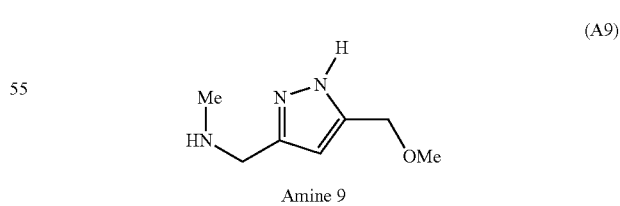

Amine 9

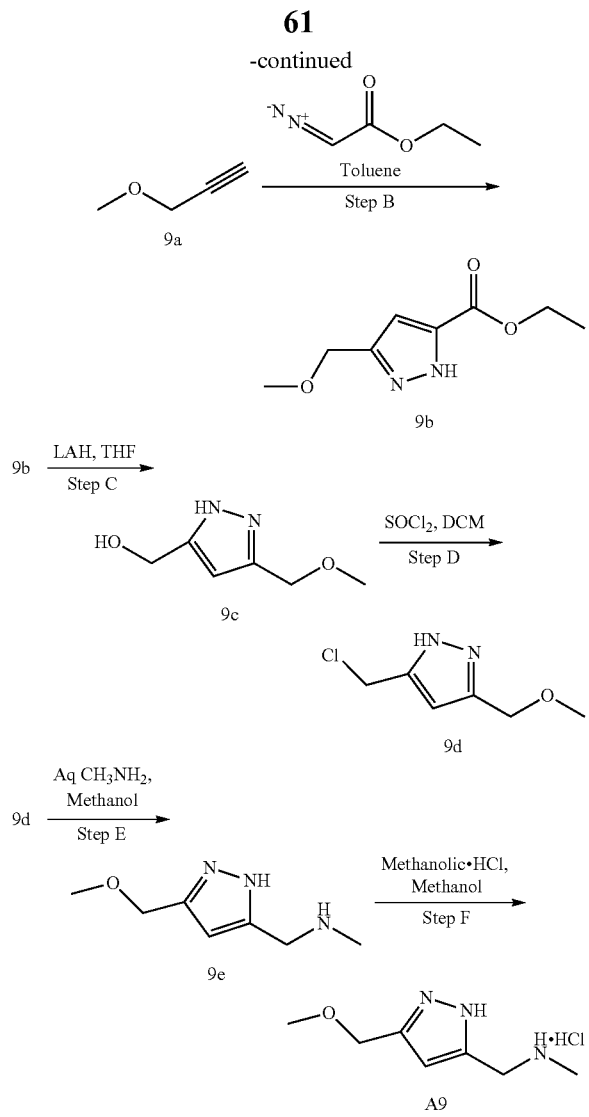

Step A 3-methoxyprop-1-yne (9a)

To a stirred solution of prop-2-yn-1-ol (500.0 g, 8.919 mol) in water (400 mL) was added 50% aqueous sodium hydroxide solution (970.0 g, 24.25 mol) followed by drop wise addition of dimethylsulfate (660.0 g, 5.33 mol) at 0° C. The resulting reaction mixture was heated to 60° C. and stirred for 2 h. The reaction progress was monitored by TLC (10% methanol in dichloromethane, using $KMnO_4$ to visualize the spots). $R_f$ values of starting material and product are 0.1 and 0.8 respectively. After completion of the reaction (TLC), the reaction mixture was concentrated under reduced pressure to afford compound 9a (500.0 g), which was used as such in the next step without further purification.

Step B Ethyl 3-(methoxymethyl)-1H-pyrazole-5-carboxylate (9b)

To a stirred solution of compound 9a (250.0 g, 3.571 mol) in toluene (2.5 L) was added ethyldiazo acetate (448.2 g, 3.928 mol) at room temperature and heated to reflux temperature for 4 hrs. The reaction progress was monitored by TLC (5% methanol in dichloromethane, using 254 nm UV light to visualize the spots). $R_f$ values of starting material and product are 0.5 and 0.3 respectively. After completion of the reaction (TLC), the reaction mixture was concentrated under reduced pressure to afford crude compound 9b. The crude compound 9b was triturated with petroleum ether (500 mL), filtered and dried further to afford compound 9b (300.0 g).

Step C (3-(methoxymethyl)-1H-pyrazol-5-yl)methanol (9c)

To a stirred suspension of lithium aluminum hydride (8.2 g, 0.217 mol) in tetrahydrofuran (150 mL) was added the solution of compound 9b (10.0 g, 0.05 mol) in tetrahydrofuran (150 mL) under nitrogen atmosphere at 0° C. The resulting reaction mixture was allowed to room temperature and stirred for 16 h. The reaction progress was monitored by (10% methanol in dichloromethane, using 254 nm UV light to visualize the spots). $R_f$ values of starting material and product are 0.6 and 0.4 respectively. After completion of the reaction (TLC), reaction mixture was quenched with ice-cold water (100 mL), ethyl acetate (200 mL) under cooling condition and stirred for 30 min. Reaction mixture was filtered through celite bed, washed with ethyl acetate and the organic layer was washed with brine (100 mL), dried over sodium sulfate. The solvent was evaporated under reduced pressure to afford compound 9c (3.0 g).

Step D 5-(chloromethyl)-3-(methoxymethyl)-1H-pyrazole (9d)

To a stirred solution of compound 9c (100.0 g, 0.704 mol) in dichloromethane (1.0 L) was added thionyl chloride (200 mL) at 0° C. and stirred for 1 hr. The reaction progress was monitored by TLC (10% methanol in dichloromethane, using 254 nm UV light to visualize the spots). $R_f$ values of starting material and product are 0.4 and 0.6 respectively. After completion of the reaction (TLC), reaction mixture was concentrated under reduced pressure to afford crude compound 9d (100.0 g), which was used as such in the next step without further purification.

Step E 1-(3-(methoxymethyl)-1H-pyrazol-5-yl)-N-methylmethanamine (9e)

To a stirred solution of compound 9d (100.0 g, 0.625 mol) in methanol (1.0 L) was added aqueous methyl amine (1.5 L) at −10° C. and stirred for 1 hr. The reaction progress was monitored by TLC (10% methanol in dichloromethane, using 254 nm UV light to visualize the spots). $R_f$ values of starting material and product are 0.6 and 0.2 respectively After completion of the reaction (TLC), reaction mixture was concentrated under reduced pressure to afford crude compound 9e. The crude compound 9e was adsorbed on 200 g of 100-200 neutral alumina, which was loaded over a pre-packed column with silica gel [120 mm×600 cm width and height of column, loaded with 1.2 kg of 100-200 silica gel]. Elution started with 5% methanol/dichloromethane and finished with 10% methanol/dichloromethane (added a drop of ammonia). All the pure fractions were collected and concentrated under reduced pressure to afford compound 9e (50.0 g).

Step F 1-(5-(methoxymethyl)-1H-pyrazol-3-yl)-N-methylmethanamine (A9.HCl)

To a stirred solution of compound 9e (80.0.0 g, 0.516 mol) in methanol (400 mL) was added drop wise methanolic. HCl (400 mL) at 0° C. and stirred for 1 h. The reaction progress was monitored by TLC (20% methanol in dichloromethane, using 254 nm UV light to visualize the spots). $R_f$ values of starting material and product were 0.4 and 0.0, respectively. After completion of the reaction (TLC), the reaction mixture was concentrated under reduced pressure to afford crude compound A9.HCl. The crude compound A9.HCl was triturated with diethyl ether (300 mL) to afford compound A9.HCl (30.0 g).

IR (KBr, cm$^{-1}$): 3429.26, 2943.84, 2762.30, 1618.41, 1464.12, 1195.16, 1158.39 and 1099.62; $^1$H NMR (400 MHz, DMSO-d$_6$) δ: 9.14 (bs, 3H), 6.39 (s, 1H), 4.40 (s, 2H), 4.073 (t, J=5.6 Hz, 1H), 3.26 (s, 3H), 2.54-2.49 (m, 3H); $^{13}$C NMR (100.57 MHz, DMSO-d$_6$) δ: 142.80, 141.46, 105.45, 64.81, 57.56, 44.11 and 31.83; LC-MS: 96.80%, (m/z=156.1 [(M−HCl)+H]$^+$.

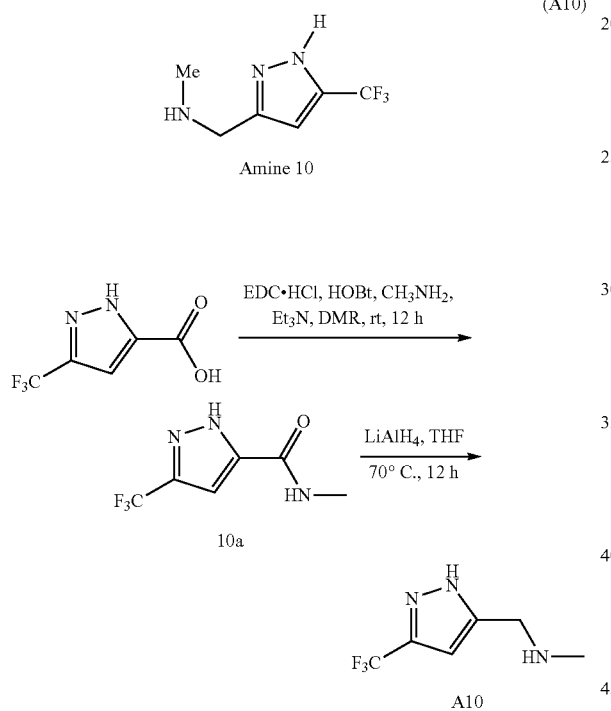

N-methyl-1-(5-(trifluoromethyl)-1H-pyrazol-3-yl)methanamine (A10) was prepared in the manner as described in the preparation of A8 utilizing 3-(trifluoromethyl)-1H-pyrazole-5-carboxylic acid (commercially available from Matrix Scientific, Columbia, S.C., USA).

$^1$H NMR (400 MHz, CD$_3$OD): δ 6.56 (s, 1H), 3.78 (s, 2H), 2.36 (s, 3H). Molecular Formula: C$_6$H$_8$F$_3$N$_3$; LC-MS purity: 94.7%; Expected 179.1; Observed: 180.2 (M+1).

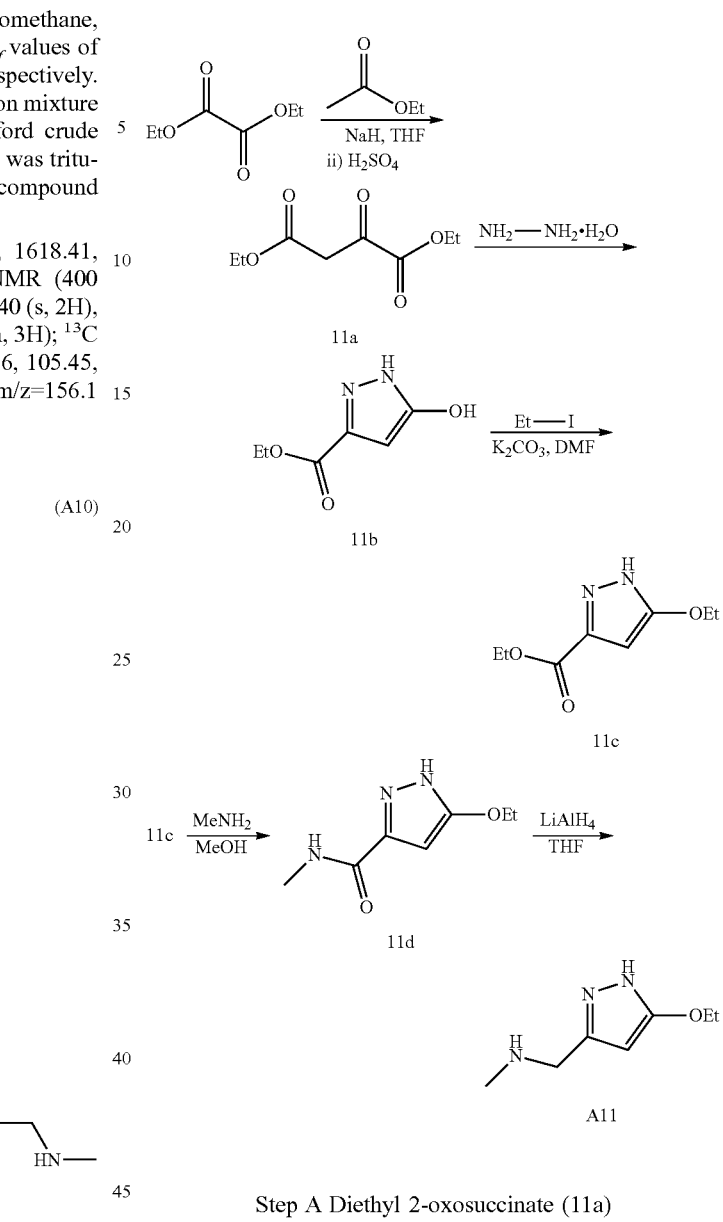

Step A Diethyl 2-oxosuccinate (11a)

To a solution of sodium hydride (14 g, 60% w/w, 580 mmol) in THF at 65° C.; a solution of diethyl oxalate (43 g, 295 mmol) in ethyl acetate (20 g, 295 mmol) and was added drop wise using an addition funnel for about 2 h until the reaction mixture turned pale yellow. The reaction mixture was slowly brought to room temperature and stirred for additional 1 h. The reaction mixture was cooled to 0° C. and acidified with concentrated H$_2$SO$_4$ until pH 3. The reaction mixture was filtered through a celite bed and concentrated under reduced pressure to get 11a as a pale yellow liquid.

Step B Ethyl 5-hydroxy-1H-pyrazole-3-carboxylate (11b)

Compound 11b was prepared from 11a in an analogous manner to that described for the preparation of 5b from 5a.

$^1$H NMR (400 MHz, CDCl$_3$): δ 6.2 (s, 1H), 4.44 (q, J=7.16 Hz, 2H), 1.41 (t, J=7.12 Hz, 3H). Molecular Formula: C$_6$H$_8$N$_2$O$_3$; LC-MS purity: 78%; Expected: 157.2; Observed: 156.7 (M+1).

Step C Ethyl 5-ethoxy-1H-pyrazole-3-carboxylate (11c)

To a solution of 11b (1 g, 6.5 mmol) in DMF (15 mL) at 0° C., potassium carbonate (0.9 g, 6.4 mmol) was added followed by the addition of ethyl iodide (1 g, 6.4 mmol). The reaction mixture was stirred at room temperature for 3 h. The reaction mixture was poured into water and extracted with ethyl acetate. The organic layer was washed with water and brine successively, dried over anhydrous $Na_2SO_4$, and then concentrated under reduced pressure. The crude mass was purified by column chromatography using 15% ethyl acetate in petroleum ether (v/v) to yield 11c (800 mg).

$^1$H NMR (300 MHz, DMSO-$d_6$): δ 13.07 (s, 1H), 6.19 (s, 1H), 4.29-4.15 (m, 2H), 4.08 (q, J=7.05 Hz, 2H), 1.37-1.26 (m, 6H). Molecular Formula: $C_8H_{12}N_2O_3$; LC-MS purity: 63%; Expected: 184.7; Observed: 185.2 (M+1).

Step D 5-ethoxy-N-methyl-1H-pyrazole-3-carboxamide (11d)

The compound 11d was prepared from 11c following an analogous protocol as described for the synthesis of 7b from 7a.

$^1$H NMR (400 MHz, DMSO-$d_6$): δ 12.57 (s, 1H), 8.31 (s, 1H), 6.16 (s, 1H), 4.08 (q, J=7.00 Hz, 2H), 2.88 (s, 3H), 1.27 (t, J=7.00 Hz, 3H). Molecular Formula: $C_7H_{11}N_3O_2$; LC-MS purity: 85.5%; Expected: 169.1; Observed: 170 (M+1).

Step E 1-(5-ethoxy-1H-pyrazol-3-yl)-N-methyl-methanamine (A11)

The compound A11 was prepared from 11d following the protocol as in the synthesis of A7 from 7b.

$^1$H NMR (400 MHz, DMSO-$d_6$): δ 11.5 (s, 1H), 5.43 (s, 1H), 4.12 (s, 2H), 4.05-4.0 (m, 2H), 2.66 (s, 3H), 1.25 (t, J=7.00 Hz, 3H). Molecular Formula: $C_2H_{13}N_3O$; LC-MS purity: 80.4%; Expected: 155.4; Observed: 156.2 (M+1).

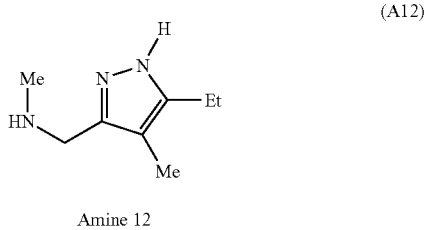 [SMILES: CCc1[nH]nc(CNC)c1C]

Amine 12

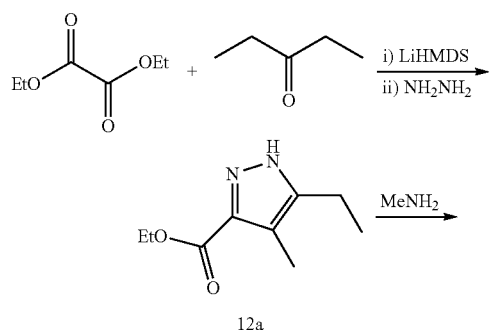

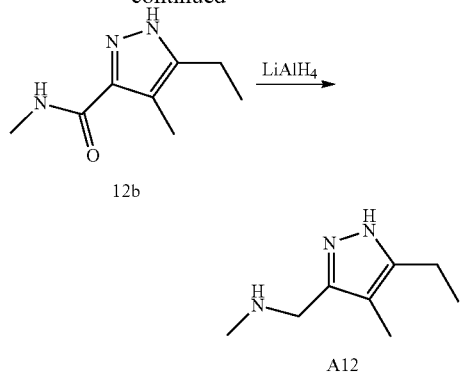

Step A Ethyl 5-ethyl-4-methyl-1H-pyrazole-3-carboxylate (12a)

To a solution of 3-pentanone (5.0 g, 58.1 mmol) and diethyl oxalate (7.8 g, 69.7 mmol) in diethyl ether (100 mL) LiHMDS (1 M, 58 mL, 58 mmol) was added at −78° C. and stirred for 2 h at the same temperature. The reaction mixture was warmed to room temperature over a period of 1 h and then stirred at room temperature for 2 h. The reaction mixture was quenched with saturated $NH_4Cl$ solution and extracted with ethyl acetate. The organic layer was dried over anhydrous $Na_2SO_4$ and evaporated to dryness. The crude product was taken to the next step without further purification.

The crude compound (5 g, 27.1 mmol) was dissolved in ethanol (100 mL) and hydrazine hydrate (15 mL, 32.6 mmol) was added at 0° C. The reaction mixture was stirred at room temperature for 2 h. It was filtered through a celite bed and concentrated under reduced pressure and the residue was purified by column chromatography using 30% ethyl acetate in petroleum ether (v/v) to yield 12a (4.12 g).

$^1$H NMR (300 MHz, DMSO-$d_6$): δ 3.73 (s, 3H), 2.59-2.40 (m, 2H), 2.09 (s, 3H), 1.11 (t, J=7.59 Hz, 3H).

Step B 5-ethyl-N,4-dimethyl-1H-pyrazole-3-carboxamide (12b)

The compound 12b was prepared from 12a following an analogous protocol to that described in the synthesis of 7b from 7a.

$^1$H NMR (300 MHz, DMSO-$d_6$): δ 12.66 (s, 1H), 7.92 (s, 1H), 2.68 (d, J=4.77 Hz, 3H), 2.56 (q, J=7.56 Hz, 2H), 2.09 (s, 3H), 1.12 (t, J=7.56 Hz, 3H). Molecular Formula: $C_8H_{13}N_3O$; LC-MS purity: 86.7%; Expected: 167; Observed: 168 (M+1).

Step C 1-(5-ethyl-4-methyl-1H-pyrazol-3-yl)-N-methylmethanamine (A12)

The compound A12 was prepared from 12b following an analogous protocol to that described in the synthesis of 7 from 7b.

Molecular Formula: $C_8H_{15}N_3$; LC-MS purity: 23%; Expected: 153; Observed: 154 (M+1).

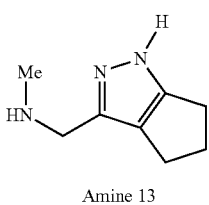

Amine 13

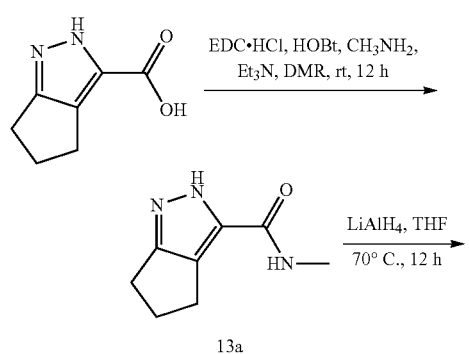

N-methyl-1-(1,4,5,6-tetrahydrocyclopenta[c]pyrazol-3-yl)methanamine (A13) was prepared in a similar manner that is described for the preparation of A8.

$^1$H NMR (400 MHz, CD$_3$OD): δ 3.70 (s, 2H), 2.68-2.60 (m, 4H), 2.48-2.43 (m, 2H), 2.38 (s, H). Molecular Formula: C$_8$H$_{13}$N$_3$; LC-MS purity: 93.7%; Expected: 151.2; Observed: 152.2 (M+1).

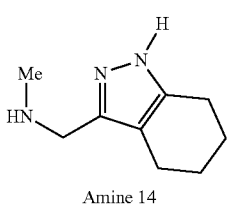

Amine 14

N-methyl-1-(4,5,6,7-tetrahydro-1H-indazol-3-yl)methanamine (A14) was prepared in an analogous manner to that described for preparation of A8.

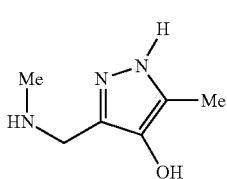

Amine 15

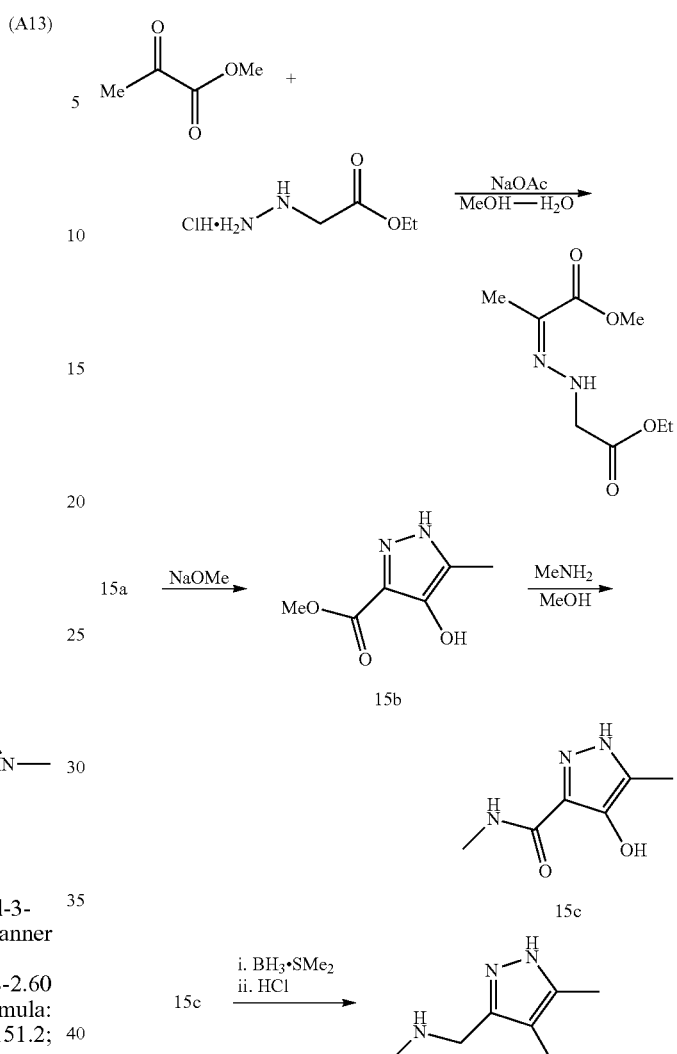

Step A (Z)-methyl 2-(2-(2-ethoxy-2-oxoethyl)hydrazono)propanoate (15a)

To a solution of sodium acetate (8.03 g, 98 mmol) and ethyl pyruvate (11.37 g, 98 mmol) in methanol (140 mL) and water (50 mL), ethyl hydrazinoacetate monohydrochloride (15 g, 98 mmol) was added and the reaction mixture was stirred overnight at room temperature. The solvent was evaporated and the residue was dissolved in water and pH was adjusted to 7 by the addition of 1.5M NaOH solution. The crude compound was extracted with chloroform and the combined organic layers were washed with water and brine successively, dried over anhydrous Na$_2$SO$_4$ and concentrated under reduced pressure. The crude product 15a (15 g) was directly taken to the next step without further purification.

$^1$H NMR (300 MHz, CD$_3$OD): δ 6.15 (s, 1H), 4.20-4.10 (m, 4H), 3.30 (s, 2H), 1.97 (s, 3H), 1.32-1.28 (m, 6H). Molecular Formula: C$_9$H$_{16}$N$_2$O$_4$; LC-MS purity: 77.4%; Expected: 216.2; Observed: 217 (M+1).

Step B Methyl 4-hydroxy-5-methyl-1H-pyrazole-3-carboxylate (15b)

Freshly cut sodium metal (4.4 g, 190 mmol) was added to anhydrous methanol (100 mL) very slowly over a period of 1 h at 0° C. A solution of 15a (15 g, 69 mmol) in methanol (50 mL) was added and heated to reflux for 4 h. The reaction mixture was cooled to room temperature and concentrated under reduced pressure. The crude mass was dissolved in water and the pH was adjusted to 7 using conc. HCl. The solution was extracted with chloroform and the combined organic layers were washed with water and brine successively, dried over anhydrous $Na_2SO_4$ and concentrated under reduced pressure. The crude mass was purified by column chromatography using 5% methanol in dichloromethane to yield 15b (6 g).

$^1$H NMR (300 MHz, $CD_3OD$): δ 3.86 (s, 3H), 2.16 (d, J=9.90 Hz, 3H). Molecular Formula: $C_7H_{10}N_2O_3$; LC-MS purity: 97.8%; Expected: 156; Observed: 157 (M+1).

Step C 4-hydroxy-N,5-dimethyl-1H-pyrazole-3-carboxamide (15c)

The compound 15c was prepared from 15b following an analogous protocol to that described for the synthesis of 7b from 7a.

Step D 5-methyl-3-((methylamino)methyl)-1H-pyrazol-4-ol (A15)

To a solution of 15c (500 mg, 3.2 mmol) in THF (15 mL) was added Borane-dimethylsulfide (1.3 mL, 1.6 mmol) at 0° C. The reaction mixture was refluxed overnight. The reaction mixture was cooled to 0° C. and conc. HCl (2 mL) was added. The reaction mixture was further refluxed for 2 h. The reaction mixture was concentrated and the crude product was purified by column chromatography using 35% methanol in dichloromethane to yield A15.

$^1$H NMR (400 MHz, DMSO-$d_6$): δ 3.37 (d, J=2.50 Hz, 2H), 2.5 (s, 3H), 2.15 (s, 3H). Molecular Formula: $C_6H_{11}N_3O$; LC-MS purity: 48.3%; Expected: 141.1; Observed: 111.2 (M–30).

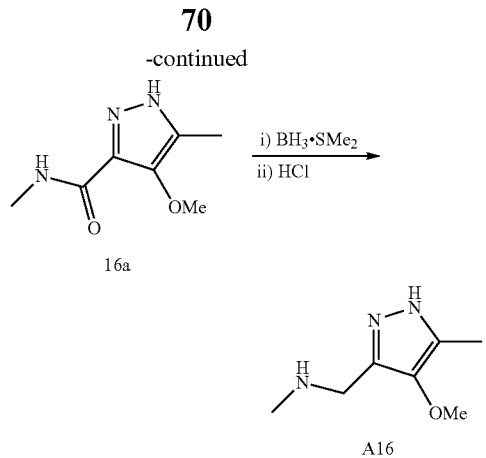

Step A 4-methoxy-N,5-dimethyl-1H-pyrazole-3-carboxamide (16a)

To a solution of 15c (500 mg, 3.2 mmol) in DMF at 0° C. was added potassium carbonate (440 mg, 3.2 mmol) followed by the addition of methyl iodide (450 mg, 3.2 mmol). The reaction mixture was stirred at room temperature for 3 h. The reaction mixture was poured in water and extracted with ethyl acetate. The organic layer was separated and washed with water and brine successively, dried over anhydrous $Na_2SO_4$ and concentrated under reduced pressure. The crude product was purified by column chromatography using 15% ethyl acetate in petroleum ether (v/v) to yield 16a (400 mg).

1H NMR (300 MHz, DMSO-$d_6$): δ 12.72 (s, 1H), 7.75 (s, 1H), 3.74-3.68 (m, 3H), 2.87-2.67 (m, 3H), 2.12 (s, 3H). Molecular Formula: $C_7H_{11}N_3O_2$; LC-MS purity: 64%; Expected: 169; Observed: 170 (M+1).

Step B 1-(4-methoxy-5-methyl-1H-pyrazol-3-yl)-N-methylmethanamine (A16)

The compound A16 was prepared following an analogous protocol to that described for the synthesis of 15 from 15c.

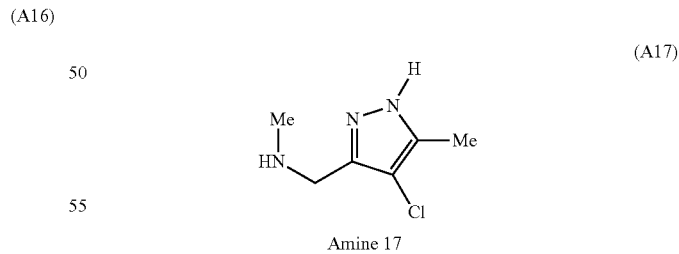

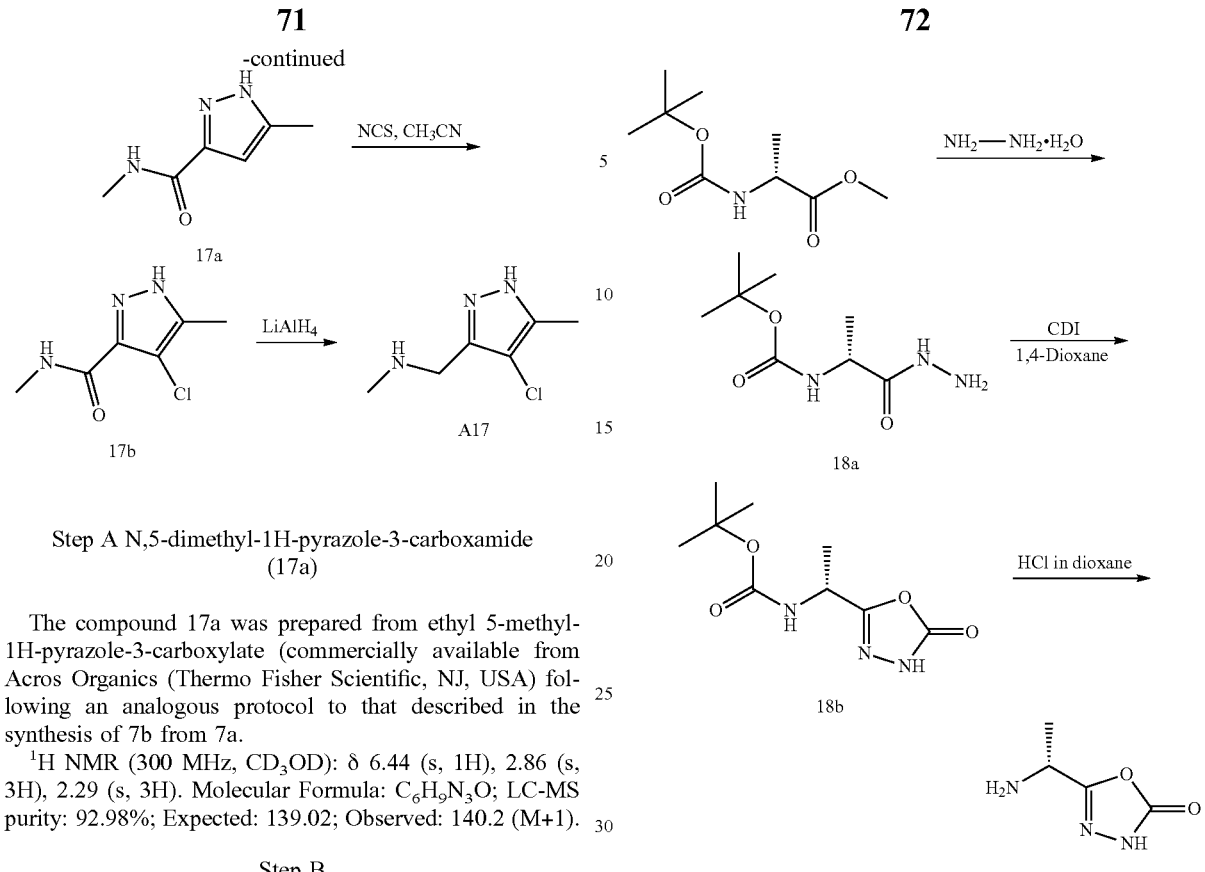

Step A N,5-dimethyl-1H-pyrazole-3-carboxamide (17a)

The compound 17a was prepared from ethyl 5-methyl-1H-pyrazole-3-carboxylate (commercially available from Acros Organics (Thermo Fisher Scientific, NJ, USA) following an analogous protocol to that described in the synthesis of 7b from 7a.

$^1$H NMR (300 MHz, CD$_3$OD): δ 6.44 (s, 1H), 2.86 (s, 3H), 2.29 (s, 3H). Molecular Formula: C$_6$H$_9$N$_3$O; LC-MS purity: 92.98%; Expected: 139.02; Observed: 140.2 (M+1).

Step B 4-chloro-N,5-dimethyl-1H-pyrazole-3-carboxamide (17b)

A solution of 17a (600 mg, 4.3 mmol) and N-Chlorosuccinimide (863 mg, 6.4 mmol) in acetonitrile (20 mL) was sonicated for 2 to 3 h at 35° C. The reaction mixture was concentrated and the crude mass was purified by column chromatography using 2% methanol in dichloromethane to yield 17b (600 mg).

$^1$H NMR (300 MHz, CD$_3$OD): δ 2.87 (s, 3H), 2.24 (s, 3H). Molecular Formula: C$_6$H$_8$ClN$_3$O; LC-MS purity: 81.5%; Expected: 173; Observed: 174 (M+1).

Step C 1-(4-chloro-5-methyl-1H-pyrazol-3-yl)-N-methylmethanamine (A17)

The compound A17 was prepared from 17b following an analogous protocol to that described for the synthesis of A7 from 7b.

$^1$H NMR (300 MHz, CD$_3$OD): δ 3.82 (s, 2H), 2.45 (s, 3H), 2.23 (s, 3H). Molecular Formula: C$_6$H$_{11}$ClN$_3$; LC-MS purity: 90.7%; Expected: 159.1; Observed: 160.2 (M+1).

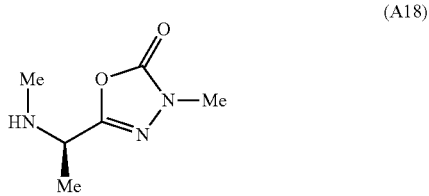

Amine 18

Step A (R)-tert-butyl (1-hydrazinyl-1-oxopropan-2-yl)carbamate (18a)

A solution of N-Boc D-Alanine methyl ester (15 g, 73.891 mmol) and hydrazine hydrate (11.08 g, 221.674 mmol) in methanol (200 mL) was heated at 80° C. for 6 h. The reaction mixture was cooled to room temperature and the volatiles were removed under reduced pressure. The crude mass was dissolved in ethyl acetate and washed with water and brine, dried over anhydrous Na$_2$SO$_4$ and evaporated to dryness to afford 18a (11.4 g) which was used as such for next step.

Step B (R)-tert-butyl(1-(5-oxo-4,5-dihydro-1,3,4-oxadiazol-2-yl)ethyl)carbamate (18b)

A mixture of crude 18a (11.4 g, 55.66 mmol) and CDI (9.01 g, 55.665 mmol) in 1,4-dioxane (150 mL) was heated at 110° C. for 6 h. The reaction mixture was cooled to room temperature and the volatiles were removed under reduced pressure. The residue was dissolved in ethyl acetate and washed with water and brine, dried over anhydrous Na$_2$SO$_4$ and concentrated to dryness. The crude mass was purified by flash column chromatography over silica gel using 50% ethyl acetate in petroleum ether to yield 18b (9 g).

$^1$H NMR (300 MHz, DMSO-d$_6$): δ 7.46 (d, J=7.70 Hz, 1H), 4.60-4.46 (m, 1H), 1.37 (s, 9H), 1.30 (d, J=7.00 Hz, 3H).

Step C (R)-3-methyl-5-(1-(methylamino)ethyl)-1,3,4-oxadiazol-2(3H)-one (A18)

The compound A18 was prepared from 18b following an analogous protocol to that described for the synthesis of 4-E from 4-E1.

Molecular Formula: $C_4H_7N_3O_2$; LC-MS purity: 95.8%; Expected: 129; Observed: 130 (M+1).

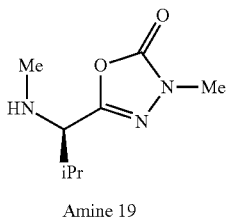

Amine 19 (A19)

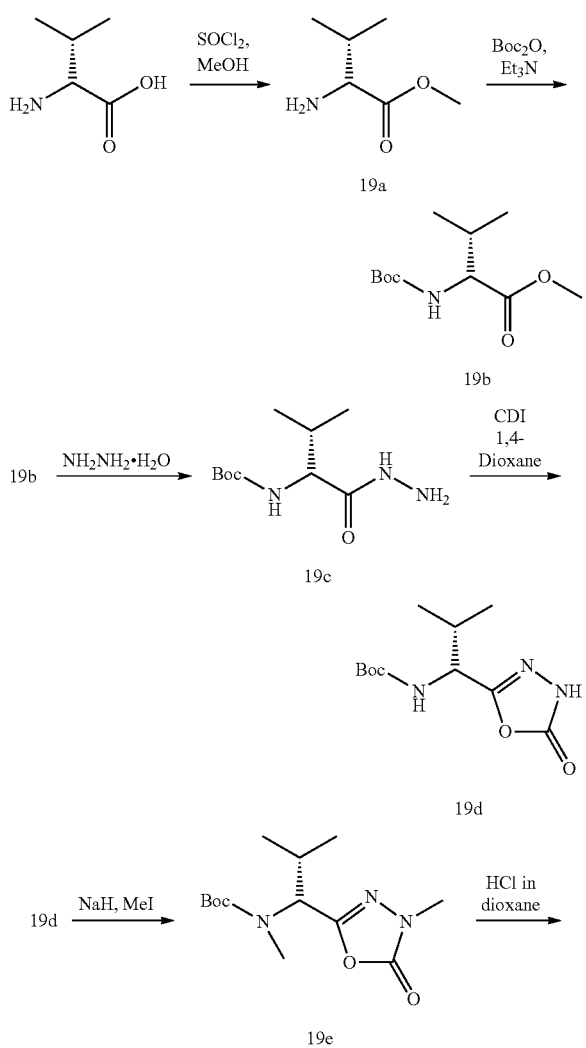

Step A (S)-methyl 2-amino-3-methylbutanoate (19a)

To a stirred solution of D-valine (10 g, 0.00854 mol) in methanol (100 mL) at 0° C. was added $SOCl_2$ (20 mL). The reaction mixture was refluxed for 6 h. After the complete conversion of the starting material, the reaction mixture was cooled to room temperature and the volatiles were removed under reduced pressure. The crude product (19a) thus obtained was taken as such for next step.

Step B (S)-methyl 2-((tert-butoxycarbonyl)amino)-3-methylbutanoate (19b)

To a solution of the crude 19a (11.19 g, 0.00854 mol) in $CH_2Cl_2$ (200 mL) at 0° C. was added triethylamine (61.8 mL, 0.427 mol) and Di-tert-butyl dicarbonate ($Boc_2O$, 27.8 g, 0.128 mol). The reaction mixture was warmed to room temperature and stirred overnight. To the reaction mixture was added dichloromethane. The organic layer washed with water and brine, dried over anhydrous $Na_2SO_4$ and concentrated to dryness. The residue was purified by column chromatography over silica gel using 10% ethyl acetate in hexane (v/v) to yield 19b (15.5 g).
$^1H$ NMR (400 MHz, DMSO-$d_6$): δ 7.18 (d, J=8.00 Hz, 1H), 3.83 (t, J=6.80 Hz, 1H), 3.68 (s, 3H), 2.03-1.94 (m, 1H), 1.47 (s, 9H), 0.91-0.86 (m, 6H).

Step C (S)-tert-butyl (1-hydrazinyl-3-methyl-1-oxobutan-2-yl)carbamate (19c)

The compound 19c was prepared from 19b following an analogous protocol to that described for the synthesis of 18a.
$^1H$ NMR (400 MHz, DMSO-$d_6$): δ 9.04 (s, 1H), 6.66 (d, J=9.20 Hz, 1H), 4.31-4.21 (bs, 2H), 3.67 (t, J=8.80 Hz, 1H), 1.87-1.74 (m, 1H), 1.37 (s, 9H), 0.82 (d, J=5.60 Hz, 6H).

Step D (S)-tert-butyl (2-methyl-1-(5-oxo-4,5-dihydro-1,3,4-oxadiazol-2-yl)propyl) carbamate (19d)

A mixture of crude 19c (1 g, 4.32 mmol) and CDI (1.055 g, 6.49 mmol) in 1,4-dioxane (20 mL) was heated at 110° C. overnight. The reaction mixture was cooled to room temperature and the residue was purified by flash column chromatography over silica gel using 50% ethyl acetate in petroleum ether to afford 19d (0.6 g).
$^1H$ NMR (400 MHz, DMSO-$d_6$): δ 12.20 (s, 1H), 7.47 (d, J=8.10 Hz, 1H), 4.20-4.14 (m, 1H), 2.03-1.96 (m, 1H), 1.36 (s, 9H), 0.90-0.81 (m, 6H), 0.81-0.90 (m, 6H), 1.36 (s, 9H), 1.96-2.03 (m, 1H), 4.14-4.20 (m, 1H), 7.47 (d, J=8.10 Hz, 1H), 12.20 (s, 1H). Molecular Formula: $C_{11}H_{19}N_3O_4$; LC-MS purity: 98.6%; Expected: 257.1; Observed: 202 (M-$^tBu$).

Step E (R)-3-methyl-5-(2-methyl-1-(methylamino)propyl)-1,3,4-oxadiazol-2(3H)-one (A19)

The compound A19 was prepared from 19d following an analogous protocol to that described for the synthesis of 2-B from 2-B1.

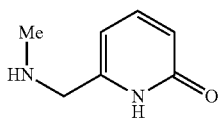

Amine 20 (A20)

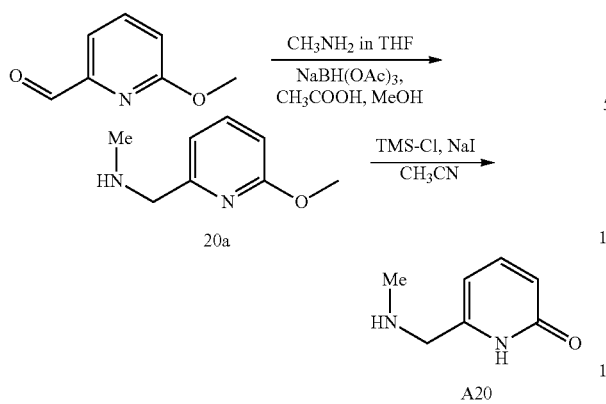

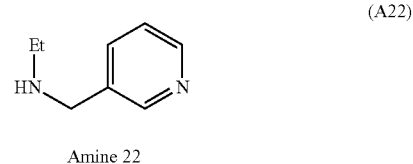

Amine 22

N-methyl-1-(pyridin-3-yl)methanamine (A21) was synthesized following the procedure disclosed in J Med Chem 2011, 54, 6040.

N-(pyridin-3-ylmethyl)ethanamine (A22) was synthesized following the procedure in J Med Chem 2011, 54, 6040.

Step A
1-(6-methoxypyridin-2-yl)-N-methylmethanamine (20a)

To a solution of 6-methoxypicolinaldehyde (10 g, 72.9 mmol) in MeOH (100 mL) was added methyl amine (182 mL, 364.9 mmol, 2M solution in THF) followed by acetic acid (22 mL, 364.9 mmol) at 0° C. and the reaction mixture was stirred for 12 h at room temperature. The reaction mixture was cooled to 0° C. and Sodium tri-acetoxy borohydride (18 g, 87.6 mmol) was added. The reaction mixture was stirred for 2 h at room temperature. The reaction was quenched with ice and the solvent was removed under reduced pressure. The crude mass was purified by flash column chromatography (neutral alumina) using 1:9 MeOH—CHCl$_3$ to yield 20a (8 g).

$^1$H NMR (400 MHz, DMSO-d$_6$): δ 7.64 (t, J=8.00 Hz, 1H), 6.97 (d, J=8.00 Hz, 1H), 6.65 (d, J=8.00 Hz, 1H), 3.82 (s, 3H), 3.71 (s, 2H), 2.32 (s, 3H). Molecular Formula: C$_8$H$_{12}$N$_2$O; LC-MS purity: 96%; Expected: 152.1; Observed: 153 (M+1).

Step B 6-((methylamino)methyl)pyridin-2(1H)-one (A20)

To a solution of 20a (8 g, 52.6 mmol) in acetonitrile (100 mL) was added NaI (19.7 g, 131.5 mmol) and TMS-Cl (14.2 g, 131.5 mol) into a closed tube at room temperature. The reaction mixture was stirred for 30 min at room temperature. The reaction mixture was heated to 75° C. for 3 h. The solvents were removed under reduced pressure and the crude mass was purified by flash column chromatography with 1:9 MeOH— CHCl$_3$ to yield A20.

$^1$H NMR (400 MHz, CD$_3$OD): δ 7.66 (t, J=10.40 Hz, 1H), 6.72 (d, J=8.00 Hz, 1H), 6.63 (d, J=12.00 Hz, 1H), 4.21 (s, 2H), 2.80 (s, 3H). Molecular Formula: C$_7$H$_{10}$N$_2$O; LC-MS purity: 80.2%; Expected: 138.1; Observed: 139 (M+1).

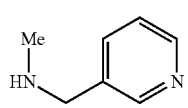

Amine 21

Amine 23

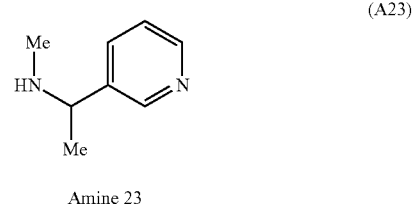

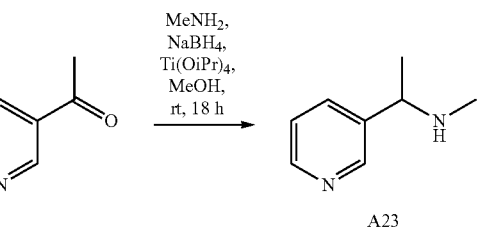

N-methyl-1-(pyridin-3-yl)ethanamine (A23)

To a stirred solution of 3-acetyl pyridine (2 g, 16.51 mmol) in THF (30 mL) methylamine (12.3 mL, 24.77 mmol, 2M solution in THF) was added at 0° C. followed by the drop wise addition of titanium isopropoxide (9.8 mL, 33.03 mmol). The reaction mixture was stirred overnight at room temperature. The reaction mixture was concentrated, added methanol (40 mL) and cooled to 0° C. NaBH$_4$ (1.24 g, 33.03 mmol) was added and was stirred for 2 h at room temperature. The reaction was quenched with ice, filtered and solids were washed thoroughly with methanol. The filtrate was evaporated to dryness under reduced pressure and the residue was purified by automated flash chromatography using 12-40% methanol in dichloromethane to obtain A23 as pale yellow liquid.

$^1$H NMR (300 MHz, DMSO-d$_6$): δ 8.49 (d, J=1.80 Hz, 1H), 8.43-8.40 (m, 1H), 7.73-7.69 (m, 1H), 7.34-7.30 (m, 1H), 3.61-3.59 (m, 1H), 2.01 (s, 3H), 1.23 (d, J=6.60 Hz, 3H).

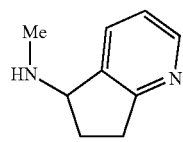

Amine 24

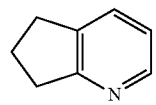

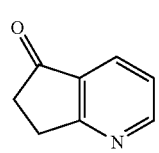 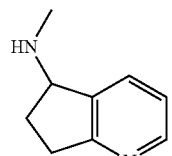

24a      A24

Step A 6,7-dihydro-5H-cyclopenta[b]pyridin-5-one (24a)

To a solution of 6,7-dihydro-5H-cyclopenta[b]pyridine (10 g, 83.99 mmol) [commercially available from Sigma-Aldrich, St. Louis, Mo., USA] in a mixture of acetic acid and sulfuric acid (5:1, 60 mL), was added $CrO_3$ (16.7 g, 167.1 mmol) dissolved in acetic acid (30 mL). The reaction mixture was stirred overnight at room temperature. The reaction mixture was cooled to 0° C. and the pH was adjusted to ~ (approximately) 11 using ammonium hydroxide and then extracted with dichloro-methane. The combined organic layers were washed with water and brine, and dried over anhydrous $Na_2SO_4$. The solvent was evaporated under reduced pressure and the crude mass was purified by column chromatography using 50% ethyl acetate in petroleum ether (v/v) to afford 24a (5 g).

Molecular Formula: $C_8H_7NO$; LC-MS purity: 94.1%; Expected: 133; Observed: 134.2 (M+1).

Step B N-methyl-6,7-dihydro-5H-cyclopenta[b]pyridin-5-amine (A24)

Compound A24 was prepared from 24a following an analogous protocol to that described for the preparation of 23.

$^1$H NMR (400 MHz, $CD_3OD$): δ 8.37 (q, J=5.00 Hz, 1H), 7.85 (d, J=7.60 Hz, 1H), 7.26 (q, J=7.60 Hz, 1H), 4.25 (t, J=6.64 Hz, 1H), 3.15-3.09 (m, 1H), 2.98-2.9 (m, 1H), 2.52-2.47 (m, 1H), 2.44 (s, 3H), 2.0-1.93 (m, 1H). Molecular Formula: $C_9H_{12}N_2$; LC-MS purity: 86.5%; Expected: 148.6; Observed: 149.2 (M+1).

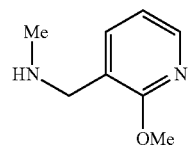

Amine 25

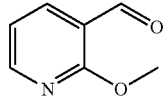 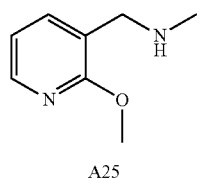

1-(2-methoxypyridin-3-yl)-N-methylmethanamine (A25)

Compound A25 was prepared from 2-methoxynicotinaldehyde (commercially available from Matrix Scientific, Columbia, S.C., USA) while following an analogous protocol to that described for the preparation of 20a.

$^1$H NMR (300 MHz, DMSO-$d_6$): δ 8.03 (d, J=4.90 Hz, 1H), 7.65 (d, J=7.20 Hz, 1H), 6.93-6.97 (m, 1H), 3.85 (s, 3H), 3.60 (s, 2H), 2.13 (s, 3H). Molecular Formula: $C_8H_{12}N_2O$; LC-MS purity: 91.6%; Expected: 152.1; Observed: 153.2 (M+1).

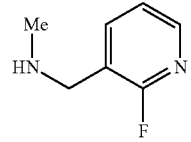

Amine 26

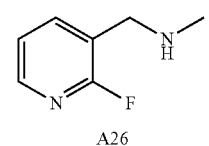

1-(2-fluoropyridin-3-yl)-N-methylmethanamine (A26)

To a stirred solution of 2-fluoro-3-pyridine carboxaldehyde (400 mg, 3.2 mmol) [commercially available from Frontier Scientific Inc., Logan, Utah, USA] in methanol (4 mL), methylamine (8 mL, 16 mmol, 2M solution in THF) was added at 0° C. Acetic acid (0.92 mL, 16 mmol) was added drop wise and the reaction mixture was stirred for 2 h at room temperature. The reaction mixture was cooled to 0° C. and PS—NaCNBH₃ (400 mg, polymer bound) was added. The reaction mixture was stirred for 1 h at room temperature and filtered through a small cotton bed. The filtrate was concentrated under reduced pressure and purified by automated flash chromatography using 10-12% methanol in dichloromethane to obtain the desired product A26 as pale brown solid.

¹H NMR (400 MHz, DMSO-d₆): δ 8.11 (d, J=4.80 Hz, 1H), 7.97-7.92 (m, 1H), 7.34-7.31 (m, 1H), 3.65 (s, 2H), 2.27 (s, 3H). Molecular Formula: C₇H₉FN₂; LC-MS purity: 81.3%; Expected: 140.2; Observed: 141.2 (M+1).

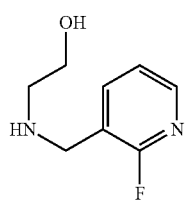

Amine 27

(A27)

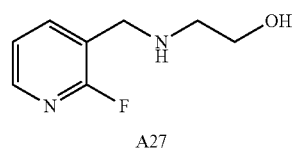

A27

2-(((2-fluoropyridin-3-yl)methyl)amino)ethanol (A27)

Compound A27 was prepared following an analogous protocol to that described for the synthesis of 20a.

¹H NMR (300 MHz, DMSO-d₆): δ 8.09 (d, J=4.70 Hz, 1H), 7.99-7.93 (m, 1H), 7.33-7.30 (m, 1H), 3.72 (s, 2H), 3.44 (t, J=5.70 Hz, 2H), 2.55 (t, J=5.70 Hz, 3H). Molecular Formula: C₈H₁₁FN₂O; LC-MS purity: 91%; Expected: 170.2; Observed: 171.1 (M+1).

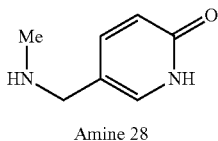

Amine 28

(A28)

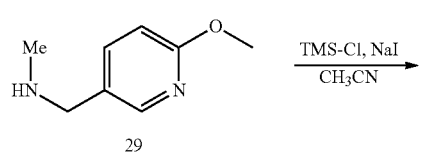

29

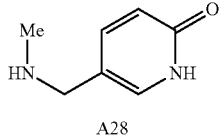

A28

5-((methylamino)methyl)pyridin-2(1H)-one (A28)

The compound A28 was prepared from 29 following an analogous protocol to that described for the synthesis of 20 from 20a.

¹H NMR (400 MHz, DMSO-d₆): δ 7.41 (dd, J=2.80 and 9.40 Hz, 1H), 7.21 (d, J=2.40 Hz, 1H), 6.28 (d, J=8.00 Hz, 1H), 3.37 (bs, 1H), 3.34 (bs, 1H), 2.21 (s, 3H). Molecular Formula: C₇H₁₀N₂O; LC-MS purity: 90.2%; Expected: 138.1; Observed: 277 (2M+1).

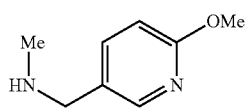

Amine 29

A29

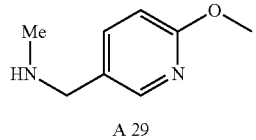

A 29

1-(6-methoxypyridin-3-yl)-N-methylmethanamine (A29)

The compound A29 was prepared from 6-methoxynicotinaldehyde [commercially available from Frontier Scientific Inc., Logan, Utah, USA] following the similar procedure as described for the preparation of 20a.

¹H NMR (400 MHz, DMSO-d₆): δ 8.02 (s, 1H), 7.62 (dd, J=2.80 and 11.40 Hz, 1H), 6.74 (d, J=11.20 Hz, 1H), 3.80 (s, 3H), 3.53 (s, 2H), 2.20 (s, 3H). Molecular Formula: C₈H₁₂N₂O; LC-MS purity: 94%; Expected: 152.1; Observed: 153 (M+1).

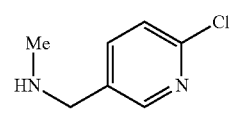

Amine 30

A30

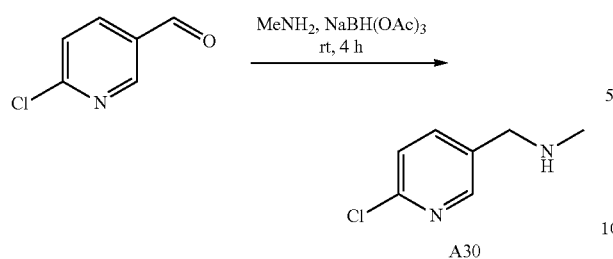

1-(6-chloropyridin-3-yl)-N-methylmethanamine (A30)

Compound A30 was prepared from 6-chloronicotinaldehyde [commercially available from Matrix Scientific, Columbia, S.C., USA] following an analogous protocol to that described for the preparation of 20a.

$^1$H NMR (400 MHz, DMSO-$d_6$): δ 8.34-8.33 (m, 1H), 7.81-7.79 (m, 1H), 7.48-7.76 (m, 1H), 3.66 (s, 2H), 2.24 (s, 3H). Molecular Formula: $C_7H_9ClN_2$; LC-MS purity: 92.6%; Expected: 156.6; Observed: 156.6 (M).

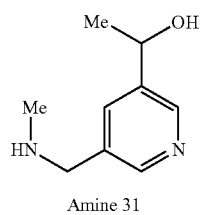

Amine 31

Step A
1-(5-bromopyridin-3-yl)-N-methylmethanamine (31a)

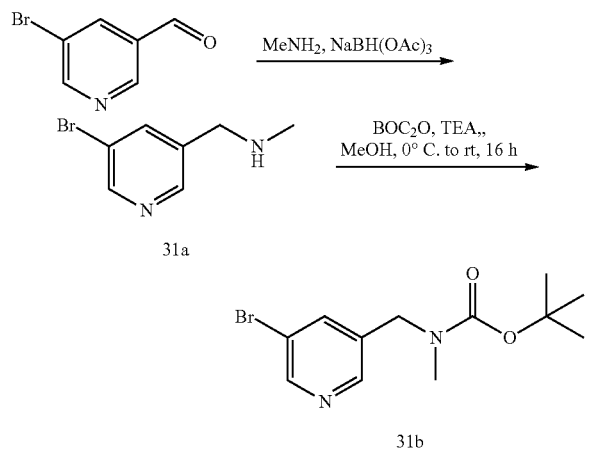

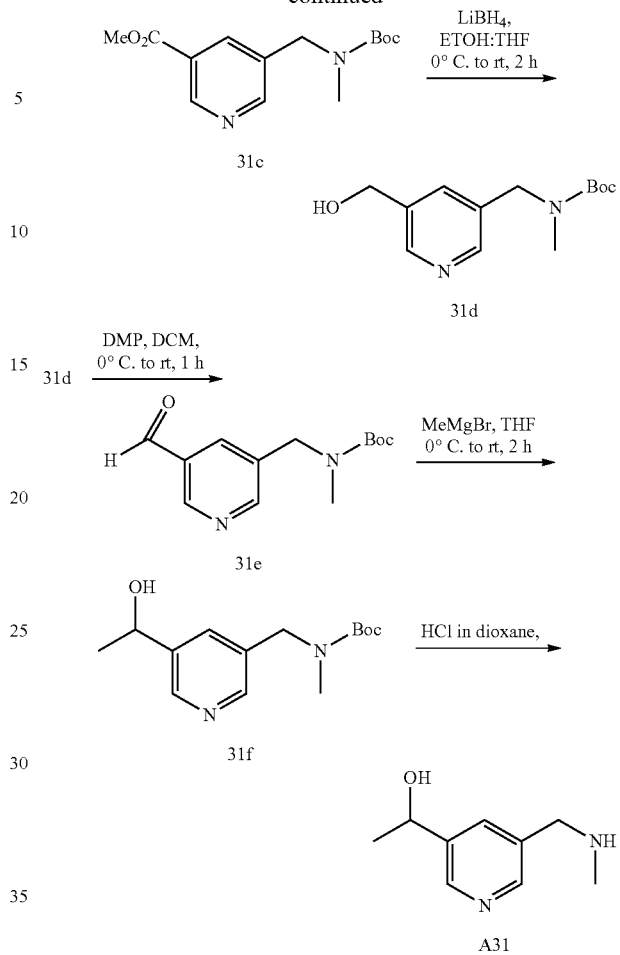

Compound 31a was prepared from 5-bromo nicotinaldehyde (Matrix Scientific, Columbia, S.C., USA) following an analogous protocol to that described for the preparation of 20a.

$^1$H NMR (300 MHz, DMSO-$d_6$): δ 8.56 (d, J=2.30 Hz, 1H), 8.49 (d, J=1.60 Hz, 1H), 8.00 (t, J=2.00 Hz, 1H), 3.68 (s, 2H), 2.25 (s, 3H). Molecular Formula: $C_7H_9BrN_2$; LC-MS purity: 96.8%; Expected: 201.1; Observed: 202.8 (M+H+1).

Step B Tert-butyl ((5-bromopyridin-3-yl)methyl)(methyl)carbamate (31b)

To a stirred solution of 31a (1 g, 4.97 mmol) in methanol (10 mL) triethylamine (3.3 mL, 24.8 mmol) was added at 0° C. followed by the drop wise addition of Boc anhydride (1.7 mL, 7.5 mmol). The reaction mixture was stirred overnight at room temperature under nitrogen atmosphere. The reaction mixture was concentrated under reduced pressure. The residue was diluted with ethyl acetate, successively washed with water and brine. The organic layer was dried over anhydrous $Na_2SO_4$, evaporated to dryness under reduced pressure to obtain 31b (800 mg) as colorless gummy mass.

$^1$H NMR (400 MHz, $CD_3OD$): δ 8.59 (d, J=1.80 Hz, 1H), 8.43 (d, J=1.50 Hz, 1H), 7.92 (t, J=2.00 Hz, 1H), 4.47 (s, 2H), 2.91 (s, 3H), 1.46 (s, 9H). Molecular Formula: $C_{12}H_{17}BrN_2O_2$; LC-MS purity: 98.4%; Expected: 301.1; Observed: 301.1 (M).

Step C Methyl 5-(((tert-butoxycarbonyl)(methyl)amino)methyl)nicotinate (31c)

To a stirred solution of 31b (800 mg, 2.65 mmol) in MeOH (20 mL), sodium acetate (653 mg, 7.96 mmol) was added at room temperature and degassed with nitrogen. $PdCl_2(dppf).2CH_2Cl_2$ (433 mg, 0.53 mmol) was added to the reaction mixture. The reaction mixture was heated at 70° C. for 3 h and carbon monoxide was purged through. The reaction mixture was cooled to room temperature and filtered through a celite bed. The filtrate was concentrated under reduced pressure and the residue was purified by automated flash chromatography using 30% ethyl acetate in petroleum ether to obtain 31c (350 mg) as colorless gummy mass.

$^1$H NMR (400 MHz, $CD_3OD$): δ 9.05 (s, 1H), 8.66 (d, J=2.00 Hz, 1H), 8.30 (s, 1H), 4.55 (s, 2H), 3.97 (s, 3H), 2.91 (s, 3H), 1.47 (s, 9H). Molecular Formula: $C_{14}H_{20}N_2O_4$; LC-MS purity: 95%; Expected: 280.3; Observed: 281 (M+1).

Step D Tert-butyl ((5-(hydroxymethyl)pyridin-3-yl)methyl)(methyl)carbamate (31d)

To a stirred solution of 31c (500 mg, 1.78 mmol) in EtOH:THF (5:2, 5 mL), $LiBH_4$ (1.78 mL, 3.56 mmol, 2M solution in THF) was added drop wise at 0° C. The reaction mixture was stirred for 2 h at room temperature under nitrogen. The reaction was quenched with water and extracted with ethyl acetate. The combined organic layer was washed successively with water and brine. The organic layer was dried over anhydrous $Na_2SO_4$, concentrated under reduced pressure and the residue was purified by automated flash chromatography using 85-90% ethyl acetate in petroleum ether to obtain 31d (250 mg) as a colorless gummy mass. Molecular Formula: $C_{13}H_{20}N_2O_3$; LC-MS purity: 97.2%; Expected: 252.3; Observed: 253 (M+1).

Step E Tert-butyl ((5-formylpyridin-3-yl)methyl)(methyl)carbamate (31e)

To a stirred solution of 31d (250 mg, 0.99 mmol) in $CH_2Cl_2$ (5 mL), Dess-Martin periodinane (840 mg, 1.98 mmol) was added at 0° C. The reaction mixture was stirred for 1 h at room temperature under nitrogen. The reaction as quenched with saturated $NaHCO_3$ solution and extracted with ethyl acetate. The combined organic layer was successively washed with saturated $Na_2S_2O_3$ solution, saturated $NaHCO_3$, water and brine. The organic layer was dried over anhydrous $Na_2SO_4$ and evaporated to dryness under reduced pressure to obtain 31e (140 mg) as colorless gummy mass.

Molecular Formula: $C_{13}H_{18}N_2O_3$; LC-MS purity: 97.5%; Expected: 250.2; Observed: 251 (M+1).

Step F Tert-butyl ((5-(1-hydroxyethyl)pyridin-3-yl)methyl)(methyl)carbamate (31f)

To a stirred solution of 31e (140 mg, 0.56 mmol) in THF (2 mL), MeMgBr (0.56 mL, 1.7 mmol, 3M solution in ether) was added at 0° C. The reaction mixture was stirred for 2 h at room temperature. The reaction mixture was cooled to 0° C., quenched with saturated $NH_4Cl$ solution and extracted with ethyl acetate. The combined organic layers were washed successively with water and brine, dried over anhydrous $Na_2SO_4$ and evaporated to dryness under reduced pressure to obtain 31f (140 mg) as colorless gummy mass.

Molecular Formula: $C_{14}H_{22}N_2O_3$; LC-MS purity: 97%; Expected: 166.3; Observed: 267 (M+1).

Step G 1-(5-((methylamino)methyl)pyridin-3-yl)ethanol (A31)

The compound A31 was prepared from 31f following the same procedure as in the synthesis of A5 from 5f.

Molecular Formula: $C_9H_{14}N_2O$; LC-MS purity: 77.3%; Expected: 166.2; Observed: 167.2 (M+1).

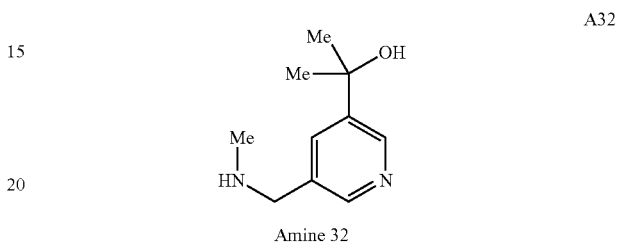

Amine 32

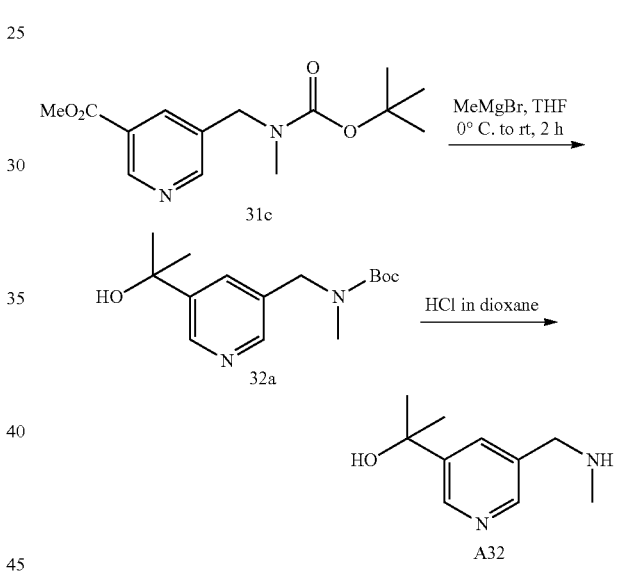

Step A Tert-butyl ((5-(2-hydroxypropan-2-yl)pyridin-3-yl)methyl)(methyl) carbamate (32a)

To a stirred solution of 31c (210 mg, 0.75 mmol) in THF (4 mL), MeMgBr (0.75 mL, 2.24 mmol, 3M solution in ether) was added at 0° C. The reaction mixture was stirred for 2 h at room temperature. The reaction mixture was cooled to 0° C., quenched with saturated $NH_4Cl$ solution and was extracted with dichloromethane. The combined organic layers were washed successively with water and brine, dried over anhydrous $Na_2SO_4$, concentrated under reduced pressure. The crude mass was purified by automated flash chromatography using 40% ethyl acetate in pet-ether to obtain tertiary alcohol 32a (140 mg) as pale yellow liquid.

$^1$H NMR (400 MHz, $CD_3OD$): δ 8.60 (d, J=2.10 Hz, 1H), 8.32 (d, J=1.90 Hz, 1H), 7.88 (bs, 1H), 4.50 (s, 2H), 2.89 (s, 3H), 1.56 (s, 6H), 1.48 (s, 9H). Molecular Formula: $C_{15}H_{24}N_2O_3$; LC-MS purity: 98.4%; Expected: 280.3; Observed: 281.2 (M+1).

Step B 2-(5-((methylamino)methyl)pyridin-3-yl) propan-2-ol (A32)

Compound A32 was prepared from 32a following the same procedure as in the synthesis of A5 from 5f.
Molecular Formula: $C_{10}H_{16}N_2O$; LC-MS purity: 77.3%; Expected: 180.2; Observed: 181 (M+1).

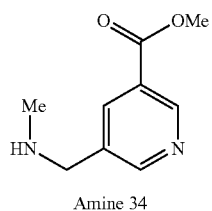

Amine 34

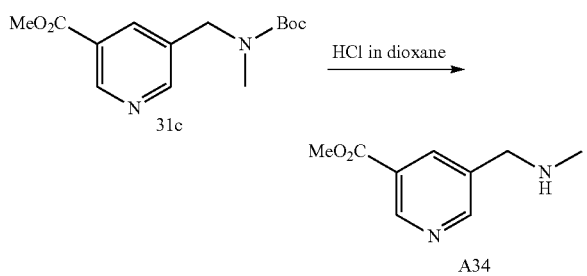

Methyl 5-((methylamino)methyl)nicotinate (A34)

Compound A34 was prepared from 31c following the same procedure as in the synthesis of A5 from 5f.
Molecular Formula: $C_9H_{12}N_2O_2$; LC-MS purity: 97.8%; Expected: 180.3; Observed: 181.1 (M+1).

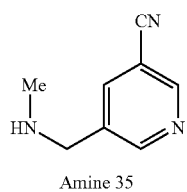

Amine 35

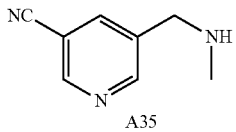

Step A Tert-butyl ((5-cyanopyridin-3-yl)methyl) (methyl)carbamate (35a)

To a stirred solution of 31b (1.5 g, 4.98 mmol) in DMF (10 mL) Zinc cyanide (0.87 g, 7.47 mmol), Xanthphos (0.17 g, 0.29 mmol) and N,N,N$^1$,N$^1$-tetramethyl ethylenediamine (0.57 g, 4.98 mmol) were added at room temperature and degassed with nitrogen for 15 min. Pd$_2$(dba)$_3$ (0.31 g, 0.34 mmol) was added and again degassed. The reaction mixture was stirred under nitrogen at 160° C. for 30 min. After cooling, the reaction mixture was passed through a celite bed and washed with EtOAc. The organic layer was washed with water and brine. The organic layer was dried over anhydrous Na$_2$SO$_4$ and evaporated to dryness under reduced pressure to obtain 35a (0.7 g) as a colorless liquid.
$^1$H NMR (400 MHz, CDCl$_3$): δ 8.81 (s, 1H), 8.72 (bs, 1H), 7.86 (bs, 1H), 4.48 (s, 2H), 2.88 (s, 3H), 1.49 (s, 9H).
Molecular Formula: $C_{13}H_{17}N_3O_2$; LC-MS purity: 96.7%; Expected: 247.3; Observed: 248.3 (M+1).

Step B 5-((methylamino)methyl)nicotinonitrile (A35)

Compound A35 was prepared from 35a following an analogous protocol to that described for the synthesis of 21-I from 21-I1.
Molecular Formula: $C_8H_9N_3$; LC-MS purity: 67.5%; Expected: 147.2; Observed: 148.2 (M+1).

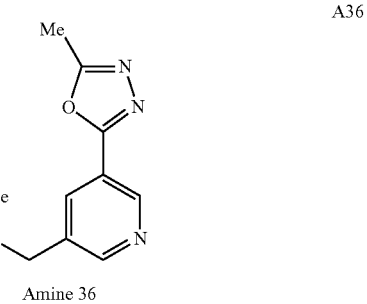

Amine 36

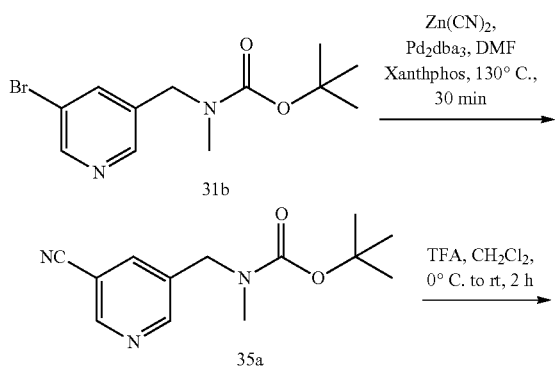

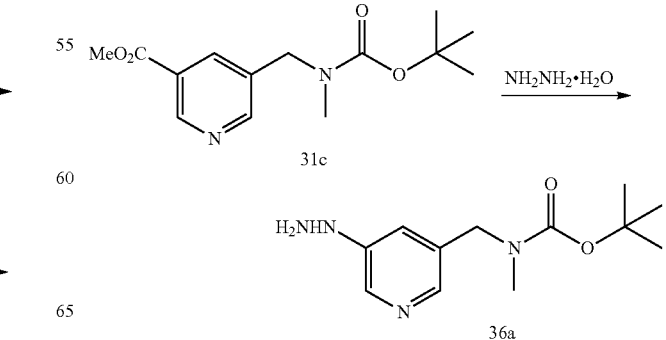

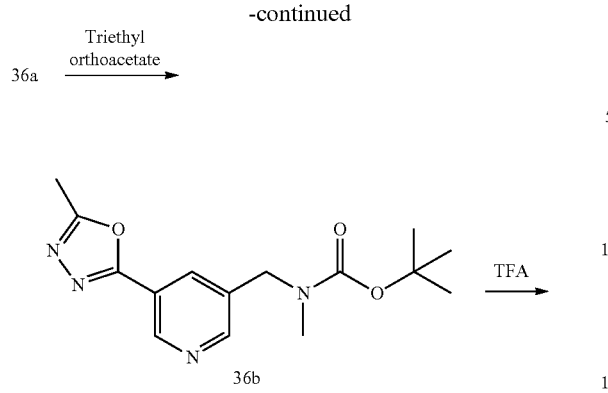

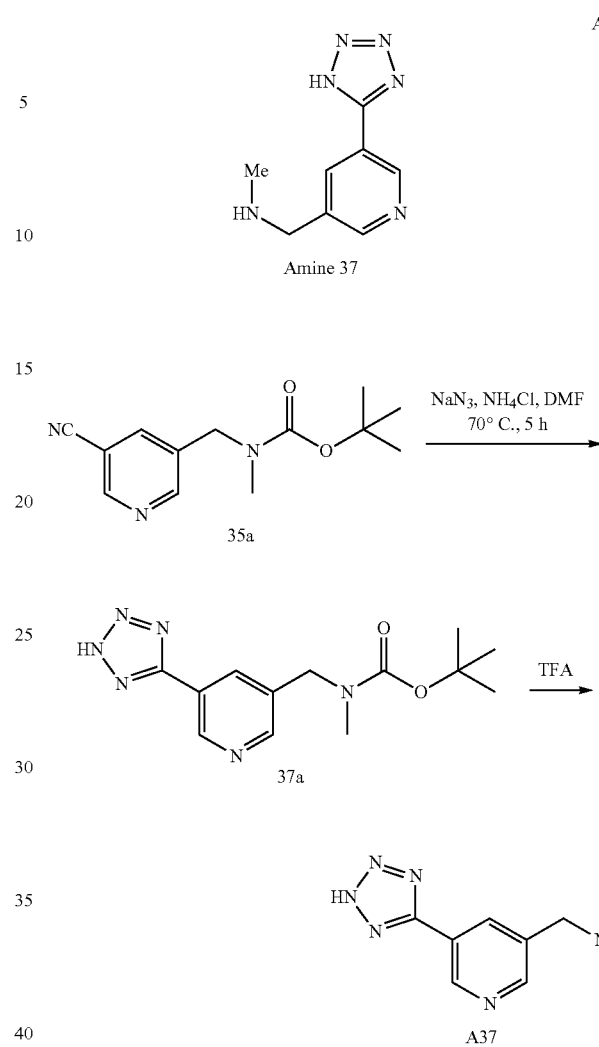

Step A Tert-butyl ((5-(hydrazinecarbonyl)pyridin-3-yl)methyl)(methyl) carbamate (36a)

Compound 36a was prepared from 31c in an analogous protocol to that described for the synthesis of 18a.

$^1$H NMR (400 MHz, DMSO-d$_6$): δ 8.90-8.85 (m, 1H), 8.56-8.50 (m, 1H), 8.10-7.95 (m, 1H), 4.44 (s, 2H), 2.81 (s, 3H), 1.37 (s, 9H). Molecular Formula: C$_{13}$H$_{20}$N$_4$O$_3$; LC-MS purity: 83.1%; Expected: 280.3; Observed: 281 (M+1).

Step B Tert-butyl methyl((5-(5-methyl-1,3,4-oxadiazol-2-yl)pyridin-3-yl)methyl) carbamate (36b)

To a stirred solution of 36a (500 mg, 1.78 mmol) in EtOH (1 mL) was added triethylorthoacetate (8 mL) at room temperature. The reaction mixture was stirred overnight at 90° C. The reaction mixture was concentrated under reduced pressure and co-evaporated with toluene. The crude mass was purified by automated flash chromatography using 70-80% ethyl acetate in petroleum ether to furnish 36b (350 mg) as a pale yellow gummy mass.

$^1$H NMR (300 MHz, DMSO-d$_6$): δ 9.05-9.00 (m, 1H), 8.65-8.60 (m, 1H), 8.15-8.10 (m, 1H), 4.49 (s, 2H), 2.83 (s, 3H), 2.59 (s, 3H), 1.38 (s, 9H). Molecular Formula: C$_{15}$H$_{20}$N$_4$O$_3$; LC-MS purity: 99.2%; Expected: 304.3; Observed: 305.2 (M+1).

Step C N-methyl-1-(5-(5-methyl-1,3,4-oxadiazol-2-yl)pyridin-3-yl)methanamine (A36)

Compound A36 was prepared from 36b following an analogous protocol to that described for the synthesis of 21-I from 21-I1.

Molecular Formula: C$_{10}$H$_{12}$N$_4$O; LC-MS purity: 77.2%; Expected: 204.2; Observed: 205.2 (M+1).

Step A Tert-butyl ((5-(2H-tetrazol-5-yl)pyridin-3-yl)methyl)(methyl) carbamate (37a)

To a stirred solution of 35a (150 mg, 0.60 mmol) in DMF (5 mL), sodium azide (0.2 g, 3.03 mmol) and ammonium chloride (0.32 g, 6.07 mmol) were added at 0° C. The reaction mixture was stirred for 5 h at 70° C. The reaction was quenched with water and was concentrated under reduced pressure and co-evaporated with toluene. The crude mass was purified by preparative HPLC to obtain 37a (150 mg) as white solids.

Molecular Formula: C$_{13}$H$_{18}$N$_6$O$_2$; LC-MS purity: 98.8%; Expected: 290.3; Observed: 291.2 (M+1).

Step B 1-(5-(1H-tetrazol-5-yl)pyridin-3-yl)-N-methylmethanamine (A37)

Compound A37 was prepared from 37a following an analogous protocol to that described for the synthesis of 21-I from 21-I1.

Molecular Formula: C$_8$H$_{10}$N$_6$; LC-MS purity: 98.8%; Expected: 190.2; Observed: 191.1 (M+1).

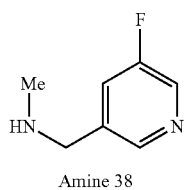

Amine 38

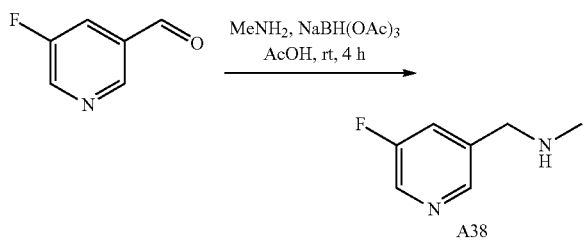

1-(5-fluoropyridin-3-yl)-N-methylmethanamine (A38)

Compound 38 was prepared from 5-fluoronicotinaldehyde [commercially available from Matrix Scientific, Columbia, S.C., USA] in the manner analogous to the procedure described for the preparation of 20a.

$^1$H NMR (400 MHz, DMSO-$d_6$): δ 8.44 (d, J=2.70 Hz, 1H), 8.40 (s, 1H), 7.66 (d, J=10.00 Hz, H), 3.72 (s, 2H), 2.26 (s, 3H). Molecular Formula: $C_7H_9FN_2$; LC-MS purity: 74.2%; Expected: 140.1; Observed: 141.2 (M+1).

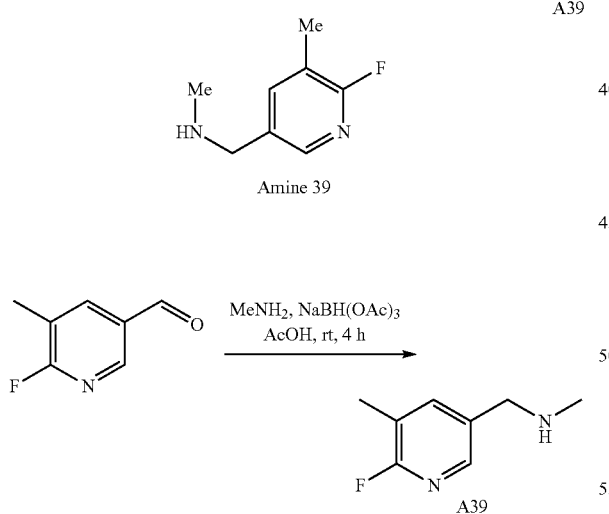

1-(6-fluoro-5-methylpyridin-3-yl)-N-methylmethanamine (A39)

Compound A39 was prepared from 6-fluoro-5-methylnicotinaldehyde [commercially available from Frontier Scientific Inc., Logan, Utah, USA] in an analogous manner to that described for the preparation of 20a.

$^1$H NMR (300 MHz, DMSO-$d_6$): δ 7.95-7.90 (m, 1H), 7.77-7.74 (m, 1H), 3.61 (s, 2H), 2.23 (s, H), 2.22 (s, 3H). Molecular Formula: $C_8H_{11}FN_2$; LC-MS purity: 89.7%; Expected: 154.1; Observed: 155.2 (M+1).

Amine 40

Amine N-methyl-1-(pyrazin-2-yl)methanamine (A40) was commercially purchased from Matrix Scientific, Columbia, S.C., USA.

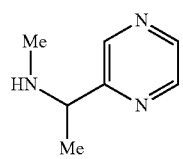

Amine 41

Amine N-methyl-1-(pyrazin-2-yl)ethanamine (A41) was prepared in an analogous manner to that described for the synthesis of amine A23.

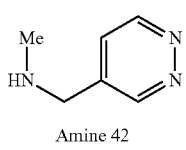

Amine 42

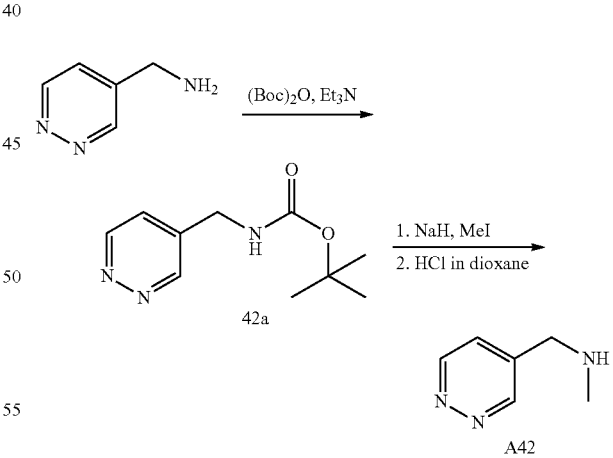

Step A Tert-butyl (pyridazin-4-ylmethyl)carbamate (42a)

Compound 42a was prepared following an analogous protocol to that described for the synthesis of 19b from 19a.

$^1$H NMR (300 MHz, DMSO-$d_6$): δ 9.13 (d, J=5.30 Hz, 1H), 9.10 (s, 1H), 7.48-7.46 (m, 1H), 4.17 (d, J=5.90 Hz,

2H), 1.38 (s, 9H). Molecular Formula: $C_{10}H_{15}N_3O_2$; LC-MS purity: 91.7%; Expected: 209.2; Observed: 210.2 (M+1).

Step B N-methyl-1-(pyridazin-4-yl)methanamine (A42)

Compound A42 was prepared from 42a following the synthetic protocol of 2-B from 2-B1.

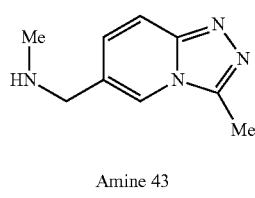

Amine 43

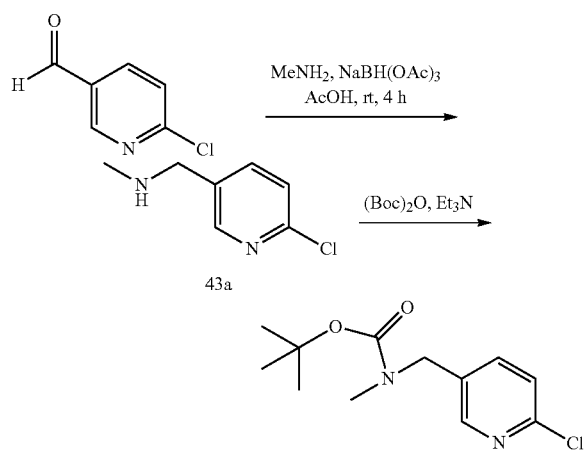

Step A
1-(6-chloropyridin-3-yl)-N-methylmethanamine (43a)

Compound 43a was prepared from 6-chloronicotinaldehyde (commercially available from Matrix Scientific, Columbia, S.C., USA) following an analogous protocol to that described for the synthesis of 20a.

$^1$H NMR (400 MHz, DMSO-$d_6$): δ 8.34 (s, 1H), 7.83-7.80 (m, 1H), 7.49 (d, J=8.20 Hz, 1H), 3.70 (s, 2H), 2.27 (s, 3H). Molecular Formula: $C_7H_9ClN_2$; LCMS purity: 74.5%; Expected: 156.6; Observed: 157.6 (M+1).

Step B Tert-butyl ((6-chloropyridin-3-yl)methyl)(methyl)carbamate (43b)

Compound 43b was prepared following an analogous protocol to that described for the synthesis of 19b from 19a.

$^1$H NMR (300 MHz, CDCl$_3$): δ 8.27 (s, 1H), 7.32 (m, 1H), 7.26 (m, 1H), 4.40 (s, 2H), 2.84 (bs, 3H), 1.45 (s, 9H). Molecular Formula: $C_{12}H_{17}ClN_2O_2$; LCMS purity: 98.5%; Expected: 256.7; Observed: 257.7 (M+1).

Step C Tert-butyl ((6-hydrazinylpyridin-3-yl)methyl)(methyl)carbamate (43c)

Compound 43b (500 mg) was added to hydrazene hydrate (1.5 mL) at room temperature and the reaction temperature was slowly raised to 130° C. and was stirred for 7 h. The reaction mixture was concentrated under reduced pressure and co-evaporated with toluene. The residue was purified by automated flash chromatography using 10-25% methanol in dichloromethane to obtain 43c (0.3 g) as colorless liquid.

Molecular Formula: $C_{12}H_{20}N_4O_2$; LCMS purity: 62.8%; Expected: 252.3; Observed: 253.3 (M+1).

Step D Tert-butyl methyl((3-methyl-[1,2,4]triazolo[4,3-a]pyridin-6-yl)methyl) carbamate (43d)

To a stirred solution of 43c (300 mg) in triethyl orthoacetate (11.6 mL) TFA (0.07 mL) was added at 0° C. The reaction temperature was slowly raised to 70° C. and was stirred for 3 h. The reaction mixture was concentrated under reduced pressure and co-evaporated with toluene. The residue was purified by automated flash chromatography using 5-15% methanol in dichloromethane to furnish 43d (0.2 g) as colorless liquid.

Molecular Formula: $C_{14}H_{20}N_4O_2$; LCMS purity: 98%; Expected: 276.3; Observed: 277.3 (M+1).

Step E N-methyl-1-(3-methyl-[1,2,4]triazolo[4,3-a]pyridin-6-yl)methanamine (A43)

Compound A43 was prepared following similar protocol as in the synthesis of 2-B from 2-B2. Molecular Formula: $C_9H_{12}N_4$; LCMS purity: 97.8%; Expected: 176.2; Observed: 177.2 (M+1).

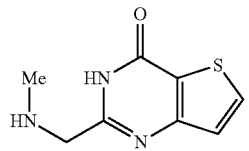

Amine 44

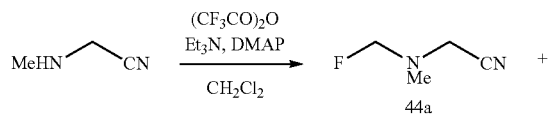
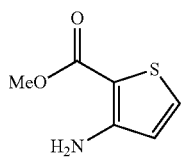
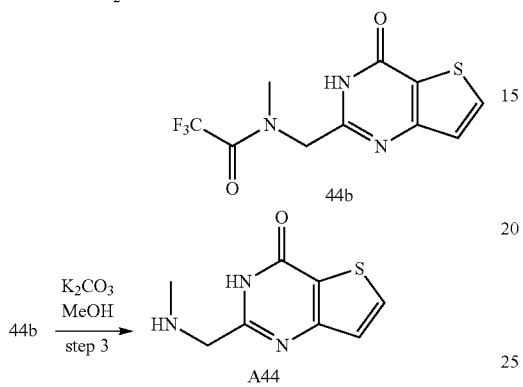

Step A N-(cyanomethyl)-2,2,2-trifluoro-N-methylacetamide (44a)

To a solution of methylamino acetonitrile (1 g, 1.43 mmol) in $CH_2Cl_2$ (10 mL) were added $Et_3N$ (3.97 mL, 2.85 mmol), catalytic amount of DMAP (10 mg) and trifluoroacetic anhydride (2.39 mL, 1.71 mmol) and the reaction mixture was stirred at room temperature for 1 h. The reaction mixture was diluted with dichloromethane, washed with 1.5N HCl solution and water, dried over anhydrous $Na_2SO_4$ and evaporated to dryness under reduced pressure to provide 44a (2.2 g).

$^1$H NMR (300 MHz, $CDCl_3$): δ 4.41 (s, 2H), 3.31 (s, 3H).

Step B 2,2,2-trifluoro-N-methyl-N-((4-oxo-3,4-dihydrothieno[3,2-d]pyrimidin-2-yl)methyl)acetamide (44b)

Compound 44b was prepared from 44a in an analogous protocol to that described for the synthesis of 2-B from 2-B2.

$^1$H NMR (300 MHz, DMSO-$d_6$): δ12.60 (bs, 1H), 8.16 (m, 1H), 7.32 (d, J=5.00 Hz, 1H), 4.60 (s, 2H), 3.24 (s, 3H). Molecular Formula: $C_{10}H_8F_3N_3O_2S$; LCMS purity: 97%; Expected: 291.2; Observed: 292.1 (M+1).

Step C 2-((methylamino)methyl)thieno[3,2-d]pyrimidin-4(3H)-one (A44)

To a solution of 44b (200 mg, 0.69 mmol) in MeOH (5 mL) was added $K_2CO_3$ (190 mg, 1.37 mmol) and the reaction mixture was stirred at room temperature for 2 h. The reaction mixture was concentrated under reduced pressure. The crude mass was dissolved in a solution of 10% MeOH—$CH_2Cl_2$ and was filtered. The filtrate was evaporated to dryness under reduced pressure to provide A44.

$^1$H NMR (400 MHz, DMSO-$d_6$): δ12.9 (bs, 1H), 9.34 (bs, 1H), 8.25 (d, J=5.00 Hz, 1H), 7.41 (d, J=5.00 Hz, 1H), 4.22 (s, 2H), 2.68 (s, 3H). Molecular Formula: $C_8H_9N_3OS$; LCMS purity: 97%; Expected: 195.2; Observed: 196 (M+1).

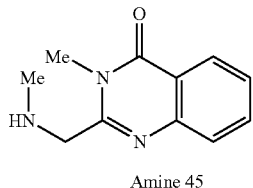

Amine 45

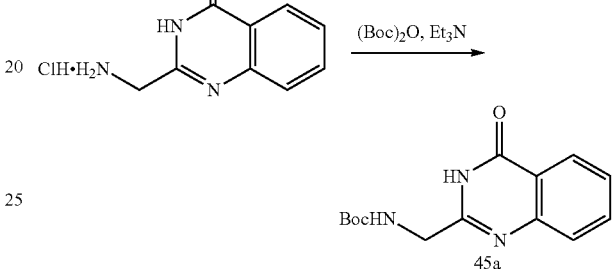
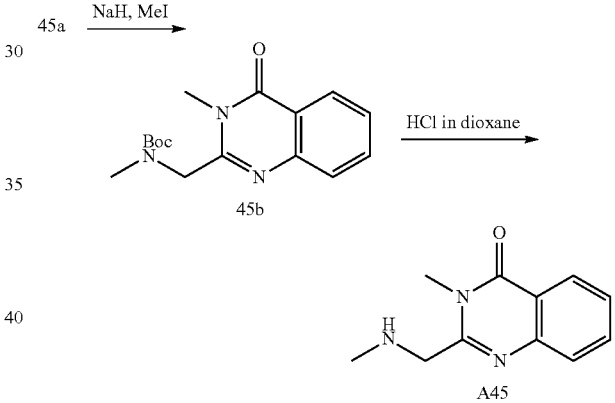

2-((methylamino)methyl)thieno[3,2-d]pyrimidin-4(3H)-one (A45)

Compound A45 was prepared from 2-(aminomethyl)quinazolin-4(3H)-one hydrochloride (commercially available from Chembridge Corporation, San diego, Calif. USA) in an analogous manner to that described for the preparation of A44.

Molecular Formula: $C_{11}H_{13}N_3O$; LCMS purity: 83.8%; Expected: 203.2; Observed: 203.9 (M+1).

EXAMPLES

Exemplified compounds of the present invention are those compounds that are identified by the suffix A after the example number. For instance, Example n-A, where n is equal to 1 through 45, such as, for example, Example 1-A, Example 2-A, Example 3-A, etc. through Example 45-A. Similarly, comparative examples are identified by use of the Suffix B through S after the example number. For instance, the following compounds denote comparative examples: Example 1-B, and Examples 4-B, 4-E, 4-F, 4-G, 4-Q, and 4-R.

Example 1-A

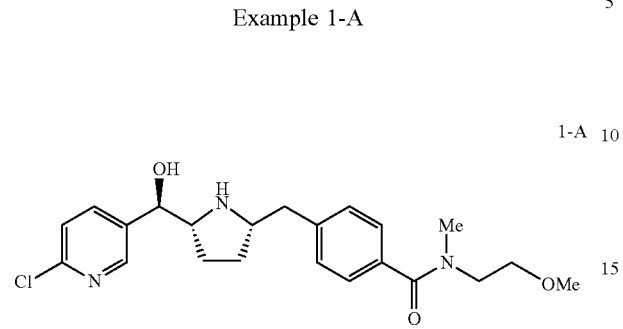

1-A 4-(((2S,5R)-5-((R)-(4-chlorophenyl)(hydroxy)methyl)pyrrolidin-2-yl)methyl)-N-(2-methoxyethyl)-N-methylbenzamide (1-A)

Compound 1-A was prepared from Amine 1 (A1) in the manner of example 4-E.

$^1$H NMR (400 MHz, DMSO-d$_6$): δ 9.47 (bs, 1H), 8.76 (bs, 1H), 8.47 (d, J=2.08 Hz, 1H), 7.90 (dd, J=8.20 and 2.04 Hz, 1H), 7.56 (d, J=8.20 Hz, 1H), 7.35-7.30 (m, 4H), 6.49 (d, J=3.84 Hz, 1H), 4.87 (dd, J=8.04 and 3.68 Hz, 1H), 3.69-3.55 (m, 4H), 3.39-3.28 (m, 3H), 3.20-3.17 (m, 3H), 2.99-2.94 (m, 4H), 1.92-1.88 (m, 1H), 1.77-1.69 (m, 3H). Molecular Formula: C$_{22}$H$_{28}$ClN$_3$O$_3$; LC-MS purity: 97.4%; Expected: 417.2; Observed: 418 (M+1).

Example 1-B

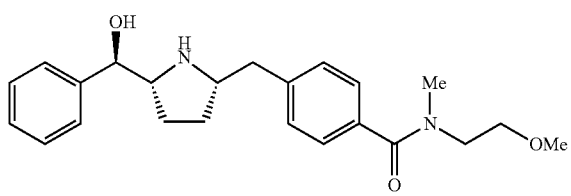

1-B 4-(((2S,5R)-5-((R)-hydroxy(phenyl)methyl)pyrrolidin-2-yl)methyl)-N-(2-methoxyethyl)-N-methylbenzamide (1-B)

Compound 1-B was prepared in a manner analogous to that described in Example 45-A.

$^1$H NMR (400 MHz, DMSO-d6): δ7.33-7.18 (9H, m), 4.23 (1H, d, J=7 Hz), 3.54-3.49 (5H, m), 3.27-3.15 (6H, m), 2.93 (3H, s), 2.74-2.63 (2H, m), 1.63-1.59 (1H, m), 1.42-1.22 (3H, m). Molecular Formula: C$_{23}$H$_{30}$N$_2$O$_3$; LCMS purity: >98%; Expected: 382.5; Observed: 383.2 (M+1).

Example 2-A

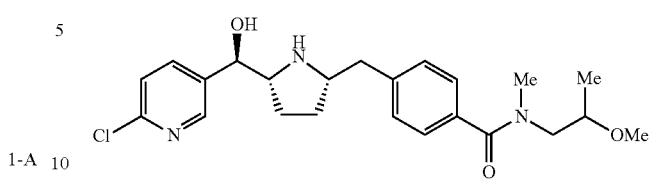

TFA salt 4-(((2S,5R)-5-((R)-(6-chloropyridin-3-yl)(hydroxy)methyl)pyrrolidin-2-yl)methyl)-N-(2-methoxypropyl)-N-methylbenzamide, triflic acid salt (2-A)

Compound 2-A was prepared from A in the manner of Example 2-B.

1H NMR (400 MHz, CD$_3$OD): δ 8.46 (s, 1H), 7.94-7.91 (m, 1H), 7.52 (d, J=8.2 Hz, 1H), 7.43-7.38 (m, 4H), 4.85 (d, J=8.28 Hz, 2H), 3.84-3.80 (m, 2H), 3.59-3.51 (m, 2H), 3.39 (s, 2H), 3.23-3.19 (m, 2H), 3.10-3.04 (m, 3H), 2.13-2.11 (m, 1H), 1.90-1.87 (m, 3H), 1.32-1.28 (m, 3H), 1.19-0.45 (m, 3H). Molecular Formula: C$_{23}$H$_{30}$ClN$_3$O$_3$; LC-MS purity: 97.3%; Expected: 431.9; Observed: 432 (M+1).

Example 2-B

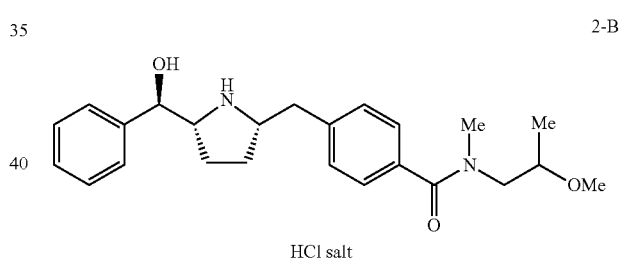

2-B

HCl salt

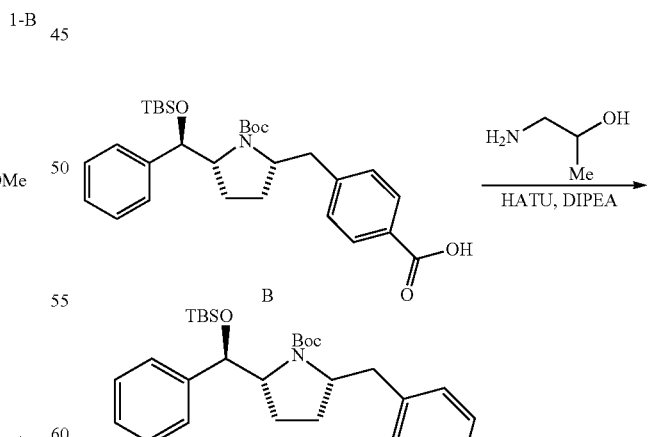

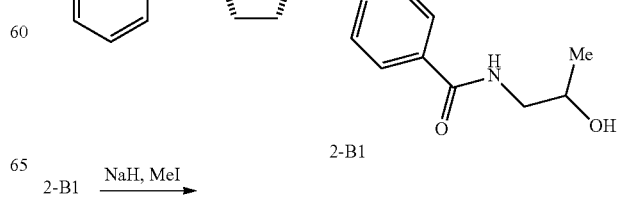

2-B1

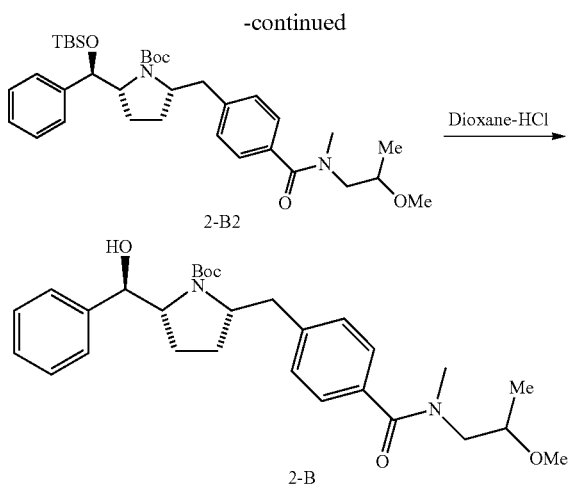

Step A (2R,5S)-tert-butyl 2-((R)-((tert-butyldimethylsilyl)oxy)(phenyl)methyl)-5-(4-((2-hydroxypropyl)carbamoyl)benzyl)pyrrolidine-1-carboxylate (2-B1)

To a solution of acid B (250 mg, 0.47 mmol) in dichloromethane (3 mL) HATU (272 mg, 0.71 mmol) was added followed by the addition of DIPEA (0.24 mL, 1.43 mmol) and the solution was stirred for 10 min. 1-Aminopropan-2-ol (commercially available, 0.04 mL, 0.52 mmol) in dichloromethane (2 mL) was added to the solution at 0° C. and stirred at room temperature for 3 h. The reaction mixture was diluted with dichloromethane and washed successively with water, saturated sodium bicarbonate solution and brine. The organic fraction was dried over anhydrous $Na_2SO_4$ and concentrated under reduced pressure. The residue was purified by automated flash chromatography using 30% ethyl acetate in petroleum ether (v/v) to furnish 2-B1 (265 mg).

$^1$H NMR (300 MHz, $CDCl_3$): δ 7.61-7.59 (m, 2H), 7.34-7.28 (m, 5H), 6.94-6.91 (m, 2H), 6.53-6.51 (m, 1H), 5.27-5.25 (m, 1H), 4.05-4.03 (m, 2H), 3.84-3.81 (m, 2H), 3.65-3.68 (m, 2H), 2.64-2.55 (m, 1H), 2.83-2.80 (m, 1H), 2.61-2.57 (m, 2H), 1.96-1.87 (m, 4H), 1.59 (s, 9H), 1.12 (d, J=6.6 Hz, 3H), 0.92 (s, 9H), 0.12 (s, 3H), −0.1 (s, 3H). Molecular Formula: $C_{33}H_{50}N_2O_5Si$; LC-MS purity: 87.3%; Expected: 583; Observed: 483 (M-Boc).

Step B (2R,5S)-tert-butyl 2-((R)-((tert-butyldimethylsilyl)oxy)(phenyl)methyl)-5-(4-((2-methoxypropyl)(methyl)carbamoyl)benzyl)pyrrolidine-1-carboxylate (2-B2)

To a solution of 2-B1 (265 mg, 0.45 mmol) in THF (3 mL) NaH (27.3 mg, 1.1 mmol) was added at 0° C. and stirred for 30 min. To the suspension methyl iodide (130 mg, 0.91 mmol) was added at 0° C. and stirred for 1 h. The reaction was quenched with saturated $NH_4Cl$ solution and extracted with ethyl acetate. The organic fraction was washed with water and brine, dried over anhydrous $Na_2SO_4$ and concentrated under reduced pressure. The crude mass was purified by column chromatography using 15% ethyl acetate in petroleum ether (v/v) to yield 2-B2 (250 mg).

$^1$H NMR (300 MHz, $CDCl_3$): δ 7.61-7.59 (m, 2H), 7.34-7.28 (m, 5H), 6.94-6.91 (m, 2H), 6.53-6.51 (m, 1H), 5.27-5.25 (m, 1H), 4.05-4.03 (m, 2H), 3.97-3.95 (m, 3H), 3.84-3.81 (m, 2H), 3.64-3.61 (m, 5H), 2.64-2.55 (m, 1H), 2.81-2.8 (m, 1H), 2.61-2.57 (m, 2H), 1.96-1.87 (m, 4H), 1.59 (s, 9H), 1.12 (d, J=6.6 Hz, 3H), 0.92 (s, 9H), 0.12 (s, 3H), −0.1 (s, 3H). Molecular Formula: $C_{35}H_{54}N_2O_5Si$; LC-MS purity: 99%; Expected: 610.9; Observed: 555 (M-$^t$Bu).

Step C 4-(((2S,5R)-5-((R)-hydroxy(phenyl)methyl)pyrrolidin-2-yl)methyl)-N-(2-methoxypropyl)-N-methylbenzamide, hydrochloride salt (2-B)

To a solution of 2-B2 (230 mg, 0.37 mmol) in 1,4-dioxane (1 mL) was added HCl in dioxane (4 mL). The reaction mixture was stirred at room temperature for 1 h. The reaction mixture was evaporated to dryness and the crude mass was purified by HPLC to obtain 2-B.

$^1$H NMR (400 MHz, $CD_3OD$): δ 7.44-7.33 (m, 9H), 4.74 (d, J=8.64 Hz, 1H), 3.83-3.79 (m, H), 3.39-3.34 (m, 3H), 3.32 (s, 3H), 3.25-3.21 (m, 2H), 3.14-3.03 (m, 4H), 2.10-2.06 (m, 1H), 1.87-1.78 (m, 3H), 1.21 (d, J=6.16 Hz, 1.5H), 0.96 (d, 6.04 Hz, 1.5H). Molecular Formula: $C_{24}H_{32}N_2O_3$; LC-MS purity: 98.6%; Expected: 396.5; Observed: 397 (M+1).

The two isomers were separated by chiral HPLC (EtOH: Hexane (95:5), 0.8 mL/min).

Isomer I-2-B $^1$H NMR (400 MHz, $CD_3OD$): δ 7.31-7.28 (m, 9H), 5.15-5.03 (m, 1H), 4.21 (d, J=7.16 Hz, 1H), 3.52-3.40 (m, 1H), 3.33-3.19 (m, 4H), 3.14-3.08 (m, 1H), 2.95 (s, 9H), 2.75-2.67 (m, 3H), 1.68-1.56 (m, 1H), 1.48-1.37 (m, 1H), 1.42-1.28 (m, 2H), 1.1 (s, 1.5H), 0.9 (s, 1.5H). Molecular Formula: $C_{24}H_{32}N_2O_3$; LC-MS purity: 95.3%; Expected: 396.5; Observed: 397 (M+1).

Isomer II-2-B $^1$H NMR (400 MHz, $CD_3OD$): δ 7.33-7.21 (m, 9H), 5.12 (bs, 1H), 4.22 (d, J=7.2 Hz, 1H), 3.65-3.55 (m, 1H), 3.52-3.40 (m, 2H), 3.33-3.19 (m, 5H), 3.18-3.06 (m, 1H), 2.94 (s, 9H), 2.71-2.68 (m, 2H), 1.65-1.5$^a$ (m, 1H), 1.48-1.21 (m, 4H), 1.1 (s, 1.5H), 0.87-0.85 (s, 1.5H). Molecular Formula: $C_{24}H_{32}N_2O_3$; LC-MS purity: 96.5%; Expected: 396.5; Observed: 397 (M+1).

Example 3-A

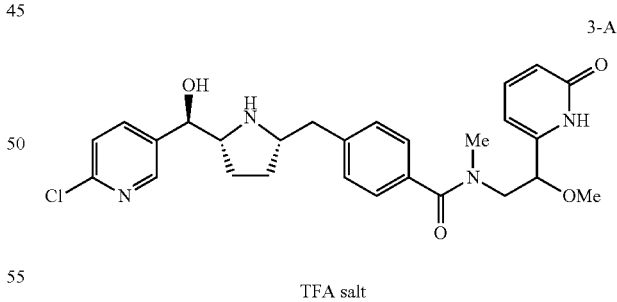

TFA salt 4-(((2S,5R)-5-((R)-(6-chloropyridin-3-yl)(hydroxy)methyl)pyrrolidin-2-yl)methyl)-N-(2-methoxy-2-(6-oxo-1,6-dihydropyridin-2-yl)ethyl)-N-methylbenzamide, triflic acid salt (3-A)

Compound 3-A was prepared in an analogous manner of that of Example 2-B.

1H NMR (400 MHz, $CD_3OD$): δ 8.39 (d, J=1.88 Hz, 1H), 8.2 (s, 1H), 7.82 (dd, J=8.21 and 2.30 Hz, 1H), 7.47 (d, J=8.20 Hz, 1H), 7.40-7.38 (m, 1H), 7.21-7.16 (m, 4H), 6.28-6.02 (m, 2H), 4.46 (bs, 1H), 4.38-4.23 (m, 1H), 3.87-3.61 (m, 3H), 3.27-3.19 (m, 3H), 2.99-2.85 (m, 4H), 2.7-2.63 (m, 3H), 1.68-1.63 (m, 1H), 1.73-1.72 (m, 2H), 1.28-1.23 (m, 1H). Molecular Formula: $C_{27}H_{31}ClN_4O_4$; LC-MS purity: 98.4%; Expected: 511; Observed: 512.2 (M+1).

3.21-3.20 (m, 2H), 3.19-3.02 (m, 3H), 2.29-2.20 (m, 1H), 1.85-1.73 (m, 3H). Molecular Formula: $C_{28}H_{33}N_3O_4$; LC-MS purity: 99.6%; Expected: 475; Observed: 476 (M+1).

Example 4-A

Example 3-B

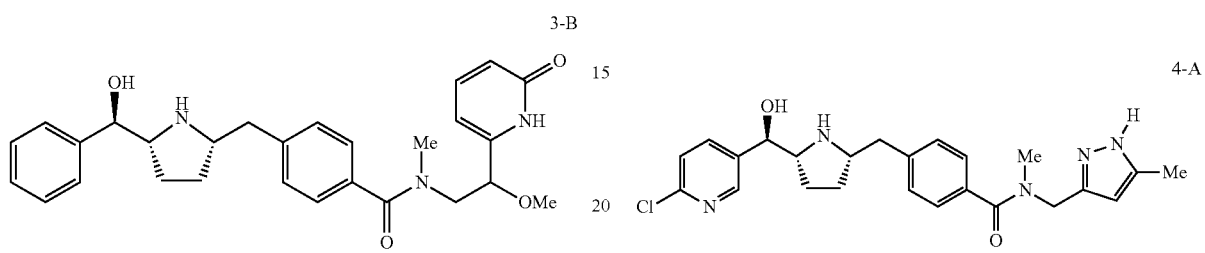

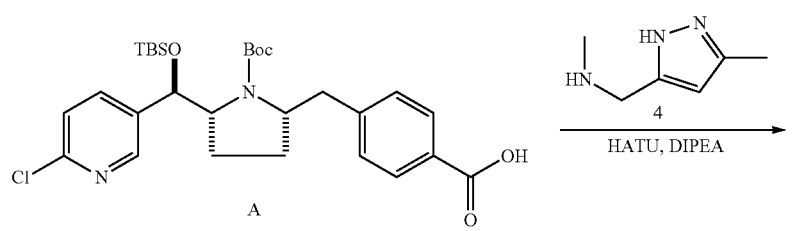

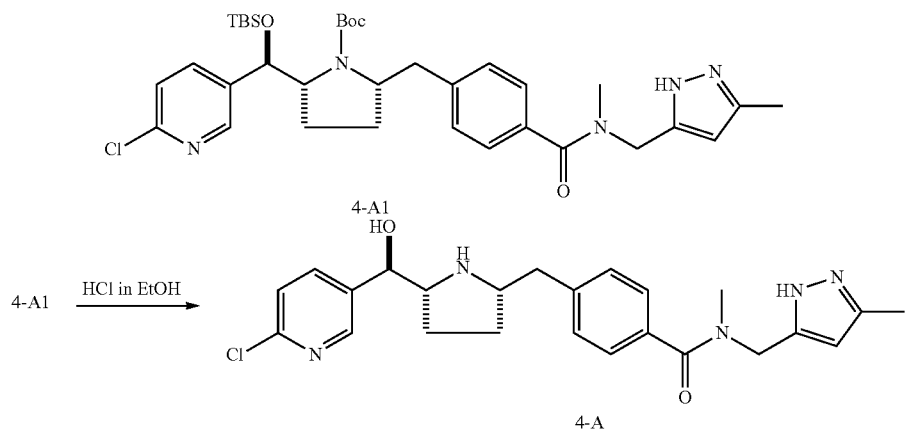

4-(((2S,5R)-5-((R)-hydroxy(phenyl)methyl)pyrrolidin-2-yl)methyl)-N-(2-methoxy-2-(6-oxo-1,6-dihydropyridin-2-yl)ethyl)-N-methylbenzamide, formic acid salt (3-B)

Compound 3-B was prepared in an analogous manner to that of example 2-B.

$^1$H NMR (400 MHz, CD$_3$OD): δ 7.59-7.55 (m, 1H), 7.45-7.39 (m, 7H), 7.30 (t, J=7.4 Hz, 1H), 7.07 (d, J=6.44 Hz, 1H), 6.51-6.30 (m, 2H), 4.82-4.23 (m, 1H), 4.55-4.29 (m, 1H), 3.93-3.67 (m, 4H), 3.49-3.48 (m, 2H), 3.28 (s, 3H),

Step A (2R,5S)-tert-butyl 2-((R)-((tert-butyldimethylsilyl)oxy)(6-chloropyridin-3-yl)methyl)-5-(4-(methyl((3-methyl-1H-pyrazol-5-yl)methyl)carbamoyl) benzyl)pyrrolidine-1-carboxylate (4-A1)

To a stirred cold (0° C.) solution of acid A (11.0 g, 0.02 mol) in DMF (60 mL) HATU (15.32 g, 0.04 mol) was added slowly portion wise over a period of 15 min followed by portion wise addition of HOAT (0.68 g, 0.005 mol) and drop-wise addition of DIPEA (10.3 mL, 0.06 mol) over 15 min at the same temperature. The reaction mixture was stirred at 0° C. for 30 min. After 30 min, pyrazole amine 4 (7.36 g, 0.06 mol) was added portion wise and the reaction mixture was allowed to warm to room temperature and stirred for 16 h. The reaction mixture was concentrated under vacuum. The crude residue was dissolved in dichloromethane and washed with saturated NaHCO$_3$ solution, water and brine, successively. The organic layer was dried over anhydrous Na$_2$SO$_4$ and concentrated to dryness. The crude product was purified by flash chromatography using 40% ethyl acetate in hexane (v/v) to afford 4-A1 as off-white solid (10 g) which was taken to the next step without further characterization.

Step B 4-(((2S,5R)-5-((R)-(6-chloropyridin-3-yl)(hydroxy)methyl) pyrrolidin-2-yl)methyl)-N-methyl-N-((5-methyl-1H-pyrazol-3-yl)methyl)benzamide (4-A)

Compound 4-A1 was dissolved in ethanol (100 mL) and ethanolic HCl (100 mL) was added at 0° C. and stirred for 6 h. The solvent was removed under reduced pressure. The crude mass was dissolved in water (150 mL) and washed with EtOAc (4×200 mL) followed by dichloromethane (4×200 mL) to get rid of all the soluble impurities. The aqueous layer was then cooled to 0° C. and the pH was adjusted to 8-9 using saturated NaHCO$_3$ solution. The aqueous layer was extracted with 2% MeOH in dichloromethane (4×200 mL). The combined organic layers was washed with brine (2×200 mL), dried over anhydrous Na$_2$SO$_4$ and concentrated to dryness under reduced pressure to afford 4-A as white solid.

$^1$H NMR (400 MHz, CD$_3$OD): δ 8.36 (s, 1H), 7.83 (d, J=8.00 Hz, 1H), 7.44-7.33 (m, 5H), 6.09-5.95 (m, 1H), 4.67 (s, 1H), 4.53-4.45 (m, 2H), 3.35-3.33 (m, 1H), 3.28-3.23 (m, 1H), 3.02-2.86 (m, 3H), 2.84-2.78 (m, 2H), 2.28 (s, 3H), 1.82-1.75 (m, 1H), 1.58-1.52 (m, 2H), 1.48-1.43 (m, 1H). Molecular Formula: C$_{24}$H$_{28}$ClN$_5$O$_2$; LC-MS purity: 99.8%; Expected: 453.9; Observed: 454.9 (M+1).

Example 4-B

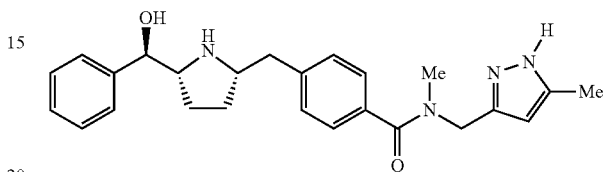

4-B

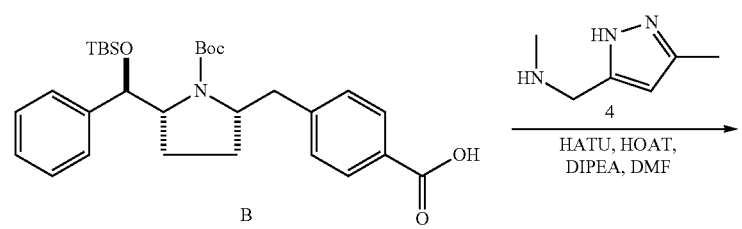

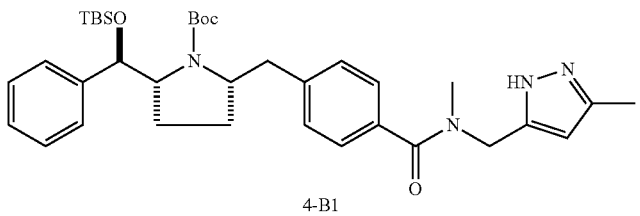

4-B1

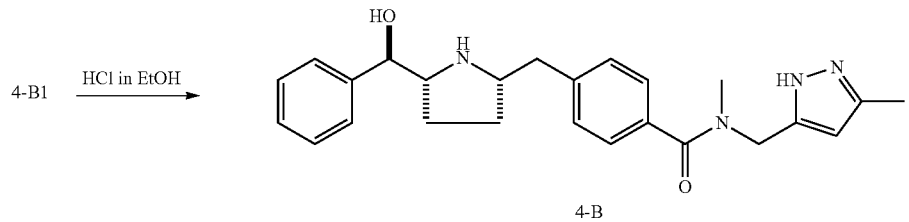

Step A (2R,5S)-tert-butyl 2-((R)-((tert-butyldimethylsilyl)oxy)(phenyl)methyl)-5-(4-(methyl((3-methyl-1H-pyrazol-5-yl)methyl)carbamoyl)benzyl)pyrrolidine-1-carboxylate (4-B1)

To a stirred cold (0° C.) solution of acid B (13.0 g, 0.025 mol) in DMF (150.0 mL) HATU (18.9 g, 0.05 mol) was added slowly portion wise over a period of 15 min followed by portion wise addition of HOAT (0.84 g, 0.006 mol) and drop-wise addition of DIPEA (44.7 mL, 0.25 mol) over 15 min at the same temperature. The reaction mixture was stirred at 0° C. for 30 min. After 30 min, pyrazole amine 4

(9.28 g, 0.07 mol) was added portion wise and the reaction mixture was allowed to warm to room temperature and stirred for 16 h. The reaction mixture was concentrated under vacuum. The crude residue was dissolved in dichloromethane and washed with saturated NaHCO₃ solution, water and brine, successively. The organic layer was dried over anhydrous Na₂SO₄ and concentrated to dryness. The crude product was purified by flash chromatography using 40% ethyl acetate in hexane (v/v) to afford 4-B1 as off-white solid (11.5 g) which was taken to the next step without further characterization.

Step B 4-(((2S,5R)-5-((R)-hydroxy(phenyl)methyl)pyrrolidin-2-yl)methyl)-N-methyl-N-((5-methyl-1H-pyrazol-3-yl)methyl)benzamide (4-B)

Compound 4-B1 was dissolved in ethanol (100 mL) and ethanolic HCl (100 mL) was added at 0° C. and stirred for 6 h. The solvent was removed under reduced pressure. The crude mass was dissolved in water (150 mL) and washed with EtOAc (4×200 mL) followed by dichloromethane (4×200 mL) to get rid of all the soluble impurities. The aqueous layer was then cooled to 0° C. and the pH was adjusted to 8-9 using saturated NaHCO₃ solution. The aqueous layer was extracted with 2% MeOH in dichloromethane (4×200 mL). The combined organic layers was washed with brine (2×200 mL), dried over anhydrous Na₂SO₄ and concentrated to dryness under reduced pressure to afford 4-B (5.5 g) as white solid.

¹H NMR (400 MHz, CD₃OD): δ 7.50-7.48 (m, 1H), 7.46-7.33 (m, 7H), 7.32-7.28 (m, 1H), 5.96 (s, 1H), 4.67 (s, 1H), 4.66 (d, J=8.00 Hz, 1H), 4.44 (s, 1H), 3.71-3.66 (m, 2H), 3.14-3.12 (m, 1H), 3.03 (s, 2H), 3.01-2.98 (m, 2H), 2.28 (s, 3H), 2.03-1.99 (m, 1H), 1.92 (s, 3H), 1.79-1.76 (m, 3H). Molecular Formula: C₂₅H₃₀N₄O₂; LC-MS purity: 99.48%; Expected: 418.4; Observed: 419.2 (M+1).

Example 4-E

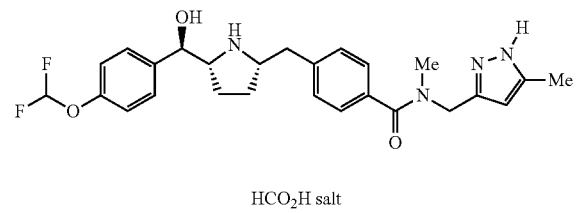

HCO₂H salt

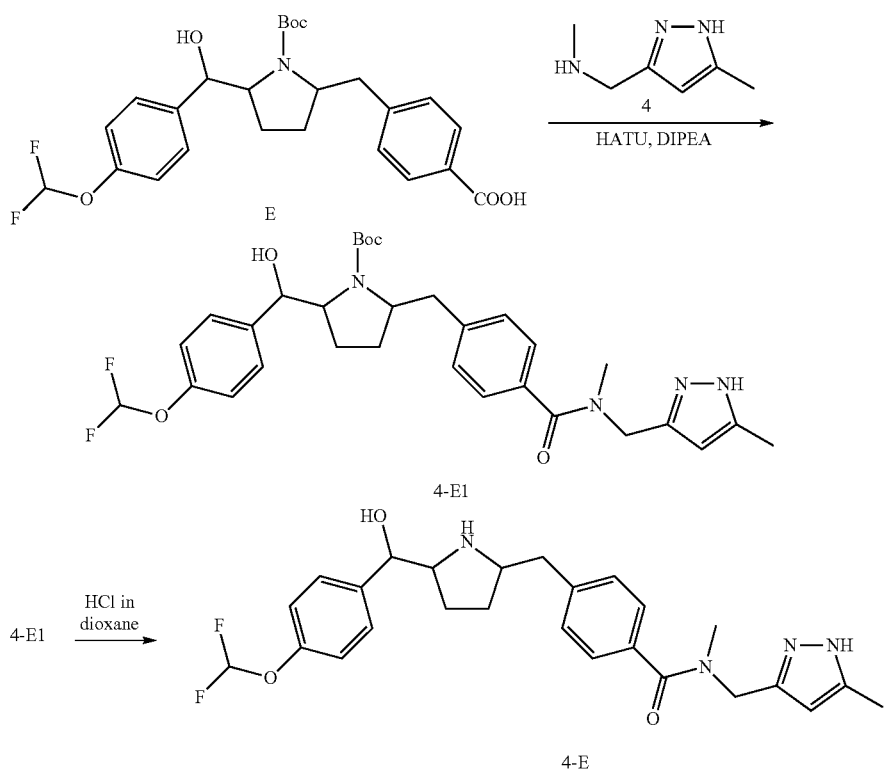

Step A Tert-butyl 2-((4-(difluoromethoxy)phenyl)(hydroxy)methyl)-5-(4-(methyl((5-methyl-1H-pyrazol-3-yl)methyl)carbamoyl)benzyl)pyrrolidine-1-carboxylate (4-E1)

To a stirred solution of E (50 mg, 0.104 mmol) in DMF (2 mL), DIPEA (0.09 mL, 0.523 mmol) and HATU (60 mg, 0.157 mmol) were added at room temperature and the reaction mixture was stirred for 15 min. Amine 4 (34 mg, 0.261 mmol) was added to the reaction mixture and was further stirred overnight at room temperature. The reaction mixture was diluted with ethyl acetate, washed successively with water and brine. The organic layer was dried over anhydrous Na₂SO₄ and concentrated under reduced pressure to obtain the desired product 4-E1 as brown solid.

Molecular Formula: $C_{31}H_{38}F_2N_4O_5$; LCMS purity: 71.56%; Expected: 584.65; Observed: 584.8 (M+1).

Step B 4-(((2S,5R)-5-((R)-(4-(difluoromethoxy)phenyl)(hydroxy)methyl)pyrrolidin-2-yl)methyl)-N-methyl-N-((5-methyl-1H-pyrazol-3-yl)methyl)benzamide, formic acid salt (4-E)

To a solution of 4-E1 (90 mg, 0.154 mmol) in $CH_3OH$ (2 mL), was added HCl in dioxane (2 mL) at 0° C. and the reaction mixture was slowly raised to room temperature and stirred for 2 h. The reaction mixture was concentrated under reduced pressure and co-evaporated with toluene. The crude product was purified by preparative HPLC to yield 4-E as white solid.

$^1$H NMR (400 MHz, $CD_3OD$): δ 8.51 (s, 1H), 7.49-7.38 (m, 6H), 7.17 (d, J=8.52 Hz, 2H), 6.83 (t, J=73.88 Hz, 1H), 6.08 (s, 0.5H), 5.97 (s, 0.5H), 4.73-4.67 (m, 2H), 4.43 (s, 1H), 3.76-3.72 (m, 2H), 3.19-3.13 (m, 1H), 3.06-3.01 (m, 2H), 2.93 (s, 3H), 2.29 (s, 3H), 2.11-2.09 (m, 1H), 1.82-1.80 (m, 3H). Molecular Formula: $C_{26}H_{30}F_2N_4O_3$; LCMS purity: 97%; Expected: 484.5; Observed: 485.4 (M+1).

Example 4-F

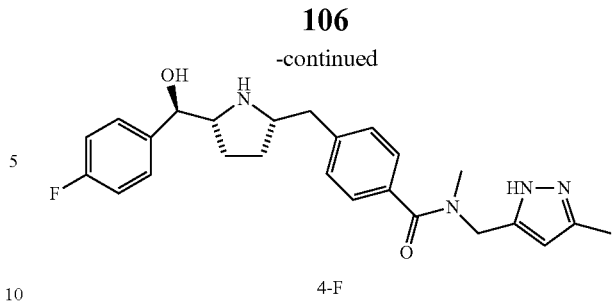

4-F

HCO$_2$H salt

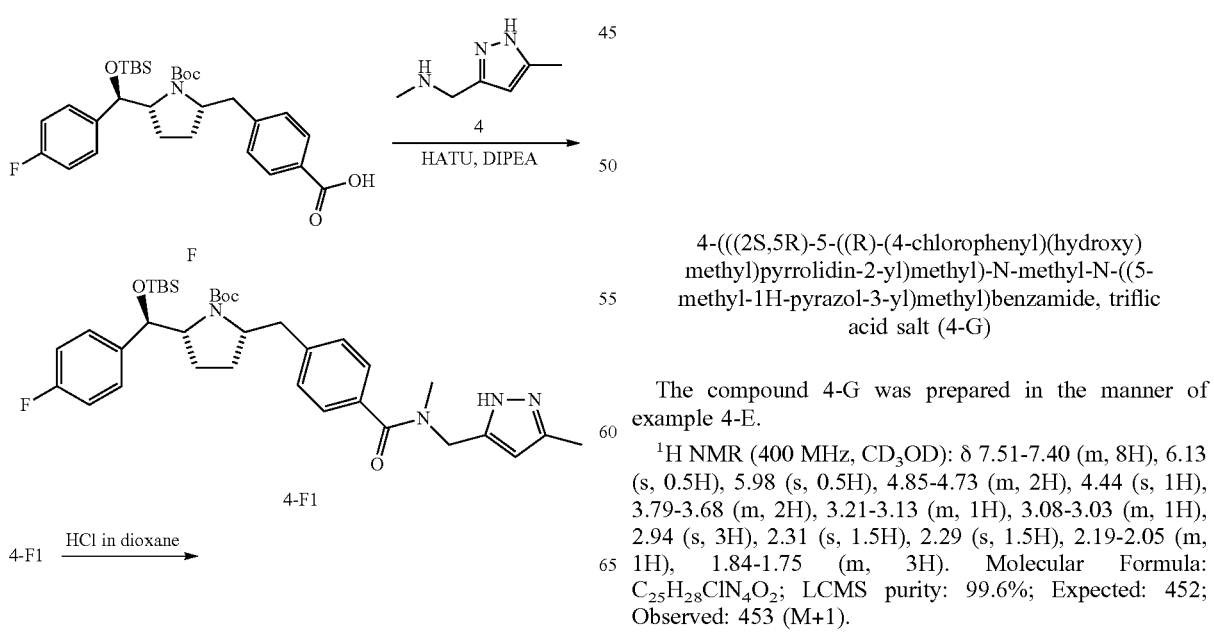

Step A 4-(((2S,5R)-5-((R)-(4-fluorophenyl)(hydroxy)methyl)pyrrolidin-2-yl)methyl)-N-methyl-N-((5-methyl-1H-pyrazol-3-yl)methyl)benzamide, formic acid salt (4-F)

Compound 4-F was prepared in an analogous manner to that as in the example 4-E.

$^1$H NMR (400 MHz, $CD_3OD$): δ 8.50 (s, 1H), 7.51-7.45 (m, 3H), 7.40-7.38 (m, 2H), 7.13 (t, J=8.64 Hz, 2H), 6.08-5.97 (m, 1H), 4.73 (d, J=8.52 Hz, 1H), 4.67 (s, 1H), 4.43 (s, 1H), 3.78-3.74 (m, 2H), 3.20-3.17 (m, 1H), 3.07-3.03 (m, 2H), 2.93 (s, 2H), 2.28 (s, 3H), 2.09-2.05 (m 1H), 1.37-1.29 (m, 3H). Molecular Formula: $C_{25}H_{29}FN_4O_2$; LCMS purity: 97.5%; Expected: 436; Observed: 437 (M+1).

Example 4-G

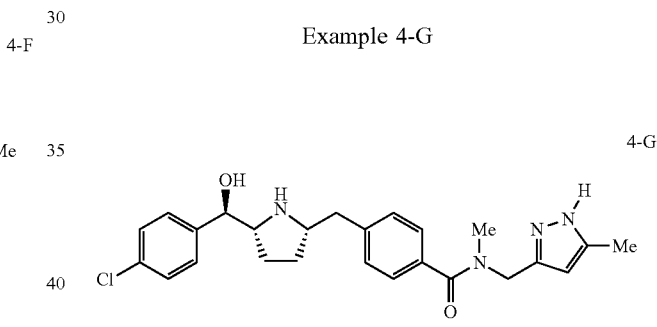

4-G

TFA salt 4-(((2S,5R)-5-((R)-(4-chlorophenyl)(hydroxy)methyl)pyrrolidin-2-yl)methyl)-N-methyl-N-((5-methyl-1H-pyrazol-3-yl)methyl)benzamide, triflic acid salt (4-G)

The compound 4-G was prepared in the manner of example 4-E.

$^1$H NMR (400 MHz, $CD_3OD$): δ 7.51-7.40 (m, 8H), 6.13 (s, 0.5H), 5.98 (s, 0.5H), 4.85-4.73 (m, 2H), 4.44 (s, 1H), 3.79-3.68 (m, 2H), 3.21-3.13 (m, 1H), 3.08-3.03 (m, 1H), 2.94 (s, 3H), 2.31 (s, 1.5H), 2.29 (s, 1.5H), 2.19-2.05 (m, 1H), 1.84-1.75 (m, 3H). Molecular Formula: $C_{25}H_{28}ClN_4O_2$; LCMS purity: 99.6%; Expected: 452; Observed: 453 (M+1).

Example 4-Q

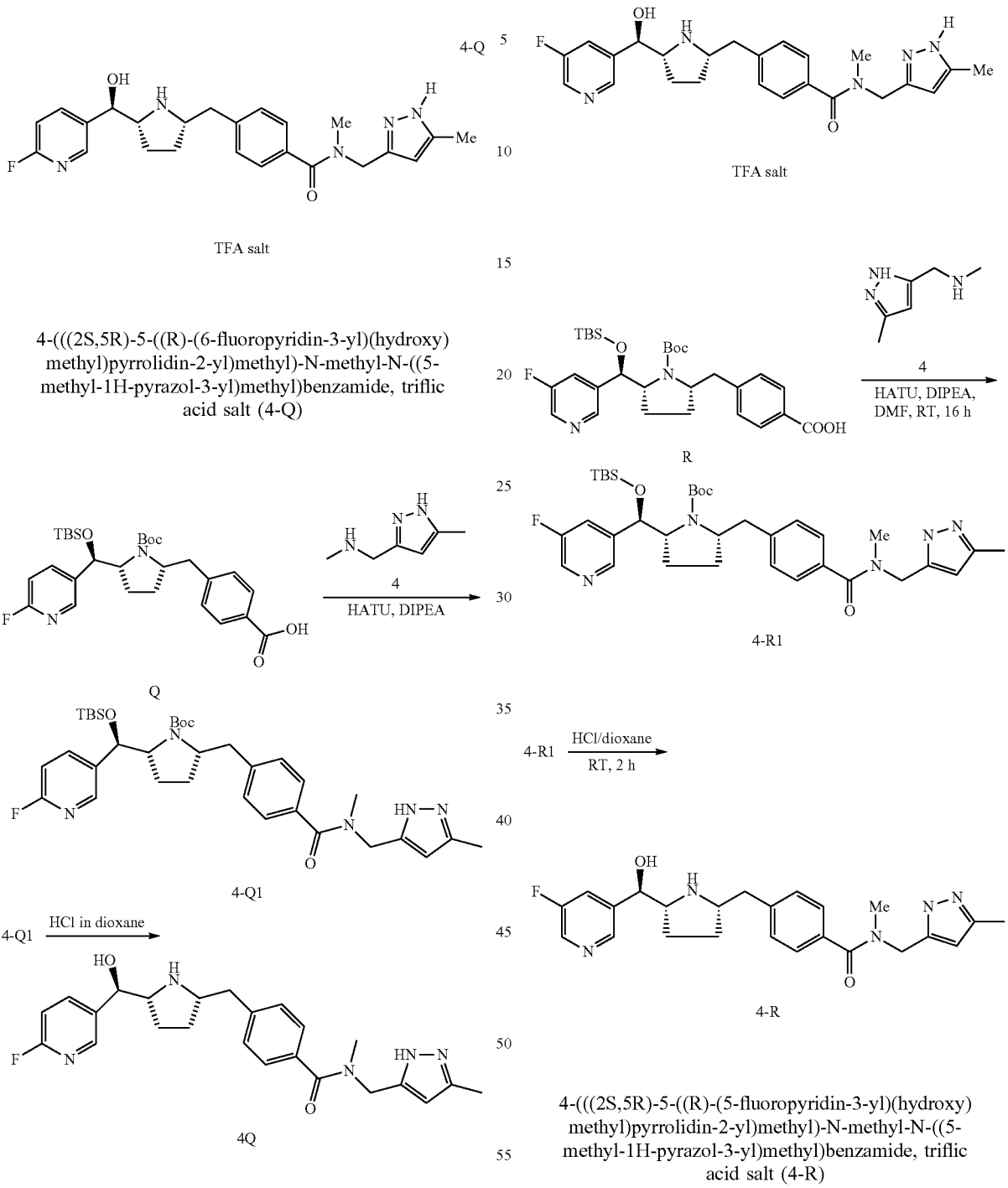

4-(((2S,5R)-5-((R)-(6-fluoropyridin-3-yl)(hydroxy)methyl)pyrrolidin-2-yl)methyl)-N-methyl-N-((5-methyl-1H-pyrazol-3-yl)methyl)benzamide, triflic acid salt (4-Q)

The compound 4-Q was prepared in the manner of example 4-E.

$^1$H NMR (400 MHz, DMSO-d$_6$): δ 8.29 (s, 1H), 8.06 (t, J=8.52 Hz, 1H), 7.56-7.49 (m, 2H), 7.40 (d, J=3.24 Hz, 2H), 7.13 (dd, J=8.44 and 2.28 Hz, 1H), 6.10-5.97 (m, 1H), 4.86 (d, J=6.48 Hz, 1H), 4.68 (s, 1H), 4.43 (s, 1H), 3.98-3.82 (m, 2H), 3.20-3.15 (m, 2H), 3.07-2.93 (m, 3H), 2.27 (d, J=4.82 Hz, 3H), 2.16-2.08 (m, 1H), 1.89-1.82 (m, 3H). Molecular Formula: C$_{24}$H$_{28}$FN$_5$O$_2$; LC-MS purity: 99.1%; Expected: 437; Observed: 438 (M+1).

4-(((2S,5R)-5-((R)-(5-fluoropyridin-3-yl)(hydroxy)methyl)pyrrolidin-2-yl)methyl)-N-methyl-N-((5-methyl-1H-pyrazol-3-yl)methyl)benzamide, triflic acid salt (4-R)

The compound 4-R was prepared in the manner of example 4-E.

$^1$H NMR (400 MHz, CD$_3$OD): δ 8.51-8.46 (m, 3H), 7.78 (d, J=8.88 Hz, 1H), 7.51-7.39 (m, 4H), 6.09 (s, 0.5H), 5.97 (s, 0.5H), 4.94 (s, 1H), 4.68 (s, 1H), 3.85-3.81 (m, 2H), 3.32-3.31 (m, 2H), 3.24-3.20 (m, 1H), 3.09 (s, 1.5H), 2.97 (s, 1.5H), 2.29 (s, 3H), 2.12-2.07 (m, 1H), 1.90-1.81 (m, 3H). Molecular Formula: C$_{25}$H$_{28}$ClN$_4$O$_2$; LCMS purity: 98.5%; Expected: 436.5; Observed: 437.3 (M+1).

Example 5-A

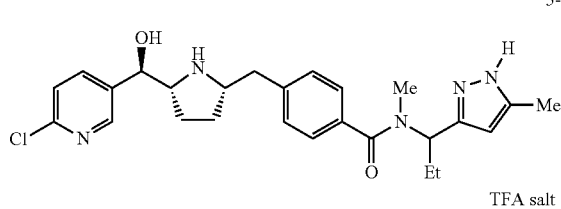

Step A (2R,5S)-tert-butyl 2-((R)-((tert-butyldimethylsilyl)oxy)(6-chloropyridin-3-yl)methyl)-5-(4-(methyl(1-(3-methyl-1H-pyrazol-5-yl)propyl)carbamoyl)benzyl)pyrrolidine-1-carboxylate (5-A1)

Compound A (200 mg, 0.357 mmol) was dissolved in dichloromethane (10 mL) and crude amine 5 (80.7 mg, 0.428 mmol) and T$_3$P (170 mg, 0.535 mmol; T$_3$P is 50% solution, hence added 340 mg) were added. The reaction mixture was cooled to 0° C. and Et$_3$N (0.25 mL, 1.78 mmol) was added. The reaction mixture was allowed to warm to room temperature and stirred overnight. After the completion, the reaction was quenched with 10% NaHCO$_3$ solution and was extracted with dichloromethane. The organic layer was washed with water and brine, dried over anhydrous Na$_2$SO$_4$ and concentrated under reduced pressure to yield 5-A1 which was taken as such for the next step.

Step B 4-(((2S,5R)-5-((R)-(6-chloropyridin-3-yl)(hydroxy)methyl)pyrrolidin-2-yl)methyl)-N-methyl-N-(1-(5-methyl-1H-pyrazol-3-yl)propyl)benzamide, triflic acid salt (5-A)

To the solution of 5-A1 (300 mg) in dioxane (10 ml) at 0° C. HCl in Dioxane (5 ml) was added and stirred at room

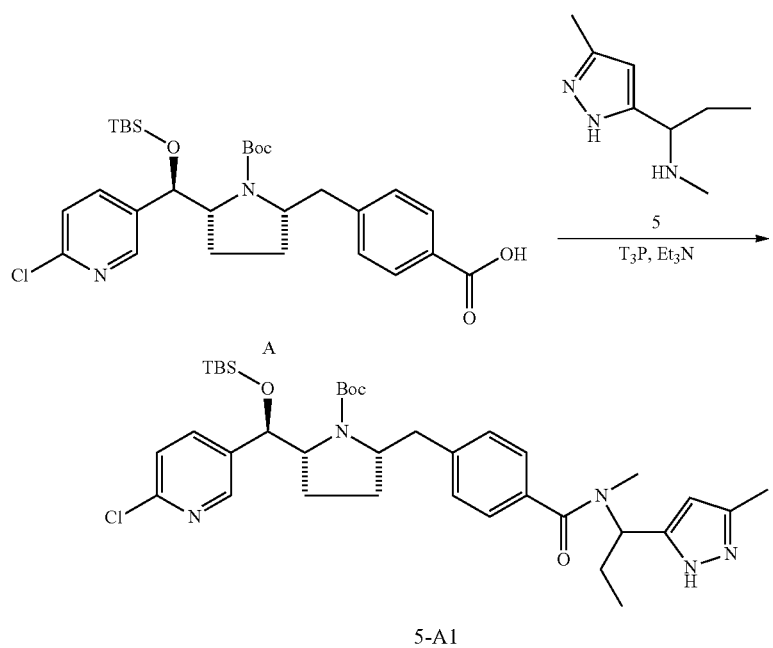

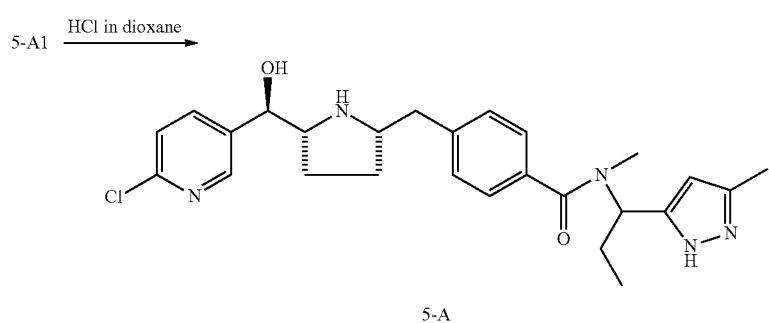

temperature for 3 h. The reaction mixture was concentrated under reduced pressure and the residue was purified by preparative HPLC to yield the product 5-A.

$^1$H NMR (400 MHz, CD$_3$OD): δ 8.46-8.47 (m, 1H), 7.94-7.91 (m, 1H), 7.52-7.39 (m, 5H), 6.19-6.06 (m, 1H), 4.86 (d, J=8.4 Hz, 1H), 4.80-4.71 (m, 1H), 3.84-3.80 (m, 2H), 3.20-3.18 (m, 1H), 3.09-3.06 (m, 1H), 2.89-2.73 (m, 3H), 2.32-2.31 (m, 3H), 2.13-2.11 (m, 3H), 1.92-1.85 (m, 3H), 1.08-0.83 (m, 3H). Molecular Formula: C$_{26}$H$_{32}$ClN$_5$O$_2$; LCMS purity: 99%; Expected: 481.2; Observed: 482 (M+1).

Example 5-H

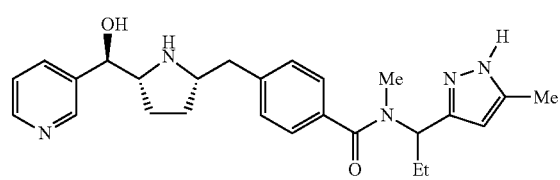

TFA salt

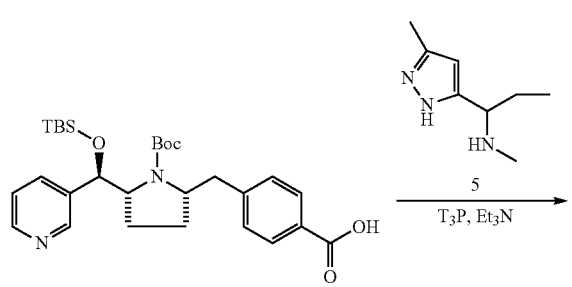

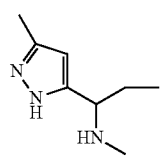

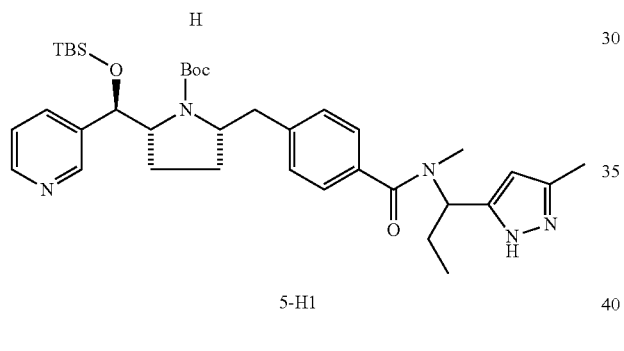

5-H1 $\xrightarrow{\text{HCl in dioxane}}$

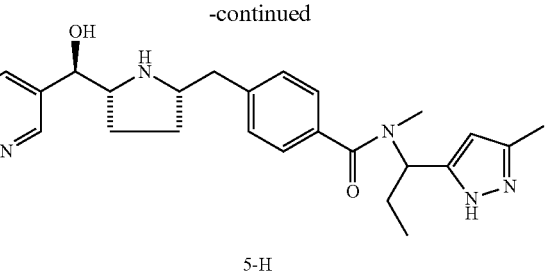

4-(((2S,5R)-5-((R)-hydroxy(pyridin-3-yl)methyl)pyrrolidin-2-yl)methyl)-N-methyl-N-(1-(5-methyl-1H-pyrazol-3-yl)propyl)benzamide, triflic acid salt (5-H)

Compound 5-H was prepared in an analogous manner described in the synthesis of Example 5-A $^1$H NMR (400 MHz, CD$_3$OD): δ 8.73 (s, 1H), 8.63-8.62 (m, 1H), 8.12 (d, J=7.6 Hz, 1H), 7.63 (t, J=7.6 Hz, 1H), 7.52-7.40 (m, 4H), 6.11-6.05 (m, 1H), 4.77-4.73 (m, 1H), 3.89-3.82 (m, 2H), 3.24-3.19 (m, 1H), 3.15-3.05 (m, 1H), 2.90-2.72 (m, 3H), 2.31 (s, 3H), 2.14-2.01 (m, 1H), 1.99-1.87 (m, 5H), 1.08-0.84 (m, 3H). Molecular Formula: C$_{26}$H$_{33}$N$_5$O$_2$; LCMS purity: 95.3%; Expected: 447.3; Observed: 448.2 (M+1).

Example 6-A

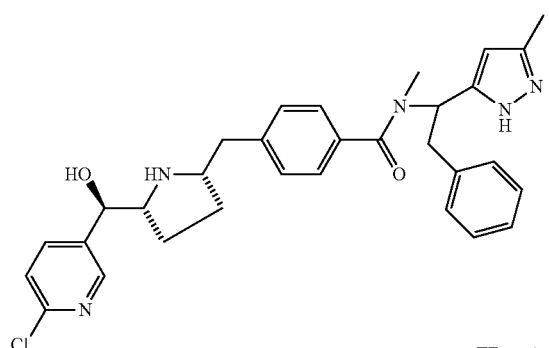

TFA salt

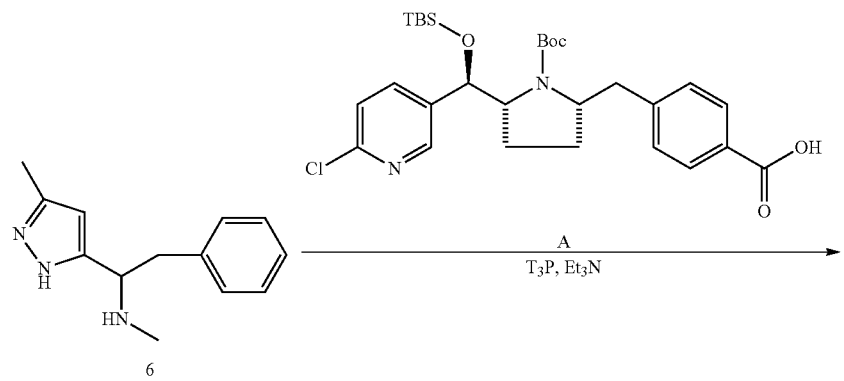

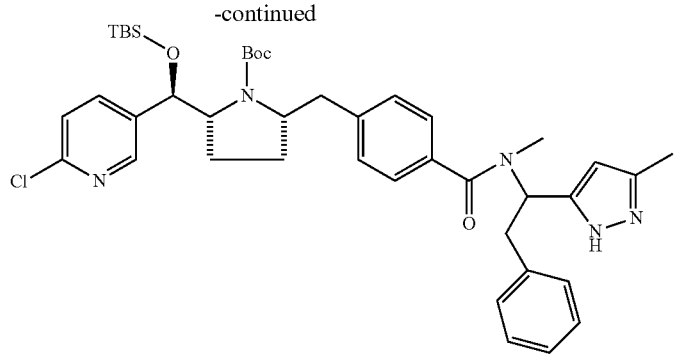

6-A1

6-A1 →[HCl in dioxane]

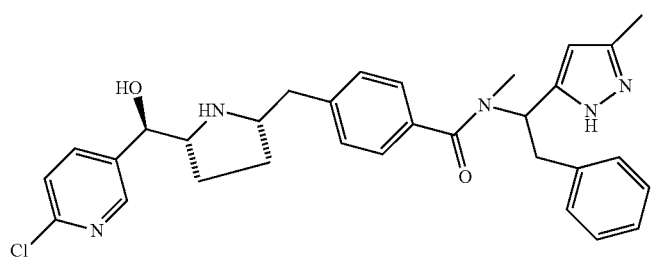

6-A 4-(((2S,5R)-5-((R)-(6-chloropyridin-3-yl)(hydroxy)methyl)pyrrolidin-2-yl)methyl)-N-methyl-N-(1-(5-methyl-1H-pyrazol-3-yl)-2-phenylethyl)benzamide, triflic acid salt (6-A)

Compound 6-A was prepared in an analogous manner as described for the synthesis of Example 5-A.

$^1$H NMR (400 MHz, DMSO-d$_6$): δ 9.50-9.30 (m, 1H), 8.54-8.49 (m, 2H), 7.91 (d, J=8.20 Hz, 1H), 7.59-7.57 (m, 1H), 7.35-7.22 (m, 4H), 7.15-7.12 (m, 1H), 7.02-6.96 (m, 2H), 6.77-6.76 (m, 1H), 6.51 (bs, 1H), 6.08-6.02 (m, 1H), 4.88-4.82 (m, 2H), 3.85-3.64 (m, 2H), 3.22-3.07 (m, 3H), 2.93-2.88 (m, 1H), 2.80 (s, 2H), 2.60-2.58 (m, 1H), 2.22-2.21 (m, 3H), 1.90-1.86 (m, 1H), 1.73-1.64 (m, 3H). Molecular Formula: C$_{31}$H$_{34}$ClN$_5$O$_2$; LCMS purity: 98.9%; Expected: 543.2; Observed: 544 (M+1).

Example 6-H

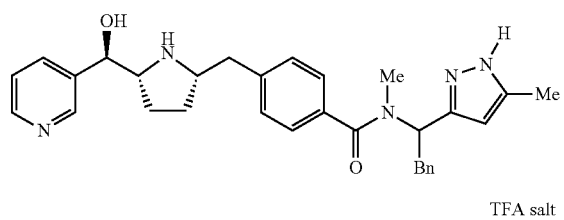

6-H

TFA salt

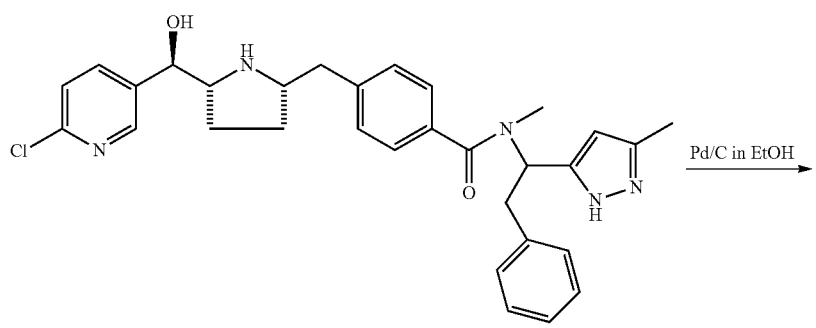

6-A →[Pd/C in EtOH]

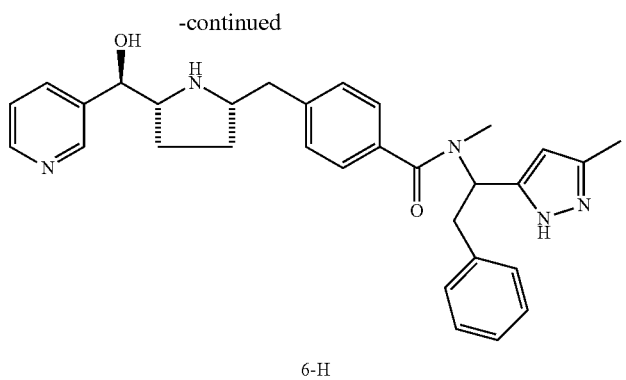

6-H

4-(((2S,5R)-5-((R)-hydroxy(pyridin-3-yl)methyl)pyrrolidin-2-yl)methyl)-N-methyl-N-(1-(5-methyl-1H-pyrazol-3-yl)-2-phenylethyl)benzamide, triflic acid salt (6-H)

Compound 6-H was prepared from 6-A in the manner as in example 9-H.

$^1$H NMR (400 MHz, CD$_3$OD): δ 8.82 (s, 1H), 8.71 (s, 1H), 8.31 (d, J=7.80 Hz, 1H), 7.84-7.80 (m, 1H), 7.41-7.39 (m, 1H), 7.36-7.24 (m, 4H), 7.22-7.19 (m, 1H), 7.04-7.01 (m, 2H), 6.82 (d, J=7.40 Hz, 1H), 6.27-6.16 (m, 1H), 5.09-4.95 (m, 3H), 3.95-3.71 (m, 2H), 3.61-3.39 (m, 2H), 3.29-3.10 (m, 3H), 3.01 (s, 3H), 2.30 (s, 3H), 2.19-2.02 (m, 1H), 2.00-1.80 (m, 3H). Molecular Formula: C$_{31}$H$_{35}$N$_5$O$_2$; LCMS purity: 98.8%; Expected: 509.3; Observed: 510 (M+1).

4-(((2S,5R)-5-((R)-(6-chloropyridin-3-yl)(hydroxy)methyl)pyrrolidin-2-yl)methyl)-N-((5-isopropyl-1H-pyrazol-3-yl)methyl)-N-methylbenzamide, hydrochloride salt (7-A)

Compound 7-A was prepared in an analogous manner to that described in Example 4-A.

$^1$H NMR (400 MHz, CD$_3$OD): δ 8.48 (d, J=1.60 Hz, 1H), 7.90-7.92 (m, 1H), 7.53-7.43 (m, 5H), 6.6 (bs, 1H), 4.91-4.89 (m, 1H), 4.12-4.09 (m, 2H), 3.85-3.83 (m, 2H), 3.24-3.23 (m, 2H), 3.14-3.10 (m, 5H), 2.12-2.10 (m, 1H), 1.91-1.88 (m, 3H), 1.34 (d, J=8.00 Hz, 6H). Exchangeable protons were not shown. Molecular Formula: C$_{26}$H$_{32}$ClN$_5$O$_2$; LC-MS purity: 96.2%; Expected: 482; Observed: 483.2 (M+1).

Example 7-A

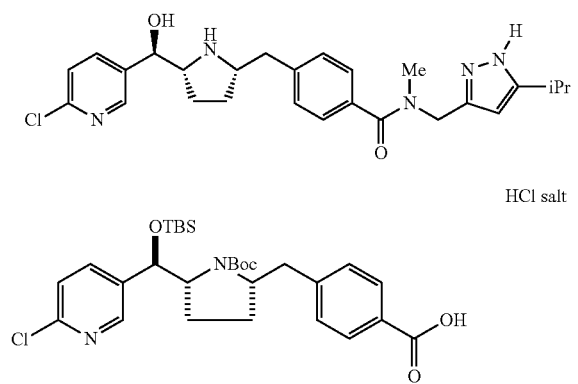

Example 7-B

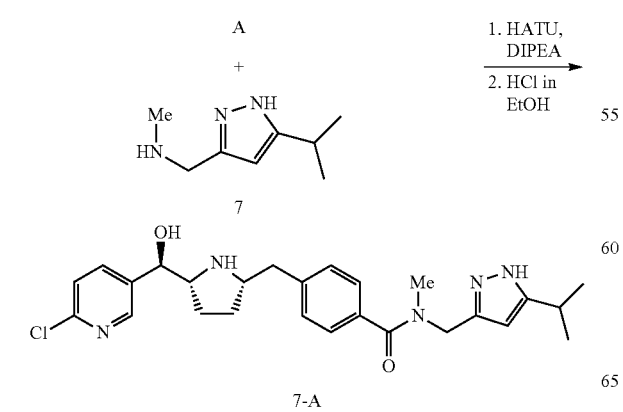

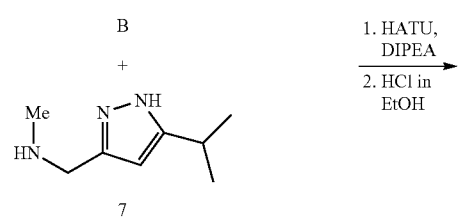

-continued

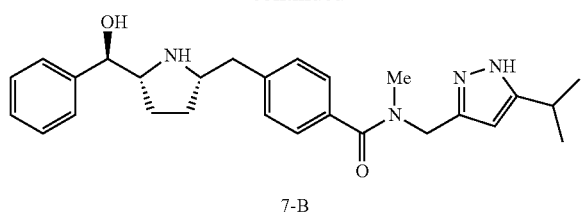

7-B 4-(((2S,5R)-5-((R)-hydroxy(phenyl)methyl)pyrrolidin-2-yl)methyl)-N-((5-isopropyl-1H-pyrazol-3-yl)methyl)-N-methylbenzamide, hydrochloride salt (7-B)

Compound 7-B was prepared in an analogous manner described for the synthesis of Example 4-A.

$^1$H NMR (400 MHz, CD$_3$OD): δ 7.50-7.32 (m, 9H), 6.60 (bs, 1H), 4.80-4.75 (m, 3H), 4.12-4.09 (m, 1H), 3.81-3.79 (m, 2H), 3.27-3.22 (m, 6H), 2.08-2.07 (m, 1H), 1.89-1.80 (m, 3H), 1.35 (d, J=8.00 Hz, 6H). Exchangeable protons were not shown. Molecular Formula: C$_{27}$H$_{34}$N$_4$O$_2$; LC-MS purity: 96.4%; Expected: 446.6; Observed: 447.2 (M+1).

Example 8-A

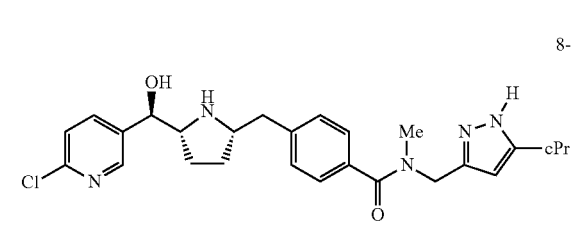

8-A

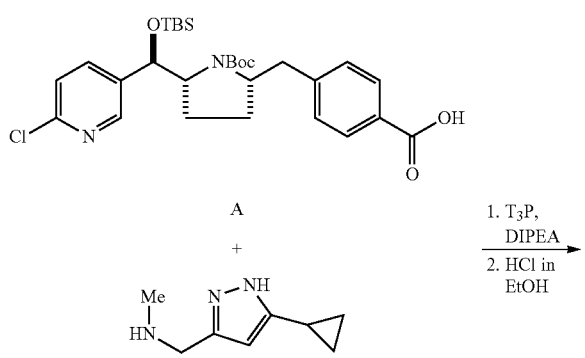

4-(((2S,5R)-5-((R)-(6-chloropyridin-3-yl)(hydroxy)methyl)pyrrolidin-2-yl)methyl)-N-((5-cyclopropyl-1H-pyrazol-3-yl)methyl)-N-methylbenzamide (8-A)

Compound 8-A was prepared in an analogous manner as described in Example 8-B.

$^1$H NMR (400 MHz, CD$_3$OD): δ 8.46 (s, 1H), 8.01 (d, J=8.00, 1H), 7.92 (d, J=8.00, 1H), 7.52-7.39 (m, 4H), 6.03 (s, 1H), 4.85 (d, J=8.00 Hz, 1H), 4.67 (s, 1H), 4.42 (s, 1H), 3.84-3.82 (m, 2H), 3.27-3.20 (m, 2H), 3.11-3.08 (m, 1H), 2.98 (s, 3H), 2.13-2.09 (m, 1H), 1.91-1.84 (m, 3H), 1.01-0.99 (m, 2H), 0.74-0.71 (m, 2H). Exchangeable protons were not shown. Molecular Formula: C$_{26}$H$_{30}$ClN$_5$O$_2$; LC-MS purity: 99.7%; Expected: 480; Observed: 480.2 (M+1).

Example 8-B

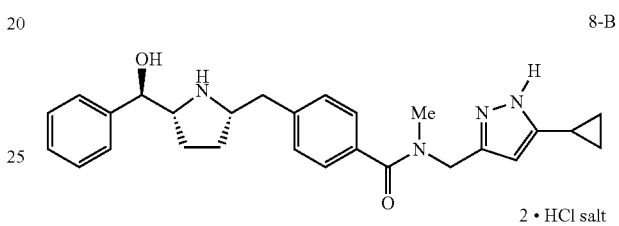

8-B

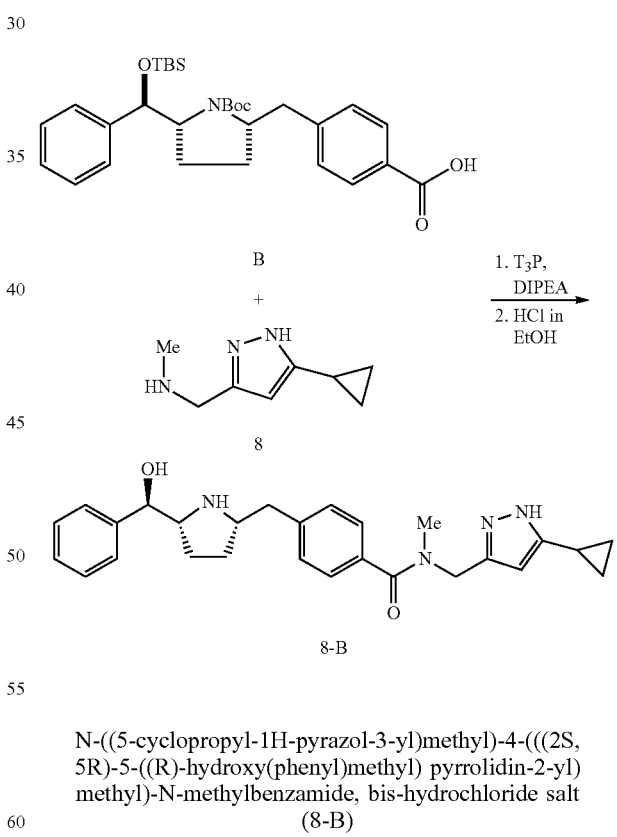

N-((5-cyclopropyl-1H-pyrazol-3-yl)methyl)-4-(((2S,5R)-5-((R)-hydroxy(phenyl)methyl) pyrrolidin-2-yl)methyl)-N-methylbenzamide, bis-hydrochloride salt (8-B)

To a solution of acid B (0.150 g, 0.286 mmol) and 8 (0.051 g, 0.47 mmol) in DMF (3 mL) DIPEA (0.15 mL, 0.857 mol) was added at 0° C. and stirred for 20 min at the same temperature. T$_3$P (0.27 mL, 0.857 mol) was added drop wise at 0° C. and was stirred at room temperature for 14 h. The reaction mass was concentrated to dryness under reduced pressure. The crude mass was dissolved in dichloromethane (25 mL) and washed with water (3×25 mL) followed by brine (25 mL). Organic layer was dried over anhydrous Na$_2$SO$_4$ and concentrated under reduced pressure. The crude mass was purified by flash chromatography using 1:9 petroleum ether in ethyl acetate to afford an intermediate amide (0.06 g). The compound was taken as such to the next step. To a solution of the intermediate amide (0.06 g, 0.091 mmol) in EtOH (5 mL) EtOH.HCl (2 mL) was added at room temperature and stirred for 2 h. The reaction mixture was concentrated to dryness under reduced pressure to afford 8-B (0.025 g) as white solids.

$^1$H NMR (400 MHz, CD$_3$OD): δ 7.47-7.32 (m, 10H), 4.79 (d, J=8.00 Hz, 1H), 3.82 (s, 2H), 3.24-3.22 (m, 3H), 3.12 (s, 3H), 2.07-2.05 (m, 2H), 1.87-1.79 (m, 4H), 1.21-1.19 (m, 2H), 1.95-1.88 (m, 2H). Exchangeable protons were not shown. Molecular Formula: C$_{27}$H$_{32}$N$_4$O$_2$; LC-MS purity: 98.2%; Expected: 444.6; Observed: 445.2 (M+1).

Example 9-A $^1$H NMR (400 MHz, DMSO-d$_6$): δ 8.39 (d, J=4.00 Hz, 1H), 8.21 (s, 1H), 7.83 (d, J=4.00 Hz, 1H), 7.47 (d, J=8.00 Hz, 2H), 7.27 (d, J=8.00 Hz, 2H), 6.15 (s, 1H), 4.46 (d, J=8.00 Hz, 2H), 4.36 (s, 2H), 3.42-3.31 (m, 4H), 3.26 (s, 3H), 2.87 (s, 3H), 2.75-2.70 (m, 1H), 2.70-2.67 (m, 1H), 1.68-1.67 (m, 1H), 1.44-4.42 (m, 2H), 1.25-1.23 (m, 1H). Molecular Formula: C$_{25}$H$_{30}$ClN$_5$O$_3$; LC-MS purity: 99.5%; Expected: 483.2; Observed: 484.2 (M+1).

Example 9-B

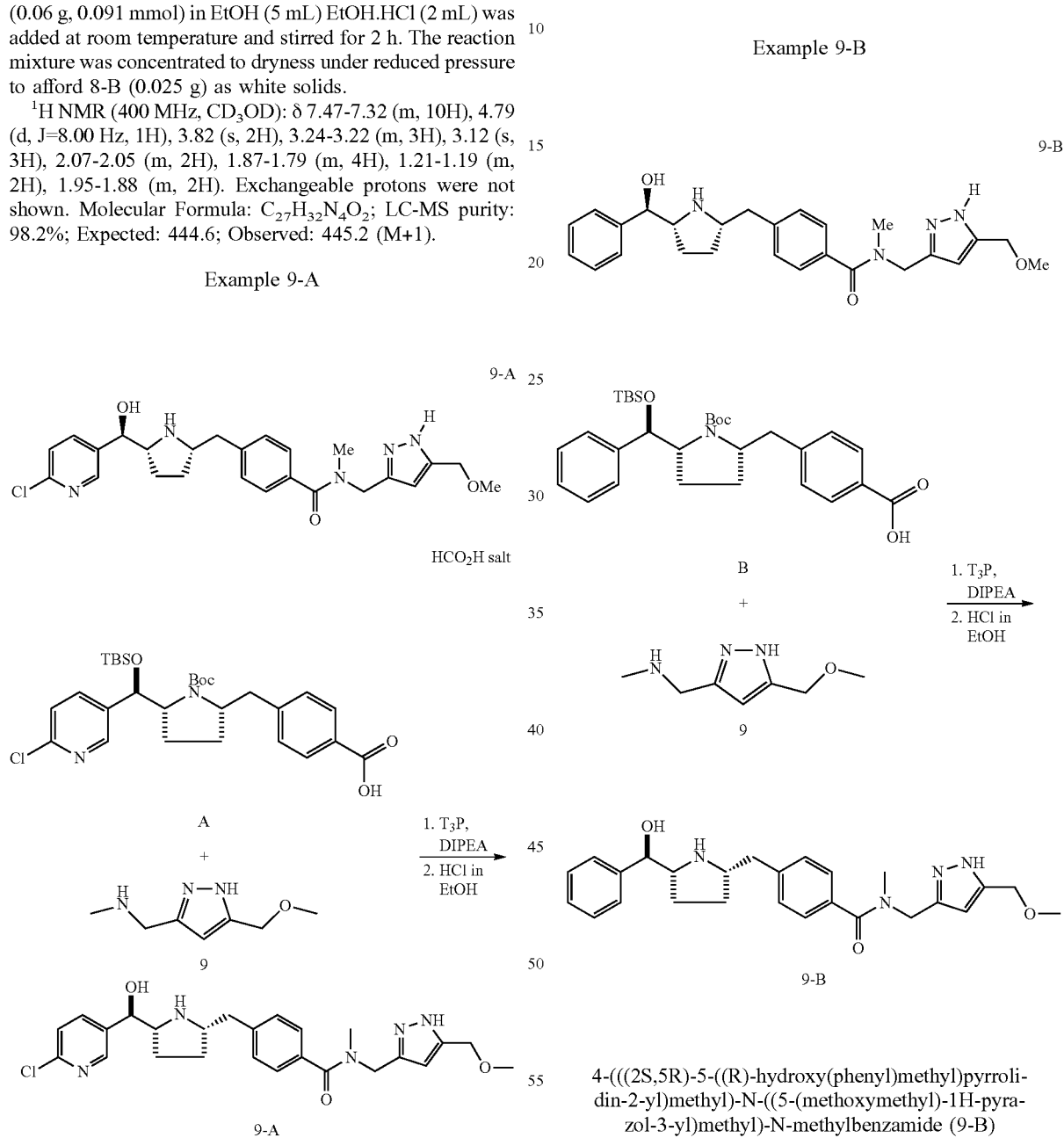

4-(((2S,5R)-5-((R)-hydroxy(phenyl)methyl)pyrrolidin-2-yl)methyl)-N-((5-(methoxymethyl)-1H-pyrazol-3-yl)methyl)-N-methylbenzamide (9-B)

4-(((2S,5R)-5-((R)-(6-chloropyridin-3-yl)(hydroxy)methyl)pyrrolidin-2-yl)methyl)-N-((5-(methoxymethyl)-1H-pyrazol-3-yl)methyl)-N-methylbenzamide, formic acid salt (9-A)

Compound 9-A was prepared in an analogous manner to that describe for the synthesis of compound of Example 8-B.

The compound 9-B was prepared in the manner as in example 8-B.

$^1$H NMR (400 MHz, DMSO-d$_6$): δ 7.35-7.12 (m, 10H), 6.15 (s, 1H), 4.37 (s, 2H), 4.30 (d, J=8.00 Hz, 2H), 3.33 (s, 3H), 3.17 (s, 2H), 2.77-2.75 (m, 1H), 2.87 (s, 3H), 2.73-2.48 (m, 2H), 1.68-1.63 (m, 2H), 1.44-1.33 (m, 2H). Molecular Formula: C$_{26}$H$_{32}$N$_4$O$_3$; LC-MS purity: 97.8%; Expected: 448.3; Observed: 449.2 (M+1).

Example 9-E

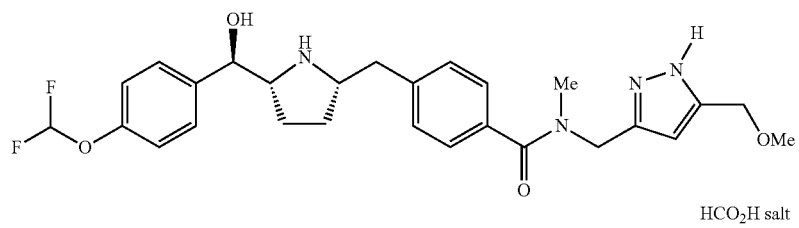 [SMILES: COCc1cc(CN(C)C(=O)c2ccc(C[C@@H]3CC[C@H]([C@H](O)c4ccc(OC(F)F)cc4)N3)cc2)n[nH]1]

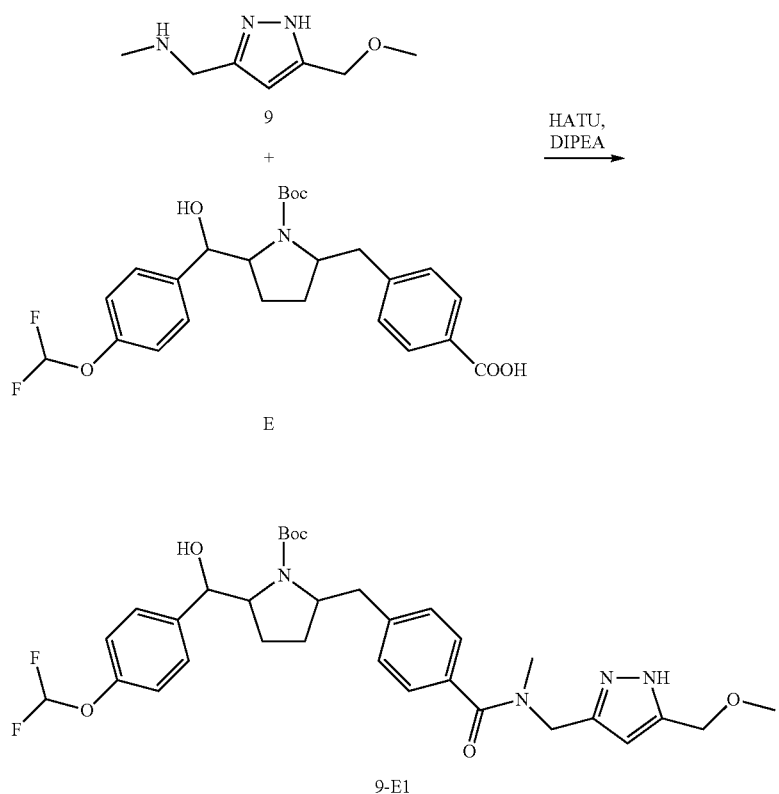

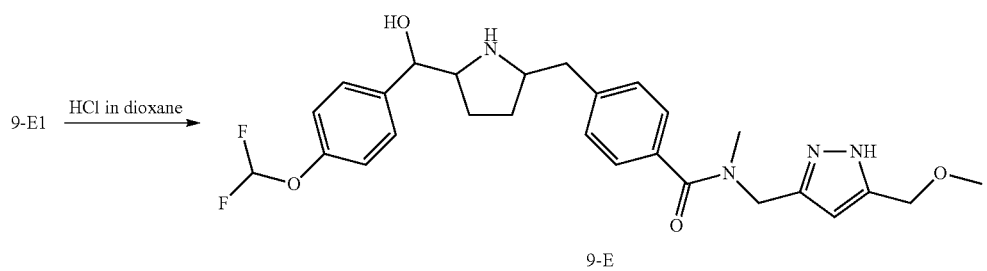

4-(((2S,5R)-5-((R)-(4-(difluoromethoxy)phenyl)(hydroxy)methyl)pyrrolidin-2-yl)methyl)-N-((5-(methoxymethyl)-1H-pyrazol-3-yl)methyl)-N-methylbenzamide, formic acid salt (9-E)

Compound 9-E was prepared in an analogous manner as described in Example 4-E.

$^1$H NMR (400 MHz, CD$_3$OD): δ 7.48-7.42 (m, 4H), 7.40 (d, J=8.00 Hz, 2H), 7.18 (d, J=8.52 Hz, 2H), 6.83 (t, J=73.88 Hz, 1H), 6.19 (bs, 1H), 4.74 (d, J=8.92 Hz, 2H), 4.49-4.47 (m, 3H), 3.83-3.80 (m, 2H), 3.32-3.80 (m, 2H), 3.18 (s, 3H), 3.10-2.98 (m, 6H), 2.11-2.09 (m, 1H), 1.84-1.82 (m, 3H). Molecular Formula: C$_{27}$H$_{32}$F$_2$N$_4$O$_4$; LC-MS purity: 96.3%; Expected: 514.6; Observed: 515.2 (M+1).

Example 9-G

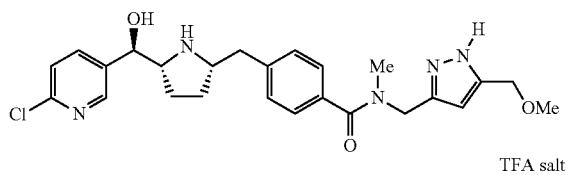

4-(((2S,5R)-5-((R)-(4-chlorophenyl)(hydroxy)
methyl)pyrrolidin-2-yl)methyl)-N-((5-(methoxym-
ethyl)-1H-pyrazol-3-yl)methyl)-N-methylbenz-
amide, triflic acid salt (9-G)

Compound 9-G was prepared in an analogous manner to that described in Example 4-E.
$^1$H NMR (400 MHz, CD$_3$OD): δ 7.48-7.39 (m, 9H), 6.32 (s, 0.5H), 6.19 (s, 0.5H), 4.74 (d, J=8.24 Hz, 2H), 4.46 (d, J=8.68 Hz, 2H), 4.85-4.73 (m, 2H), 3.81-3.75 (m, 2H), 3.49 (s, 3H), 3.22-3.17 (m, 1H), 3.14 (s, 3H), 3.08-3.03 (m, 1H), 2.11-2.07 (m, 1H), 1.85-1.80 (m, 3H). Molecular Formula: C$_{26}$H$_{30}$ClN$_4$O$_3$; LC-MS purity: 98.1%; Expected: 482; Observed: 483.3 (M+1).

Example 9-H 4-(((2S,5R)-5-((R)-hydroxy(pyridin-3-yl)methyl)
pyrrolidin-2-yl)methyl)-N-((5-(methoxymethyl)-1H-
pyrazol-3-yl)methyl)-N-methylbenzamide (9-H)

To a solution of 9-A (0.20 g, 0.22 mmol) in EtOH (5 mL) Pd/C (0.01 g) was added and the reaction mixture was stirred under H$_2$ (1 atm) for 12 h. The reaction mixture was filtered through a celite bed and the filtrate was concentrated under reduced pressure. The residue was purified by flash chromatography using 1:9 methanol-dichloromethane to afford 9-H as white solids.

$^1$H NMR (400 MHz, CD$_3$OD): δ 8.64 (s, 1H), 8.54 (d, J=4.00 Hz, 1H), 7.95 (d, J=8.00 Hz, 1H), 7.56-7.51 (m, 3H), 7.40 (d, J=8.00 Hz, 2H), 6.30 (s, 1H), 4.73 (s, 1H), 4.47 (s, 2H), 3.84-3.82 (m, 2H), 3.37 (s, 3H), 3.26-3.21 (m, 1H), 3.09-3.03 (m, 1H), 2.95 (s, 3H), 2.12-2.10 (m, 1H), 1.88-1.86 (m, 3H). Exchange-able protons were not shown. Molecular Formula: C$_{25}$H$_{31}$N$_5$O$_3$; LC-MS purity: 95.4%; Expected 449.6; Observed: 450.2 (M+1).

Example 10-A

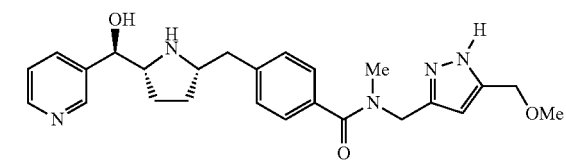

9-H

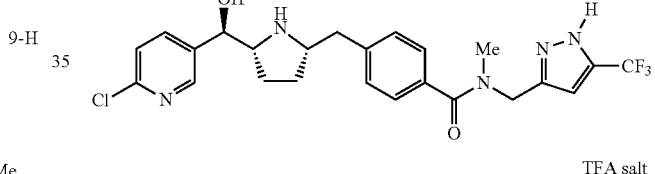

10-A

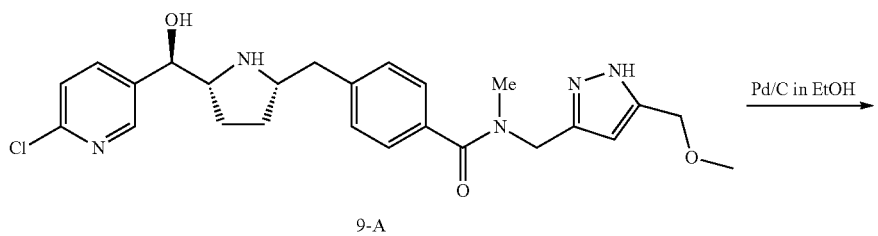

9-A

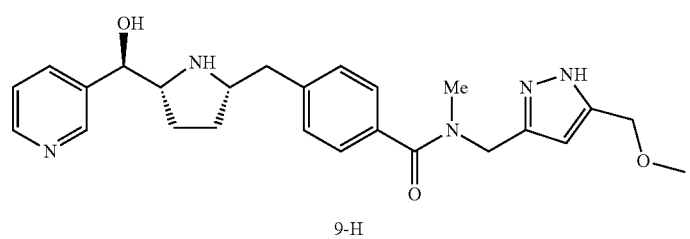

9-H

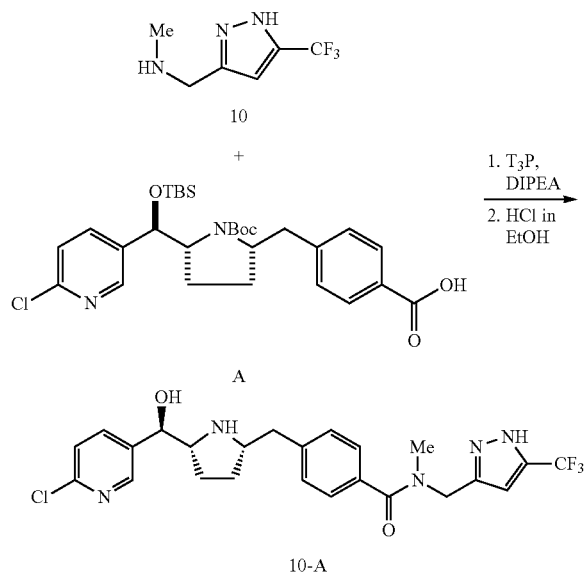

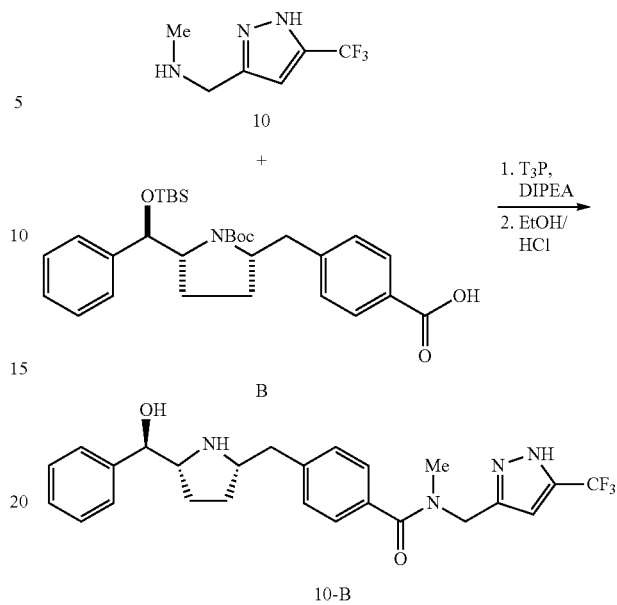

4-(((2S,5R)-5-((R)-(6-chloropyridin-3-yl)(hydroxy)methyl)pyrrolidin-2-yl)methyl)-N-methyl-N-((5-(trifluoromethyl)-1H-pyrazol-3-yl)methyl)benzamide, triflic acid salt (10-A)

Compound 10-A was prepared in an analogous manner top that shown in Example 8-B.

$^1$H NMR (400 MHz, CD$_3$OD): δ 8.47 (d, J=2.40 Hz, 1H), 7.93 (dd, J=2.40 and 8.00 Hz, 1H), 7.52-7.47 (m, 3H), 7.42-7.40 (m, 2H), 6.66 (s, 1H), 4.85 (d, J=8.00 Hz, 1H), 4.80 (s, 2H), 3.84-3.80 (m, 2H), 3.23-3.20 (m, 1H), 3.09-3.01 (m, 4H), 2.12-2.10 (m, 1H), 1.92-1.84 (m, 3H). Exchangeable protons were not shown. Molecular Formula: C$_{24}$H$_{25}$ClF$_3$N$_5$O$_2$; LC-MS purity: 98.8%; Expected 507.9; Observed: 509 (M+1).

Example 10-B

Preparation of 4-(((2S,5R)-5-((R)-hydroxy(phenyl)methyl)pyrrolidin-2-yl)methyl)-N-methyl-N-((5-(trifluoromethyl)-1H-pyrazol-3-yl)methyl)benzamide (10-B)

Compound 10-B was prepared in an analogous manner to the synthesis scheme described in Example 8-B.

$^1$H NMR (400 MHz, CD$_3$OD): δ 7.45-7.25 (m, 9H), 6.65 (s, 1H), 4.80 (s, 2H), 4.47 (d, J=8.00 Hz, 2H), 3.42-3.40 (m, 1H), 3.02 (s, 3H), 2.93-2.88 (m, 2H), 1.83-1.81 (m, 1H), 1.57-1.52 (m, 3H). Exchangeable protons were not shown. Molecular Formula: C$_{25}$H$_{27}$F$_3$N$_4$O$_2$; LC-MS purity: 96%; Expected 472.5; Observed: 473.2 (M+1).

Example 10-H

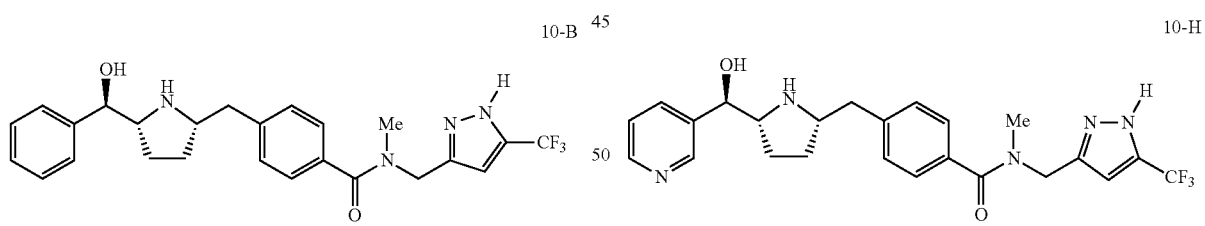

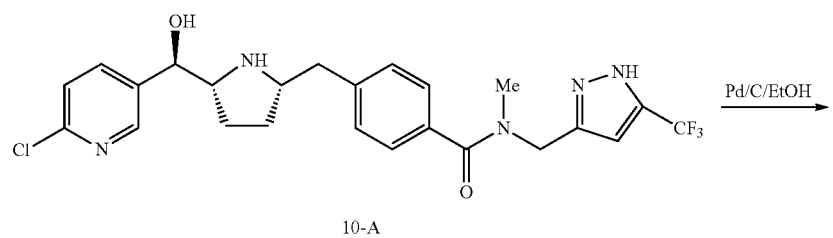

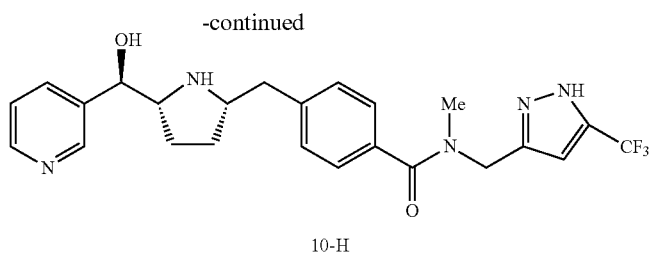

10-H 4-(((2S,5R)-5-((R)-hydroxy(pyridin-3-yl)methyl)pyrrolidin-2-yl)methyl)-N-methyl-N-((5-(trifluoromethyl)-1H-pyrazol-3-yl)methyl)benzamide (10-H)

Compound 10-H was prepared from 10-A utilizing an analogous synthesis route as described in Example 9-H.

$^1$H NMR (400 MHz, CD$_3$OD): δ 8.64 (s, 1H), 8.54 (dd, J=1.60 and 4.80 Hz, 1H), 7.51-7.49 (m, 3H), 7.43-7.41 (m, 2H), 6.67 (s, 1H), 4.82 (d, J=8.00 Hz, 1H), 3.80-3.77 (m, 2H), 3.21-3.18 (m, 2H), 3.07-3.03 (m, 4H), 2.08-2.05 (m, 1H), 1.84-1.83 (m, 3H), 1.30-1.28 (m, 2H). Exchangeable protons were not shown. Molecular Formula: C$_{24}$H$_{26}$F$_3$N$_5$O$_2$; LC-MS purity: 96.74%; Expected 473.5; Observed: 474.2 (M+1).

Example 11-A

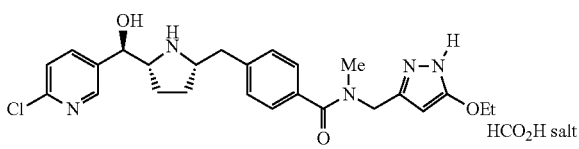

11-A

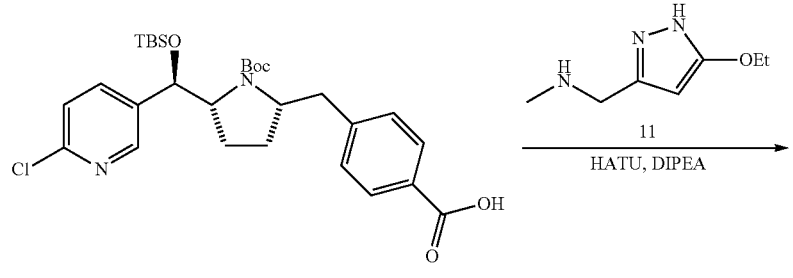

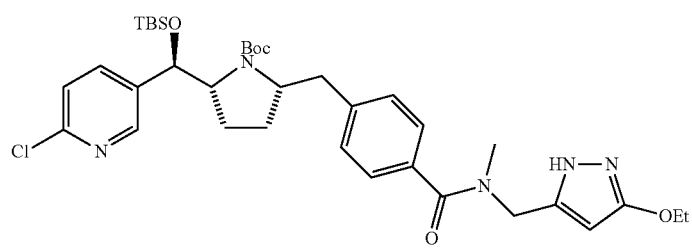

11-A1

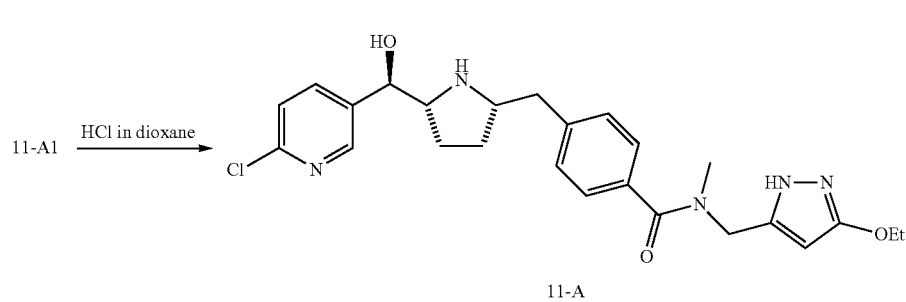

11-A

4-(((2S,5R)-5-((R)-(6-chloropyridin-3-yl)(hydroxy)methyl)pyrrolidin-2-yl)methyl)-N-((5-ethoxy-1H-pyrazol-3-yl)methyl)-N-methylbenzamide, formic acid salt (11-A)

Compound 11-A was prepared utilizing an analogous synthesis route to that described in Example 4-E.

$^1$H NMR (400 MHz, CD$_3$OD): δ 8.47-8.39 (m, 2H), 7.97-7.87 (m, 1H), 7.55-7.51 (m, 1H), 7.51-7.47 (m, 2H), 4.83 (d, J=8.12 Hz, 2H), 4.66 (s, 1H), 4.44 (s, 1H), 4.13 (q, J=6.90 Hz, 2H), 3.97-3.72 (m, 2H), 3.38-3.18 (m, 1H), 3.12-2.95 (m, 4H), 2.20-2.08 (m, 1H), 1.89-1.85 (m, 3H), 1.36 (t, J=7.04 Hz, 3H).; Molecular Formula: C$_{25}$H$_{30}$ClN$_5$O$_3$; LC-MS purity: 98.8%; Expected: 483.4; Observed: 484.2 (M+1).

Example 11-B

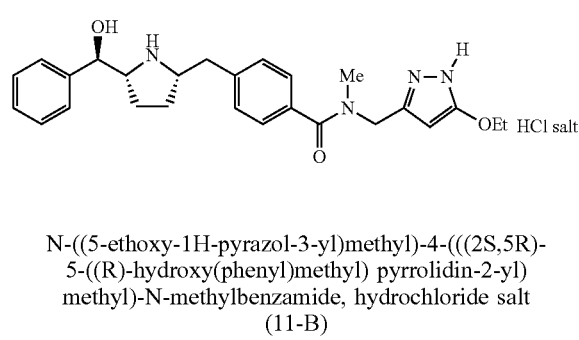

N-((5-ethoxy-1H-pyrazol-3-yl)methyl)-4-(((2S,5R)-5-((R)-hydroxy(phenyl)methyl) pyrrolidin-2-yl)methyl)-N-methylbenzamide, hydrochloride salt (11-B)

Compound 11-B was prepared utilizing an analogous synthesis route to that described in Example 4-E.

$^1$H NMR (400 MHz, CD$_3$OD): δ 7.50-7.35 (m, 9H), 6.06 (s, 1H), 4.73 (d, J=8.72 Hz, 1H), 4.50 (s, 1H), 4.26-4.19 (m, 3H), 3.82-3.80 (m, 3H), 3.23-3.22 (m, 2H), 3.15-3.10 (m, 1H), 3.06 (s, 3H), 2.10-2.04 (m, 2H), 1.87-1.80 (m, 3H), 1.42-1.41 (m, 3H). Molecular Formula: C$_{26}$H$_{32}$N$_4$O$_3$; LC-MS purity: 95.8%; Expected: 448.5; Observed: 449.4 (M+1).

Example 12-A

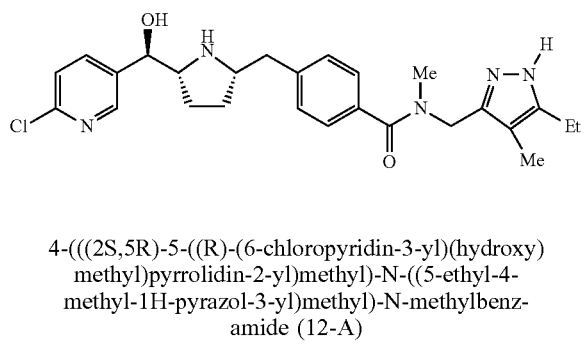

4-(((2S,5R)-5-((R)-(6-chloropyridin-3-yl)(hydroxy)methyl)pyrrolidin-2-yl)methyl)-N-((5-ethyl-4-methyl-1H-pyrazol-3-yl)methyl)-N-methylbenzamide (12-A)

Compound 12-A was prepared utilizing an analogous synthesis route to that described in Example 12-B.

$^1$H NMR (400 MHz, CD$_3$OD): δ 8.44 (d, J=2.20 Hz, 1H), 7.92 (dd, J=8.28 and 2.2 Hz, 1H), 7.60-7.52 (m, 2H), 7.49-7.30 (m, 3H), 4.89-4.70 (m, 2H), 3.80-3.62 (m, 2H), 3.60 (d, J=10.70 Hz, 1H), 3.21-3.12 (m, 1H), 3.10-2.97 (m, 2H), 2.90-2.85 (m, 2H), 2.70-2.56 (m, 2H), 2.04 (s, 3H), 1.89-1.72 (m, 3H), 1.42-1.30 (m, 1H), 1.27-1.11 (m, 3H). Molecular Formula: C$_{26}$H$_{32}$ClN$_5$O$_2$; LC-MS purity: 96.2%; Expected: 481.1; Observed: 482 (M+1).

Example 12-B

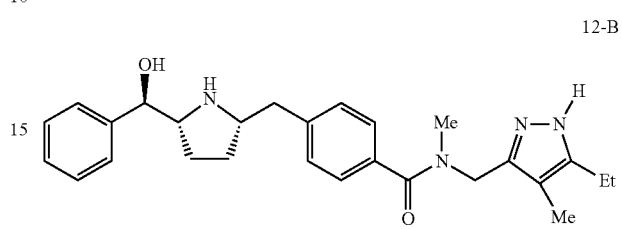

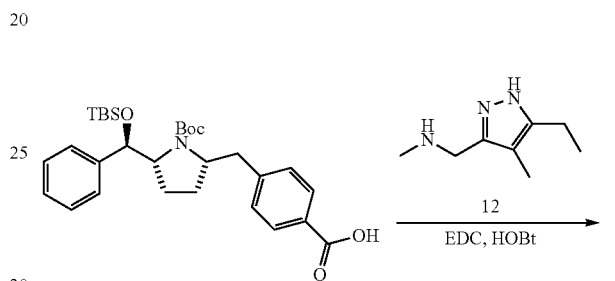

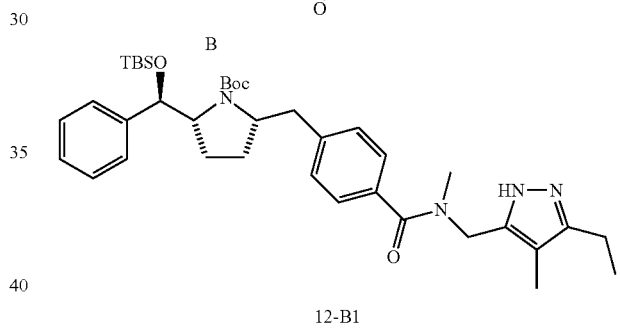

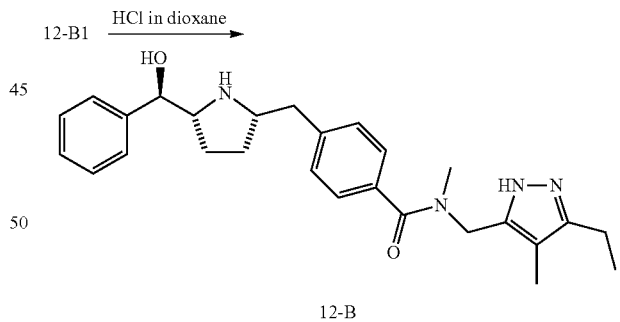

Step 1 (2R,5S)-tert-butyl 2-((R)-((tert-butyldimethylsilyl)oxy)(phenyl)methyl)-5-(4-(((3-ethyl-4-methyl-1H-pyrazol-5-yl)methyl)(methyl)carbamoyl)benzyl) pyrrolidine-1-carboxylate (12-B1)

To a solution of Acid B (150 mg, 0.28 mmol) in DMF (5 mL) was added EDC.HCl (136 mg, 0.71 mmol) followed by the addition of HOBt (22 mg, 0.14 mmol) and triethyl amine (0.1 mL, 0.71 mmol). To this solution amine 12 (52 mg, 0.34 mmol) in DMF (1 mL) was added at 0° C. and the reaction mixture was stirred at room temperature for 3 h. The reaction mixture was diluted with dichloromethane and washed consecutively with water, saturated sodium bicarbonate solution and brine. The organic layer was dried over anhydrous $Na_2SO_4$ and concentrated under reduced pressure. The crude mass was purified by column chromatography using 25% ethyl acetate in petroleum ether (v/v) to provide 12-B1 (70 mg). Molecular Formula: $C_{38}H_{56}N_4O_4Si$; LC-MS purity: 89.8%; Expected: 661; Observed: 661 (M).

Step B N-((5-ethyl-4-methyl-1H-pyrazol-3-yl)methyl)-4-(((2S,5R)-5-((R)-hydroxy (phenyl)methyl)pyrrolidin-2-yl)methyl)-N-methylbenzamide (12-B)

Compound 12-B was prepared utilizing an analogous synthesis route to that described for making 2-B from 2-B2.

$^1$H NMR (400 MHz, $CD_3OD$): δ 7.66-7.30 (m, 9H), 4.80-4.71 (m, 2H), 3.91-3.75 (m, 2H), 3.27-3.21 (m, 1H), 3.19-3.05 (m, 1H), 3.00-2.80 (m, 3H), 2.70-2.55 (m, 2H), 2.10-1.99 (m, 3H), 1.90-1.71 (m, 4H), 1.30-1.12 (m, 3H). Molecular Formula: $C_{27}H_{34}N_4O_2$; LC-MS purity: 99.2%; Expected: 446; Observed: 447.2 (M+1).

Example 13-A 4-(((2S,5R)-5-((R)-(6-chloropyridin-3-yl)(hydroxy)methyl)pyrrolidin-2-yl)methyl)-N-methyl-N-((1,4,5,6-tetrahydrocyclopenta[c]pyrazol-3-yl)methyl)benzamide, triflic acid salt (13-A)

Compound 13-A was prepared utilizing an analogous synthesis route to that described for making 8-B.

$^1$H NMR (400 MHz, $CD_3OD$): δ 8.47 (s, 1H), 7.93-7.91 (m, 1H), 7.53-7.40 (m, 4H), 7.23-7.11 (m, 1H), 7.19-7.16 (m, 1H), 4.86-4.84 (m, 1H), 4.73-4.66 (m, 2H), 3.82-3.73 (m, 2H), 3.07-2.99 (m, 4H), 2.76-2.73 (m, 3H), 2.66-2.63 (m, 3H), 2.13-2.11 (m, 1H), 1.92-1.87 (m, 3H), 1.32-1.29 (m, 1H). Exchangeable protons were not shown. Molecular Formula: $C_{26}H_{30}ClN_5O_2$; LC-MS purity: 95.6%; Expected: 480; Observed: 481 (M+1).

Example 13-B

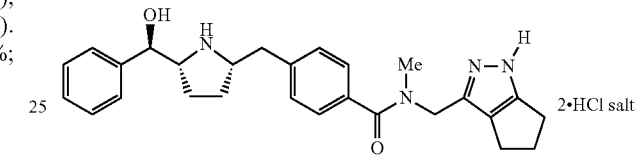

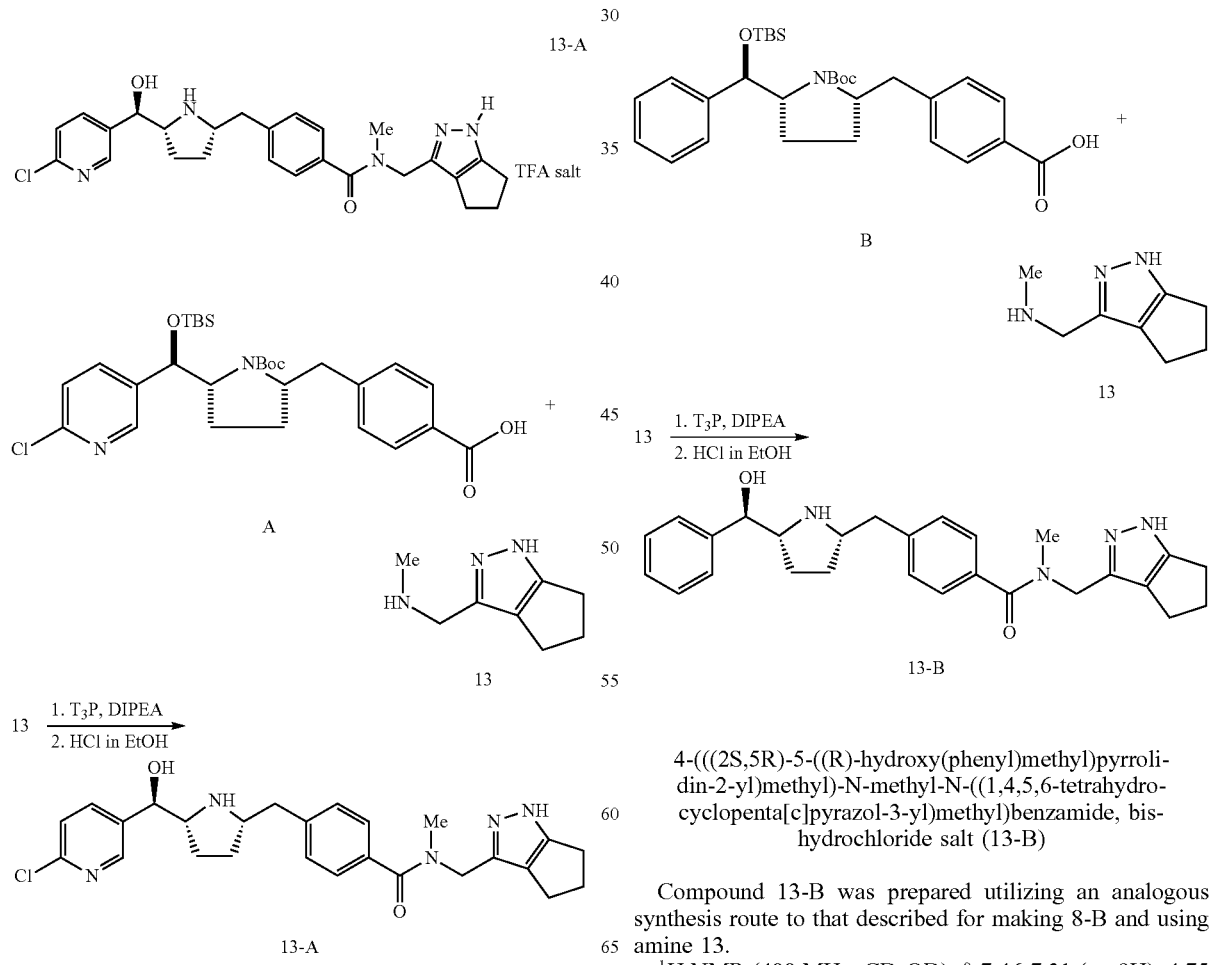

4-(((2S,5R)-5-((R)-hydroxy(phenyl)methyl)pyrrolidin-2-yl)methyl)-N-methyl-N-((1,4,5,6-tetrahydrocyclopenta[c]pyrazol-3-yl)methyl)benzamide, bis-hydrochloride salt (13-B)

Compound 13-B was prepared utilizing an analogous synthesis route to that described for making 8-B and using amine 13.

$^1$H NMR (400 MHz, $CD_3OD$): δ 7.46-7.31 (m, 9H), 4.75 (d, J=8.00 Hz, 1H), 3.82-3.78 (m, 3H), 3.20-3.11 (m, 6H), 2.69-2.54 (m, 6H), 2.09-2.07 (m, 1H), 1.84-1.82 (m, 3H). Exchangeable protons were not shown. Molecular Formula: C₂₇H₃₂N₄O₂; LC-MS purity: 97.9%; Expected: 444.6; Observed: 445.2 (M+1).

Example 14-A

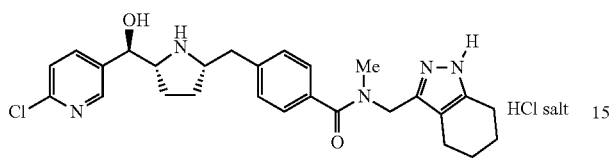

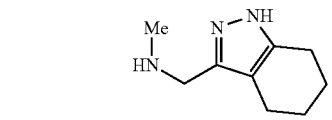

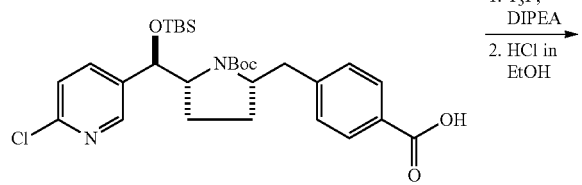

4-(((2S,5R)-5-((R)-(6-chloropyridin-3-yl)(hydroxy)methyl)pyrrolidin-2-yl)methyl)-N-methyl-N-((4,5,6,7-tetrahydro-1H-indazol-3-yl)methyl)benzamide, hydrochloride salt, 14-A Compound 14-A was prepared utilizing an analogous synthesis route to that described for making 8-B.

¹H NMR (400 MHz, CD₃OD): δ 8.48 (s, 1H), 7.96-7.94 (m, 1H), 7.51-7.46 (m, 5H), 4.85 (d, J=8.00 Hz, 1H), 3.89-3.85 (m, 2H), 0.00 (s, 3H), 2.80-2.65 (m, 4H), 2.11-2.09 (m, 2H), 1.91-1.87 (m, 8H), 1.48-1.42 (m, 2H). Molecular Formula: C₂₇H₃₂ClN₅O₂; LC-MS purity: 97.5%; Expected: 494; Observed: 495.4 (M+1).

Example 14-H

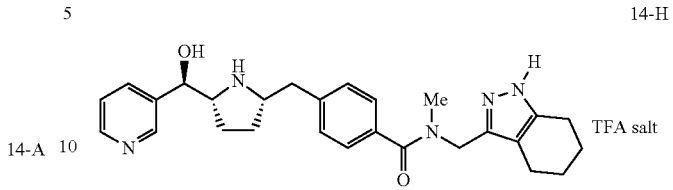

4-(((2S,5R)-5-((R)-hydroxy(pyridin-3-yl)methyl)pyrrolidin-2-yl)methyl)-N-methyl-N-((4,5,6,7-tetrahydro-1H-indazol-3-yl)methyl)benzamide, triflic acid salt (14-H)

Compound 14-H was prepared from 14-A in an analogous synthesis route to that described in Example 9-H.

¹H NMR (400 MHz, CD₃OD): δ 8.71 (s, 1H), 8.61 (d, J=4.00 Hz, 1H), 8.09 (d, J=8.00 Hz, 1H), 7.62-7.59 (m, 1H), 7.53-7.51 (m, 1H), 7.47-7.41 (m, 3H), 4.73-4.49 (m, 1H), 3.89-3.86 (m, 2H), 3.25-3.21 (m, 1H), 3.15-3.09 (m, 1H), 2.99-0.00 (m, 3H), 2.67-2.65 (m, 1H), 2.54-2.52 (m, 1H), 2.29-2.27 (m, 1H), 2.14-2.12 (m, 1H), 1.91-1.85 (m, 6H), 1.34-1.30 (m, 4H). Exchangeable protons were not shown. Molecular Formula: C₂₇H₃₃N₅O₂; LC-MS purity: 90.1%; Expected: 459.6; Observed: 460.4 (M+1).

Example 15-A

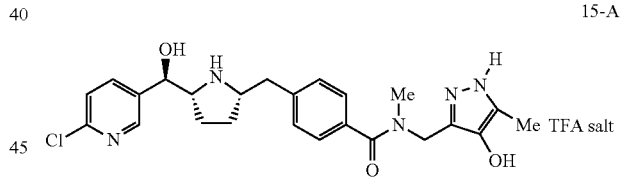

4-(((2S,5R)-5-((R)-(6-chloropyridin-3-yl)(hydroxy)methyl)pyrrolidin-2-yl)methyl)-N-((4-hydroxy-5-methyl-1H-pyrazol-3-yl)methyl)-N-methylbenzamide, triflic acid salt (15-A)

Compound 15-A was prepared utilizing an analogous synthesis route to that described in Example 4-E.

¹H NMR (400 MHz, CD₃OD): δ 8.47 (d, J=2.08 Hz, 1H), 7.94 (dd, J=8.20 and 2.16 Hz, 1H), 7.60-7.49 (m, 3H), 7.41 (d, J=7.56 Hz, 1H), 4.89 (d, J=8.20 Hz, 1H), 4.64-4.45 (m, 2H), 3.87-3.81 (m, 2H), 3.25-3.15 (m, 1H), 3.1-3.02 (m, 1H), 3.01 (s, 3H), 2.24 (s, 3H), 2.15-2.0 (m, 1H), 1.92-1.83 (m, 3H). Molecular Formula: C₂₄H₂₈ClN₅O₃; LC-MS purity: 97.5%; Expected: 469.2; Observed: 470.2 (M+1).

Example 15-B

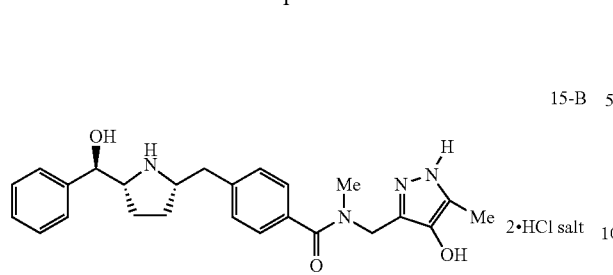

4-(((2S, 5R)-5-((R)-hydroxy(phenyl)methyl)pyrrolidin-2-yl)methyl)-N-((4-hydroxy-5-methyl-1H-pyrazol-3-yl)methyl)-N-methylbenzamide, bis-hydrochloride salt (15-B)

Compound 15-B was prepared utilizing an analogous synthesis route to that described in Example 4-E.

1H NMR (400 MHz, CD$_3$OD): δ 7.58-7.32 (m, 9H), 4.82-4.72 (m, 2H), 3.92-3.76 (m, 2H), 3.28-3.20 (m, 2H), 3.18-3.02 (m, 5H), 2.36 (s, 3H), 2.18-2.02 (m, 1H), 1.97-1.78 (m, 3H). Molecular Formula: C$_{25}$H$_{30}$N$_4$O$_3$; LC-MS purity: 97.1%; Expected: 434.2; Observed: 435.2 (M+1).

Example 16-A

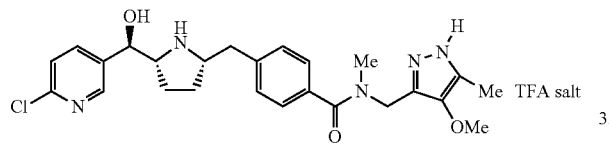

4-(((2S,5R)-5-((R)-(6-chloropyridin-3-yl)(hydroxy)methyl)pyrrolidin-2-yl)methyl)-N-((4-methoxy-5-methyl-1H-pyrazol-3-yl)methyl)-N-methylbenzamide, triflic acid salt (16-A)

Compound 16-A was prepared utilizing an analogous synthesis route to that described in Example 4-E.

$^1$H NMR (400 MHz, CD$_3$OD): δ 8.45 (d, J=2.32 Hz, 1H), 7.93 (dd, J=7.9 and 2.3 Hz, 1H), 7.62-7.55 (m, 1H), 7.53-7.46 (m, 1H), 7.45-7.4 (m, 1H), 7.39-7.30 (m, 2H), 4.86 (d, J=8.16 Hz, 1H), 4.74 (s, 1H), 4.44 (s, 1H), 3.90-3.8 (m, 2H), 3.33 (s, 1.5H), 3.3 (s, 1.5H), 3.25-3.15 (m, 1H), 3.1-3.0 (m, 1H), 2.99 (s, 1.5H), 2.92 (s, 1.5H), 2.25-2.2 (m, 3H), 2.18-2.07 (m, 1H), 1.92-1.80 (m, 3H). Molecular Formula: C$_{25}$H$_{30}$ClN$_5$O$_3$; LC-MS purity: 99.4%; Expected: 483.2; Observed: 484.2 (M+1).

Example 16-B

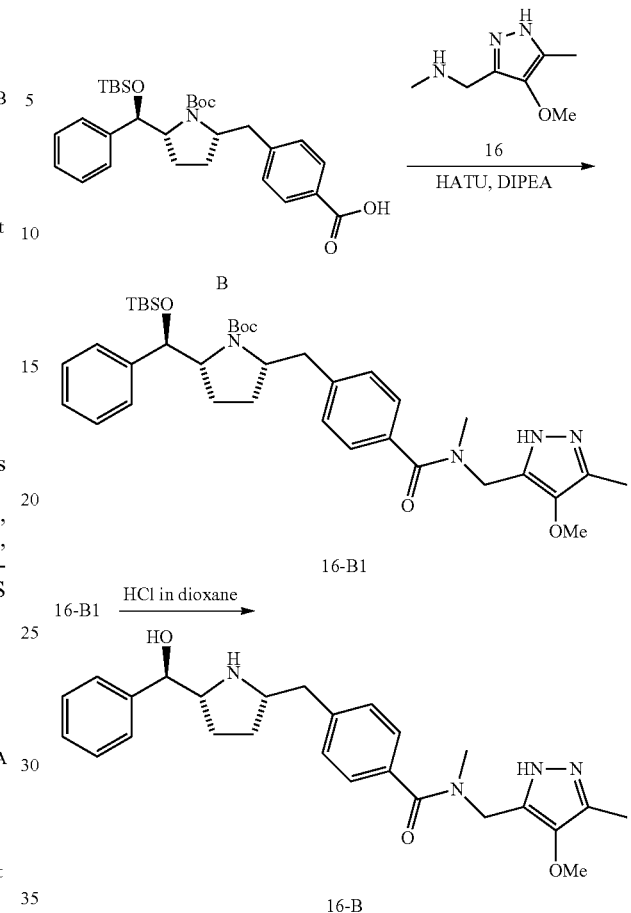

4-(((2S,5R)-5-((R)-hydroxy(phenyl)methyl)pyrrolidin-2-yl)methyl)-N-((4-methoxy-5-methyl-1H-pyrazol-3-yl)methyl)-N-methylbenzamide (16-B)

The compound 16-B was prepared was prepared utilizing an analogous synthesis route to that described in Example 4-E.

$^1$H NMR (400 MHz, CD$_3$OD): δ 7.67-7.55 (m, 1H), 7.52-7.29 (m, 8H), 4.81-4.7 (m, 2H), 4.46 (s, 1H), 3.9-3.72 (m, 3H), 3.65 (s, 1H), 3.38-3.20 (m, 1H), 3.15-3.05 (m, 1H), 3.02-2.85 (m, 3H), 2.24 (s, 3H), 2.17-1.97 (m, 1H), 1.92-1.72 (m, 3H). Molecular Formula: C$_{26}$H$_{32}$N$_4$O$_3$; LC-MS purity: 96.1%; Expected: 448.2; Observed: 449.2 (M+1).

Example 17-A

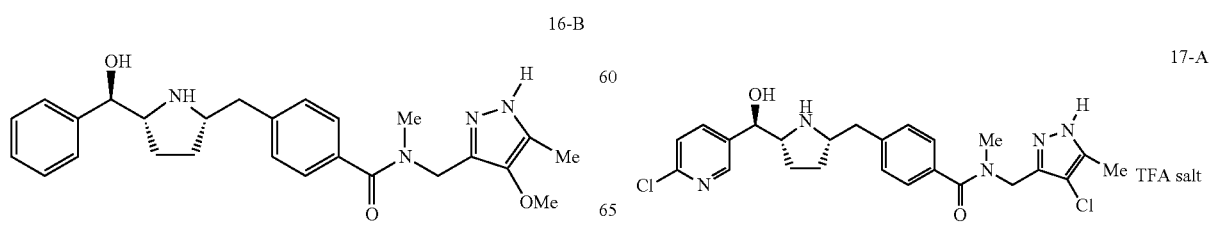

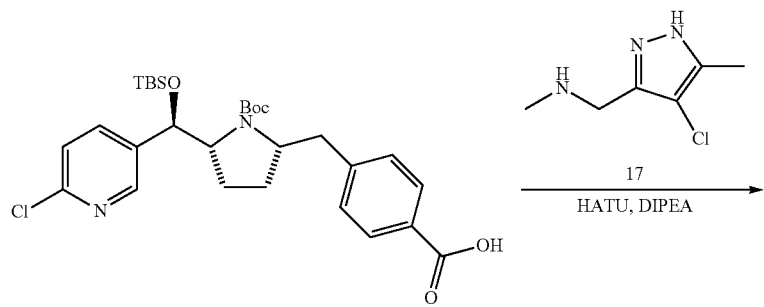

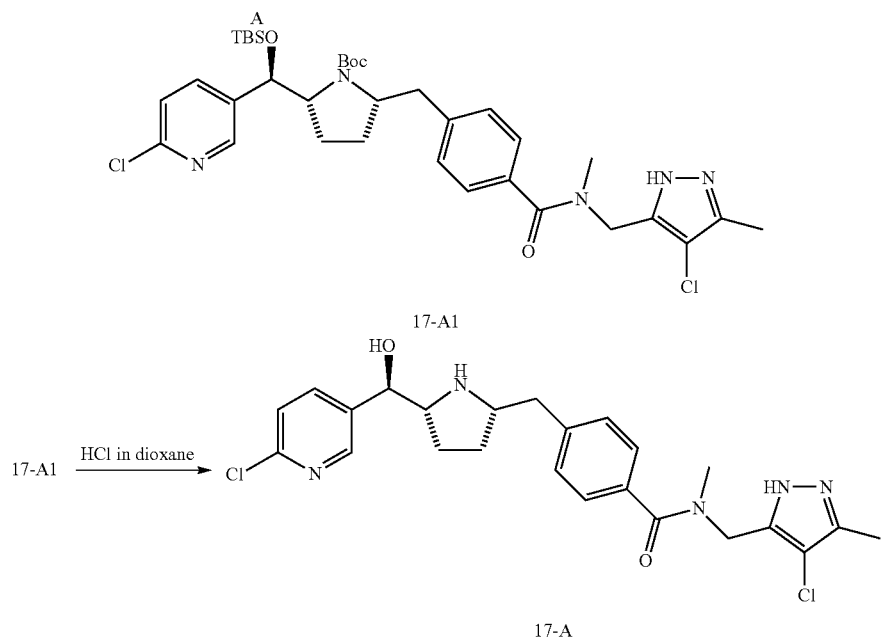

N-((4-chloro-5-methyl-1H-pyrazol-3-yl)methyl)-4-(((2S,5R)-5-((R)-(6-chloropyridin-3-yl)(hydroxy)methyl)pyrrolidin-2-yl)methyl)-N-methylbenzamide, triflic acid salt (17-A)

Compound 17-A was prepared was prepared utilizing an analogous synthesis route to that described in Example 4-E.

$^1$H NMR (400 MHz, CD$_3$OD): δ 8.46 (d, J=2.30 Hz, 1H), 7.92 (dd, J=8.28 and 2.30 Hz, 1H), 7.55-7.46 (m, 3H), 7.39 (d, J=8.12 Hz, 2H), 4.85-4.83 (m, 1H), 4.77-4.50 (m, 1H), 3.83-3.81 (m, 2H), 3.30-3.22 (m, 1H), 4.77-4.50 (m, 1H), 3.3-3.22 (m, 1H), 3.2-3.13 (m, 2H), 3.03-2.99 (m, 3H), 2.31-2.26 (m, 3H), 2.22-2.11 (m, 1H), 1.87-1.82 (m, 3H). Molecular Formula: C$_{24}$H$_{27}$Cl$_2$N$_5$O$_2$; LC-MS purity: 99.1%; Expected: 488; Observed: 490 (M+2).

Example 17-B

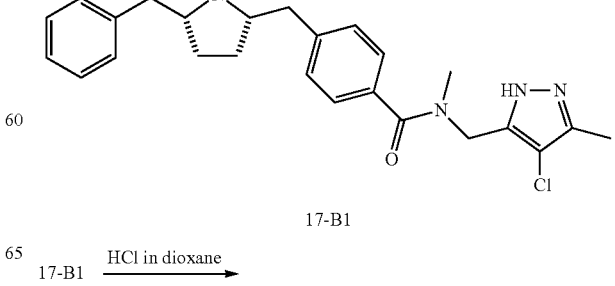

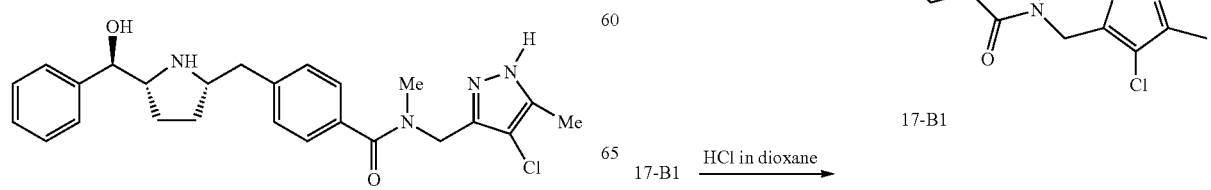

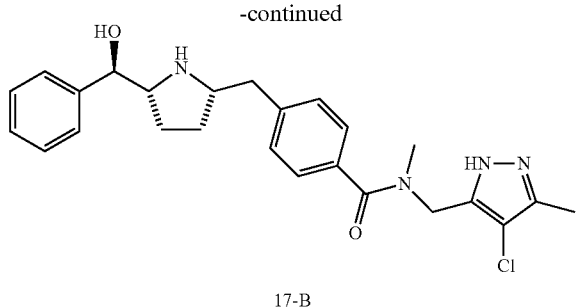
17-B
N-((4-chloro-5-methyl-1H-pyrazol-3-yl)methyl)-4-(((2S,5R)-5-((R)-hydroxy(phenyl) methyl)pyrrolidin-2-yl)methyl)-N-methylbenzamide (17-B)
Compound 17-B was prepared was prepared utilizing an analogous synthesis route to that described in Example 4-E.
$^1$H NMR (400 MHz, CD$_3$OD): δ 7.54-7.31 (m, 9H), 4.77 (s, 1H), 4.70 (d, J=8.56 Hz, 1H), 4.51 (s, 1H), 3.77-3.73 (m, 2H), 3.20-3.18 (m, 1H), 3.15-3.06 (m, 1H), 3.01-2.89 (m, 3H), 2.26-2.23 (m, 3H), 2.07-2.05 (m, 1H), 1.80-1.77 (m, 3H). Molecular Formula: C$_{25}$H$_{29}$ClN$_4$O$_2$; LC-MS purity: 97.6%; Expected: 452; Observed: 453 (M+1).
Example 18-A
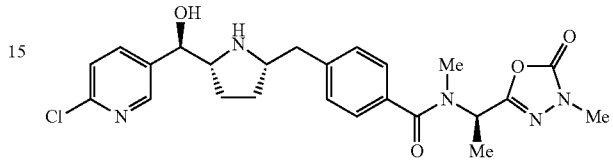
18-A
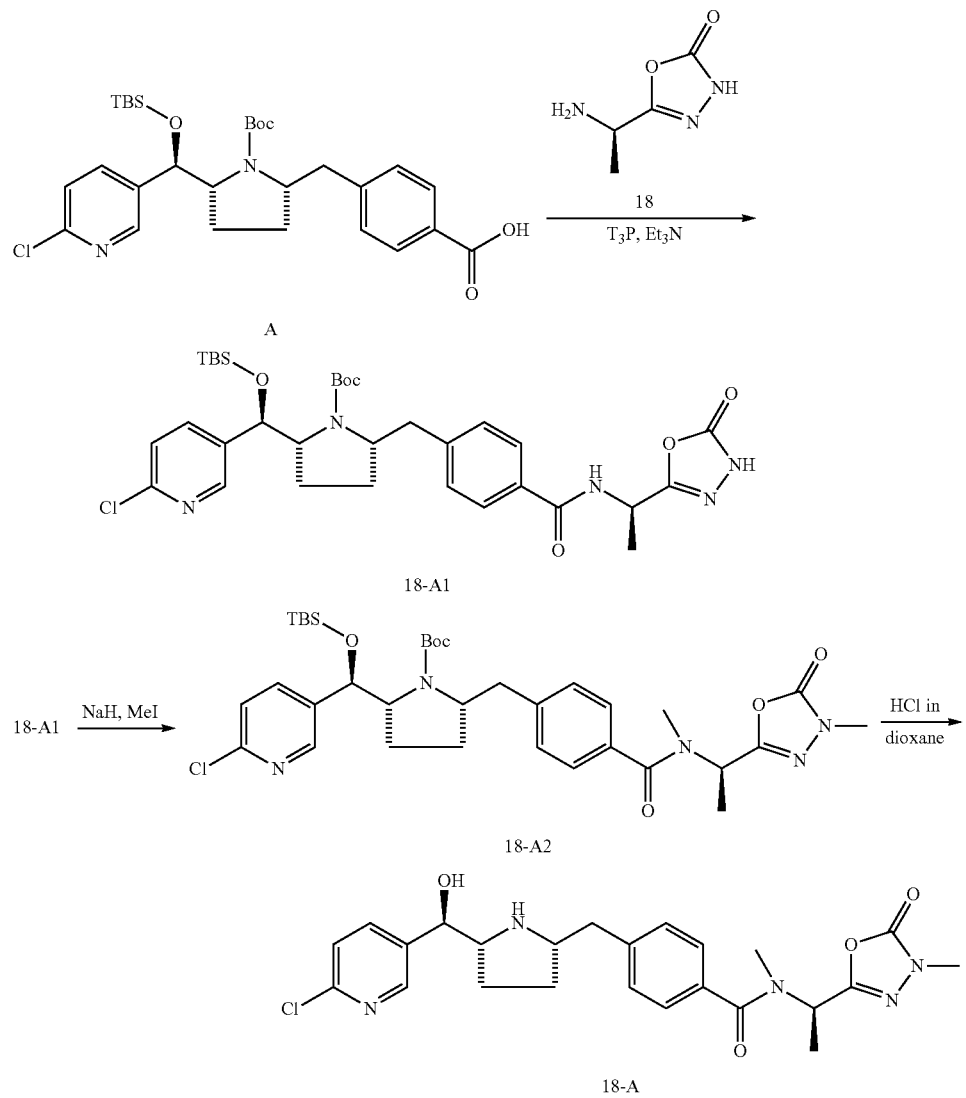

Step A (2R,5S)-tert-butyl 2-((R)-((tert-butyldimethylsilyl)oxy)(6-chloropyridin-3-yl)methyl)-5-(4-(((R)-1-(5-oxo-4,5-dihydro-1,3,4-oxadiazol-2-yl)ethyl)carbamoyl)benzyl)pyrrolidine-1-carboxylate (18-A1)

Compound 18-A1 was prepared following an analogous procedure described for the synthesis of compound 5-A1.

$^1$H NMR (400 MHz, DMSO-d$_6$, 80° C.): δ 11.93 (s, 1H), 8.58 (d, J=7.60 Hz, 1H), 8.29 (d, J=2.00 Hz, 1H), 7.76 (d, J=8.00 Hz, 3H), 7.54 (d, J=8.20 Hz, 1H), 7.07 (d, J=8.00 Hz, 2H), 5.32 (d, J=4.70 Hz, 1H), 5.10-5.01 (m, 1H), 4.10-4.05 (m, 1H), 3.90-3.82 (m, 1H), 2.89-2.85 (m, 1H), 1.90-1.77 (m, 2H), 1.63-1.55 (m, 2H), 1.46 (s, 9H), 1.30-1.15 (m, 2H), 0.88 (s, 9H), 0.11 (s, 3H), −0.03 (s, 3H). Molecular Formula: C$_{33}$H$_{46}$ClN$_5$O$_6$Si; LC-MS purity: 97.4%; Expected: 671; Observed: 672 (M+1).

Step B (2R,5S)-tert-butyl 2-((R)-((tert-butyldimethylsilyl)oxy)(6-chloropyridin-3-yl)methyl)-5-(4-(methyl((R)-1-(4-methyl-5-oxo-4,5-dihydro-1,3,4-oxadiazol-2-yl)ethyl)carbamoyl)benzyl)pyrrolidine-1-carboxylate (18-A2)

Compound 18-A2 was prepared from 18-A1 following an analogous procedure as described for the synthesis of 2-B2 from 2-B1.

$^1$H NMR (400 MHz, DMSO-d$_6$, 80° C.): δ 8.29 (d, J=2.20 Hz, 1H), 7.75 (dd, J=2.30 and 8.20 Hz, 1H), 7.54 (d, J=8.20 Hz, 1H), 7.31 (d, J=8.00 Hz, 2H), 7.06 (d, J=8.00 Hz, 2H), 5.33 (d, J=5.00 Hz, 1H), 4.03-4.12 (m, 1H), 3.87-3.88 (m, 1H), 3.32 (s, 3H), 2.81-2.87 (m, 1H), 2.80 (s, 3H), 1.78-1.92 (m, 2H), 1.55-1.65 (m, 2H), 1.48 (s, 3H), 1.46 (s, 9H), 1.24-1.30 (m, 2H), 0.91 (s, 9H), 0.11 (s, 3H), −0.03 (s, 3H). Molecular Formula: C$_{35}$H$_{50}$ClN$_5$O$_6$Si; LC-MS purity: 99.2%; Expected: 699.32; Observed: 700 (M+1).

Step C 4-(((2S,5R)-5-((R)-(6-chloropyridin-3-yl)(hydroxy)methyl)pyrrolidin-2-yl)methyl)-N-methyl-N—((R)-1-(4-methyl-5-oxo-4,5-dihydro-1,3,4-oxadiazol-2-yl)ethyl)benzamide (18-A)

Compound 18-A was prepared as TFA salt from 18-A2 following an analogous procedure described in synthesis of 2-B from 2-B2.

The TFA salt of 18-A was dissolved in minimum amount of water (20 mL) and to this turbid solution sodium bicarbonate was added slowly with cooling (pH~8). The product was then extracted with dichlormethane (4×50 mL). The combined organic layer was dried over anhydrous Na$_2$SO$_4$ and evaporated to dryness under reduced pressure to furnish 18-A as free base.

$^1$H NMR (400 MHz, DMSO-d$_6$): δ 8.36 (d, J=2.00 Hz, 1H), 7.80 (dd, J=2.20 and 8.20 Hz, 1H), 7.45 (d, J=8.20 Hz, 1H), 7.37-7.31 (m, 2H), 7.30-7.26 (m, 2H), 5.70-4.85 (bs, 2H, OH and NH), 4.38 (d, J=6.30 Hz, 1H), 3.31 (d, J=6.30 Hz, 3H), 3.26-3.21 (m, 1H), 3.20-3.13 (m, 1H), 2.80 (s, 3H), 2.70-2.59 (m, 3H), 1.65-1.55 (m, 1H), 1.49-1.42 (m, 3H), 1.41-1.34 (m, 2H), 1.20-1.10 (m, 1H). Molecular Formula: C$_{24}$H$_{28}$ClN$_5$O$_4$; LC-MS purity: 99.6%; Expected: 485.2; Observed: 486 (M+1). HPLC Chiral Purity-99.15%.

Example 18-B

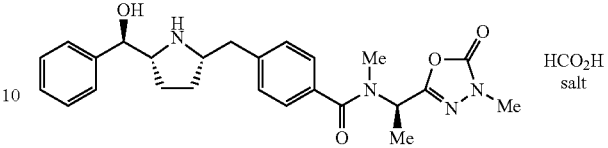

18-B · HCO$_2$H salt

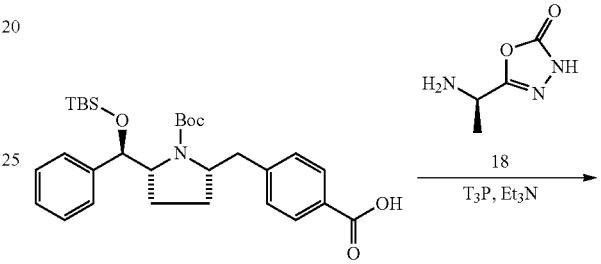

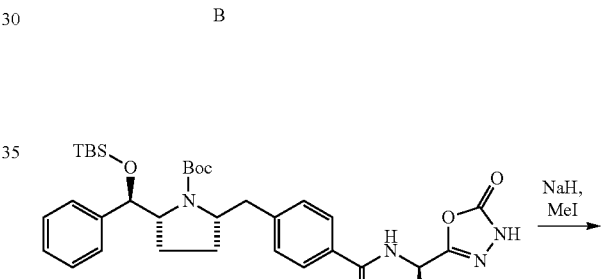

18-B1

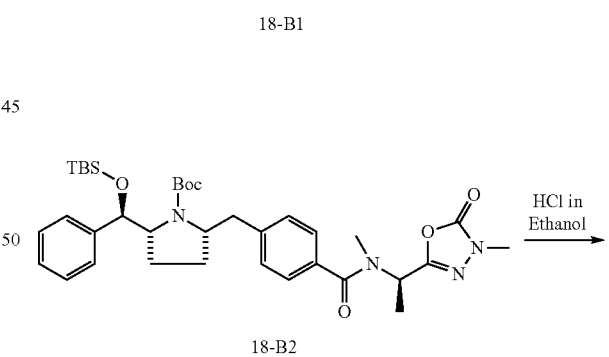

18-B2

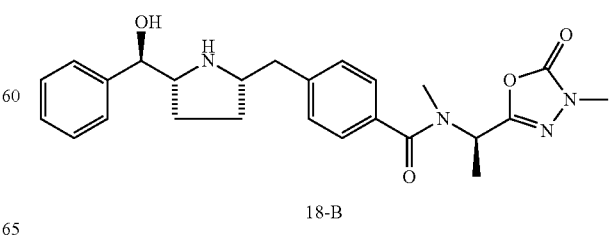

18-B

Step A ((2R,5S)-tert-butyl 2-((R)-((tert-butyldimethylsilyl)oxy)(phenyl)methyl)-5-(4-(((R)-1-(5-oxo-4,5-dihydro-1,3,4-oxadiazol-2-yl)ethyl)carbamoyl)benzyl) pyrrolidine-1-carboxylate (18-B1)

Compound 18-B1 was prepared following an analogous procedure described for the synthesis of 5-A1.
Molecular Formula: $C_{34}H_{48}N_4O_6Si$; LC-MS purity: 62.7%; Expected: 636.9; Observed: 537 (M+1-Boc), 659.2 (M+Na).

Step B (2R,5S)-tert-butyl 2-((R)-((tert-butyldimethylsilyl)oxy)(phenyl)methyl)-5-(4-(methyl((R)-1-(4-methyl-5-oxo-4,5-dihydro-1,3,4-oxadiazol-2-yl) ethyl) carbamoyl)benzyl)pyrrolidine-1-carboxylate (18-B2)

Compound 18-B2 was prepared from 18-B1 following an analogous procedure described for the synthesis of 2-B2 from 2-B1.
$^1$H NMR (400 MHz, DMSO-$d_6$): δ 7.39-7.30 (m, 7H), 6.95-6.91 (m, 2H), 5.30-5.16 (m, 2H), 4.11-4.10 (m, 2H), 3.85-3.54 (m, 3H), 3.1-2.98 (m, 4H), 1.89-1.78 (m, 2H), 1.50-1.43 (m, 3H), 1.24-1.15 (m, 9H), 0.91 (s, 9H), 0.01 (s, 3H), −0.01 (s, 3H). Molecular Formula: $C_{36}H_{52}N_4O_6Si$; LC-MS: Expected: 664.9; Observed: 566 (M+1-Boc).

Step C 4-(((2S,5R)-5-((R)-hydroxy(phenyl)methyl) pyrrolidin-2-yl)methyl)-N-methyl-N—((R)-1-(4-methyl-5-oxo-4,5-dihydro-1,3,4-oxadiazol-2-yl) ethyl)benzamide, formic acid salt (18-B)

Compound 18-B was prepared as the formic acid salt from 18-B2 following an analogous procedure described for the synthesis of 4-A from 4-A1.
$^1$H NMR (400 MHz, DMSO-$d_6$): δ 7.49-7.33 (m, 9H), 4.70 (d, J=8.40 Hz, 1H), 3.82-3.75 (m, 2H), 3.37 (s, 3H), 3.19-3.18 (m, 1H), 3.10-2.98 (m, 1H), 2.93 (s, 3H), 1.85-1.78 (m, 4H), 1.65-1.50 (m, 3H). Molecular Formula: $C_{25}H_{30}N_4O_4$; LC-MS purity: 95.5%; Expected: 450.5; Observed: 451 (M+1).

Example 18-G

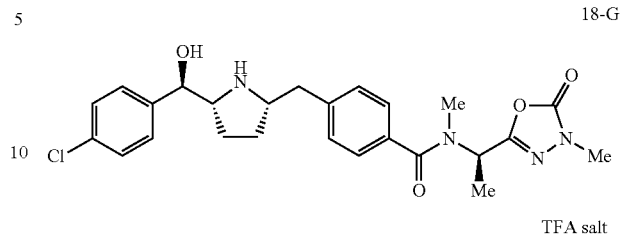

4-(((2S,5R)-5-((R)-(4-chlorophenyl)(hydroxy) methyl)pyrrolidin-2-yl)methyl)-N-methyl-N—((R)-1-(4-methyl-5-oxo-4,5-dihydro-1,3,4-oxadiazol-2-yl) ethyl)benzamide, triflic acid salt (18-G)

Compound 18-G was prepared in an analogous manner as described in Example 4-E.
$^1$H NMR (400 MHz, CD$_3$OD): δ 7.49-7.40 (m, 9H), 4.75 (d, J=8.56 Hz, 1H), 3.80-3.76 (m, 2H), 3.39 (s, 3H), 3.22-3.19 (m, 1H), 3.09-3.06 (m, 1H), 2.93 (bs, 3H), 2.11-2.09 (m, 1H), 1.88-1.82 (m, 3H), 1.60-1.55 (m, 3H). Molecular Formula: $C_{25}H_{29}ClN_4O_4$; LC-MS purity: 97.6%; Expected: 485; Observed: 485.2 (M+1).

Example 19-A

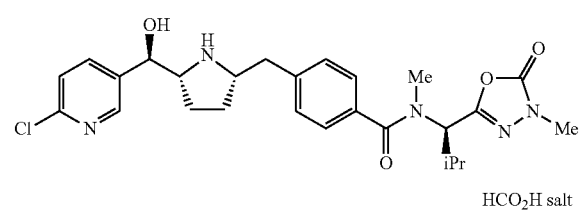

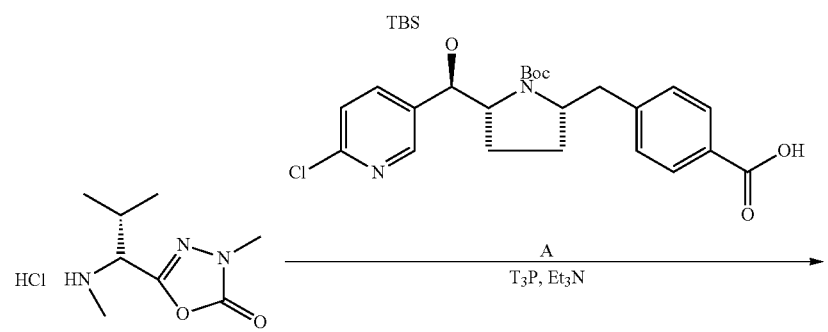

-continued

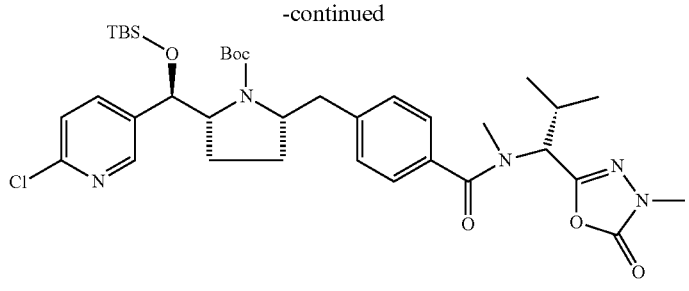

19-A1

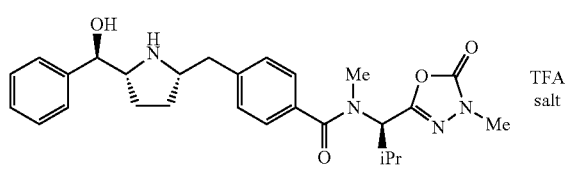

19-A

4-(((2S,5R)-5-((R)-(6-chloropyridin-3-yl)(hydroxy)methyl)pyrrolidin-2-yl)methyl)-N-methyl-N—((R)-2-methyl-1-(4-methyl-5-oxo-4,5-dihydro-1,3,4-oxadiazol-2-yl)propyl) benzamide, formic acid salt (19-A)

Compound 19-A was prepared in an analogous manner as described in Example 5-A.

$^1$H NMR (400 MHz, CD$_3$OD): δ 8.46 (s, 1H), 7.92-7.94 (m, 1H), 7.52 (d, J=8.40 Hz, 1H), 7.46-7.43 (m, 4H), 5.39-5.36 (m, 1H), 4.86 (d, J=7.60 Hz, 1H), 3.85-3.83 (m, 2H), 3.41 (s, 3H), 3.09-3.01 (m, 2H), 2.91 (s, 3H), 2.50-2.41 (m, 1H), 2.13-2.11 (m, 1H), 1.94-1.81 (m, 3H), 1.13-1.07 (m, 3H), 0.85-0.84 (m, 3H). Molecular Formula: C$_{26}$H$_{32}$ClN$_5$O$_4$; LC-MS purity: 99%; Expected: 513.2; Observed: 514 (M+1).

Example 19-B

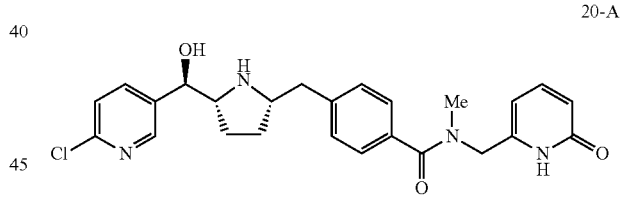

19-B

4-(((2S,5R)-5-((R)-hydroxy(phenyl)methyl)pyrrolidin-2-yl)methyl)-N-methyl-N—((R)-2-methyl-1-(4-methyl-5-oxo-4,5-dihydro-1,3,4-oxadiazol-2-yl)propyl)benzamide, triflic acid salt (19-B)

Compound 19-B was prepared in an analogous manner as described in Example 5-A.

$^1$H NMR (400 MHz, CD$_3$OD): δ 7.47-7.35 (m, 9H), 5.47-5.35 (m, 1H), 4.74 (d, J=8.60 Hz, 1H), 3.82-3.80 (m, 2H), 3.41 (s, 3H), 3.31-3.21 (m, 3H), 3.09-2.91 (m, 4H), 2.59-2.47 (m, 1H), 2.18-2.09 (m, 1H), 1.85-1.82 (m, 3H), 1.13-1.07 (m, 3H), 0.93-0.84 (m, 3H). Molecular Formula: C$_{27}$H$_{34}$N$_4$O$_4$; LC-MS purity: 99.6%; Expected: 478.3; Observed: 479.2 (M+1).

Example 20-A

20-A

4-(((2S,5R)-5-((R)-(6-chloropyridin-3-yl)(hydroxy)methyl)pyrrolidin-2-yl)methyl)-N-methyl-N-((6-oxo-1,6-dihydropyridin-2-yl)methyl)benzamide (20-A)

Compound 20-A was prepared in an analogous manner to that described for compound 8-B.

$^1$H NMR (400 MHz, CD$_3$OD): δ 8.50 (bs, 1H), 8.45 (s, 1H), 7.96-7.90 (m, 1H), 7.62-7.50 (m, 3H), 7.43-7.33 (m, 2H), 6.50-6.47 (m, 1H), 6.40-6.38 (m, 1H), 4.82 (d, J=8.00 Hz, 1H), 4.63 (s, 1H), 3.76-3.74 (m, 2H), 3.26-3.18 (m, 2H), 3.13 (s, 3H), 2.08-2.05 (m, 1H), 1.84-1.82 (m, 3H). Molecular Formula: C$_{25}$H$_{27}$ClN$_4$O$_3$; LC-MS purity: 97.9%; Expected: 466.9, Observed: 467.1 (M+1).

Example 20-B

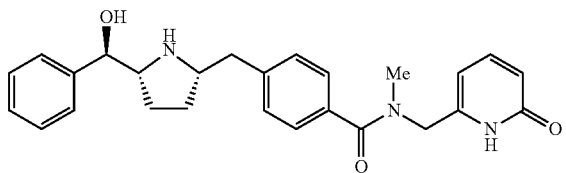

20-B

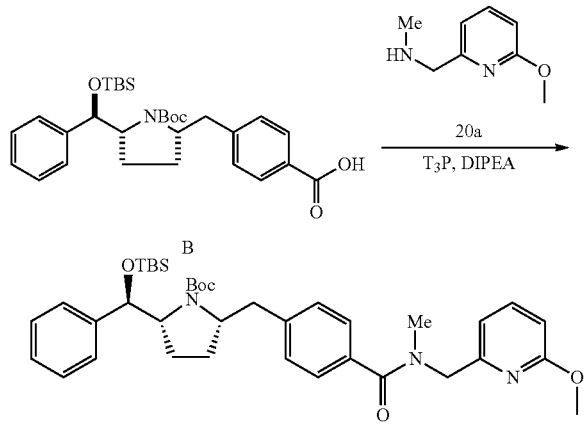

Step A (2R,5S)-tert-butyl 2-((R)-((tert-butyldimethylsilyl)oxy)(phenyl)methyl)-5-(4-(((6-methoxypyridin-2-yl)methyl)(methyl)carbamoyl)benzyl)pyrrolidine-1-carboxylate (20-B1)

Compound 20-B1 was prepared following an analogous procedure described for the synthesis of compound 8-B1.

Step B 4-(((2S,5R)-5-((R)-hydroxy(phenyl)methyl)pyrrolidin-2-yl)methyl)-N-methyl-N-((6-oxo-1,6-dihydropyridin-2-yl)methyl)benzamide (20-B)

Compound 20-B was prepared from 20-B1 following an analogous procedure described for the synthesis of compound 20 from 20a.

$^1$H NMR (400 MHz, DMSO-d$_6$): δ 8.24 (s, 1H), 7.44-7.43 (m, 2H), 7.36-7.23 (m, 8H), 6.25 (d, J=12.00 Hz, 1H), 6.11 (d, J=8.00 Hz, 1H), 4.38 (d, J=8.00 Hz, 2H), 3.25-3.27 (m, 1H), 3.17 (s, 2H), 2.95 (s, 3H), 2.87-2.86 (m, 1H), 2.79-2.77 (m, 1H), 1.71-1.69 (m, 1H), 1.50-1.37 (m, 3H). Molecular Formula: C$_{26}$H$_{28}$N$_3$O$_3$; LC-MS purity: 96.4%; Expected: 430.2; Observed: 431.2 (M+1).

Example 20-E

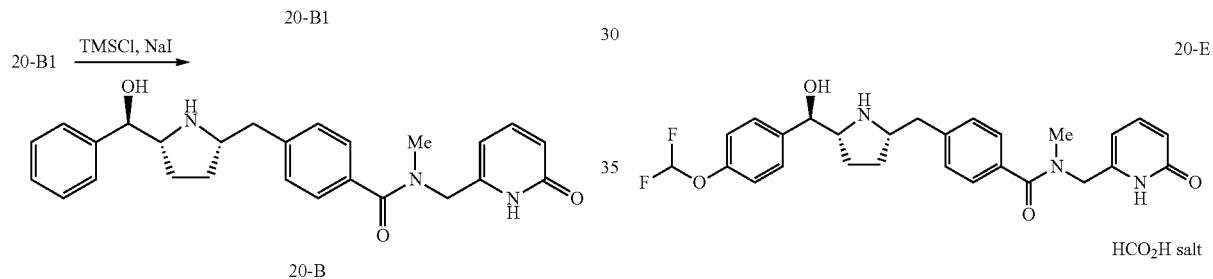

20-E

HCO$_2$H salt

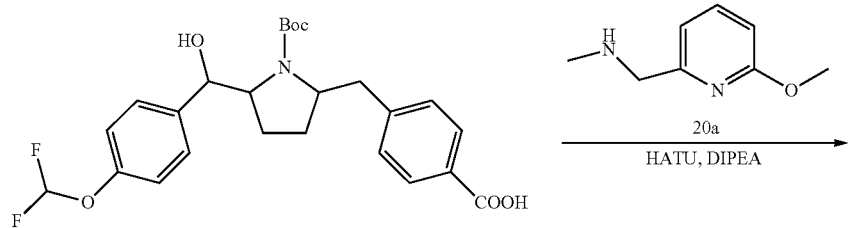

E

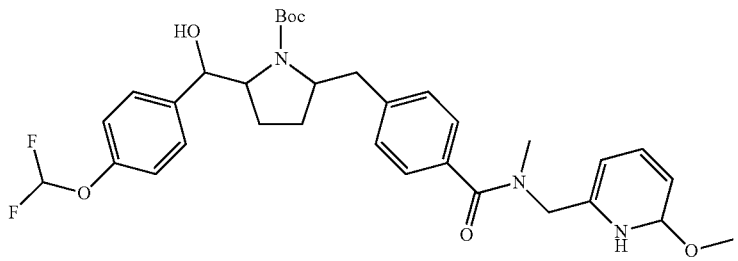

20-E1

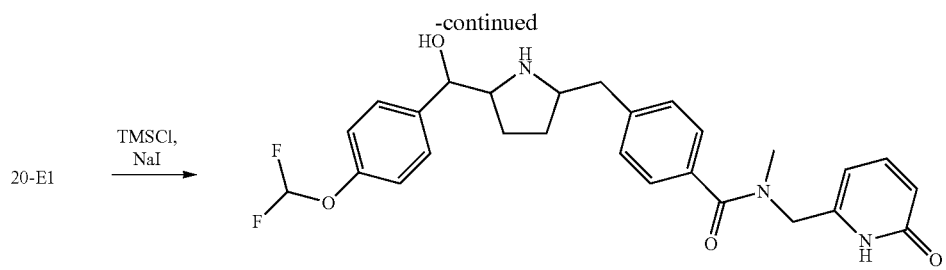

20-E

Step A Tert-butyl 2-((4-(difluoromethoxy)phenyl)(hydroxy)methyl)-5-(4-((((6-methoxy-1,6-dihydropyridin-2-yl)methyl)(methyl)carbamoyl)benzyl) pyrrolidine-1-carboxylate (20-E1)

Compound 20-E1 was prepared following an analogous procedure as described for the synthesis of 4-E1.
Molecular Formula: $C_{33}H_{41}F_2N_3O_6$; LC-MS purity: 44.64%; Expected: 613.69, Observed: 555.8 (M+1-$^t$Bu).

Step B 4-(((2S,5R)-5-((R)-(4-(difluoromethoxy)phenyl)(hydroxy)methyl)pyrrolidin-2-yl)methyl)-N-methyl-N-((6-oxo-1,6-dihydropyridin-2-yl)methyl)benzamide, formic acid salt (20-E)

Compound 20-E was prepared from 20-E1 following an analogous procedure as described in the synthesis of 20 from 20a.
$^1$H NMR (400 MHz, CD$_3$OD): δ 8.48 (s, 1H), 7.61-7.39 (m, 7H), 7.18 (d, J=8.44 Hz, 2H), 6.84 (t, J=73.84 Hz, 1H), 6.50-6.38 (m, 2H), 4.74 (d, J=8.44 Hz, 1H), 4.63 (s, 2H), 3.80-3.76 (m, 2H), 3.19-3.12 (m, 1H), 3.06-2.93 (m, 4H), 2.12-2.08 (m, 1H), 1.82 (bs, 3H). Molecular Formula: $C_{27}H_{29}F_2N_3O_4$; LC-MS purity: 97.8%; Expected: 497.5; Observed: 497.

Example 20-G

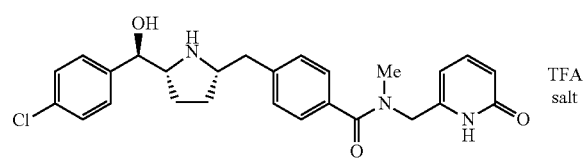

20-G

4-(((2S,5R)-5-((R)4-chlorophenyl)(hydroxy)methyl)pyrrolidin-2-yl)methyl)-N-methyl-N-((6-oxo-1,6-dihydropyridin-2-yl)methyl)benzamide, triflic acid salt (20-G)

Compound 20-G was prepared from compound 20 utilizing an analogous procedure to that describe in Example 4-E.
$^1$H NMR (400 MHz, CD$_3$OD): δ 7.61-7.54 (m, 2H), 7.46-7.34 (m, 6H), 6.51-6.46 (m, 1H), 6.42-6.36 (m, 1H), 4.74 (d, J=8.48 Hz, 1H), 4.62 (bs, 2H), 3.79-3.75 (m, 2H), 3.32-3.14 (m, 2H), 3.05 (s, 3H), 2.19-2.04 (m, 1H), 1.91-1.79 (m, 3H). Molecular Formula: $C_{26}H_{28}ClN_3O_3$; LC-MS purity: 98.5%; Expected: 466; Observed: 466.0 (M).

Example 21-A

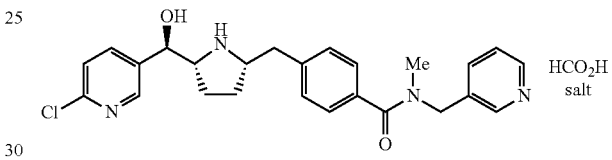

21-A

4-(((2S,5R)-5-((R)-(6-chloropyridin-3-yl)(hydroxy)methyl)pyrrolidin-2-yl)methyl)-N-methyl-N-(pyridin-3-ylmethyl)benzamide, formic acid salt (21-A)

Compound 21-A was prepared utilizing an analogous procedure as described in Example 5-A.
$^1$H NMR (400 MHz, DMSO-d$_6$): δ 8.59 (m, 1H), 8.51 (d, J=4.20 Hz, 1H), 8.41 (d, J=2.20 Hz, 1H), 8.16 (s, 1H), 7.84 (dd, J=2.40 and J=8.30 Hz, 1H), 7.75 (m, 1H), 7.50 (d, J=8.20 Hz, 1H), 7.40-7.28 (m, 5H), 4.69 (bs, 2H), 4.54 (d, J=7.10 Hz, 2H), 2.89 (s, 3H), 2.84-2.75 (m, 2H), 1.72 (m, 1H), 1.50 (m, 3H), 1.24 (m, 1H). Molecular Formula: $C_{25}H_{27}ClN_4O_2$; LC-MS purity: 98.5%; Expected: 451; Observed: 451.2 (M+1).

Example 21-B

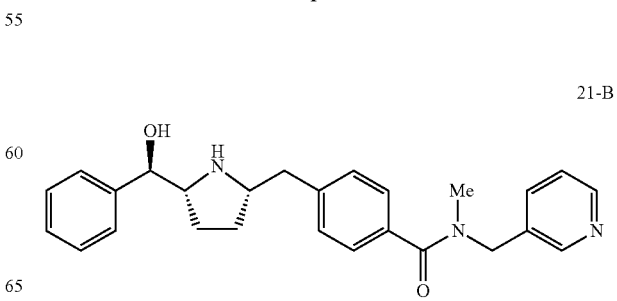

21-B

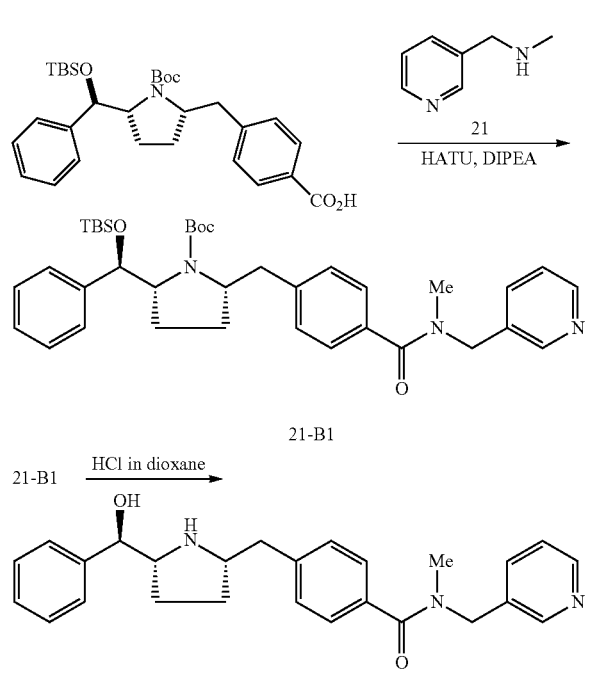

21-B1

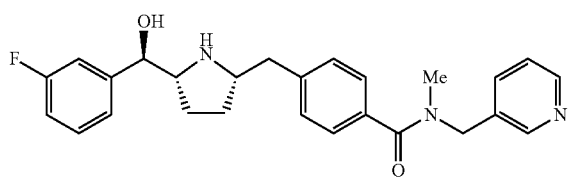

21-B

4-(((2S,5R)-5-((R)-hydroxy(phenyl)methyl)pyrrolidin-2-yl)methyl)-N-methyl-N-(pyridin-3-ylmethyl)benzamide (21-B)

Compound 21-B was prepared in an analogous manner to that described in Example 4-E.

$^1$H NMR (400 MHz, CD3OD): δ 8.61-8.58 (m, 1H), 8.53-8.48 (m, 2H), 7.91-7.89 (m, 1H), 7.48-7.32 (m, 9H), 4.81 (s, 2H), 4.73-4.71 (m, 1H), 4.62 (bs, 1H), 3.80-3.71 (m, 2H), 3.23-3.18 (m, 1H), 3.07-3.02 (m, 1H), 3.02-2.98 (m, 3H), 2.04-2.04 (m, 1H), 1.90-1.81 (m, 3H). Molecular Formula: $C_{26}H_{29}N_3O_2$; LC-MS purity: 91.77%; Expected: 415.22; Observed: 416.2 (M+1).

Example 21-C

21-C

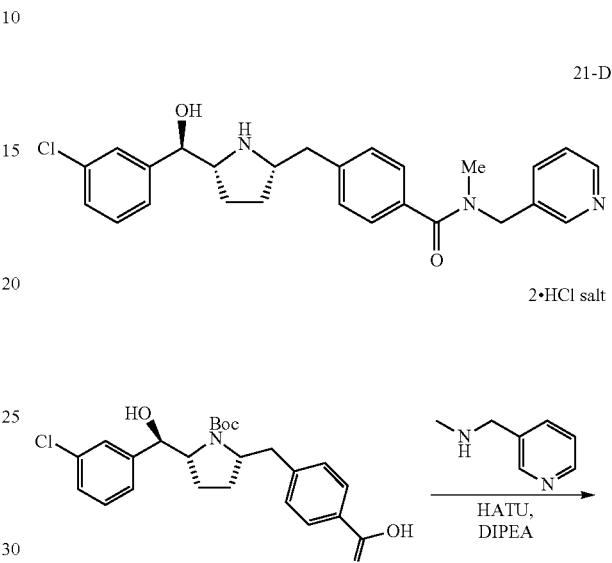

4-(((2S,5R)-5-((R)-(3-fluorophenyl)(hydroxy)methyl)pyrrolidin-2-yl)methyl)-N-methyl-N-(pyridin-3-ylmethyl)benzamide (21-C)

Compound 21-C was prepared from core C and Amine 21 utilizing an analogous synthesis route to that described in Example 4-E.

$^1$H NMR (400 MHz, DMSO-$d_6$): δ 9.54 (bs, 1H), 9.02-9.01 (m, 1H), 8.82-8.77 (m, 2H), 8.32 (bs, 1H), 7.89 (bs, 1H), 7.47-7.42 (m, 4H), 7.18-7.17 (m, 2H), 7.15-7.13 (m, 1H), 4.85-4.80 (m, 2H), 3.65-3.62 (m, 4H), 3.25-3.23 (m, 1H), 3.03-2.98 (m, 4H), 1.89-1.84 (m, 1H), 1.76-1.72 (m, 2H), 1.65-1.60 (m, 1H). Molecular Formula: $C_{25}H_{27}FN_4O_2$; LC-MS purity: 99.3%; Expected: 433.5; Observed: 434.2 (M+1).

Example 21-D

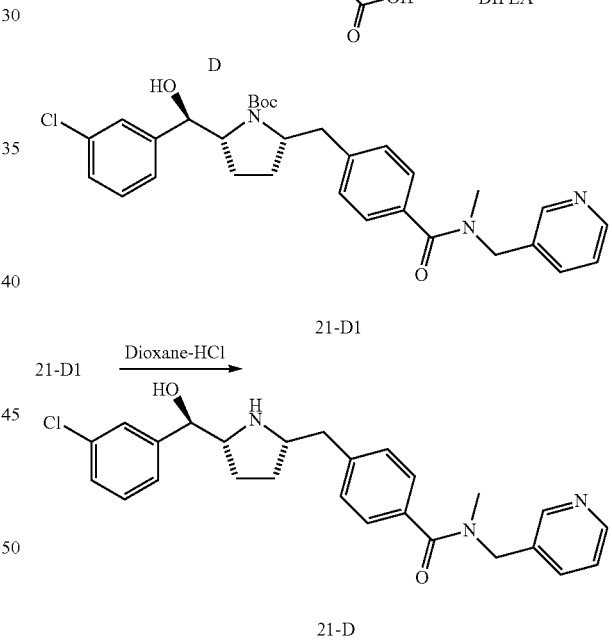

4-(((2S,5R)-5-((R)-(3-chlorophenyl)(hydroxy)methyl)pyrrolidin-2-yl)methyl)-N-methyl-N-(pyridin-3-ylmethyl)benzamide, bis-hydrochloride salt (21-D)

Compound 21-D was prepared from Core Acid D and Amine 21 utilizing an analogous chemical synthesis to that described in Example 4-E.

$^1$H NMR (400 MHz, CD$_3$OD): δ 8.93 (s, 1H), 8.86-8.8 (m, 1H), 8.69-8.62 (m, 1H), 8.17-8.07 (m, 1H), 7.58-7.52 (m, 3H), 7.48-7.40 (m, 2H), 7.40-7.33 (m, 3H), 4.94 (s, 2H), 4.77 (d, J=8.20 Hz, 2H), 3.89-3.72 (m, 3H), 3.29-3.21 (m, 2H), 3.17-3.05 (m, 4H), 2.15-2.02 (m, 1H), 1.94-1.81 (m, 3H). Molecular Formula: $C_{26}H_{28}ClN_3O_2$; LC-MS purity: 96%; Expected: 449.2; Observed: 450.2 (M+1).

Example 21-F

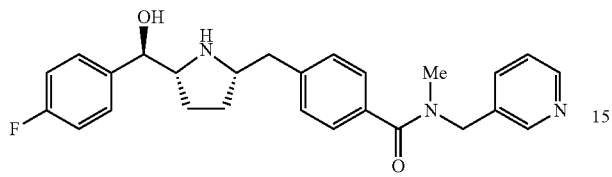

21-F 4-(((2S,5R)-5-((R)-(4-fluorophenyl)(hydroxy)methyl)pyrrolidin-2-yl)methyl)-N-methyl-N-(pyridin-3-ylmethyl)benzamide (21-F)

Compound 21-F was prepared from Core Acid F and Amine 21 utilizing an analogous procedure as described in Example 4-E.
$^1$H NMR (400 MHz, CD$_3$OD): δ 8.82-8.21 (m, 1H), 8.69-8.63 (m, 1H), 8.22-8.21 (m, 1H), 7.74-7.65 (m, 1H), 7.51-7.42 (m, 6H), 7.14 (t, J=8.24 Hz, 1H), 4.8-4.62 (m, 2H), 4.82-4.7 (m, 2H), 3.36-3.31 (m, 2H), 3.14-3.11 (m, 4H), 2.94-2.90 (m, 1H), 2.82-2.78 (m, 1H), 2.18-2.06 (m, 1H), 1.92-1.73 (m, 3H). Molecular Formula: $C_{26}H_{28}FN_3O_2$; LC-MS purity: 99.1%; Expected: 433.2; Observed: 434 (M+1).

Example 21-G

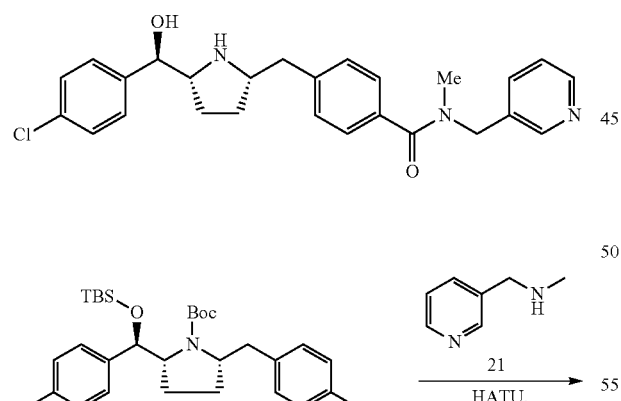

21-G1

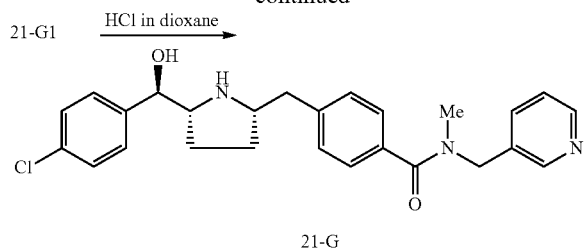

21-G 4-(((2S,5R)-5-((R)-(4-chlorophenyl)(hydroxy)methyl)pyrrolidin-2-yl)methyl)-N-methyl-N-(pyridin-3-ylmethyl)benzamide (21-G)

Compound 21-G was prepared in an analogous manner to that disclosed in Example 4-E
$^1$H NMR (400 MHz, CD$_3$OD): δ 8.60-8.50 (m, 2H), 7.91-7.89 (m, 1H), 7.46-7.35 (m, 9H), 7.91-4.91 (s, 2H), 4.49-4.45 (m, 1H), 3.54-3.44 (m, 2H), 2.99-2.93 (m, 1H), 2.90 (s, 3H), 2.87-2.83 (m, 1H), 1.94-1.83 (m, 1H), 1.68-1.56 (m, 3H). Molecular Formula: $C_{26}H_{28}ClN_3O_2$; LC-MS purity: 96.4%; Expected: 450; Observed: 450.2 (M+1).

Example 21-H

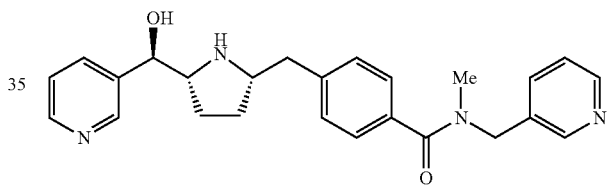

3·HCl salt

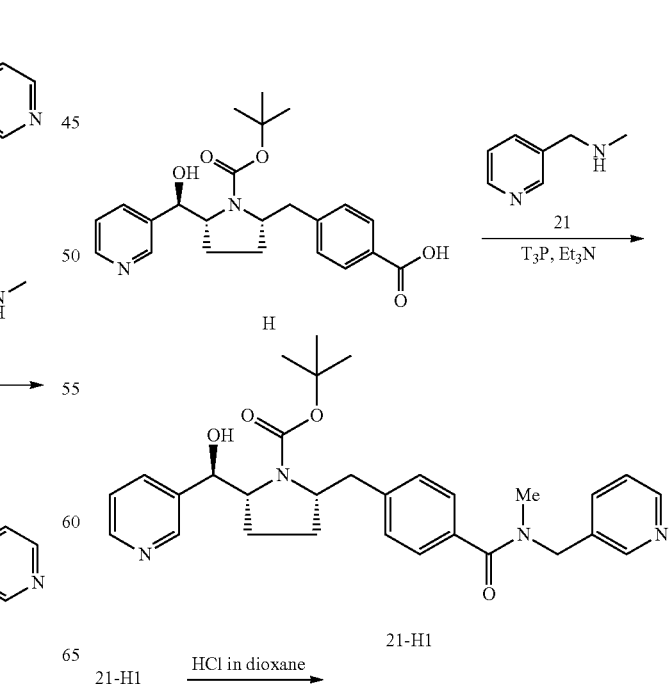

21-H1

-continued

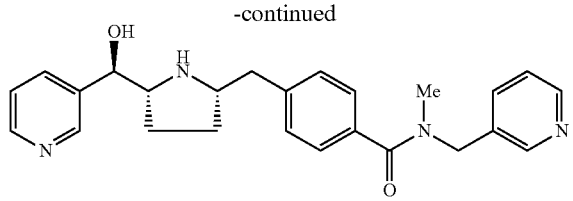

21-H 4-(((2S,5R)-5-((R)-hydroxy(pyridin-3-yl)methyl)pyrrolidin-2-yl)methyl)-N-methyl-N-(pyridin-3-ylmethyl)benzamide, tris-hydrochloride salt (21-H)

Compound 21-H was prepared in an analogous manner as described in Example 5-A.

$^1$H NMR (400 MHz, DMSO-d$_6$): δ 8.65 (s, 1H), 8.57-8.54 (m, 4H), 7.86 (d, J=8.00 Hz, 1H), 7.48-7.45 (m, 4H), 7.34 (d, J=6.40 Hz, 1H), 6.41 (bs, 1H), 4.79 (d, J=8.40 Hz, 1H), 4.71 (bs, 2H), 3.70 (m, 3H), 3.16 (m, 2H), 2.97 (m, 1H), 2.89 (s, 3H), 1.93 (m, 1H), 1.70 (m, 3H). Molecular Formula: C$_{25}$H$_{28}$N$_4$O$_2$; LC-MS purity: 97.2%; Expected: 416.5; Observed: 417.2 (M+1).

Example 21-I

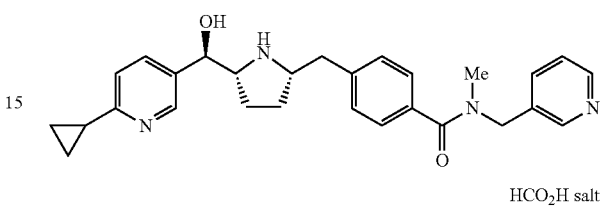

21-I

HCO$_2$H salt

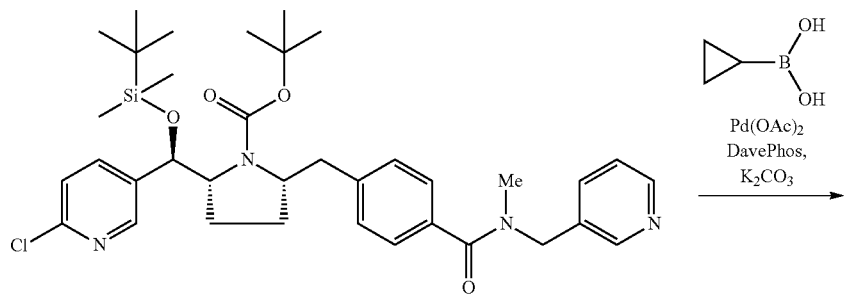

21-A1

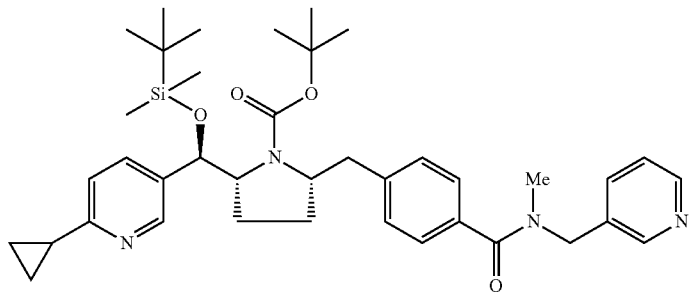

21-I1

21-I1 →[TFA, MeOH]

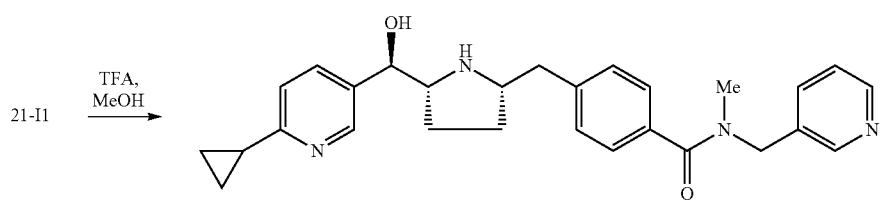

21-I

Step A (2R,5S)-tert-butyl 2-((R)-((tert-butyldimethylsilyl)oxy)(6-cyclopropylpyridin-3-yl)methyl)-5-(4-(methyl(pyridin-3-ylmethyl)carbamoyl)benzyl)pyrrolidine-1-carboxylate (21-I1)

To a stirred solution of 21-A1 (300 mg, 0.45 mmol) in toluene (4 mL), K$_3$PO$_4$ (125 mg, 0.70 mmol) in H$_2$O (0.8 mL) was added and was degassed bubbling Argon. To this reaction mixture, 2-dicyclohexyl phosphino-2'-(N,N-dimethylamino)biphenyl (DavePhos, 35.5 mg, 0.09 mmol) was added and degassed once again and finally Pd(OAc)$_2$ (20 mg, 0.09 mmol) was added. The reaction mixture was heated to 120° C. and stirred overnight under Argon atmosphere. The reaction mixture was filtered through a small celite bed and filtrate was concentrated under reduced pressure. The crude product was dissolved in ethyl acetate and washed with water and brine. The organic layer was dried over anhydrous Na$_2$SO$_4$, evaporated to dryness and purified by preparative HPLC to obtain the desired product 21-I1 (120 mg) as off white solid.

$^1$H NMR (400 MHz, DMSO-d$_6$): δ 8.49 (d, J=4.60 Hz, 1H), 8.24 (s, 1H), 8.14 (s, 1H), 7.71 (m, 1H), 7.53 (d, J=7.00 Hz, 1H), 7.40-7.32 (m, 4H), 6.95 (bs, 2H), 5.30 (bs, 1H), 4.65 (bs, 1H), 4.00 (m, 1H), 3.76 (bs, 1H), 2.84 (s, 3H), 2.07 (m, 1H), 1.80 (m, 2H), 1.44 (bs, 11H), 1.30 (t, J=10.70 Hz, 1H), 0.91 (m, 5H), 0.87 (s, 9H), 0.07 (s, 3H), −0.08 (s, 3H). Molecular Formula: C$_{39}$H$_{54}$N$_4$O$_4$Si; LC-MS purity: 97.5%; Expected: 671; Observed: 672.2 (M+1).

Step B 4-(((2S,5R)-5-((R)-(6-cyclopropylpyridin-3-yl)(hydroxy)methyl)pyrrolidin-2-yl)methyl)-N-methyl-N-(pyridin-3-ylmethyl)benzamide, formic acid salt 21-I To a stirred solution of 21-I1 (120 mg) in MeOH (0.5 mL), TFA (2 mL) was added at 0° C. The reaction mixture was stirred at room temperature for overnight. The reaction mixture was concentrated under reduced pressure and co-evaporated with toluene. The crude product was purified by preparative HPLC to obtain the desired product 21-I as off-white solid.

$^1$H NMR (400 MHz, DMSO-d$_6$): δ 8.53 (m, 1H), 8.51 (d, J=4.80 Hz, 1H), 8.38 (m, 1H), 8.16 (s, 1H), 7.75 (m, 1H), 7.62-7.60 (m, 1H), 7.41 (m, 2H), 7.31-7.25 (m, 3H), 4.69 (bs, 2H), 4.49 (m, 2H), 3.44 (m, 2H), 2.93 (s, 1H), 2.88 (s, 3H), 2.82 (m, 1H), 2.08 (m, 1H), 1.77 (m, 1H), 1.50 (m, 3H), 0.94-0.86 (m, 3H). Molecular Formula: C$_{28}$H$_{32}$N$_4$O$_2$; LC-MS purity: 98.5%; Expected: 456.6; Observed: 457.2 (M+1).

Example 21-J

21-J

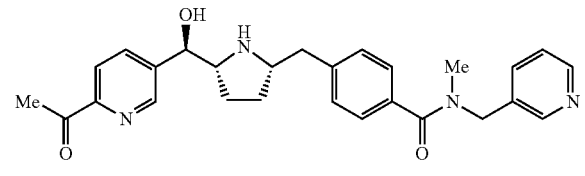

HCO$_2$H salt

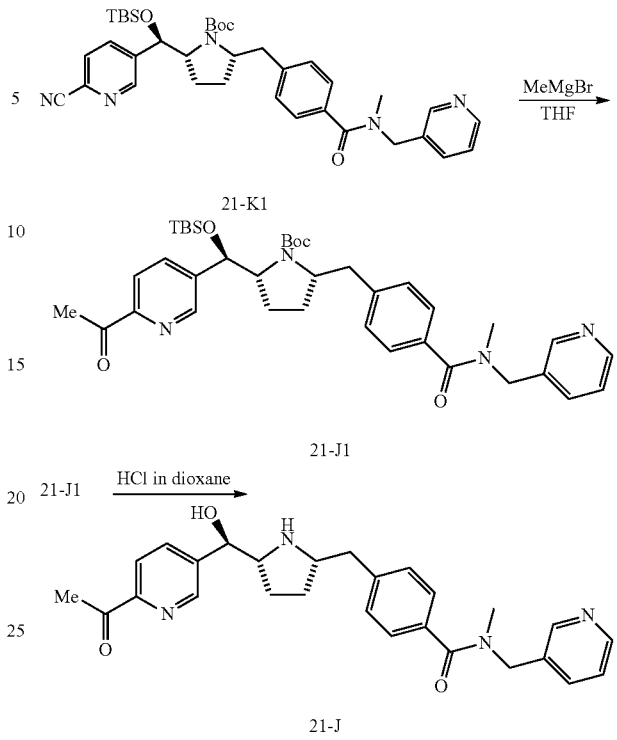

Step A (2R,5S)-tert-butyl 2-((R)-(6-acetylpyridin-3-yl)((tert-butyldimethylsilyl)oxy) methyl)-5-(4-(methyl(pyridin-3-ylmethyl)carbamoyl)benzyl)pyrrolidine-1-carboxylate (21-J1)

To a solution of 21-K1 (150 mg, 0.23 mmol) in THF (1 mL) methyl magnesium bromide (3M, 0.09 mL, 0.27 mmol) was added drop wise at −20° C. The reaction mixture was slowly warmed to room temperature and stirred for 2 h. The reaction was quenched with saturated NH$_4$Cl solution and extracted with ethyl acetate. The organic layer was washed with water and brine, dried over anhydrous Na$_2$SO$_4$ and concentrated under reduced pressure. The crude product was purified by purified by column chromatography using 80% ethyl acetate in petroleum ether (v/v) to yield 2141 (100 mg).

Molecular Formula: C$_{38}$H$_{52}$N$_5$O$_5$Si; LC-MS purity: 49.6%; Expected: 672.9; Observed: 673 (M+1).

Step B 4-(((2S,5R)-5-((R)-(6-acetylpyridin-3-yl)(hydroxy)methyl)pyrrolidin-2-yl)methyl)-N-methyl-N-(pyridin-3-ylmethyl)benzamide, formic acid salt 21-J Compound 21-J was prepared from 21-J1 following the same procedure as in the synthesis of 2-B from 2-B2.

$^1$H NMR (400 MHz, CD$_3$OD): δ 8.71 (s, 1H), 8.59-8.50 (m, 3H), 8.13 (d, J=8.04 Hz, 1H), 8.04 (d, J=7.52 Hz, 1H), 7.91-7.89 (m, 1H), 7.47-7.40 (m, 5H), 4.89-4.80 (m, 3H), 3.81-3.77 (m, 3H), 3.16-3.13 (m, 2H), 3.08-3.05 (m, 2H), 3.01-2.98 (m, 3H), 2.08-2.04 (m, 2H), 1.84 (bs, 3H). Molecular Formula: C$_{27}$H$_{30}$N$_4$O$_3$; LC-MS purity: 99.2%; Expected: 458.5; Observed: 460 (M+1).

Example 21-K
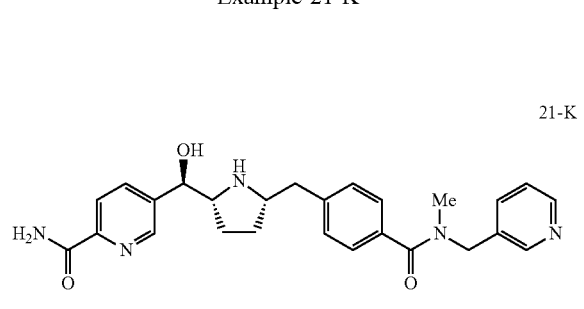
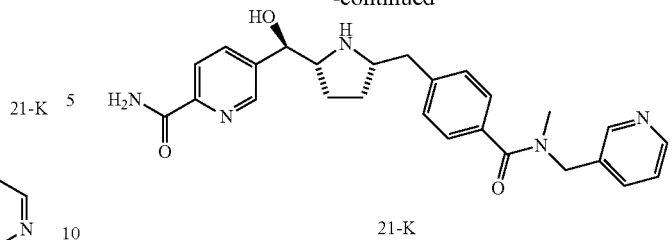
Step A 5-((R)-hydroxy((2R,5S)-5-(4-(methyl(pyridin-3-ylmethyl)carbamoyl) benzyl)pyrrolidin-2-yl) methyl)picolinamide, formic acid salt (21-K)
Compound 21-K was prepared in a manner analogous to the synthesis described in Example 4-E.
$^1$H NMR (400 MHz, CD$_3$OD): δ 8.79-8.72 (m, 2H), 8.66-8.57 (m, 2H), 8.19-8.10 (m, 2H), 8.09-8.02 (m, 1H), 7.75-7.65 (m, 2H), 7.59-7.5 (m, 2H), 7.5-7.37 (m, 3H), 6.61 (s, 1H), 3.97-3.8 (m, 4H), 3.76-3.67 (m, 2H), 2.15-2.12 (m, 1H), 2.07-2.05 (m, 3H). Molecular Formula: C$_{26}$H$_{29}$N$_5$O$_3$; LC-MS purity: 92.6%; Expected: 459.2; Observed: 460 (M+1).
Example 21-L
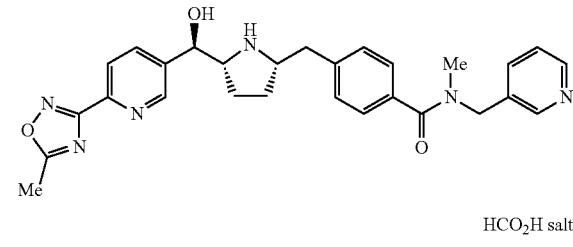
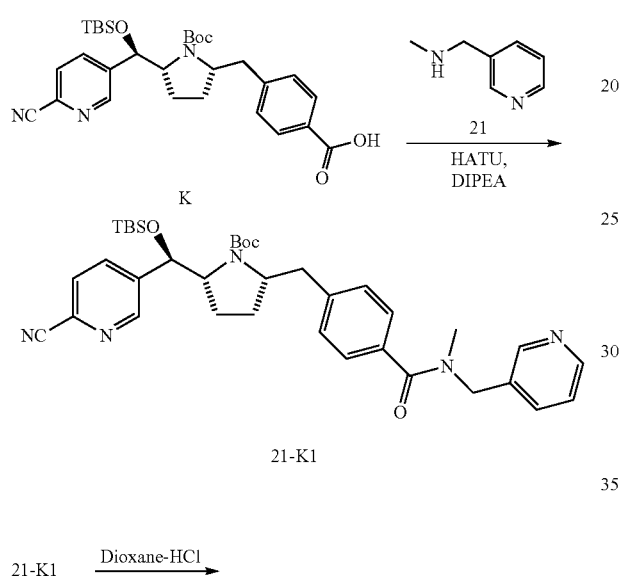
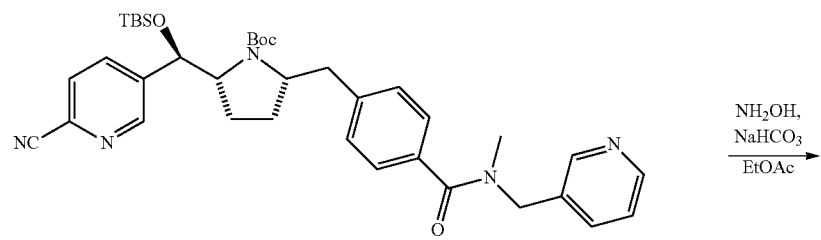
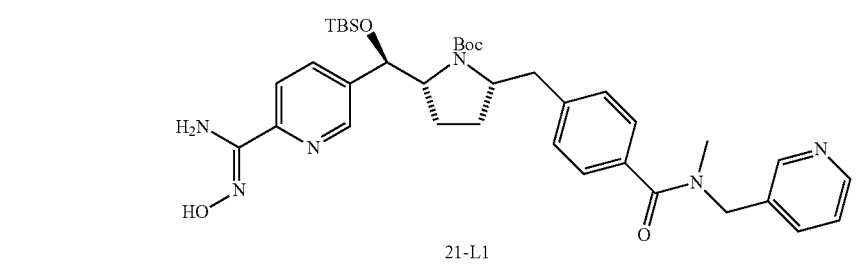

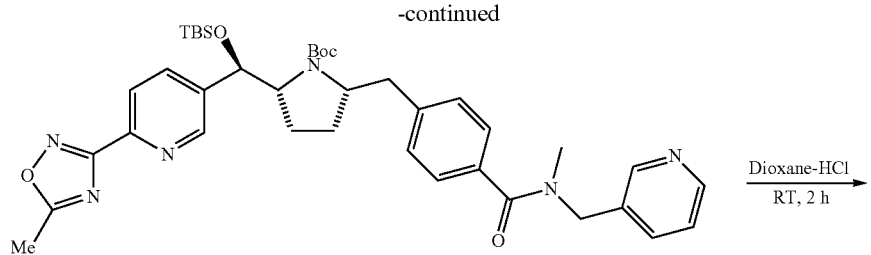

21-L2

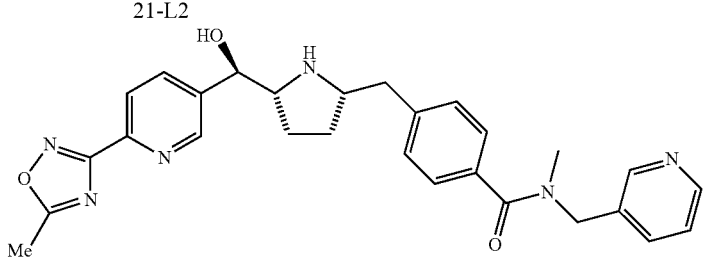

21-L

Step A (2S,5R)-tert-butyl 2-((R)-((tert-butyldimethylsilyl)oxy)(6-((Z)—N'-hydroxycarbamimidoyl)pyridin-3-yl)methyl)-5-(4-(methyl(pyridin-3-ylmethyl)carbamoyl)benzyl)pyrrolidine-1-carboxylate (21-L1)

To a solution of 21-K1 (250 mg, 0.38 mmol) in ethyl acetate (3 mL), hydroxyl amine (63 mg, 1.9 mmol) and sodium bicarbonate (160 mg, 1.9 mmol) were added and the reaction mixture was refluxed for 3 h. The solvents were removed under reduced pressure and the crude mass was dissolved in ethyl acetate. The organic layer was washed with water and brine, dried over anhydrous $Na_2SO_4$ and concentrated under reduced pressure. The residue was purified by column chromatography using 4% methanol in dichloromethane to yield 21-L1. Molecular Formula: $C_{37}H_{52}N_6O_5Si$; LC-MS purity: 98.9%; Expected: 688.9; Observed: 690 (M+1).

Step B (2R,5S)-tert-butyl 2-((R)-((tert-butyldimethylsilyl)oxy)(6-(5-methyl-1,2,4-oxadiazol-3-yl)pyridin-3-yl)methyl)-5-(4-(methyl(pyridin-3-ylmethyl)carbamoyl)benzyl)pyrrolidine-1-carboxylate (21-L2)

A solution of 21-L1 (150 mg, 0.21 mmol) in acetic anhydride (2 mL) was refluxed at 140° C. for 3 h. The solvent was removed under reduced pressure and the crude product was purified by column chromatography using 8% methanol in dichloromethane to furnish 21-L2. The compound was taken to the next step without further purification.

Step C 4-(((2S,5R)-5-((R)-hydroxy(6-(5-methyl-1,2,4-oxadiazol-3-yl)pyridin-3-yl)methyl)pyrrolidin-2-yl)methyl)-N-methyl-N-(pyridin-3-ylmethyl)benzamide, formic acid salt (21-L)

Compound 21-L was prepared from 21-L2 following an analogous procedure as described in the synthesis of 2-B from 2-B2.

$^1$H NMR (400 MHz, DMSO-$d_6$): δ 8.73 (s, 1H), 8.57 (bs, 1H), 8.50 (d, J=4.04 Hz, 1H), 8.20 (s, 1H), 8.03-8.01 (m, 1H), 7.97-7.94 (m, 1H), 7.7 (bs, 1H), 7.43-7.39 (m, 3H), 7.29-7.27 (m, 2H), 4.68 (bs, 1H), 4.52 (d, J=6.36 Hz, 1H), 3.34-3.28 (m, 2H), 2.89 (s, 3H), 2.73-2.68 (m, 5H), 1.66-1.63 (m, 1H), 1.51-1.42 (m, 3H). Molecular Formula: $C_{28}H_{30}N_6O_3$; LC-MS purity: 98%; Expected: 498.5; Observed: 499 (M+1).

Example 21-M

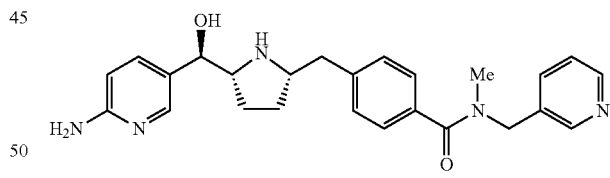

21-M

HCO$_2$H salt 4-(((2S,5R)-5-((R)-(6-aminopyridin-3-yl)(hydroxy)methyl)pyrrolidin-2-yl)methyl)-N-methyl-N-(pyridin-3-ylmethyl)benzamide (21-M)

Compound 21-M was prepared from the corresponding core acid following an analogous procedure as in the synthesis of 23-B.

Molecular Formula: $C_{25}H_{30}N_5O_2$; Expected: 432; Observed: 432 (M+1).

Example 21-N

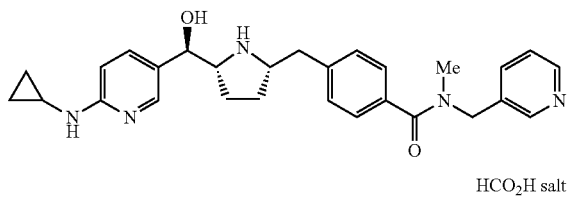

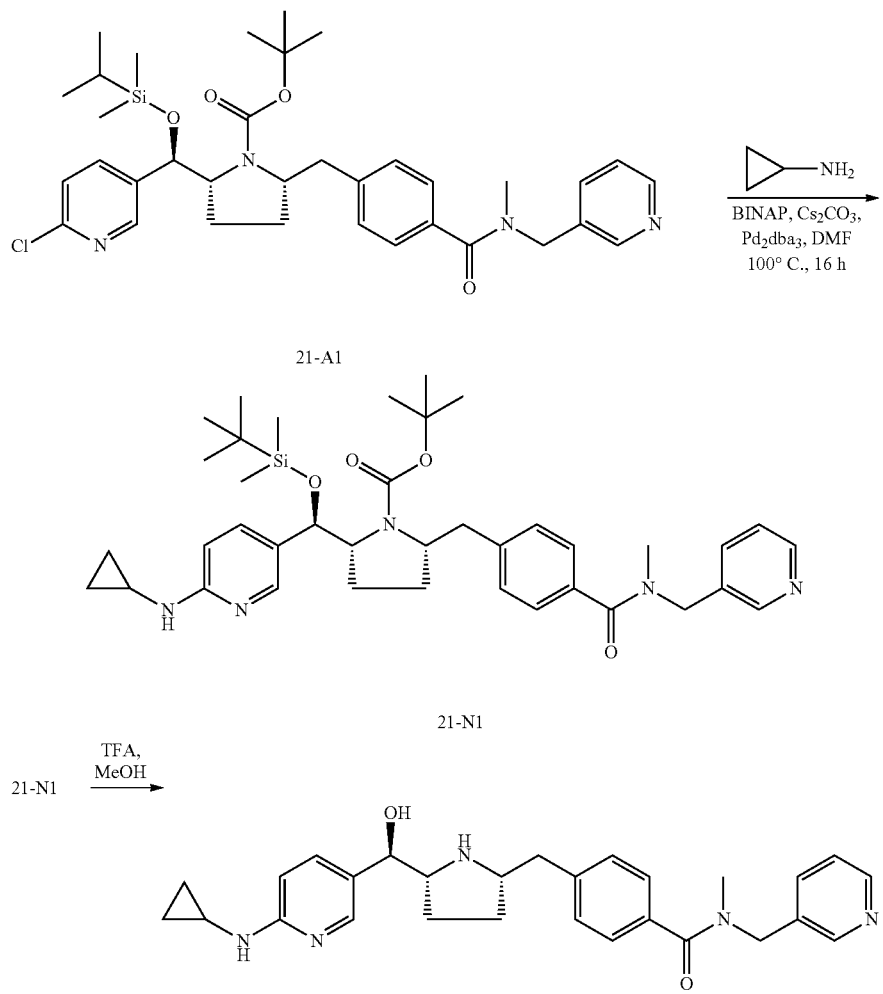

argon was bubbled for 10 min. BINAP (383 mg, 1.05 mmol) and Pd$_2$dba$_3$ (24 mg, 0.026 mmol) were added and the reaction mixture was stirred overnight at 100° C. The reaction mixture was cooled to room temperature and filtered through a celite bed. The filtrate was diluted with ethyl acetate, washed successively with water and brine. The organic layer was dried over anhydrous Na$_2$SO$_4$ and evaporated to dryness under reduced pressure. The crude product was purified by preparative HPLC to furnish the desired product 21-N1 (100 mg) as colorless liquid.

Molecular Formula: C$_{39}$H$_{55}$N$_5$O$_4$Si; LC-MS purity: 89%; Expected: 685.9; Observed: 686.4 (M+1).

Step A (2R,5S)-tert-butyl 2-((R)-((tert-butyldimethylsilyl)oxy)(6-(cyclopropylamino) pyridin-3-yl)methyl)-5-(4-(methyl(pyridin-3-ylmethyl)carbamoyl)benzyl) pyrrolidine-1-carboxylate (21-N1)

To a stirred solution of 21-A1 (350 mg, 0.78 mmol) in DMF (10 mL), cyclopropyl amine (0.7 mL) and Cs$_2$CO$_3$ (383 mg, 1.05 mmol) were added at room temperature and Step B 4-(((2S,5R)-5-((R)-(6-cyclopropylamino)pyridin-3-yl)(hydroxy)methyl) pyrrolidin-2-yl)methyl)-N-methyl-N-(pyridin-3-ylmethyl)benzamide, formic acid salt (21-N)

Compound 21-N was prepared from 21-N1 following an analogous procedure as disclosed in the synthesis of 21-I from 21-I1.

¹H NMR (400 MHz, DMSO-d₆): δ 9.47 (bs, 1H), 8.60-8.54 (m, 3H), 8.13 (s, 1H), 7.85-7.82 (m, 2H), 7.44-7.32 (m, 5H), 6.97 (d, J=8.90 Hz, 1H), 6.41 (bs, 1H), 4.71 (m, 2H), 4.52 (m, 1H), 3.68 (m, 2H), 3.16 (m, 1H), 2.96 (m, 1H), 2.88 (m, 3H), 2.63 (m, 1H), 1.92 (m, 1H), 1.72 (m, 3H), 0.87 (m, 2H), 0.56 (bs, 2H). Molecular Formula: $C_{28}H_{33}N_5O_2$; LC-MS purity: 97%; Expected: 471.5; Observed: 472.2 (M+1).

Example 21-O

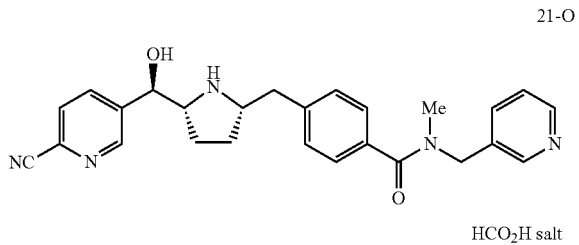 [SMILES: CN(Cc1cccnc1)C(=O)c1ccc(C[C@@H]2CC[C@H]([C@H](O)c3ccc(C#N)nc3)N2)cc1]

21-O
HCO₂H salt

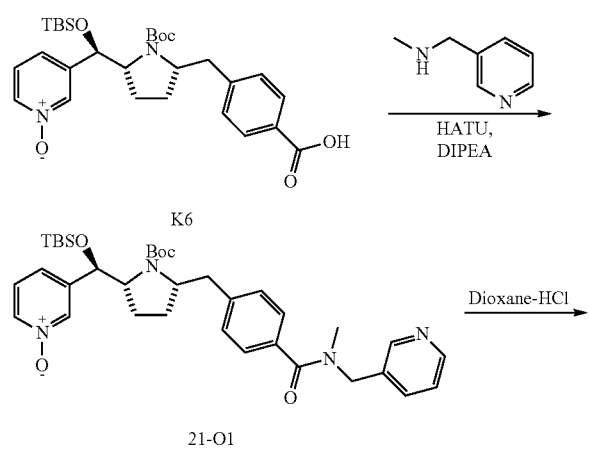

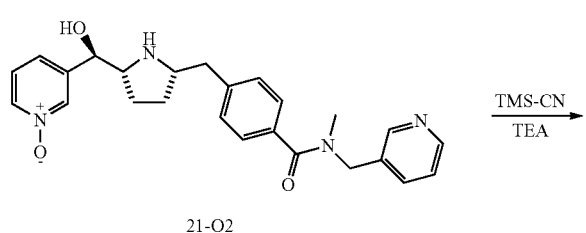

21-O

Step A 3-((R)-((2R,5S)-1-(tert-butoxycarbonyl)-5-(4-(methyl(pyridin-3-ylmethyl) carbamoyl)benzyl) pyrrolidin-2-yl)((tert-butyldimethylsilyl)oxy)methyl) pyridine1-oxide (21-O1)

Compound 21-O1 was prepared from K6 and 21 following an analogous procedure as outlined for the synthesis of 2-B1.

¹H NMR (300 MHz, CDCl₃): δ 8.56 (d, J=4.68 Hz, 2H), 8.29-8.27 (m, 1H), 8.19-8.15 (m, 1H), 7.78-7.75 (m, 1H), 7.32-7.23 (m, 5H), 7.03-7.01 (m, 1H), 4.89-4.85 (m, 1H), 4.29-4.27 (m, 1H), 4.09-4.05 (m, 1H), 3.89-3.85 (m, 1H), 3.69-3.62 (m, 3H), 3.15-3.08 (m, 3H), 2.95-2.90 (m, 2H), 1.66 (s, 9H), 1.57-1.52 (m, 3H), 0.94 (s, 9H), 1.12 (s, 3H), −0.03 (s, 3H). Molecular Formula: $C_{36}H_{51}N_4O_5Si$; LC-MS purity: 80.3%; Expected: 647.8; Observed: 648 (M+1).

Step B 3-((R)-hydroxy((2R,5S)-5-(4-(methyl(pyridin-3-ylmethyl)carbamoyl)benzyl) pyrrolidin-2-yl) methyl)pyridine 1-oxide (21-O2)

Compound 21-O2 was prepared from 21-O1 following an analogous procedure as outlined for the synthesis of 2-B from 2-B2.

¹H NMR (400 MHz, CD₃OD): δ 8.97-8.95 (m, 1H), 8.85-8.80 (m, 1H), 8.79-8.77 (m, 1H), 8.73-8.71 (m, 1H), 8.65-8.62 (m, 1H), 8.16-8.13 (m, 2H), 7.85-7.80 (m, 1H), 7.55-7.53 (m, 2H), 7.46-7.42 (m, 2H), 5.09-5.05 (m, 1H), 5.01-4.98 (m, 1H), 3.91-3.85 (m, 2H), 3.69-3.66 (m, 3H), 3.26-3.20 (m, 3H), 3.11 (s, 3H), 2.15-2.12 (m, 1H), 2.07-2.05 (m, 2H). Molecular Formula: $C_{25}H_{29}N_4O_3$; LC-MS purity: 90.9%; Expected: 433.5; Observed: 434 (M+1).

Step C 4-(((2S,5R)-5-((R)-(6-cyanopyridin-3-yl)(hydroxy)methyl)pyrrolidin-2-yl)methyl)-N-methyl-N-(pyridin-3-ylmethyl)benzamide, formic acid salt 21-O Compound 21-O was prepared from compound 21-O2 following an analogous procedure as outlined for the synthesis of K from K6.

¹H NMR (400 MHz, CD₃OD): δ 8.82 (s, 1H), 8.60 (s, 1H), 8.50 (s, 1H), 8.11 (d, J=8.20 Hz, 1H), 7.94-7.89 (m, 2H), 7.50-7.41 (m, 6H), 4.93-4.89 (m, 1H), 4.85-4.81 (m, 1H), 4.62 (s, 1H), 3.85-3.81 (m, 2H), 3.19-3.14 (m, 2H), 3.14-3.01 (m, 4H), 2.14-2.08 (m, 1H), 1.94-1.91 (m, 3H). Molecular Formula: $C_{26}H_{27}N_5O_2$; LC-MS purity: 96%; Expected: 441.5; Observed: 442 (M+1).

Example 21-P

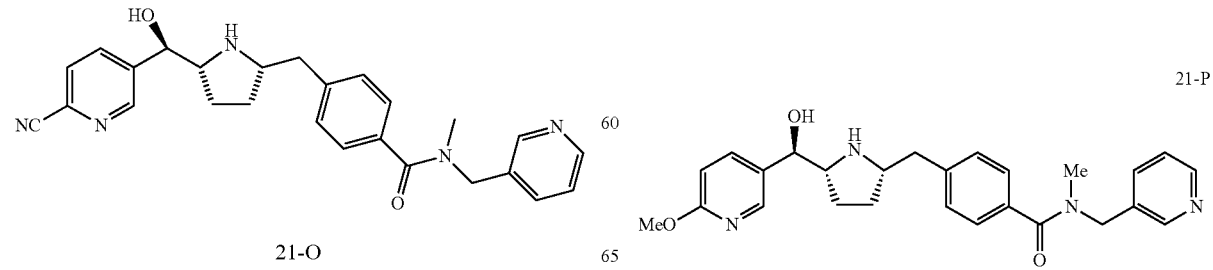

21-P

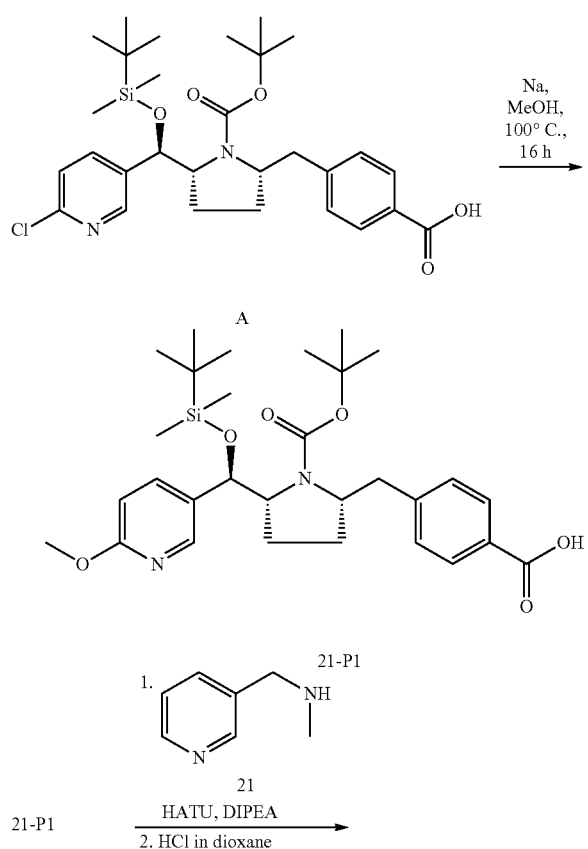

21-P1

Step A 4-(((2S,5R)-1-(tert-butoxycarbonyl)-5-((R)-((tert-butyldimethylsilyl)oxy)(6-methoxypyridin-3-yl)methyl)pyrrolidin-2-yl)methyl)benzoic acid (21-P1)

Sodium metal (400 mg) was added slowly in dry methanol (8 mL) to make freshly prepared NaOMe solution. Core Acid A (250 mg, 0.45 mmol) was added and the reaction mixture was stirred overnight at 100° C. The reaction mixture was evaporated to dryness under reduced pressure and the crude mass was purified by automated flash chromatography using 4-6% methanol in dichloromethane to furnish the desired product 21-P1 as pale yellow liquid.

$^1$H NMR (400 MHz, DMSO-$d_6$): δ 7.61-7.80 (m, 4H), 7.05-7.11 (m, 2H), 6.83-6.85 (m, 1H), 4.85-4.90 (m, 1H), 4.00-4.21 (m, 2H), 3.84 (s, 3H), 2.70-2.90 (m, 2H), 1.69-1.82 (m, 4H), 1.45 (bs, 9H), 0.89 (s, 9H), 0.09 (s, 3H), −0.07 (s, 3H). Molecular Formula: $C_{30}H_{44}N_2O_6Si$; LC-MS purity: 79.6%; Expected: 556.2; Observed: 557.2 (M+1).

Step B 4-(((2S,5R)-5-((R)-hydroxy(6-methoxypyridin-3-yl)methyl)pyrrolidin-2-yl)methyl)-N-methyl-N-(pyridin-3-ylmethyl)benzamide (21-P)

Compound 21-P was prepared from 21-P1 following an analogous protocol as disclosed in the synthesis of 4-E.

$^1$H NMR (400 MHz, CD$_3$OD): δ 8.60 (bs, 1H), 8.50 (bs, 1H), 8.13 (s, 1H), 7.90 (d, J=6.60 Hz, 1H), 7.72 (d, J=8.40 Hz, 1H), 7.48-7.39 (m, 5H), 6.81 (d, J=8.60 Hz, 1H), 4.81 (s, 1H), 4.63 (bs, 1H), 4.56 (d, J=8.00 Hz, 1H), 3.58-3.49 (m, 2H), 3.04-2.92 (m, 5H), 1.92 (m, 2H), 1.59 (m, 3H). Molecular Formula: $C_{26}H_{30}N_4O_3$; LC-MS purity: 95.6%; Expected: 446.5; Observed: 447.2 (M+1).

Example 21-R

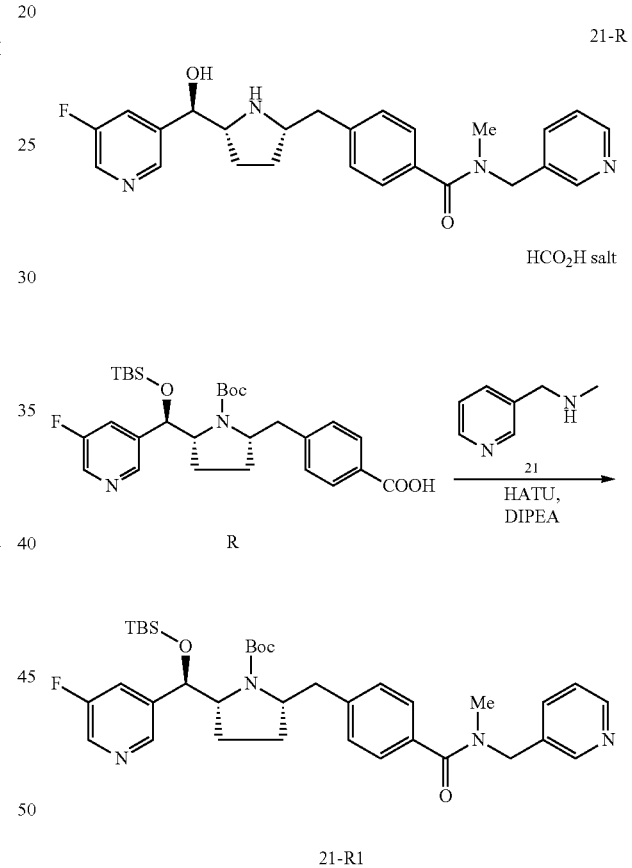

4-(((2S,5R)-5-((R)-(5-fluoropyridin-3-yl)(hydroxy)methyl)pyrrolidin-2-yl)methyl)-N-methyl-N-(pyridin-3-ylmethyl)benzamide, formic acid salt (21-R)

Compound 21-R was prepared in an analogous manner that is disclosed in Example 4-E.

$^1$H NMR (400 MHz, CD$_3$OD): δ 8.82-8.78 (m, 2H), 8.72-8.69 (m, 4H), 8.52-8.48 (m, 1H), 7.91-7.77 (m, 2H), 7.51-7.42 (m, 2H), 4.91 (s, 2H), 4.69 (s, 2H), 3.87-3.83 (m, 1H), 3.32-3.30 (m, 2H), 3.07 (s, 3H), 2.14-2.10 (m, 1H), 1.94-1.86 (m, 3H). Molecular Formula: C$_{25}$H$_{27}$FN$_4$O$_2$; LC-MS purity: 98.5%; Expected: 434.5; Observed: 435.3 (M+1).

Example 21-S

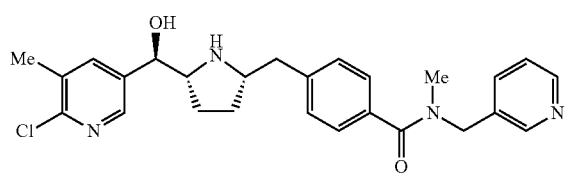

21-S

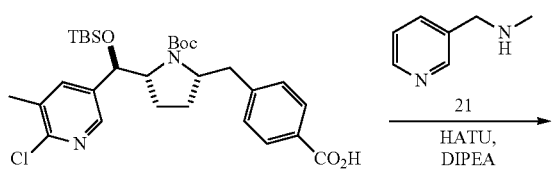

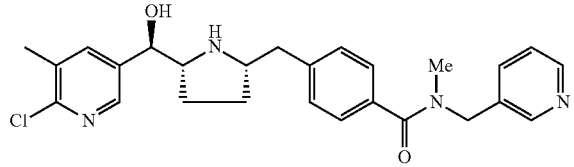

21-S 4-(((2S,5R)-5-((R)-(6-chloro-5-methylpyridin-3-yl)(hydroxy)methyl)pyrrolidin-2yl)methyl)-N-methyl-N-(pyridin-3-ylmethyl)benzamide (21-S)

Compound 21-S was prepared in an analogous manner of the chemical synthesis disclosed in Example 4-E.

$^1$H NMR (400 MHz, CD$_3$OD): δ 8.59 (s, 1H), 8.49 (s, 1H), 8.18 (s, 1H), 7.92 (s, 1H), 7.75 (s, 1H), 7.47-7.36 (m, 5H), 4.80 (s, 2H), 4.49 (d, J=6.60 Hz, 1H), 3.25 (d, J=7.30 Hz, 1H), 2.99 (s, 3H), 2.82 (d, J=6.80 Hz, 2H), 2.38 (s, 3H), 1.80 (s, 1H), 1.55-1.52 (m, 2H), 1.50-1.47 (m, 1H). Molecular Formula: C$_{26}$H$_{29}$ClN$_4$O$_2$; LC-MS purity: 98.1%; Expected: 465; Observed: 465 (M).

Example 22-A

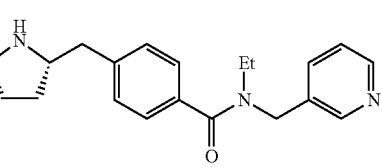

22-A

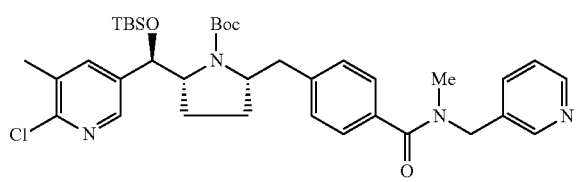

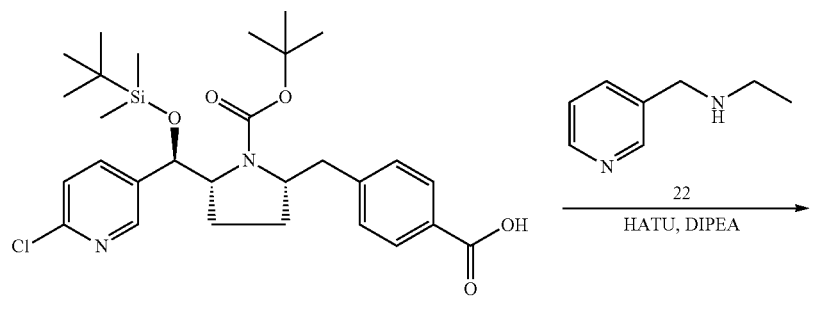

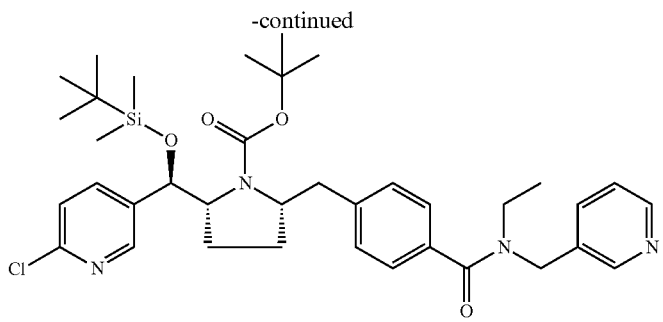

22-A1

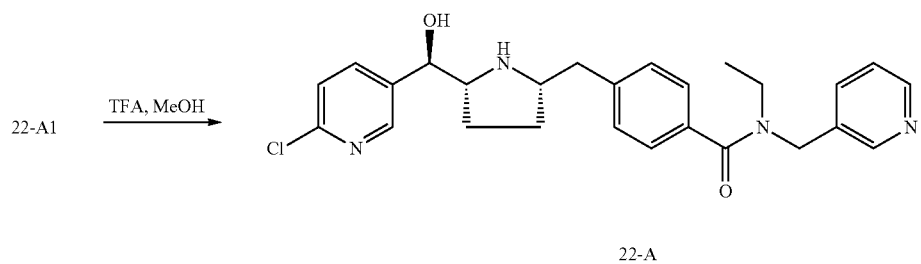

22-A

Step A (2R,5S)-tert-butyl 2-((R)-((tert-butyldimethylsilyl)oxy)(6-chloropyridin-3-yl)methyl)-5-(4-(ethyl(pyridin-3-ylmethyl)carbamoyl)benzyl)pyrrolidine-1-carboxylate (22-A1)

Compound 22-A1 was prepared in an analogous manner to that of the disclosed synthesis of compound 4-E1.

$^1$H NMR (300 MHz, DMSO-d$_6$): δ 8.50-8.63 (m, 2H), 8.25 (s, 1H), 8.01-8.09 (m, 1H), 7.72 (d, J=8.70 Hz, 2H), 7.56 (d, J=8.50 Hz, 1H), 7.32 (s, 2H), 7.06 (s, 2H), 5.76 (bs, 1H), 4.04-4.18 (m, 2H), 3.75-3.80 (m, 2H), 3.47 (bs, 2H), 1.82-1.89 (m, 2H), 1.51-1.54 (m, 2H), 1.41 (bs, 9H), 1.03 (bs, 3H), 0.87 (s, 9H), 0.10 (s, 3H), −0.09 (s, 3H). Molecular Formula: C$_{37}$H$_{51}$ClN$_4$O$_4$Si; LC-MS purity: 96.5%; Expected: 678.3; Observed: 679 (M+1).

Step B 4-(((2S,5R)-5-((R)-(6-chloropyridin-3-yl)(hydroxy)methyl)pyrrolidin-2-yl)methyl)-N-ethyl-N-(pyridin-3-ylmethyl)benzamide, formic acid salt (22-A)

Compound 22-A was prepared from 22-A1 following an analogous procedure as that disclosed for the synthesis of compound 21-I from compound 21-I1.

$^1$H NMR (400 MHz, DMSO-d$_6$): δ 8.58 (bs, 1H), 8.50 (d, J=4.40 Hz, 1H), 8.41 (bs, 1H), 8.19 (s, 1H), 7.84 (dd, J=1.60 and J=8.00 Hz, 1H), 7.74 (bs, 1H), 7.50 (d, J=8.00 Hz, 1H), 7.41-7.30 (m, 5H), 4.69 (bs, 1H), 4.56 (d, J=7.20 Hz, 1H), 3.37 (m, 3H), 2.86 (m, 1H), 2.76 (m, 1H), 1.72 (bs, 1H), 1.52 (m, 2H), 1.37 (m, 1H), 1.05 (bs, 3H). Molecular Formula: C$_{25}$H$_{26}$ClFN$_4$O$_2$; LC-MS purity: 96.5%; Expected: 464.9; Observed: 465.2 (M+1).

Example 22-B

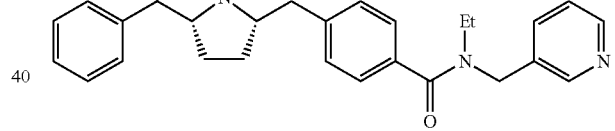

22-B

HCO$_2$H salt

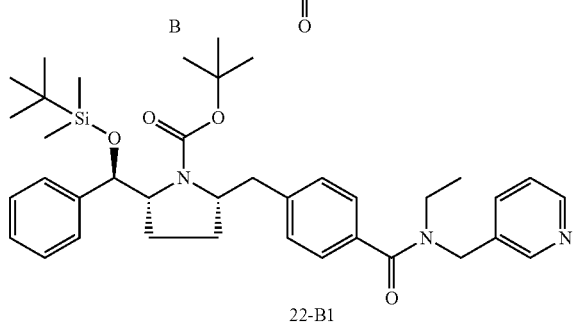

-continued

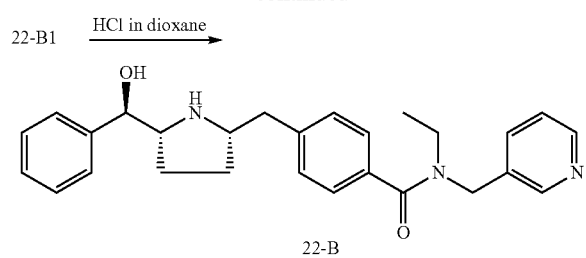

N-ethyl-4-(((2S,5R)-5-((R)-hydroxy(phenyl)methyl) pyrrolidin-2-yl)methyl)-N-(pyridin-3-ylmethyl)benzamide, formic acid salt (22-B)

Compound 22-B was prepared following an analogous procedure as that disclosed for the synthesis of Example 4-E.

$^1$H NMR (400 MHz, CD$_3$OD): δ 8.87 (bs, 1H), 8.75 (bs, 4H), 8.52 (bs, 1H), 8.00 (m, 1H), 7.48-7.34 (m, 12H), 4.75-4.72 (m, 2H), 3.81-3.79 (m, 2H), 3.45-3.44 (m, 2H), 3.30-3.20 (m, 1H), 3.12-3.05 (m, 1H), 2.12 (s, 1H), 1.85-1.81 (m, 3H), 1.19 (m, 3H). Molecular Formula: C$_{27}$H$_{31}$N$_3$O$_2$; LC-MS purity: 99.5%; Expected: 429.6; Observed: 430.2 (M+1).

Example 23-A

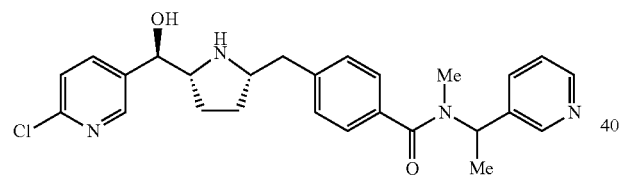

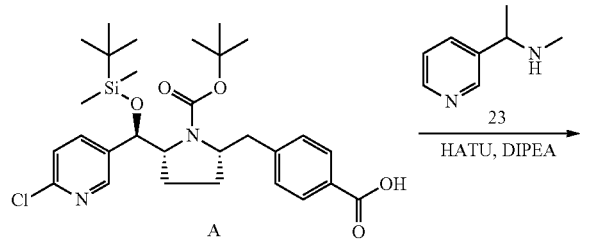

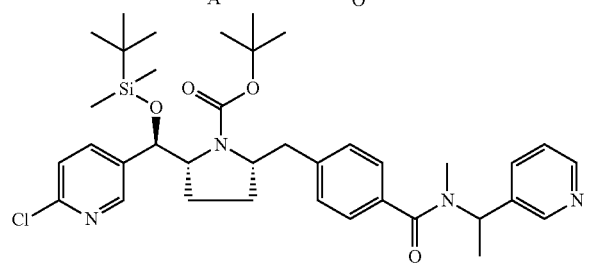

-continued

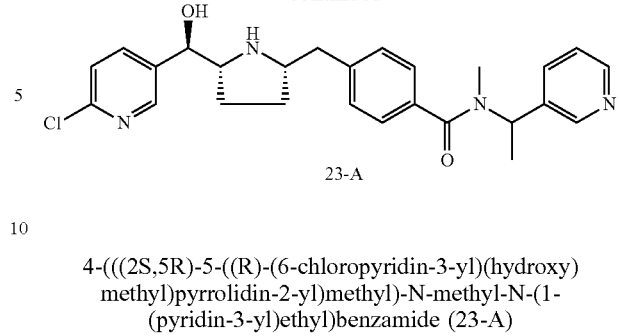

4-(((2S,5R)-5-((R)-(6-chloropyridin-3-yl)(hydroxy) methyl)pyrrolidin-2-yl)methyl)-N-methyl-N-(1-(pyridin-3-yl)ethyl)benzamide (23-A)

Compound 23-A was prepared in an analogous manner to that of compound 4-E.

$^1$H NMR (400 MHz, CD$_3$OD): δ 8.75 (bs, 1H), 8.63 (bs, 1H), 8.47 (d, J=4.00 Hz, 1H), 8.28 (bs, 1H), 7.93 (dd, J=2.40 and 8.40 Hz, 1H), 7.73 (bs, 1H), 7.53-7.42 (m, 5H), 3.87-3.81 (m, 2H), 3.25-3.20 (m, 1H), 3.13-3.05 (m, 1H), 2.84 (s, 3H), 2.12-2.09 (m, 1H), 1.92-1.84 (m, 3H), 1.75 (bs, 3H). Molecular Formula: C$_{26}$H$_{29}$ClN$_4$O$_2$; LC-MS purity: 97.9%; Expected: 464.9; Observed: 465.2 (M+1).

Example 23-B

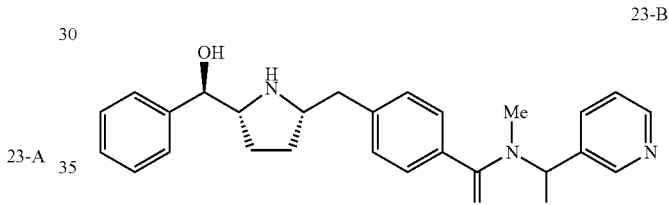

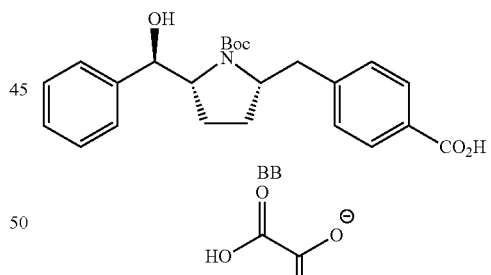

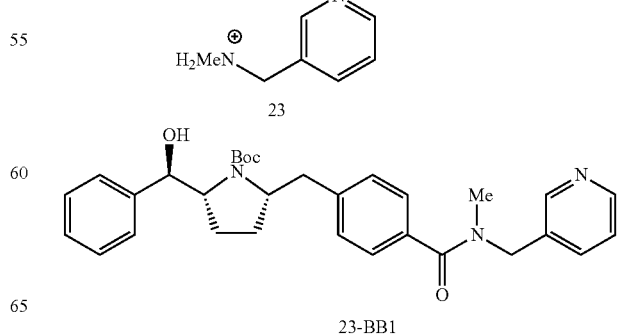

175

-continued

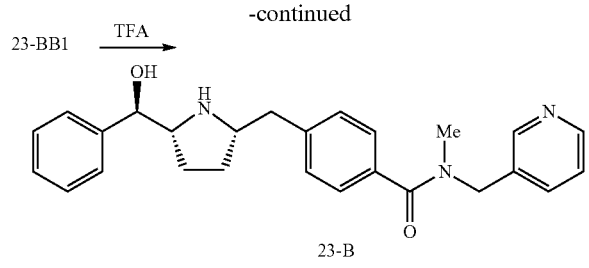

4-(((2S,5R)-5-((R)-hydroxy(phenyl)methyl)pyrrolidin-2-yl)methyl)-N-methyl-N-(1-(pyridin-3-yl)ethyl)benzamide, formic acid salt (23-B)

N-methyl-1-(pyridin-3-yl)ethanaminium carboxyformate (27.6 mg, 0.122 mmol) was added to a stirred, room temperature solution of 4-(((2S,5R)-1-(tert-butoxycarbonyl)-5-((R)-hydroxy(phenyl)methyl)pyrrolidin-2-yl)methyl)benzoic acid (0.050 g, 22 mmol) [BB], HATU (0.056 g, 0.15 mmol), and Hunig's base (0.107 mL, 0.610 mmol) in DMF (1.2 mL), and the mixture was stirred at room temperature overnight. The reaction was then concentrated in vacuo and the residue was taken up in a 3:3:1 mixture of ACN, TFA, water (1 mL:1 mL:0.33 mL), and then stirred at 55° C. overnight. The reaction mixture was then cooled to room temperature and concentrated in vacuo and purified by mass directed reverse phase chromatography using AcCN/water gradient with 0.1% formic acid modifier. Lyophilization of the desired fractions afforded the product as the formic acid salt. Molecular Formula: $C_{27}H_{32}N_3O_2$; Expected: 430; Observed: 430 (M+1).

Example 24-A

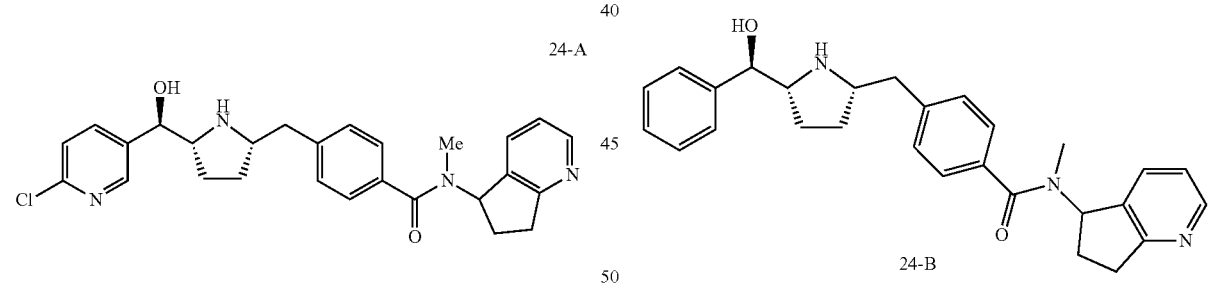

4-(((2S,5R)-5-((R)-(6-chloropyridin-3-yl)(hydroxy)methyl)pyrrolidin-2-yl)methyl)-N-(6,7-dihydro-5H-cyclopenta[b]pyridin-5-yl)-N-methylbenzamide (24-A)

Compound 24-A was prepared in an analogous manner to that disclosed in Example 4-E.

$^1$H NMR (400 MHz, DMSO-d$_6$): δ 8.40 (d, J=4.56 Hz, 1H), 8.35 (s, 1H), 7.78 (d, J=7.28 Hz, 1H), 7.67 (d, J=7.56 Hz, 1H), 7.44-7.41 (m, 3H), 7.27 (d, J=8.04 Hz, 2H), 7.24-7.21 (m, 1H), 6.13-6.1 (m, 1H), 5.37-5.25 (m, 1H), 4.37 (s, 1H), 3.31-3.17 (m, 2H), 3.11-2.98 (m, 2H), 2.68-2.67 (m, 2H), 2.64-2.62 (m, 5H), 1.61-1.57 (m, 1H), 1.41-1.28 (m, 3H). Molecular Formula: $C_{27}H_{29}N_4O_2$; LC-MS purity: 94.7%; Expected: 476; Observed: 477.4 (M+1).

176

Example 24-B

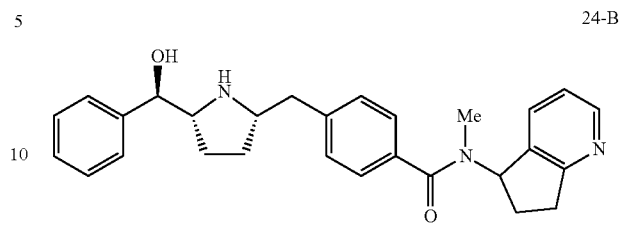

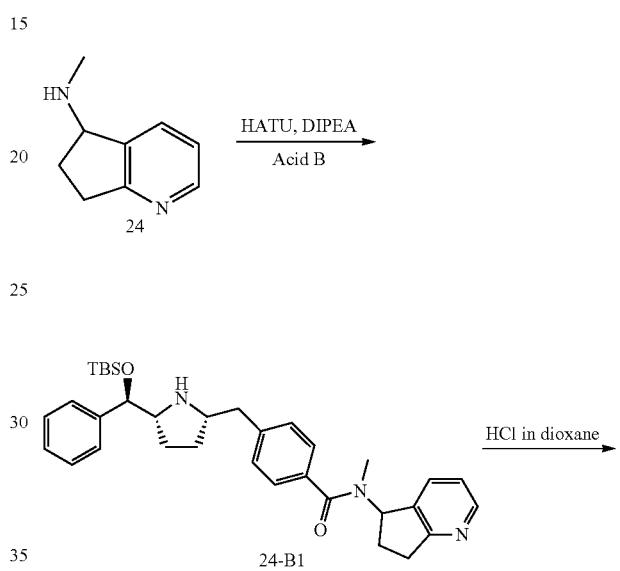

N-(6,7-dihydro-5H-cyclopenta[b]pyridin-5-yl)-4-(((2S,5R)-5-((R)-hydroxy(phenyl)methyl) pyrrolidin-2-yl)methyl)-N-methylbenzamide (24-B)

Compound 24-B was prepared in an analogous manner to that described in Example 4-E.

$^1$H NMR (400 MHz, DMSO-d$_6$): δ 8.43 (d, J=7.52 Hz, 1H), 7.69 (d, J=7.56 Hz, 1H), 7.42-7.29 (m, 2H), 7.25-7.21 (m, 8H), 5.3 (bs, 1H), 4.25-4.21 (m, 1H), 3.29-3.26 (m, 1H), 3.12-3.08 (m, 1H), 2.99-2.97 (m, 1H), 2.82-2.75 (m, 1H), 2.69-2.65 (m, 4H), 2.49-2.45 (m, 1H), 2.32-2.30 (m, 1H), 2.13-2.11 (m, 1H), 1.66-1.57 (m, 1H), 1.40-1.39 (m, 3H). Molecular Formula: $C_{29}H_{35}N_3O_2$; LC-MS purity: 98.6%; Expected: 441; Observed: 442.4 (M+1).

Example 25-A

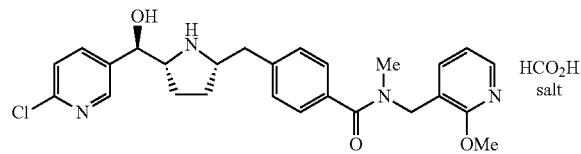

4-(((2S,5R)-5-((R)-(6-chloropyridin-3-yl)(hydroxy)
methyl)pyrrolidin-2-yl)methyl)-N-((2-methoxypyri-
din-3-yl)methyl)-N-methylbenzamide, formic acid
salt (25-A)

Compound 25-A was prepared in an analogous manner to that disclosed in Example 4-E.
$^1$H NMR (400 MHz, CD$_3$OD): δ 8.46 (bs, 2H), 8.08 (bs, 1H), 7.92 (d, J=8.40 Hz, 1H), 7.64-7.35 (m, 6H), 6.99 (dd, J=5.40 and J=6.80 Hz, 1H), 4.84 (bs, 1H), 4.72 (s, 1H), 4.50 (bs, 1H), 3.99 (bs, 1H), 3.86 (s, 1H), 3.81-3.77 (m, 2H), 3.22-3.15 (m, 1H), 3.06-3.03 (m, 1H), 2.99 (m, 4H), 2.10 (m, 1H), 1.86 (m, 3H). Molecular Formula: C$_{26}$H$_{29}$ClN$_4$O$_3$; LC-MS purity: 96.4%; Expected: 481; Observed: 481.2 (M+1).

Example 25-B

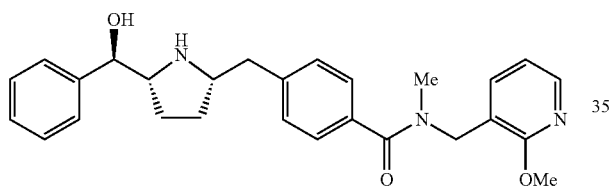

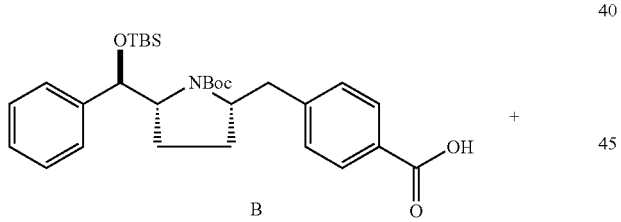

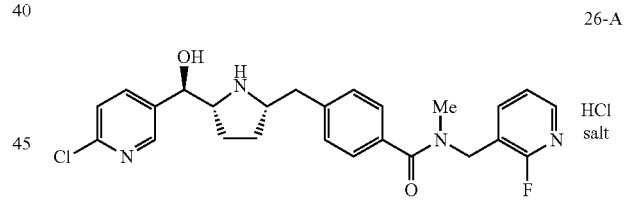

4-(((2S,5R)-5-((R)-hydroxy(phenyl)methyl)pyrroli-
din-2-yl)methyl)-N-((2-methoxypyridin-3-yl)
methyl)-N-methylbenzamide (25-B)

Compound 25-B was prepared in an analogous manner to that disclosed for compound 8-B.
$^1$H NMR (400 MHz, DMSO-d$_6$): δ 8.09 (s, 1H), 7.72-7.65 (m, 2H), 7.28-7.47 (m, 10H), 4.71 (d, J=8.00 Hz, 2H), 4.23 (s, 3H), 3.91 (s, 2H), 3.44-3.42 (m, 1H), 3.23-3.20 (m, 1H), 2.93 (s, 3H), 2.76-2.73 (m, 1H), 1.82-1.53 (m, 4H). Molecular Formula: C$_{27}$H$_{31}$N$_3$O$_3$; LC-MS purity: 95.6%; Expected: 445.2; Observed: 446.2 (M+1).

Example 26-A

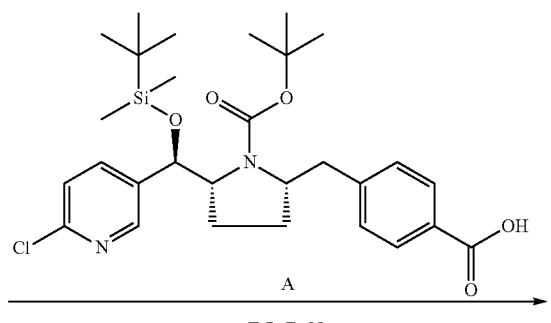

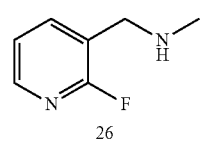

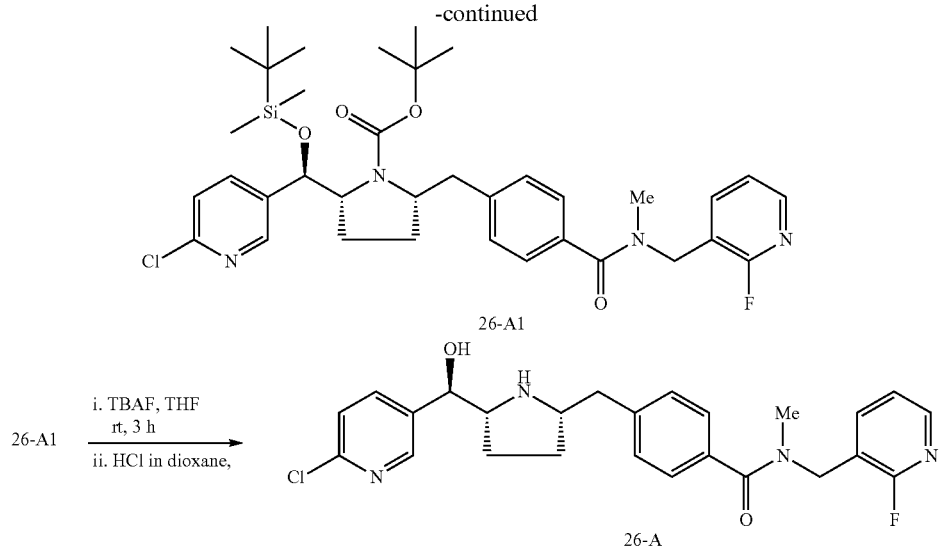

26-A1

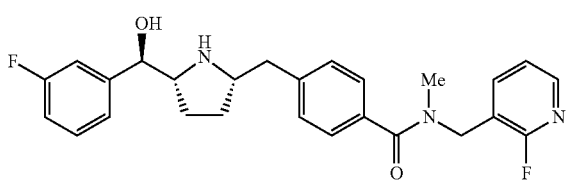

26-A

Step A (2R,5S)-tert-butyl 2-((R)-((tert-butyldimethylsilyl)oxy)(6-chloropyridin-3-yl)methyl)-5-(4-(((2-fluoropyridin-3-yl)methyl)(methyl)carbamoyl) benzyl) pyrrolidine-1-carboxylate (26-A1)

Compound 26-A1 was prepared from Core Acid A following an analogous procedure as disclosed in the synthesis of compound 5-A1.
Molecular Formula: $C_{36}H_{48}FClN_4O_4Si$; LC-MS purity: 70.5%; Expected: 683.3; Observed: 684.2 (M+1).

Step B 4-(((2S,5R)-5-((R)-(6-chloropyridin-3-yl)(hydroxy)methyl)pyrrolidin-2-yl) methyl)-N-((2-fluoropyridin-3-yl)methyl)-N-methylbenzamide, hydrochloride salt (26-A)

To a stirred solution of 26-A1 (100 mg, 0.145 mmol) in THF (1 mL) tetrabutyl ammoniumfluoride (0.29 mL, 0.29 mmol, 1M solution of THF) was added drop wise at 0° C. and the reaction mixture was stirred for 3 h at room temperature. The reaction mixture was concentrated under reduced pressure and the residue was dissolved in ethyl acetate. The ethyl acetate layer was washed with water and brine. The organic layer was dried over anhydrous $Na_2SO_4$ and concentrated under reduced pressure. The crude mass was purified by preparative HPLC to obtain the intermediate TBS-cleaved product (50 mg, LC purity 97.7%).
To the solution of the intermediate TBS-cleaved product in 1,4-dioxane (0.5 mL), HCl in 1,4-dioxane (5 mL) was added at 0° C. and stirred for 4 h at room temperature. The reaction mixture was concentrated and purified by short column chromatography using (silica gel 60-120) 20% methanol in dichloromethane to obtain the desired product 26-A as off-white solid.
$^1$H NMR (400 MHz, DMSO-$d_6$): δ 8.37 (d, J=2.10 Hz, 1H), 8.18 (d, J=4.20 Hz, 1H), 7.88 (m, 1H), 7.80 (dd, J=2.30 Hz and J=8.20 Hz, 1H), 7.45 (d, J=8.20 Hz, 1H), 7.40-7.28 (m, 5H), 5.40 (bs, 1H), 4.69 (bs, 2H), 4.39 (d, J=6.20 Hz, 1H), 3.26-3.17 (m, 2H), 2.93 (s, 3H), 2.66 (m, 2H), 1.59 (m, 1H), 1.38 (m, 2H). Molecular Formula: $C_{25}H_{26}ClFN_4O_2$; LC-MS purity: 95.6%; Expected: 469; Observed: 469.2 (M+1).

Example 26-C

26-C

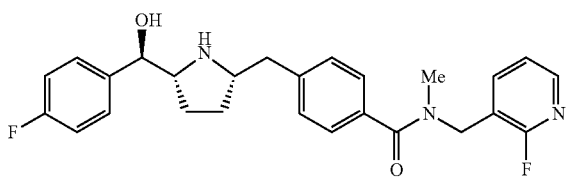

4-(((2S,5R)-5-((R)-(3-fluorophenyl)(hydroxy)methyl)pyrrolidin-2-yl)methyl)-N-((2-fluoropyridin-3-yl)methyl)-N-methylbenzamide (26-C)

Compound 26-C was prepared from Core Acid C and Amine 26 utilizing an analogous synthesis route to that disclosed in Example 4-E.
$^1$H NMR (400 MHz, DMSO-$d_6$): δ 8.17 (d, J=4.08 Hz, 1H), 7.88 (bs, 1H), 7.41-7.32 (m, 6H), 7.17-7.12 (m, 2H), 7.06-7.01 (m, 1H), 4.78-4.51 (m, 2H), 4.27 (d, J=6.76 Hz, 1H), 3.25-3.22 (m, 1H), 3.12-3.05 (m, 1H), 2.93 (s, 3H), 2.70-2.66 (m, 2H), 1.62-1.58 (m, 1H), 1.31-1.28 (m, 3H). Molecular Formula: $C_{25}H_{26}F_2N_4O_2$; LC-MS purity: 98.7%; Expected: 451.5; Observed: 454.

Example 26-F

26-F

4-(((2S,5R)-5-((R)-(4-fluorophenyl)(hydroxy)methyl)pyrrolidin-2-yl)methyl)-N-((2-fluoropyridin-3-yl)methyl)-N-methylbenzamide (26-F)

Compound 26-F was prepared from Core Acid F and Amine 26 in a similar manner as in the synthesis of Example 4-E.

$^{1}$H NMR (400 MHz, CD$_{3}$OD): δ 8.21-8.18 (m, 1H), 8.0-7.8 (m, 1H), 7.45-7.34 (m, 7H), 7.1 (t, J=8.32 Hz, 2H), 4.85-4.81 (m, 1H), 4.68-4.62 (m, 2H), 3.64-3.51 (m, 2H), 3.16-3.12 (m, 1H), 3.05-2.96 (m, 4H), 2.82-2.78 (m, 1H), 2.72-2.68 (m, 1H), 2.08-1.95 (m, 1H), 1.83-1.66 (m, 3H). Molecular Formula: C$_{26}$H$_{27}$F$_{2}$N$_{3}$O$_{2}$; LC-MS purity: 96.6%; Expected: 451.2; Observed: 452.2 (M+1).

Example 26-H

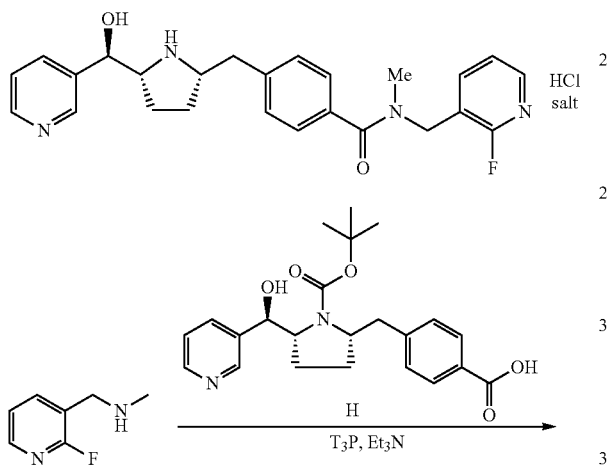

26-H1

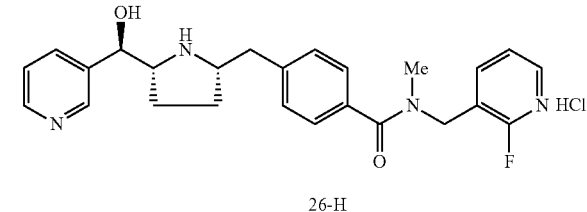

N-((2-fluoropyridin-3-yl)methyl)-4-(((2S,5R)-5-((R)-hydroxy(pyridin-3-yl)methyl) pyrrolidin-2-yl)methyl)-N-methylbenzamide, hydrochloride salt (26-H)

The compound 26-H was prepared in the manner as in example 5-A.

$^{1}$H NMR (400 MHz, DMSO-d$_{6}$): δ 8.58 (s, 1H), 8.48 (d, J=4.60 Hz, 1H), 8.18 (d, J=3.00 Hz, 1H), 7.89 (bs, 1H), 7.77 (d, J=7.50 Hz, 1H), 7.41-7.32 (m, 6H), 4.70 (bs, 1H), 4.56 (bs, 2H), 3.41 (m, 1H), 2.89 (m, 4H), 2.82 (m, 1H), 1.74 (m, 1H), 1.54-1.45 (m, 3H). Molecular Formula: C$_{25}$H$_{27}$FN$_{4}$O$_{2}$; LC-MS purity: 95%; Expected: 434.2; Observed: 435.2 (M+1).

Example 27A

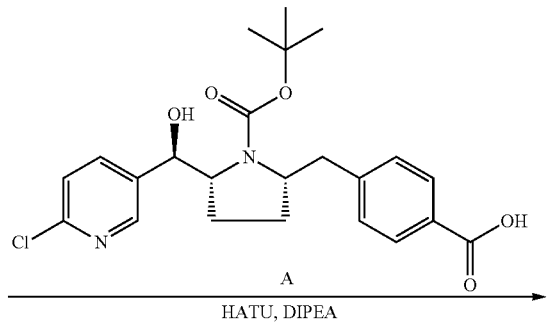

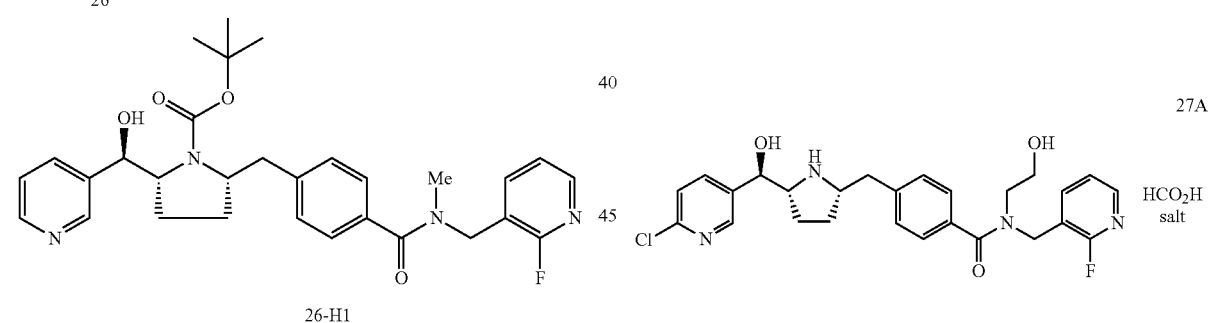

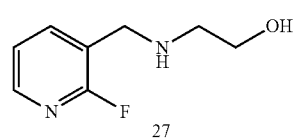

-continued

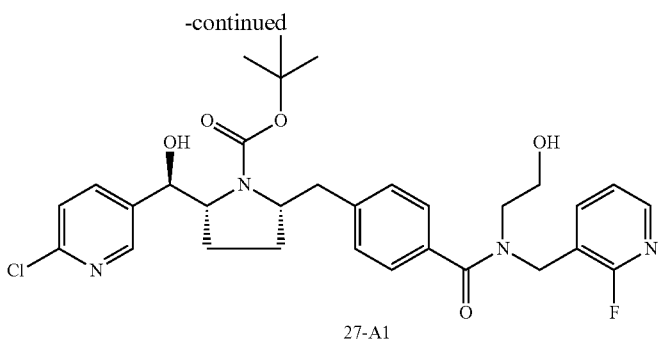

27-A1

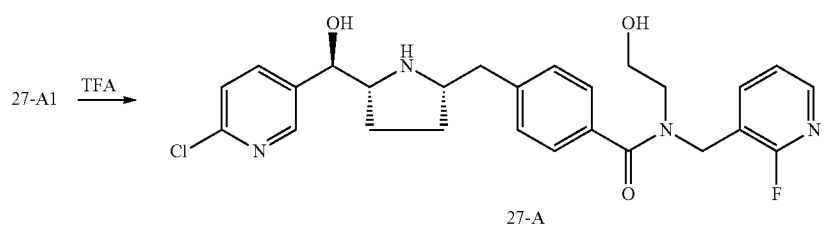

27-A

Step A (2R,5S)-tert-butyl 2-((R)-(6-chloropyridin-3-yl)(hydroxy)methyl)-5-(4-(((2-fluoropyridin-3-yl)methyl)(2-hydroxyethyl)carbamoyl)benzyl)pyrrolidine-1-carboxylate (27A1)

Compound 27-A1 was prepared from Amine A27 following an analogous procedure as disclosed for the synthesis of 4-E1.
Molecular Formula: $C_{31}H_{36}ClFN_4O_5$; LC-MS purity: 95.6%; Expected: 598.1; Observed: 599.1 (M+1).

Step B 4-(((2S,5R)-5-((R)-(6-chloropyridin-3-yl)(hydroxy)methyl)pyrrolidin-2-yl)methyl)-N-((2-fluoropyridin-3-yl)methyl)-N-(2-hydroxyethyl)benzamide, formic acid salt (27-A)

Compound 27-A was prepared from 27-A1 following an analogous procedure as disclosed for the synthesis of 21-I from 21-I1.
$^1$H NMR (400 MHz, CD$_3$OD): δ 8.47 (bs, 2H), 8.14 (bs, 1H), 8.01-7.91 (m, 2H), 7.52-7.51 (m, 2H), 7.41-7.34 (m, 3H), 4.83 (m, 2H), 4.72 (bs, 1H), 3.82-3.79 (m, 2H), 3.64 (m, 2H), 3.49 (m, 1H), 3.17-3.14 (m, 1H), 3.08-3.00 (m, 1H), 2.12-2.10 (m, 1H), 1.86 (m, 3H). Molecular Formula: $C_{26}H_{28}ClFN_4O_3$; LC-MS purity: 97.7%; Expected: 499; Observed: 499.2 (M+1).

Example 27-H

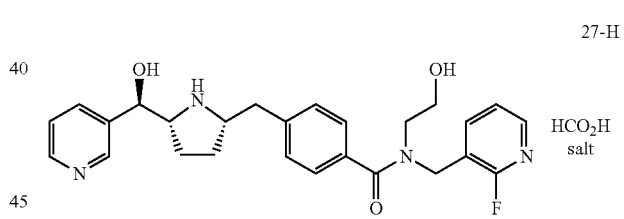

27-H

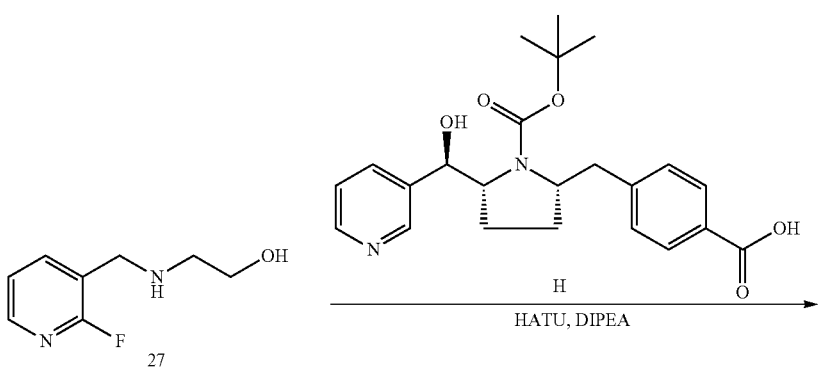

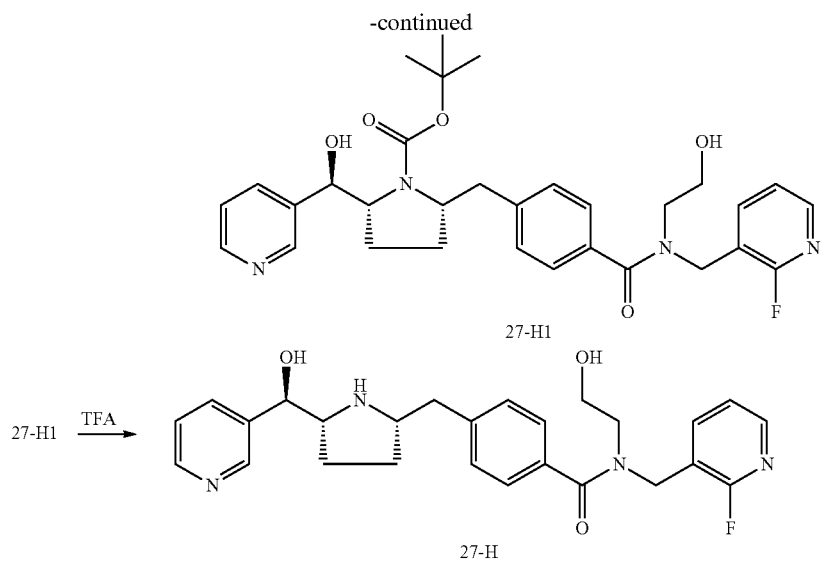

27-H1

N-((2-fluoropyridin-3-yl)methyl)-4-(((2S,5R)-5-((R)-hydroxy(pyridin-3-yl)methyl) pyrrolidin-2-yl)methyl)-N-(2-hydroxyethyl)benzamide, formic acid salt (27-H)

Compound 27-H was prepared in a manner analogous to that disclosed in Example 27-A.

$^1$H NMR (400 MHz, CD$_3$OD): δ 8.58 (bs, 1H), 8.49 (d, J=3.70 Hz, 1H), 8.23 (bs, 1H), 8.16-8.11 (m, 2H), 7.92 (m, 1H), 7.78-7.72 (m, 2H), 7.43-7.30 (m, 5H), 4.78-4.72 (m, 2H), 4.60-4.52 (m, 2H), 4.30 (bs, 1H), 3.80 (m, 1H), 3.71-3.30 (m, 4H), 2.91 (m, 1H), 2.80 (m, 1H), 1.75 (m, 1H), 1.54-1.46 (m, 3H). Molecular Formula: C$_{26}$H$_{29}$FN$_4$O$_3$; LC-MS purity: 99.5%; Expected: 464.5; Observed: 465.2 (M+1).

Example 28-A

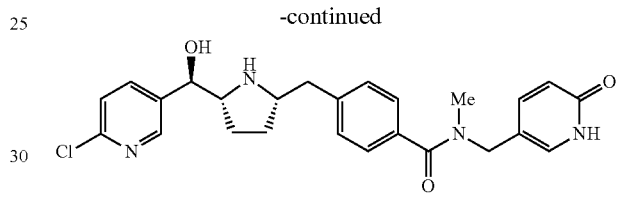

28-A 4-(((2S,5R)-5-((R)-(6-chloropyridin-3-yl)(hydroxy)methyl)pyrrolidin-2-yl)methyl)-N-methyl-N-((6-oxo-1,6-dihydropyridin-3-yl)methyl)benzamide, hydrochloride salt (28-A)

Compound 28-A was prepared in an analogous manner to that describe in Example 8-B.

$^1$H NMR (400 MHz, DMSO-d$_6$): δ 9.51 (s, 1H), 8.90 (s, 1H), 8.47 (d, J=4.00 Hz, 1H), 7.91 (d, J=4.00 Hz, 1H), 7.56 (d, J=8.00 Hz, 1H), 7.40-7.32 (m, 6H), 6.39 (d, J=12.00 Hz, 1H), 4.90 (d, J=8.00 Hz, 2H), 3.73 (s, 2H), 3.75-3.67 (m, 1H), 3.36-3.15 (m, 2H), 2.80 (s, 3H), 1.92-1.87 (m, 1H), 1.76-1.67 (m, 3H). Molecular Formula: C$_{25}$H$_{27}$ClN$_4$O$_3$; LC-MS purity: 98.3%; Expected: 466.2; Observed: 467.1 (M+1).

Example 28-C

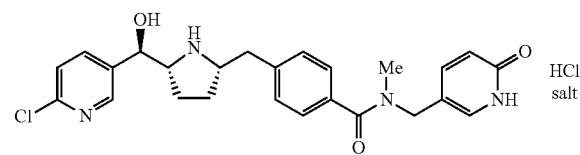

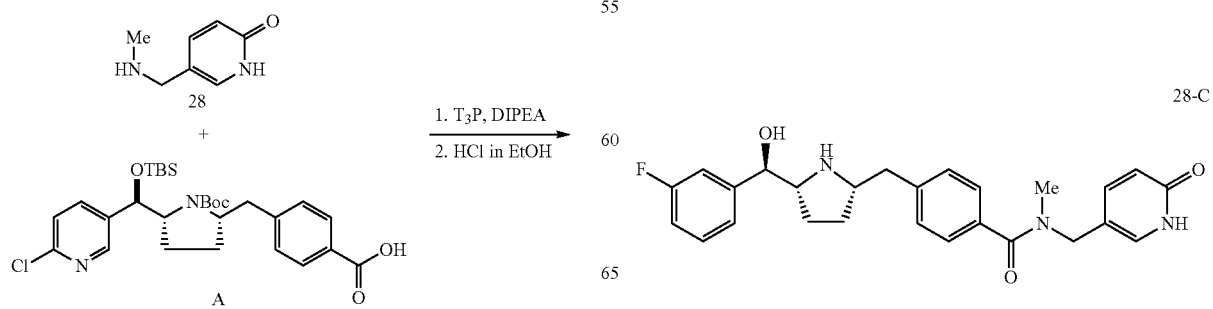

28-C 4-(((2S,5R)-5-((R)-(3-fluorophenyl)(hydroxy)methyl)pyrrolidin-2-yl)methyl)-N-methyl-N-((6-oxo-1,6-dihydropyridin-3-yl)methyl)benzamide (29-C)

Compound 28-C was prepared in a manner analogous to that describe in Example 20-E.

$^1$H NMR (400 MHz, CD$_3$OD): δ 7.77-7.65 (m, 1H), 7.56-7.37 (m, 5H), 7.30-7.19 (m, 2H), 7.12-7.05 (m, 1H), 6.62-6.56 (m, 1H), 4.82 (d, J=8.42 Hz, 1H), 4.53 (s, 2H), 4.82 (d, J=8.42 Hz, 1H), 4.53 (s, 2H), 3.86-3.71 (m, 2H), 3.35-3.30 (m, 1H), 3.24-3.19 (m, 1H), 3.08-2.94 (m, 3H), 2.57-2.50 (m, 4H), 2.17-2.05 (m, 1H), 1.20-1.16 (m, 3H). Molecular Formula: C$_{26}$H$_{28}$FN$_3$O$_3$; LC-MS purity: 99.4%; Expected: 449.2; Observed: 450.2 (M+1).

Example 28-F

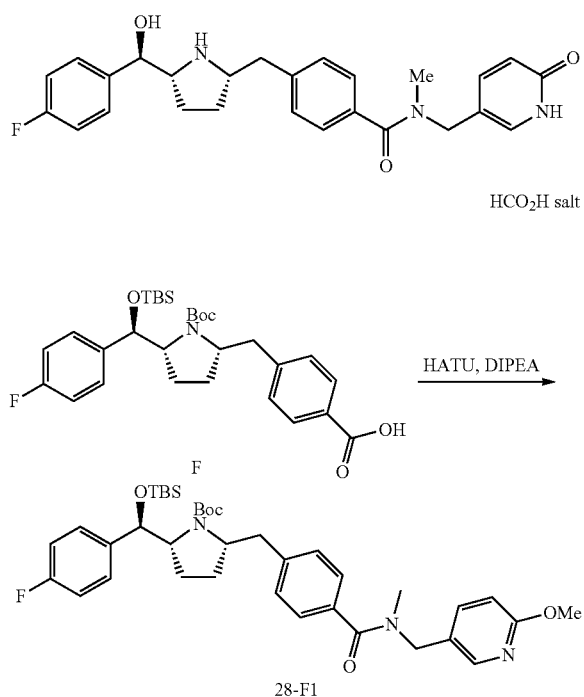

28-F

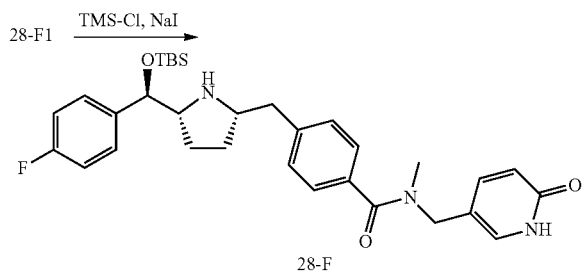

28-F 4-(((2S,5R)-5-((R)-(4-fluorophenyl)(hydroxy)methyl)pyrrolidin-2-yl)methyl)-N-methyl-N-((6-oxo-1,6-dihydropyridin-3-yl)methyl)benzamide, formic acid salt (28-F)

Compound 28-F was prepared in a manner analogous to that disclosed in Example 20-E.

$^1$H NMR (400 MHz, CD$_3$OD): δ 7.70 (d, J=9.20 Hz, 1H), 7.49-7.40 (m, 7H), 7.14 (t, J=8.70 Hz, 2H), 6.58 (d, J=9.80 Hz, 1H), 4.74 (d, J=8.60 Hz, 1H), 4.53 (s, 2H), 3.82-3.74 (m, 2H), 3.23-3.18 (m, 1H), 3.08-3.0 (m, 1H), 2.94 (s, 3H), 2.10-2.06 (m, 1H), 1.86-1.78 (m, 3H). Molecular Formula: C$_{26}$H$_{28}$FN$_3$O$_3$; LC-MS purity: 99.4%; Expected: 449.2; Observed: 450.2 (M+1).

Example 29-A

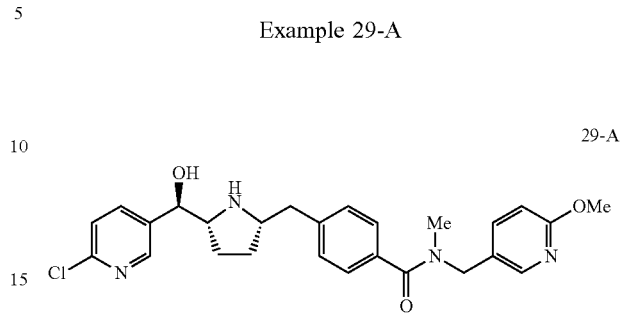

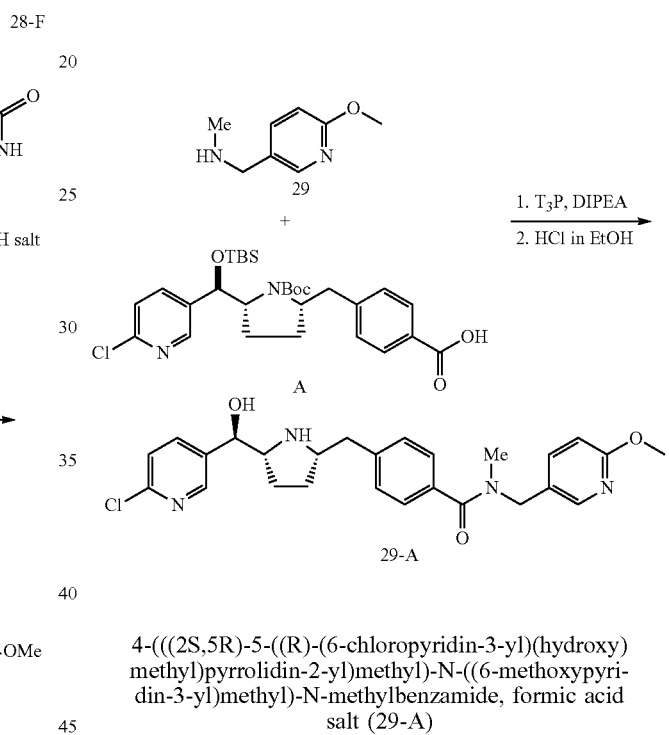

4-(((2S,5R)-5-((R)-(6-chloropyridin-3-yl)(hydroxy)methyl)pyrrolidin-2-yl)methyl)-N-((6-methoxypyridin-3-yl)methyl)-N-methylbenzamide, formic acid salt (29-A)

Compound 29-A was prepared in an analogous manner to that described in Example 8-B.

$^1$H NMR (400 MHz, CD$_3$OD): δ 8.47 (d, J=4.00 Hz, 1H), 8.16 (s, 1H), 7.93-7.91 (m, 1H), 7.77-7.75 (m, 1H), 7.52 (d, J=8.00 Hz, 1H), 7.46 (d, J=8.00 Hz, 2H), 7.40-7.42 (m, 2H), 6.86-6.84 (m, 1H), 4.86-4.84 (m, 2H), 4.69 (s, 1H), 4.50 (s, 1H), 3.91 (s, 3H), 3.84-3.82 (m, 2H), 2.13-2.11 (m, 1H), 1.89-1.87 (m, 3H). Molecular Formula: C$_{26}$H$_{29}$ClN$_4$O$_3$; LC-MS purity: 99.4%; Expected: 481; Observed: 482.2 (M+1).

Example 29-B

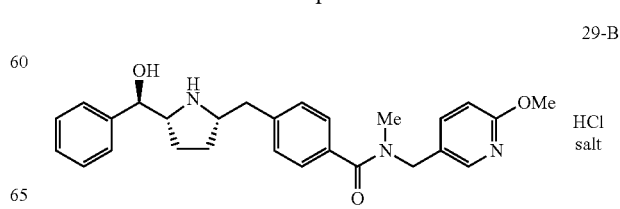

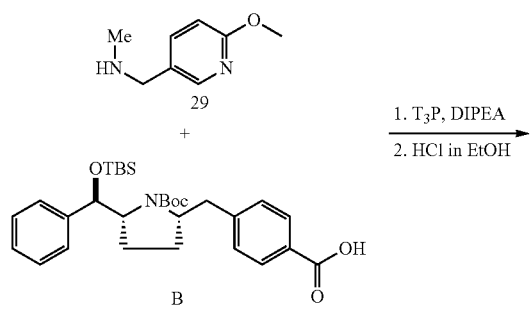
4-(((2S,5R)-5-((R)-hydroxy(phenyl)methyl)pyrrolidin-2-yl)methyl)-N-((6-methoxypyridin-3-yl)methyl)-N-methylbenzamide, hychloride salt (29-B)
Compound 29-B was prepared in an analogous manner to that described in example 8-B.
$^1$H NMR (400 MHz, DMSO-$d_6$): δ 9.47 (s, 1H), 8.77 (s, 1H), 7.67 (t, J=8.00 Hz, 1H), 7.46-7.27 (m, 10H), 6.90 (d, J=8.00 Hz, 1H), 6.71 (d, J=8.00 Hz, 1H), 4.74 (d, J=8.00 Hz, 2H), 3.91 (s, 3H), 3.21-3.15 (m, 1H), 3.05-2.90 (m, 2H), 2.93 (s, 2H), 2.87 (s, 3H), 1.88-1.86 (m, 1H), 1.68-1.55 (m, 3H). Molecular Formula: $C_{27}H_{31}N_3O_3$; LC-MS purity: 96.1%; Expected: 445.2; Observed: 446.2 (M+1).
Example 30-A
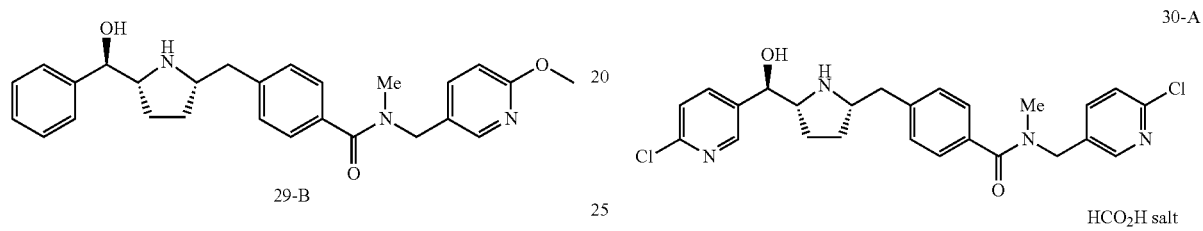
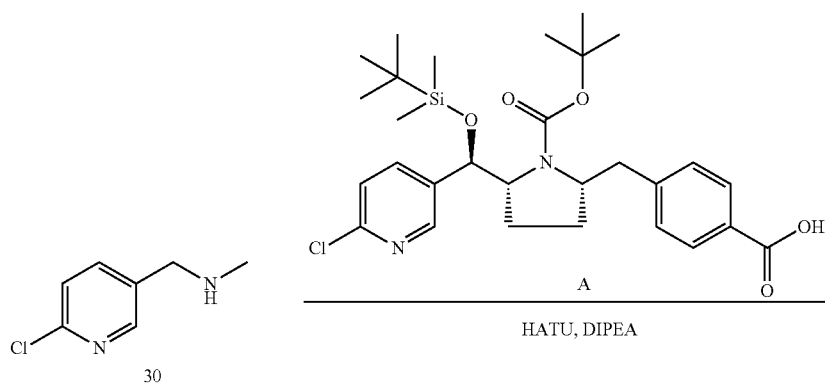
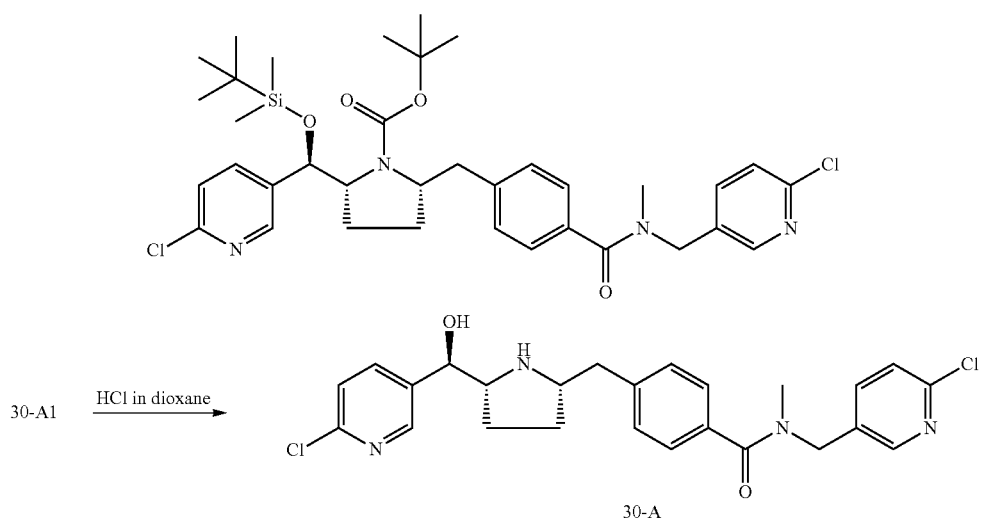

4-(((2S,5R)-5-((R)-(6-chloropyridin-3-yl)(hydroxy)methyl)pyrrolidin-2-yl)methyl)-N-((6-chloropyridin-3-yl)methyl)-N-methylbenzamide, formic acid salt (30-A)

Example 30-B

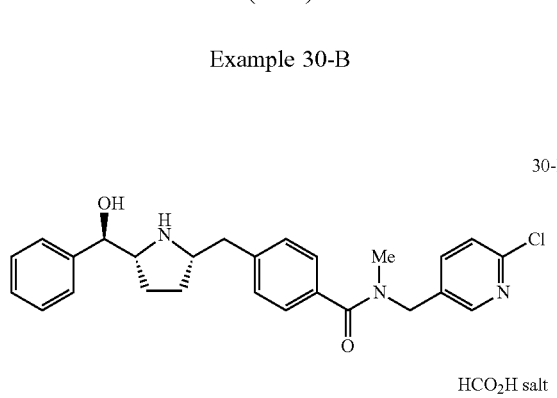

N-((6-chloropyridin-3-yl)methyl)-4-(((2S,5R)-5-((R)-hydroxy(phenyl)methyl)pyrrolidin-2-yl)methyl)-N-methylbenzamide, formic acid salt (30-B)

Compound 30-B was prepared in an analogous manner to that described for the synthesis of Example 4-E.

$^1$H NMR (400 MHz, CD$_3$OD): δ 8.42 (bs, 1H), 7.88 (d, J=7.60 Hz, 1H), 7.48-7.32 (m, 11H), 4.85 (bs, 1H), 4.73 (d, J=8.80 Hz, 2H), 4.60 (s, 1H), 3.26-3.18 (m, 1H), 3.08-3.03 (m, 1H), 2.98 (bs, 3H), 2.09-2.05 (m, 1H), 1.84-1.80 (m, 3H). Molecular Formula: C$_{26}$H$_{28}$ClN$_3$O$_2$; LC-MS purity: 97.1%; Expected: 449.2; Observed: 450 (M+1).

Example 30-F

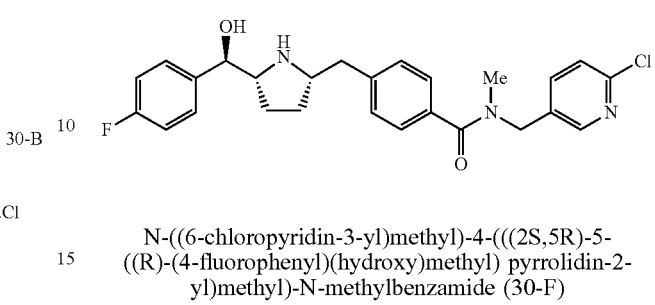

N-((6-chloropyridin-3-yl)methyl)-4-(((2S,5R)-5-((R)-(4-fluorophenyl)(hydroxy)methyl) pyrrolidin-2-yl)methyl)-N-methylbenzamide (30-F)

Compound 30-F was prepared in an analogous manner to that described for the synthesis of Example 4-E.

$^1$H NMR (400 MHz, CD$_3$OD): δ 8.43 (s, 1H), 7.97-7.8 (m, 1H), 7.91-7.85 (m, 1H), 7.52-7.45 (m, 3H), 7.42-7.35 (m, 2H), 7.13 (t, J=8.40 Hz, 2H), 4.9-4.73 (m, 2H), 3.8-3.71 (m, 3H), 3.26-3.20 (m, 2H), 3.12-3.05 (m, 2H), 3.02-2.96 (m, 2H), 2.15-2.05 (m, 1H), 1.87-1.78 (m, 3H). Molecular Formula: C$_{26}$H$_{27}$ClFN$_3$O$_2$; LC-MS purity: 95.6%; Expected: 467.2; Observed: 468.2 (M+1).

Example 31-A

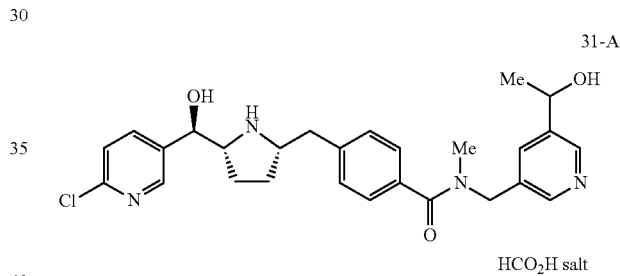

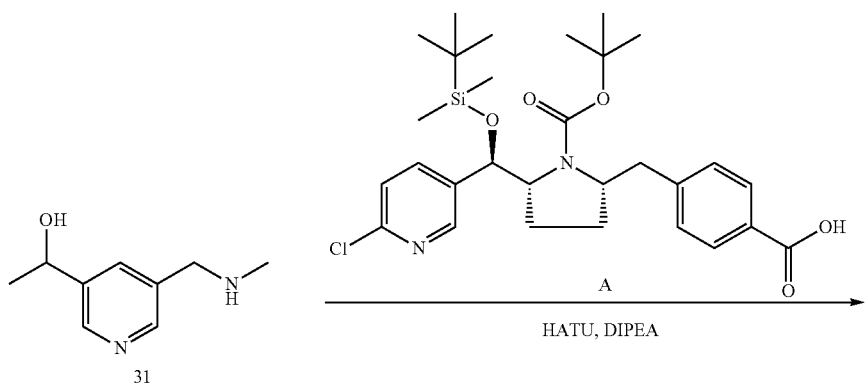

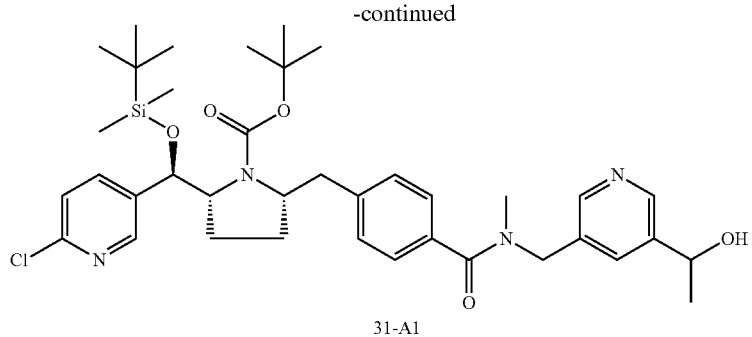

31-A1

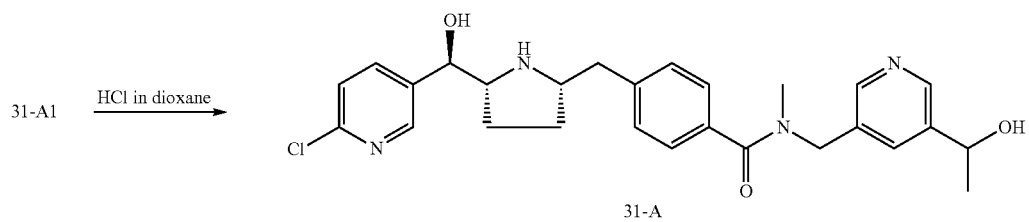

31-A ((((2S,5R)-5-((R)-(6-chloropyridin-3-yl)(hydroxy)methyl)pyrrolidin-2-yl)methyl)-N-((5-(1-hydroxyethyl)pyridin-3-yl)methyl)-N-methylbenzamide, formic acid salt (31-A)

Compound 31-A was prepared in an analogous manner to that described for the synthesis of Example 4-E.

$^1$H NMR (400 MHz, CD$_3$OD): δ 8.51-8.47 (m, 2H), 8.25 (s, 2H), 7.92-7.91 (m, 1H), 7.53-7.41 (m, 5H), 4.90 (s, 1H), 4.85-4.82 (m, 2H), 4.65 (s, 1H), 3.84-3.82 (m, 2H), 3.25-3.20 (m, 1H), 3.10-3.05 (m, 1H), 2.98 (s, 3H), 2.20-2.10 (m, 1H), 1.87-1.85 (m, 3H), 1.49 (d, J=6.40 Hz, 3H). Molecular Formula: C$_{27}$H$_{31}$ClN$_4$O$_3$; LC-MS purity: 99.3%; Expected: 495; Observed: 496.2 (M+1).

Example 31-B 4-(((2S,5R)-5-((R)-hydroxy(phenyl)methyl)pyrrolidin-2-yl)methyl)-N-((5-(1-hydroxyethyl)pyridin-3-yl)methyl)-N-methylbenzamide, formic acid salt (31-B)

Compound 31-B was prepared in an analogous manner to that described for the synthesis of Example 4-E.

$^1$H NMR (400 MHz, CD$_3$OD): δ 8.50-8.48 (m, 2H), 7.90 (bs, 1H), 7.50-7.32 (m, 8H), 4.78 (bs, 1H), 4.72 (d, J=8.80 Hz, 1H), 4.63 (s, 1H), 3.79-3.77 (m, 2H), 3.20-3.13 (m, 1H), 3.03-2.98 (m, 1H), 2.82 (s, 3H), 2.09-2.05 (m, 1H), 1.83-1.82 (m, 3H), 1.49 (d, J=8.00 Hz, 3H). Molecular Formula: C$_{28}$H$_{33}$N$_3$O$_3$; LC-MS purity: 97.3%; Expected: 459.6; Observed: 461.2 (M+1).

Example 32-A

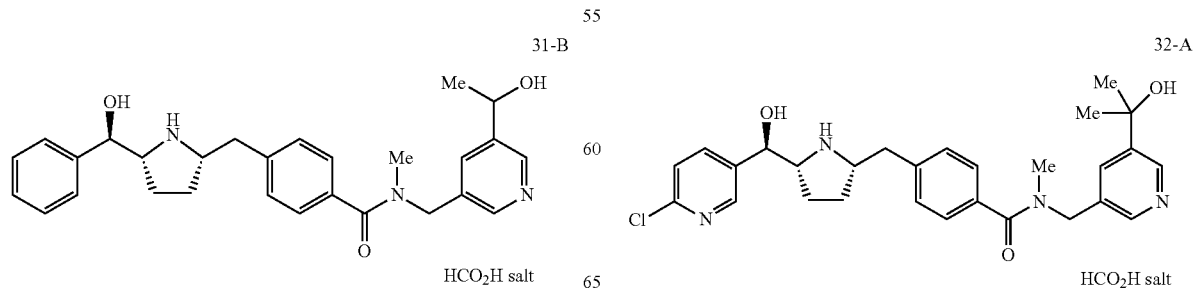

31-B

32-A

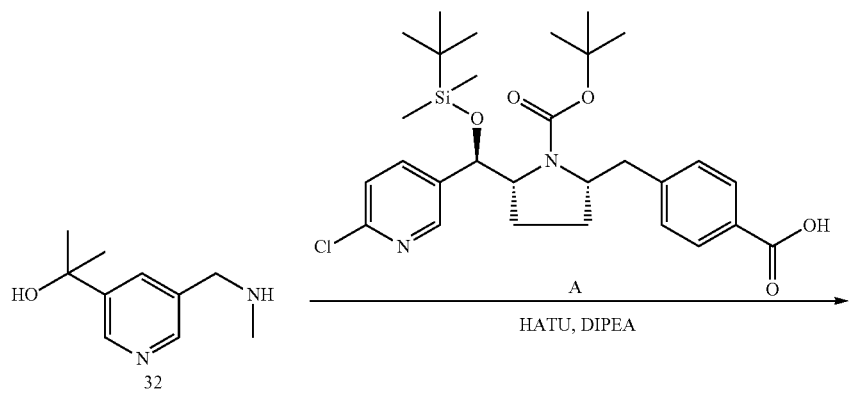

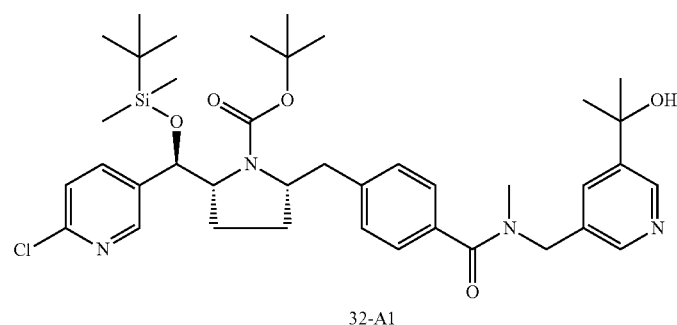

32-A1

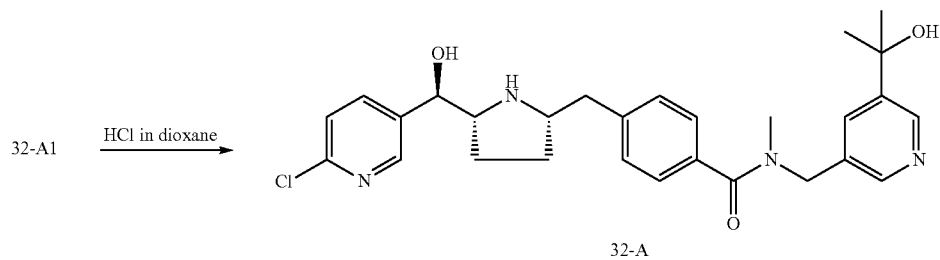

32-A 4-(((2S,5R)-5-((R)-(6-chloropyridin-3-yl)(hydroxy)
methyl)pyrrolidin-2-yl)methyl)-N-((5-(2-hydroxy-
propan-2-yl)pyridin-3-yl)methyl)-N-methylbenz-
amide, formic acid salt (32-A)

Compound 32-A was prepared in an analogous manner to that described for the synthesis of Example 4-E.

$^1$H NMR (400 MHz, CD$_3$OD): δ 8.88 (bs, 1H), 8.77 (bs, 1H), 8.68 (bs, 1H), 8.47 (d, J=2.40 Hz, 1H), 7.93 (dd, J=2.40 and 8.40 Hz, 1H), 7.54-7.43 (m, 1H), 4.94 (m, 2H), 4.87 (d, J=8.00 Hz, 1H), 3.87-3.81 (m, 2H), 3.26-3.21 (m, 1H), 3.10 (s, 3H), 3.08-3.04 (m, 1H), 2.12-2.10 (m, 1H), 1.92-1.88 (m, 3H), 1.64 (bs, 6H). Molecular Formula: C$_{28}$H$_{33}$ClN$_4$O$_3$; LC-MS purity: 99.6%; Expected: 509; Observed: 510.2 (M+1).

Example 32-B

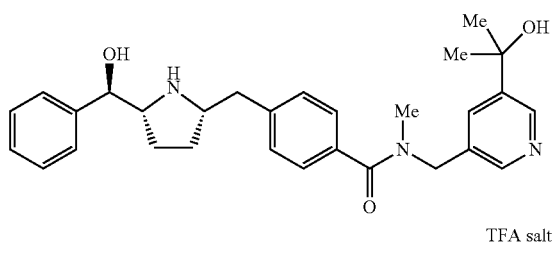

32-B

TFA salt

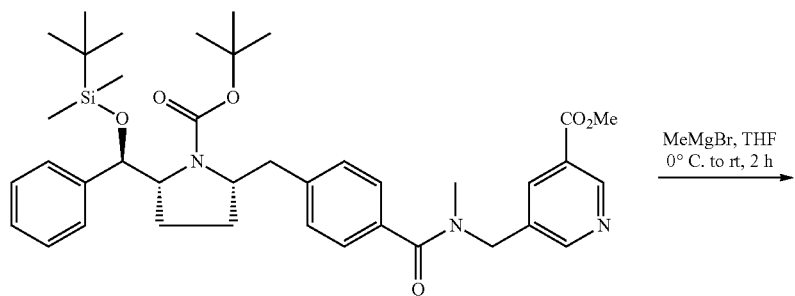

34-B2

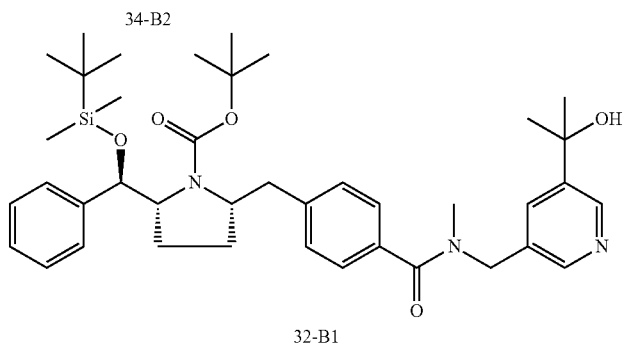

32-B1

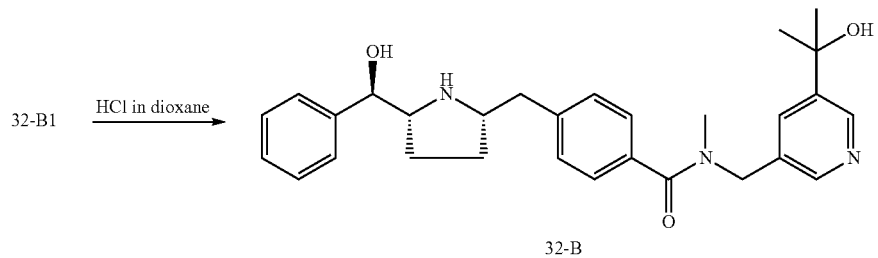

32-B

Step A (2R,5S)-tert-butyl 2-((R)-((tert-butyldimethylsilyl)oxy)(phenyl)methyl)-5-(4-(((5-(2-hydroxypropan-2-yl)pyridin-3-yl)methyl)(methyl)carbamoyl)benzyl) pyrrolidine-1-carboxylate (32-B1)

Compound 32-B1 was prepared from 34-B2 in an analogous manner as described in the synthesis of 32a from 32c.

$^1$H NMR (400 MHz, CD$_3$OD): δ 8.65-8.60 (m, 1H), 8.45-8.40 (m, 1H), 7.98-7.92 (m, 1H), 7.38-7.24 (m, 7H), 7.00 (bs, 2H), 5.45-5.25 (m, 1H), 4.85-4.62 (m, 2H), 4.14-4.12 (m, 1H), 3.90-3.80 (m, 1H), 2.97 (s, 3H), 2.75-2.65 (m, 2H), 1.95-1.85 (m, 4H), 1.58 (s, 6H), 1.56 (s, 9H), 0.94 (s, 9H), 0.12 (s, 3H), −0.01 (s, 3H). Molecular Formula: C$_{40}$H$_{57}$N$_3$O$_5$Si; LC-MS purity: 96.3%; Expected: 687.9; Observed: 688.2 (M+1).

Step B 4-(((2S,5R)-5-((R)-hydroxy(phenyl)methyl)pyrrolidin-2-yl)methyl)-N-((5-(2-hydroxypropan-2-yl)pyridin-3-yl)methyl)-N-methylbenzamide, formic acid salt (32-B)

Compound 32-B was prepared from compound 32-B1 in an analogous manner to that described in the synthesis of 2-B from 2-B2.

$^1$H NMR (400 MHz, CD$_3$OD): δ 8.84 (bs, 1H), 8.72 (bs, 1H), 8.59 (bs, 1H), 7.53-7.33 (m, 9H), 4.95-4.93 (m, 1H), 4.74 (d, J=8.80 Hz, 1H), 3.81-3.79 (m, 1H), 3.30-3.20 (m, 1H), 3.09 (s, 3H), 3.07-3.03 (m, 1H), 2.09-2.05 (m, 1H), 1.87-1.76 (m, 3H), 1.62 (m, 6H). Molecular Formula: C$_{29}$H$_{35}$N$_3$O$_3$; LC-MS purity: 98.2%; Expected: 473.5; Observed: 474.1 (M+1).

Example 32-G

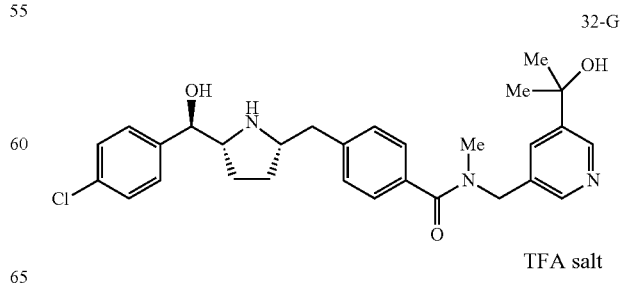

32-G

TFA salt 4-(((2S,5R)-5-((R)-(4-chlorophenyl)(hydroxy)methyl)pyrrolidin-2-yl)methyl)-N-((5-(2-hydroxypropan-2-yl)pyridin-3-yl)methyl)-N-methylbenzamide, formic acid salt (32-G)

Compound 32-G was prepared from 32 in an analogous manner to that described for the synthesis of Example 4-E.

$^1$H NMR (400 MHz, CD$_3$OD): δ 8.87 (bs, 1H), 8.76 (bs, 1H), 8.66 (bs, 1H), 7.53-7.39 (m, 8H), 4.75 (d, J=8.56 Hz, 1H), 3.80-3.71 (m, 2H), 3.25-3.20 (m, 1H), 3.10 (s, 3H), 3.06-3.04 (m, 1H), 2.16-2.07 (m, 1H), 1.89-1.80 (m, 4H), 1.63 (bs, 6H). Molecular Formula: C$_{29}$H$_{34}$ClN$_3$O$_3$; LC-MS purity: 97.8%; Expected: 508; Observed: 508.2 (M+1).

Example 33-A

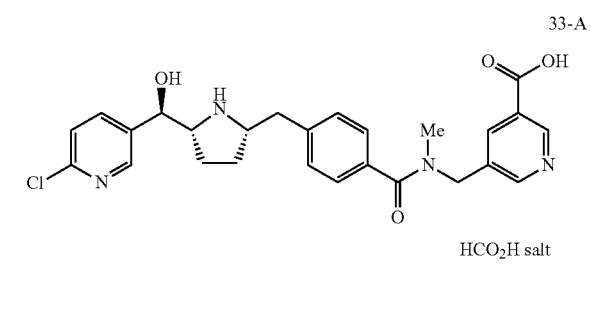 [SMILES: CN(Cc1cncc(C(=O)O)c1)C(=O)c1ccc(C[C@@H]2CC[C@H]([C@H](O)c3ccc(Cl)nc3)N2)cc1]

33-A

HCO$_2$H salt

Step A 5-((4-(((2S,5R)-1-(tert-butoxycarbonyl)-5-((R)-((tert-butyldimethylsilyl) oxy)(6-chloropyridin-3-yl)methyl)pyrrolidin-2-yl)methyl)-N-methylbenzamido)methyl)nicotinic acid (33-A1)

Compound 33-A1 was prepared in an analogous manner to that described in the synthesis of D from D3.

Molecular Formula: C$_{37}$H$_{49}$ClN$_4$O$_6$Si; LC-MS purity: 94.1%; Expected: 709.3; Observed: 711.8 (M+1).

Step B 5-((4-(((2S,5R)-5-((R)-(6-chloropyridin-3-yl)(hydroxy)methyl)pyrrolidin-2-yl)methyl)-N-methylbenzamido)methyl)nicotinic acid, formic acid salt (33-A)

Compound 33-A was prepared from 33-A1 in an analogous manner to that described in the synthesis of compound 2-B from compound 2-B2.

$^1$H NMR (400 MHz, CD$_3$OD): δ 9.04-8.99 (m, 1H), 8.67 (s, 1H), 8.47 (d, J=4.00 Hz, 1H), 8.36-8.30 (m, 2H), 7.92 (dd, J=2.36 and 8.40 Hz, 1H), 7.51 (d, J=8.00 Hz, 2H), 7.42-7.40 (m, 3H), 4.85 (d, J=8.00 Hz, 2H), 4.65 (s, 1H), 3.85-3.81 (m, 3H), 3.18-3.04 (m, 2H), 3.00 (s, 3H), 2.14-2.12 (m, 1H), 1.92-1.87 (m, 3H). Molecular Formula: C$_{26}$H$_{27}$ClN$_4$O$_4$; LC-MS purity: 96.2%; Expected: 494.9; Observed: 495.8 (M+1).

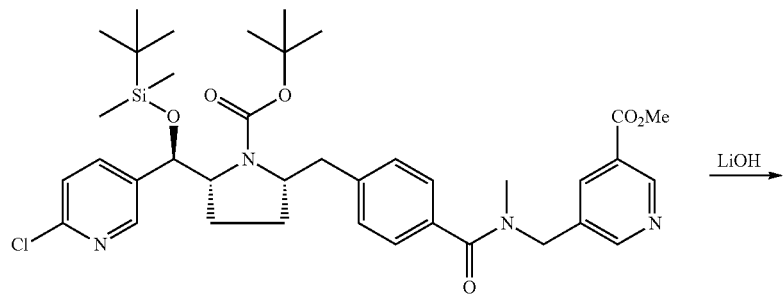

34-A1

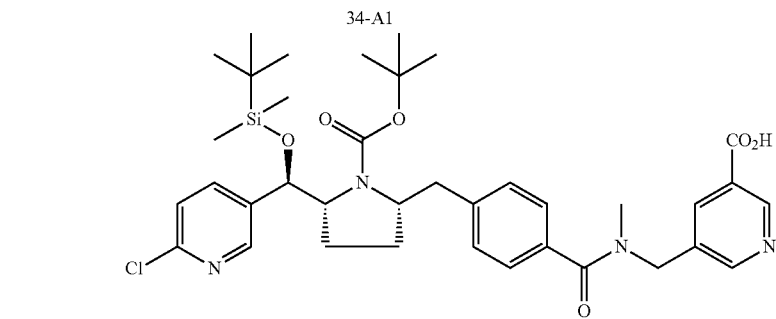

33-A1

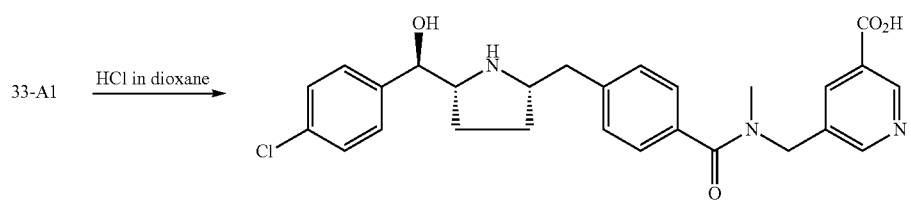

33

Example 33-B

5-((4-(((2S,5R)-5-((R)-hydroxy(phenyl)methyl)pyrrolidin-2-yl)methyl)-N-methyl benzamido)methyl) nicotinic acid, formic acid salt (33-B)

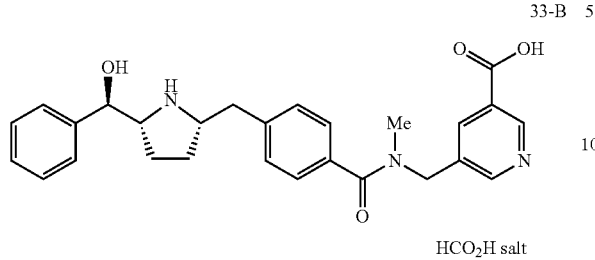

Compound 33-B was prepared from compound 34-B in an analogous manner to that described in the synthesis of compound D from compound D3.

$^1$H NMR (400 MHz, CD$_3$OD): δ 9.03-8.98 (m, 1H), 8.66 (bs, 1H), 8.36-8.26 (m, 2H), 7.63-7.24 (m, 9H), 4.86 (s, 1H), 4.73 (d, J=8.80 Hz, 1H), 4.65 (bs, 1H), 3.83-3.76 (m, 2H), 3.20-3.18 (m, 1H), 3.14-3.03 (m, 1H), 3.00 (bs, 3H), 2.14-2.07 (m, 1H), 1.84-1.77 (m, 3H). Molecular Formula: C$_{27}$H$_{29}$N$_3$O$_4$; LC-MS purity: 98.4%; Expected: 459.5; Observed: 460.2 (M+1).

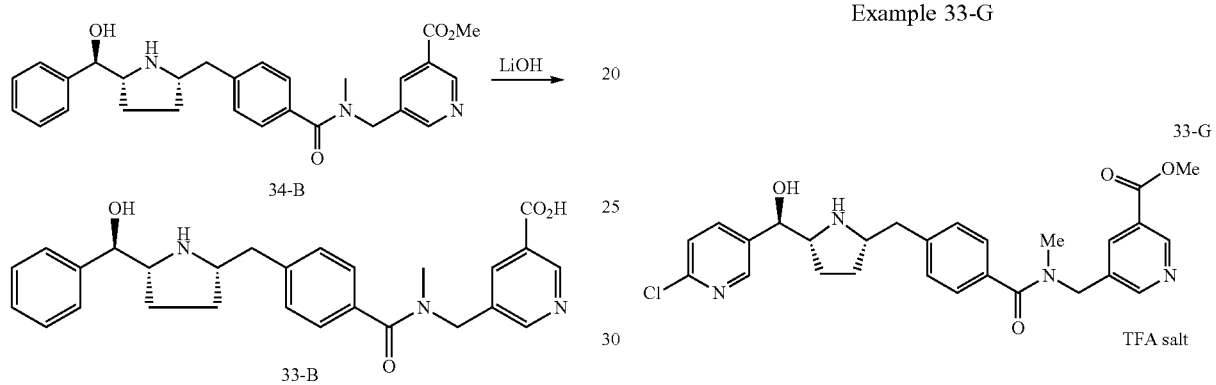

Example 33-G

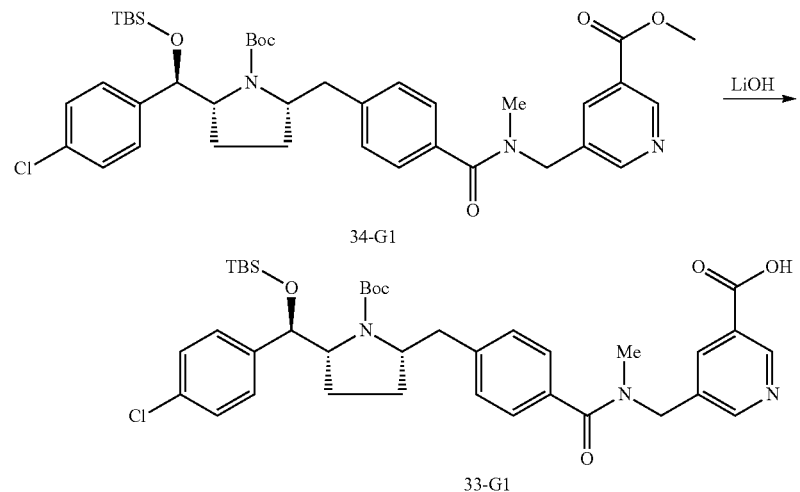

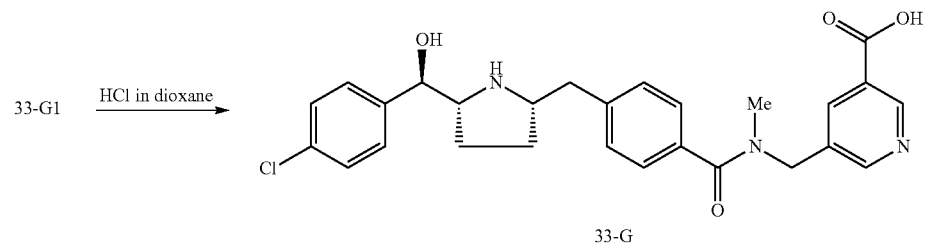

5-((4-(((2S,5R)-5-((R)-(4-chlorophenyl)(hydroxy)methyl)pyrrolidin-2-yl)methyl)-N-methylbenzamido)methyl)nicotinic acid, triflic acid salt (33-G)

Compound 33-G was prepared in an analogous manner to that described in example 33-A.

$^1$H NMR (400 MHz, CD$_3$OD): δ 9.09 (bs, 1H), 8.81 (bs, 1H), 8.52-8.46 (m, 1H), 7.51-7.40 (m, 9H), 4.74 (d, J=8.58 Hz, 1H), 4.71-4.65 (m, 1H), 3.82-3.76 (m, 2H), 3.15-3.07 (m, 3H), 3.02 (s, 3H), 2.11-2.07 (m, 1H), 1.85-1.70 (m, 3H). Molecular Formula: C$_{27}$H$_{28}$ClN$_3$O$_4$; LC-MS purity: 98.2%; Expected: 494; Observed: 494 (M).

Example 34-A

Methyl 5-((4-(((2S,5R)-5-((R)-(6-chloropyridin-3-yl)(hydroxy)methyl)pyrrolidin-2-yl) methyl)-N-methylbenzamido)methyl)nicotinate, formic acid salt (34-A)

Compound 34-A was prepared in an analogous manner to that described in Example 4-E.

$^1$H NMR (400 MHz, CD$_3$OD): δ 9.08 (bs, 1H), 8.81 (bs, 1H), 8.49-8.42 (m, 3H), 7.92 (dd, J=2.16 and 8.42 Hz, 1H), 7.52-7.41 (m, 5H), 4.83-4.81 (m, 2H), 3.98 (s, 3H), 3.79-3.73 (m, 2H), 3.18-3.16 (m, 1H), 3.07-3.05 (m, 1H), 3.02 (s, 3H), 2.16-2.05 (m, 1H), 1.98-1.85 (m, 3H). Molecular Formula: C$_{27}$H$_{29}$ClN$_4$O$_4$; LC-MS purity: 95.5%; Expected: 508.9; Observed: 509.8 (M+1).

Example 34-B

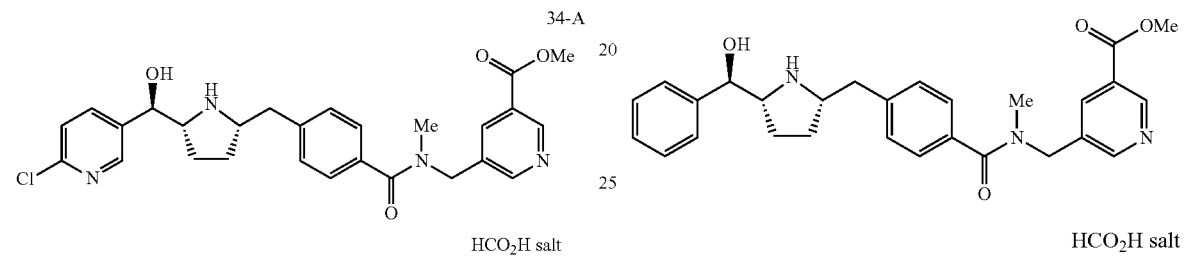

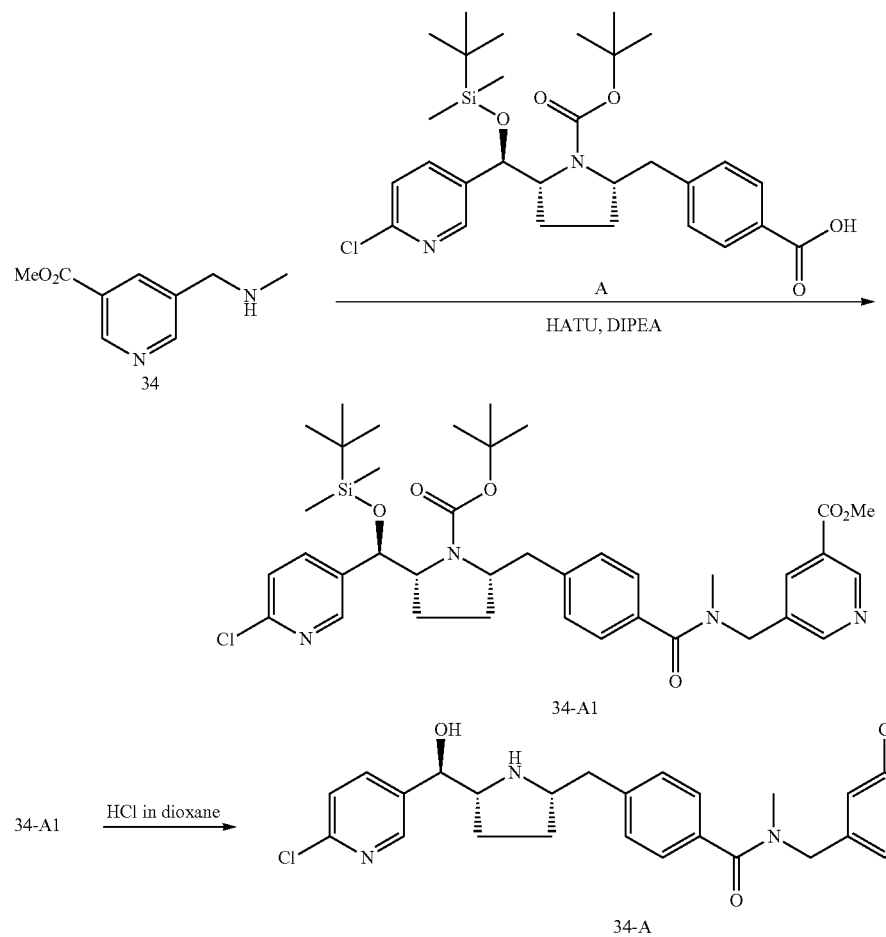

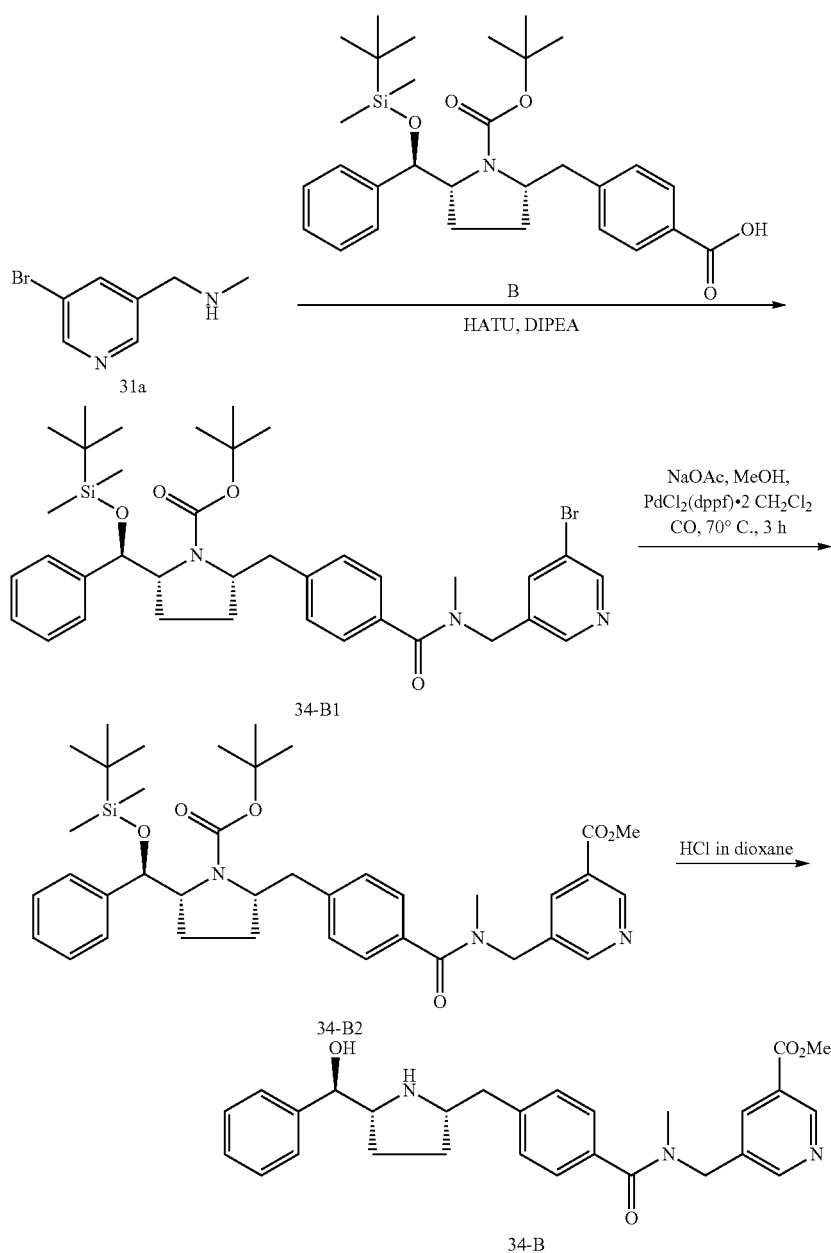

Step A (2S,5R)-tert-butyl 2-(4-(((5-bromopyridin-3-yl)methyl)(methyl)carbamoyl)benzyl)-5-((R)-((tert-butyldimethylsilyl)oxy)(phenyl)methyl)pyrrolidine-1-carboxylate (34-B1)

Compound 34-B1 was prepared following an analogous procedure that is described in the synthesis of compound 4-E1.

$^1$H NMR (400 MHz, CD$_3$OD): δ 8.61-8.55 (m, 2H), 8.05 (bs, 1H), 7.38-7.23 (m, 7H), 7.00 (bs, 2H), 5.50-5.25 (m, 1H), 4.90-4.75 (m, 2H), 4.14-4.12 (m, 1H), 3.90-3.80 (m, 1H), 3.20-3.02 (m, 2H), 2.96 (s, 3H), 1.90-1.86 (m, 4H), 1.58 (m, 9H), 0.89 (s, 9H), 0.12 (s, 3H), −0.01 (s, 3H). Molecular Formula: C$_{37}$H$_{50}$BrN$_3$O$_4$Si; LC-MS purity: 93.6%; Expected: 708.8; Observed: 652.2 (M+1-$^t$Bu).

Step B Methyl 5-((4-(((2S,5R)-1-(tert-butoxycarbonyl)-5-((R)-((tert-butyldimethylsilyl)oxy)(phenyl)methyl)pyrrolidin-2-yl)methyl)-N-methylbenzamido)methyl)nicotinate, formic acid salt (34-B)

To a stirred solution of compound 34-B1 (420 mg, 0.59 mmol) in MeOH (20 mL), sodium acetate (145 mg, 1.77 mmol) was added at room temperature and degassed with nitrogen. PdCl$_2$(dppf).2CH$_2$Cl$_2$ (96.7 mg, 0.12 mmol) was added and the reaction mixture was heated at 70° C. for 3 h under a flow of carbon monoxide. The reaction mixture was cooled to room temperature and filtered through a celite bed. The filtrate was concentrated under reduced pressure and the residue was purified by automated flash chromatography using 30% ethylacetate in petroleum ether to obtain compound 34-B2 (250 mg) as a pale yellow liquid.

¹H NMR (400 MHz, CD₃OD): δ 9.10-9.05 (m, 1H), 8.85-8.75 (m, 1H), 8.40-8.35 (m, 1H), 7.38-7.32 (m, 7H), 7.01 (bs, 2H), 5.25-5.05 (m, 1H), 4.90-4.65 (m, 2H), 4.13-4.07 (m, 1H), 3.97 (s, 3H), 3.90-3.80 (m, 1H), 2.97 (s, 3H), 2.90-2.60 (m, 2H), 1.95-1.85 (m, 4H), 1.58 (m, 9H), 0.88 (s, 9H), 0.12 (s, 3H), −0.01 (s, 3H). Molecular Formula: C₃₉H₅₃N₃O₆Si; LC-MS purity: 92.5%; Expected: 687.9; Observed: 632.2 (M+1-ᵗBu).

Step C Methyl 5-((4-(((2S,5R)-5-((R)-hydroxy(phenyl)methyl)pyrrolidin-2-yl)methyl)-N-methylbenzamido)methyl)nicotinate (34-B)

Compound 34-B was prepared from compound 34-B2 in an analogous manner to that described in the synthesis of compound 4-E from compound 4-E1.

¹H NMR (400 MHz, CD₃OD): δ 9.08 (bs, 1H), 8.81 (bs, 1H), 8.50-8.42 (m, 2H), 7.51-7.32 (m, 8H), 4.86 (s, 2H), 4.73 (d, J=8.40 Hz, 1H), 3.97 (s, 3H), 3.79-3.77 (m, 2H), 3.20-3.18 (m, 1H), 3.08-3.05 (m, 1H), 3.02 (bs, 3H), 2.09-2.07 (m, 1H), 1.83-1.80 (m, 3H). Molecular Formula: C₂₈H₃₁N₃O₄; LC-MS purity: 99%; Expected: 473.5; Observed: 474.2 (M+1).

Example 34-G

Methyl 5-((4-(((2S,5R)-5-((R)-(4-chlorophenyl)(hydroxy)methyl)pyrrolidin-2-yl)methyl)-N-methylbenzamido)methyl)nicotinate, formic acid salt (34-G)

Compound 34-G was prepared in an analogous manner to that described in the synthesis of compound 4-E.

¹H NMR (400 MHz, CD₃OD): δ 8.54 (bs, 1H), 8.35 (bs, 1H), 7.46-7.39 (m, 2H), 7.50-7.39 (m, 8H), 4.73 (d, J=8.58 Hz, 1H), 4.71-4.67 (m, 2H), 3.97 (s, 3H), 3.88-3.75 (m, 2H), 3.23-3.20 (m, 1H), 3.08-3.05 (m, 1H), 3.02 (s, 3H), 2.08-2.05 (m, 1H), 1.90-1.82 (m, 3H). Molecular Formula: C₂₈H₃₀ClN₃O₄; LC-MS purity: 99.7%; Expected: 508; Observed: 509.2 (M+1).

Example 35-A

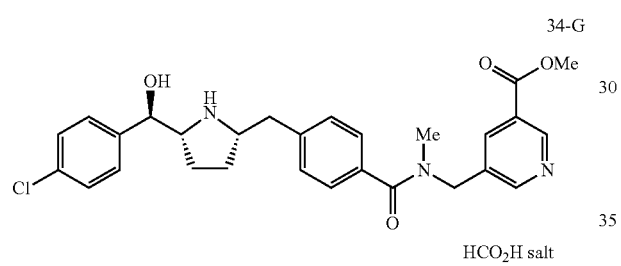

34-G

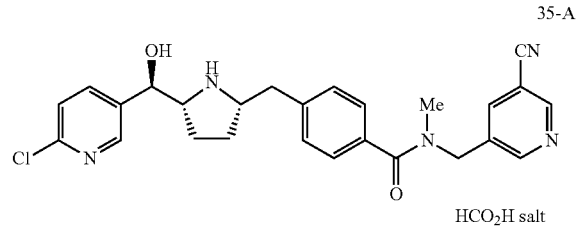 [SMILES: CN(Cc1cncc(C#N)c1)C(=O)c1ccc(C[C@@H]2CC[C@H]([C@H](O)c3ccc(Cl)nc3)N2)cc1]

35-A

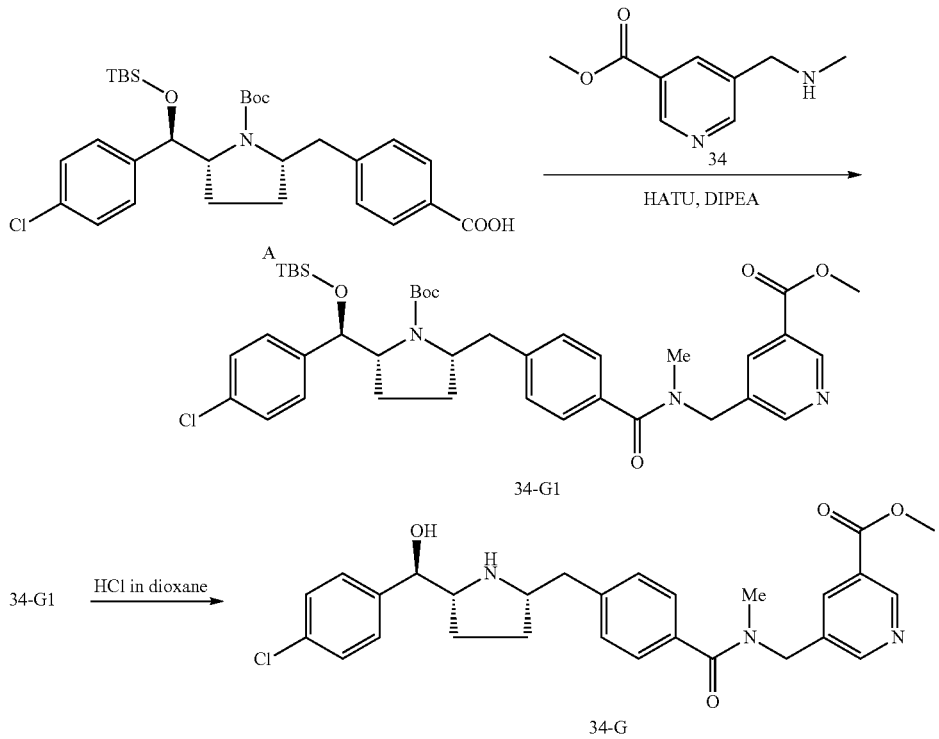

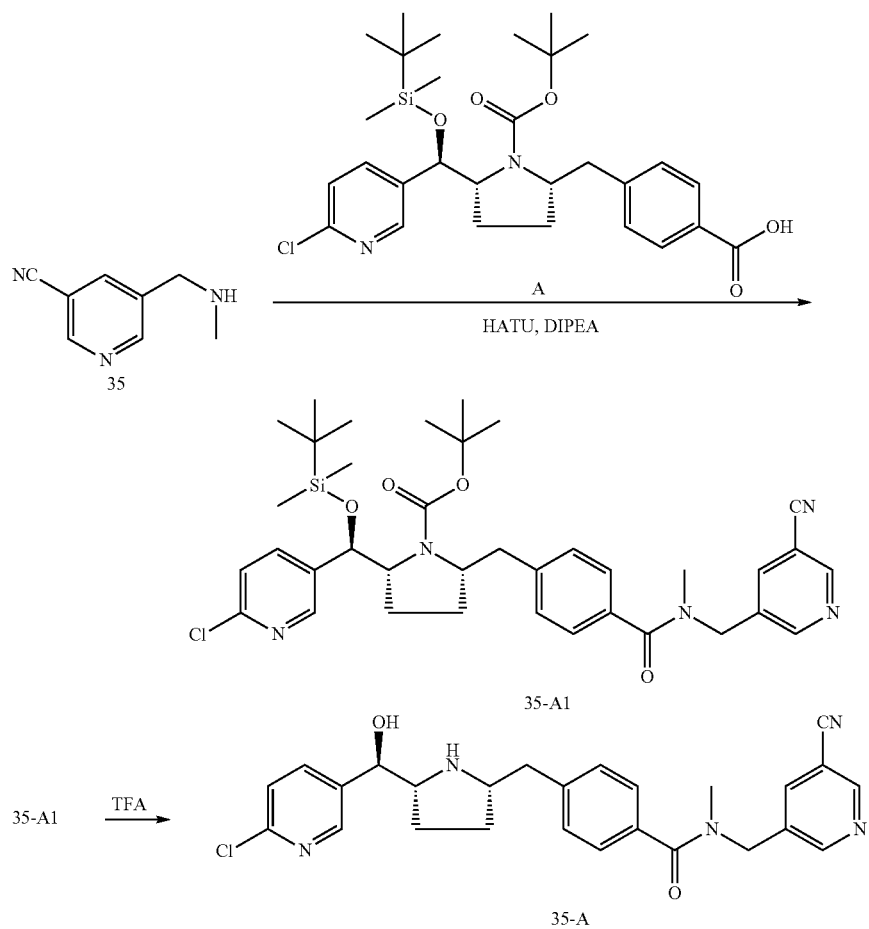
4-(((2S,5R)-5-((R)-(6-chloropyridin-3-yl)(hydroxy)methyl)pyrrolidin-2-yl)methyl)-N-((5-cyanopyridin-3-yl)methyl)-N-methylbenzamide, formic acid salt (35-A)
Compound 35-A was prepared in an analogous manner to that of Example 27-A.
$^1$H NMR (400 MHz, CD$_3$OD): δ 8.87 (m, 2H), 8.47 (d, J=2.00 Hz, 1H), 8.41 (s, 1H), 8.23 (s, 1H), 7.93 (dd, J=2.40 and 8.20 Hz, 1H), 7.51 (d, J=8.00 Hz, 2H), 7.42 (d, J=8.00 Hz, 2H), 4.84-4.82 (m, 4H), 3.82-3.78 (m, 2H), 3.30-3.08 (m, 2H), 3.04 (s, 3H), 2.11-2.10 (m, 1H), 1.90-1.81 (m, 3H). Molecular Formula: C$_{26}$H$_{26}$ClN$_5$O$_2$; LC-MS purity: 98.3%; Expected: 476; Observed: 476.2 (M+1).
Example 35-B
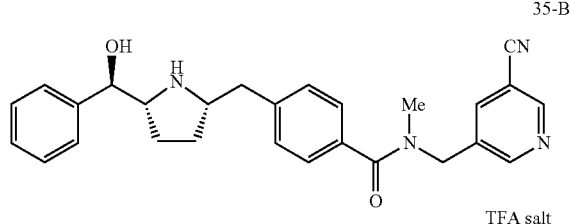 [SMILES: CN(Cc1cncc(C#N)c1)C(=O)c1ccc(C[C@@H]2CC[C@H]([C@H](O)c3ccccc3)N2)cc1]
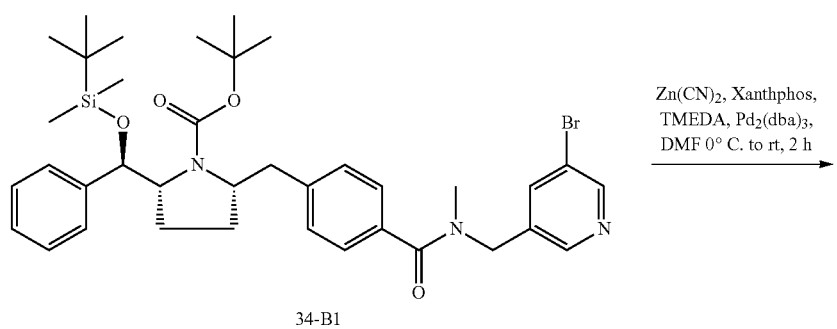

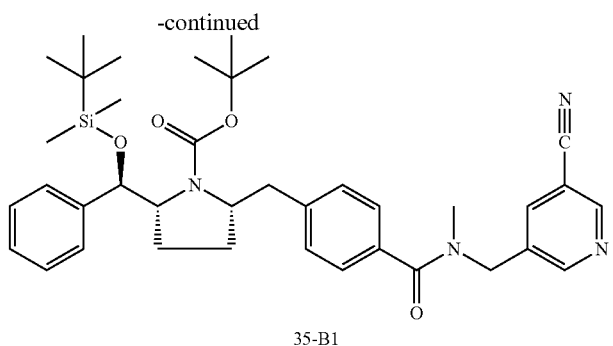

35-B1

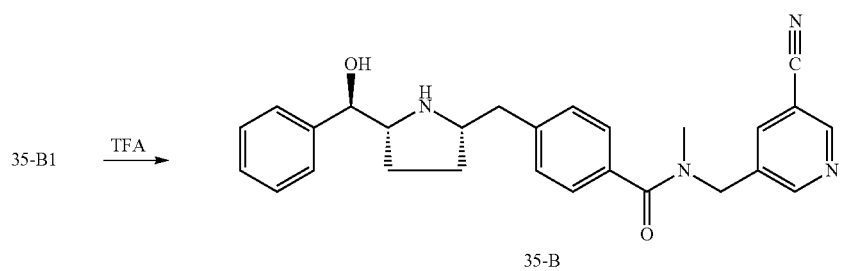

35-B

Step A (2R,5S)-tert-butyl 2-((R)-((tert-butyldimethylsilyl)oxy)(phenyl)methyl)-5-(4-(((5-cyanopyridin-3-yl)methyl)(methyl)carbamoyl)benzyl)pyrrolidine-1-carboxylate (35-B1)

To a stirred solution of compound 34-B1 (400 mg, 0.56 mmol) in DMF (10 mL), Xanthphos (19.6 mg, 0.033 mmol), N, N, N', N'-tetramethyl ethylenediamine (0.085 mL, 0.56 mmol) and $Zn(CN)_2$ (100 mg, 0.85 mmol) were added at room temperature and degassed with nitrogen followed by the addition of $Pd_2(dba)_3$ (36.2 mg, 0.04 mmol). The reaction mixture was heated at 165° C. for 2 h under nitrogen. The reaction mixture was cooled to room temperature and filtered through a celite bed. Water was added to the filtrate and extracted with ethyl acetate. The organic layer was washed successively with water and brine, dried over anhydrous $Na_2SO_4$, concentrated under reduced pressure and the residue was purified by automated flash chromatography using 30-35% ethylacetate in petroleum ether to obtain compound 35-B1 (150 mg) as a colorless gummy mass.

$^1$H NMR (400 MHz, $CD_3OD$): δ 8.85-8.80 (m, 2H), 8.21-7.99 (m, 1H), 7.27-7.24 (m, 7H), 7.01 (bs, 2H), 5.50-5.25 (m, 1H), 4.90-4.79 (m, 2H), 4.14-4.10 (m, 1H), 3.85-3.80 (m, 1H), 2.99 (s, 3H), 2.87-2.80 (m, 2H), 1.89-1.87 (m, 4H), 1.59 (s, 9H), 0.94 (s, 9H), 0.10 (s, 3H), −0.09 (s, 3H). Molecular Formula: $C_{38}H_{50}N_4O_4Si$; LC-MS purity: 97.5%; Expected: 654.9; Observed: 555.2 (M+1-Boc).

Step B N-((5-cyanopyridin-3-yl)methyl)-4-(((2S,5R)-5-((R)-hydroxy(phenyl) methyl)pyrrolidin-2-yl)methyl)-N-methylbenzamide, triflic acid salt (35-B)

Compound 35-B was prepared from compound 35-B1 following an analogous procedure as described in the synthesis of compound 21-I from compound 21-I1.

$^1$H NMR (400 MHz, $CD_3OD$): δ 8.87 (bs, 2H), 8.23 (bs, 1H), 7.53-7.34 (m, 9H), 4.83 (bs, 1H), 4.73 (d, J=8.00 Hz, 1H), 3.81-3.79 (m, 2H), 3.20-3.19 (m, 1H), 3.09-3.06 (m, 1H), 3.04 (s, 3H), 2.09-2.08 (m, 1H), 1.87-1.81 (m, 3H). Molecular Formula: $C_{27}H_{28}N_4O_2$; LC-MS purity: 98.1%; Expected: 440.5; Observed: 441.2 (M+1).

Example 36-A

36-A

TFA salt

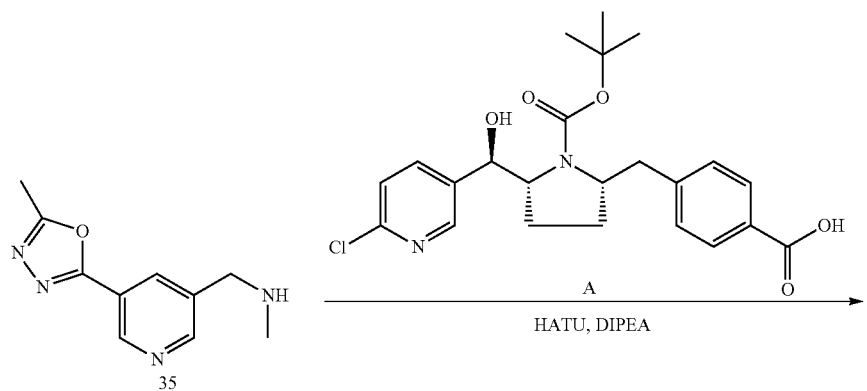

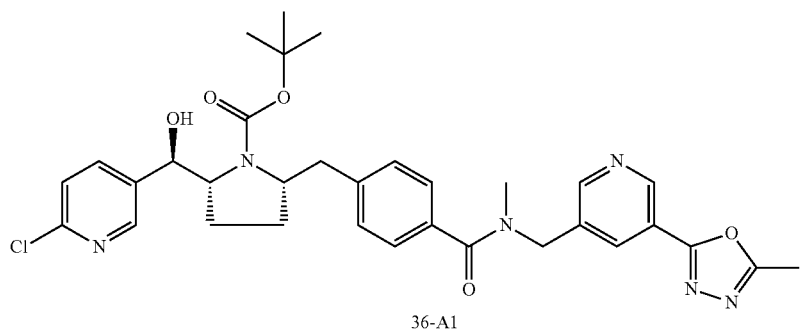

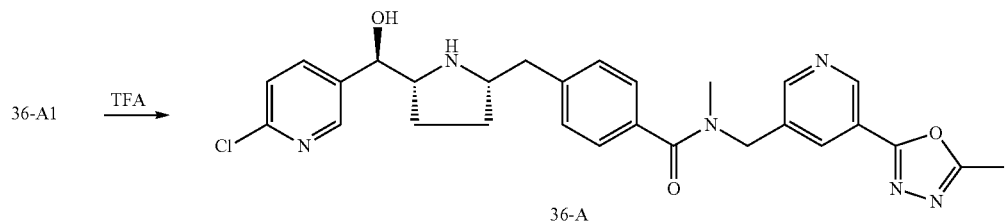

4-(((2S,5R)-5-((R)-(6-chloropyridin-3-yl)(hydroxy)methyl)pyrrolidin-2-yl)methyl)-N-methyl-N-((5-(5-methyl-1,3,4-oxadiazol-2-yl)pyridin-3-yl)methyl)benzamide, triflic acid salt (36-A)

Compound 36-A was prepared in an analogous manner to that described in Example 27-A.

$^1$H NMR (400 MHz, CD$_3$OD): δ 9.15 (bs, 1H), 8.82 (bs, 1H), 8.49-8.46 (m, 2H), 7.93 (dd, J=2.40 and 8.40 Hz, 1H), 7.52-7.42 (m, 5H), 4.86 (d, J=8.00 Hz, 1H), 4.86 (d, J=8.00 Hz, 1H), 4.75 (bs, 1H), 3.87-3.80 (m, 2H), 3.24-3.20 (m, 1H), 3.14-3.10 (m, 1H), 3.06 (s, 3H), 2.66 (s, 3H), 2.14-2.08 (m, 1H), 1.92-1.88 (m, 3H). Molecular Formula: C$_{28}$H$_{29}$ClN$_6$O$_3$; LC-MS purity: 96.1%; Expected: 533; Observed: 535.2 (M+2).

Example 36-B

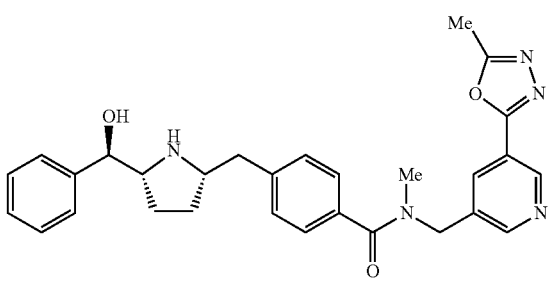

TFA salt

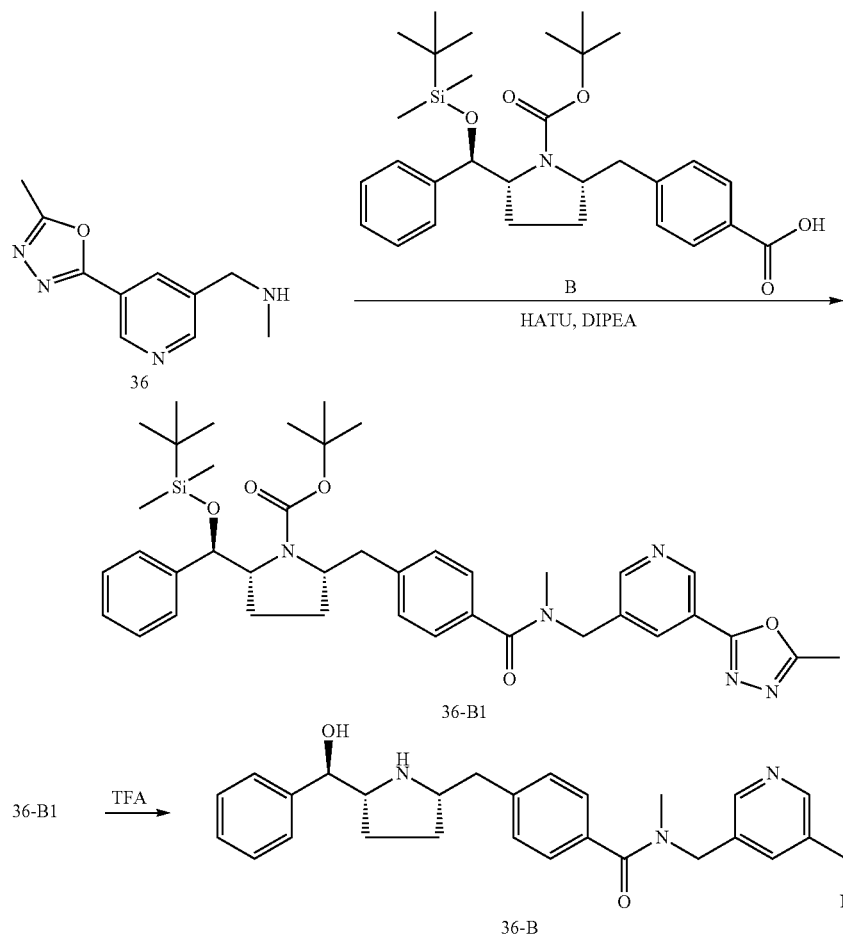

4-(((2S,5R)-5-((R)-hydroxy(phenyl)methyl)pyrrolidin-2-yl)methyl)-N-methyl-N-((5-(5-methyl-1,3,4-oxadiazol-2-yl)pyridin-3-yl)methyl)benzamide, triflic acid salt (36-B)

Compound 36-B was prepared in an analogous manner to that shown in Example 27-A.

$^1$H NMR (400 MHz, CD$_3$OD): δ 9.13 (bs, 1H), 8.81 (bs, 1H), 8.47 (bs, 1H), 7.53-7.32 (m, 9H), 4.73 (d, J=8.40 Hz, 1H), 3.98 (s, 3H), 3.81-3.77 (m, 2H), 3.25-3.15 (m, 1H), 3.14-3.07 (m, 1H), 3.06 (s, 3H), 2.10-2.02 (m, 1H), 1.84-1.81 (m, 3H). Molecular Formula: C$_{29}$H$_{31}$N$_5$O$_3$; LC-MS purity: 96.2%; Expected: 497.5; Observed: 498.2 (M+1).

N-((5-(1H-tetrazol-5-yl)pyridin-3-yl)methyl)-4-(((2S,5R)-5-((R)-(6-chloropyridin-3-yl)(hydroxy)methyl)pyrrolidin-2-yl)methyl)-N-methylbenzamide, formic acid salt (37-A)

Compound 37-A was prepared in a similar manner to that described in Example 4-E.

$^1$H NMR (400 MHz, CD$_3$OD): δ 9.16-9.13 (m, 1H), 8.60 (s, 1H), 8.45 (s, 2H), 8.34-8.24 (m, 1H), 7.91 (d, J=8.00 Hz, 1H), 7.54-7.33 (m, 5H), 4.84 (d, J=8.00 Hz, 2H), 4.68 (bs, 1H), 3.85-3.80 (m, 2H), 3.26-3.12 (m, 2H), 3.04 (s, 3H), 2.12 (m, 1H), 1.87-1.82 (m, 3H). Molecular Formula: C$_{26}$H$_{27}$ClN$_8$O$_2$; LC-MS purity: 96.1%; Expected: 519; Observed: 520.2 (M+1).

Example 37-A

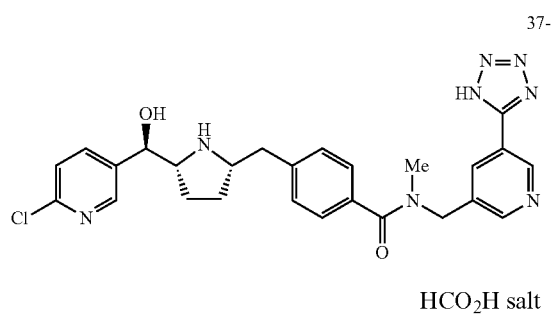

HCO$_2$H salt

Example 37-B

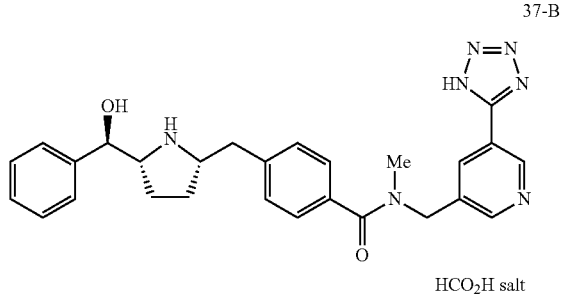 [SMILES: CN(Cc1cncc(-c2nnn[nH]2)c1)C(=O)c1ccc(C[C@@H]2CC[C@H]([C@H](O)c3ccccc3)N2)cc1]

HCO$_2$H salt

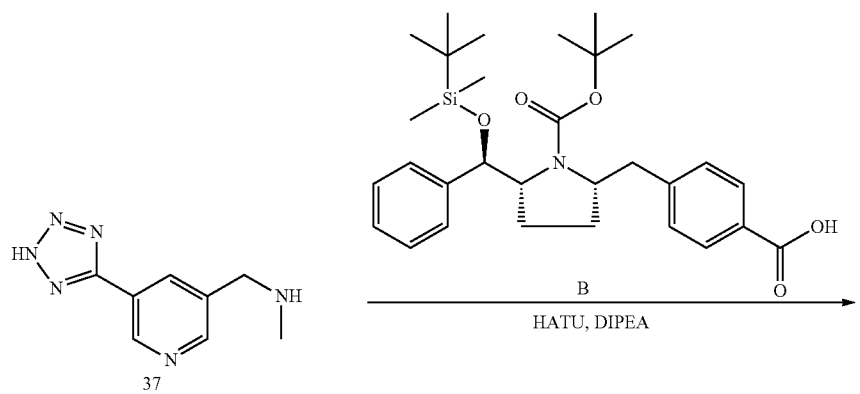
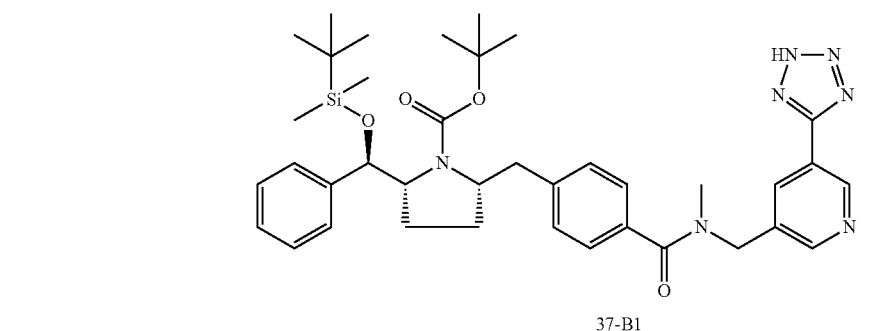
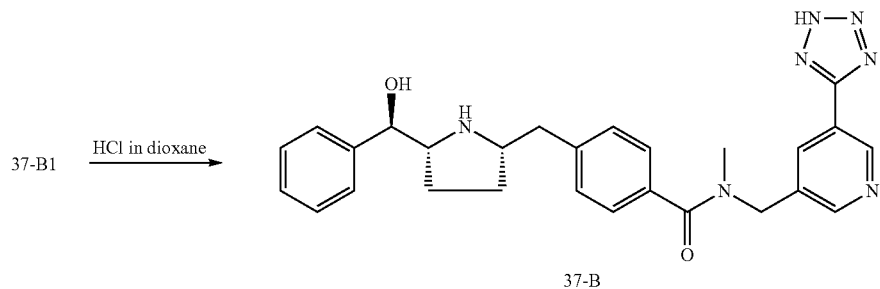
N-((5-(1H-tetrazol-5-yl)pyridin-3-yl)methyl)-4-(((2S,5R)-5-((R)-hydroxy(phenyl) methyl)pyrrolidin-2-yl)methyl)-N-methylbenzamide, formic acid salt (37-B)
Compound 37-B was prepared in an analogous manner to that shown in Example 4-E.
$^1$H NMR (400 MHz, CD$_3$OD): δ 9.16 (bs, 1H), 8.60 (s, 1H), 8.21-8.13 (m, 1H), 7.55-7.33 (m, 7H), 4.73-4.69 (m, 2H), 3.80-3.77 (m, 2H), 3.16-3.09 (m, 2H), 3.04 (bs, 3H), 2.09 (m, 1H), 1.82 (m, 3H). Molecular Formula: C$_{27}$H$_{29}$N$_7$O$_2$; LC-MS purity: 97.3%; Expected: 483.6; Observed: 484.2 (M+1).
Example 38-A
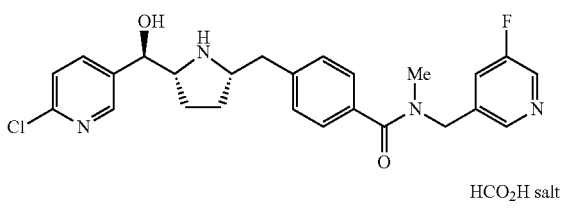
38-A
HCO$_2$H salt

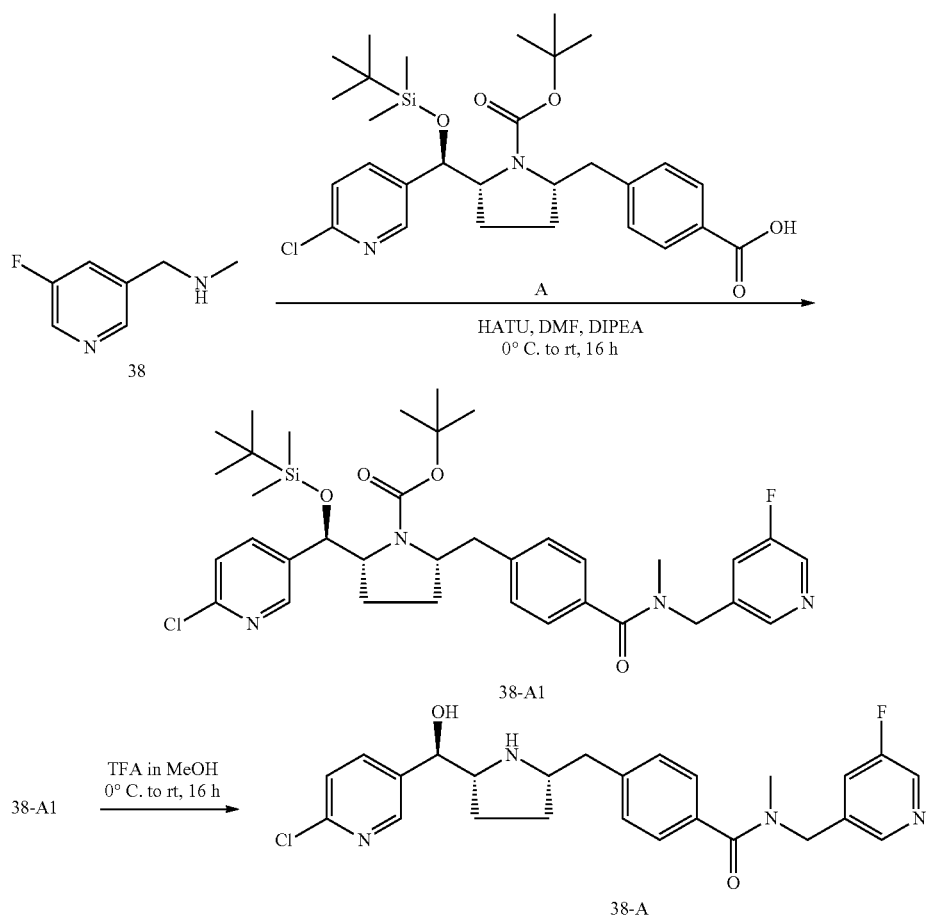

4-(((2S,5R)-5-((R)-(6-chloropyridin-3-yl)(hydroxy)methyl)pyrrolidin-2-yl)methyl)-N-((5-fluoropyridin-3-yl)methyl)-N-methylbenzamide, formic acid salt (38-A)

Compound 38-A was prepared in an analogous manner to that shown in Example 27-A.

$^1$H NMR (400 MHz, DMSO-$d_6$): δ 8.52 (d, J=2.00 Hz, 1H), 8.46 (m, 1H), 8.41 (d, J=1.60 Hz, 1H), 8.18 (s, 1H), 7.84 (dd, J=2.00 and J=8.00 Hz, 1H), 7.67 (m, 1H), 7.49 (d, J=8.40 Hz, 1H), 7.43 (bs, 2H), 7.34-7.29 (m, 2H), 4.72 (bs, 1H), 4.55 (d, J=7.20 Hz, 1H), 3.37 (bs, 2H), 2.92 (s, 3H), 2.85 (m, 1H), 2.77-2.73 (m, 1H), 1.72-1.69 (m, 1H), 1.51-1.49 (m, 2H), 1.37-1.36 (m, 1H). Molecular Formula: $C_{25}H_{26}ClFN_4O_2$; LC-MS purity: 97.6%; Expected: 468.9; Observed: 469.2 (M+1).

Example 38-B

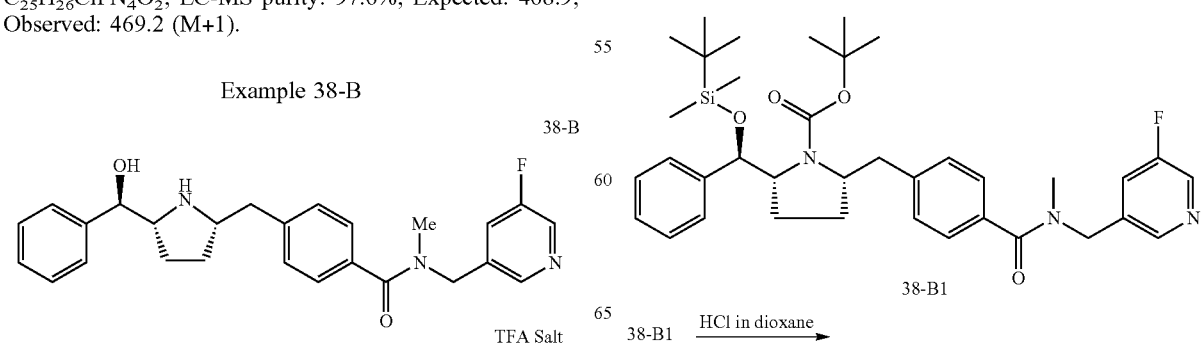

-continued
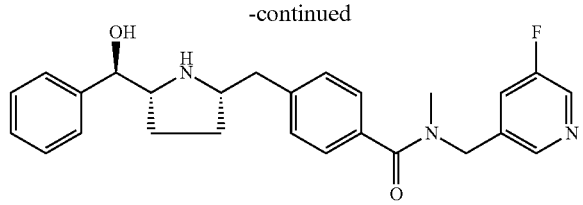
38-B
N-((5-fluoropyridin-3-yl)methyl)-4-(((2S,5R)-5-((R)-hydroxy(phenyl)methyl)pyrrolidin-2-yl)methyl)-N-methylbenzamide, triflic acid salt (38-B)
Compound 38-B was prepared in an analogous manner to that shown in Example 4-E.
$^1$H NMR (400 MHz, CD$_3$OD): δ 8.48-8.46 (m, 3H), 7.78-7.72 (m, 1H), 7.52-7.34 (m, 12H), 4.83 (s, 2H), 4.73 (d, J=8.00 Hz, 1H), 4.66 (s, 1H), 3.81-3.78 (m, 2H), 3.24-3.19 (m, 1H), 3.09-3.02 (m, 1H), 3.00 (bs, 3H), 2.10-2.05 (m, 1H), 1.87-1.81 (m, 3H). Molecular Formula: C$_{26}$H$_{28}$FN$_3$O$_2$; LC-MS purity: 95.3%; Expected: 433.5; Observed: 434.2 (M+1).
Example 39-A

4-(((2S,5R)-5-((R)-(6-chloropyridin-3-yl)(hydroxy)methyl)pyrrolidin-2-yl)methyl)-N-((6-fluoro-5-methylpyridin-3-yl)methyl)-N-methylbenzamide (39-A)

Compound 39-A was prepared in a manner analogous to that disclosed in Example 4-E.

$^1$H NMR (400 MHz, CD$_3$OD): δ 8.38-8.36 (m, 1H), 8.04 (s, 1H), 7.85-7.83 (m, 2H), 7.45-7.36 (m, 5H), 4.73 (s, 1H), 4.57 (d, J=4.00 Hz, 2H), 3.32-3.30 (m, 1H), 2.97 (s, 3H), 2.94-2.91 (m, 3H), 2.31 (s, 3H), 1.85-1.81 (m, 1H), 1.62-1.47 (m, 2H), 1.40-1.38 (m, 1H). Molecular Formula: C$_{26}$H$_{28}$ClFN$_4$O$_2$; LC-MS purity: 97.3%; Expected: 482.9; Observed: 483.2 (M+1).

(R)-((2R,5S)-5-(4-((((6-fluoro-5-methylpyridin-3-yl)methyl)(methyl)amino)methyl)benzyl)pyrrolidin-2-yl)(phenyl)methanol, formic acid salt (39-B)

Compound 39-B was prepared in an analogous manner to the synthesis described in Example 4-E.

$^1$H NMR (400 MHz, CD$_3$OD): δ 8.53 (bs, 1H), 8.05 (bs, 1H), 7.86-7.83 (m, 1H), 7.49-7.33 (m, 9H), 4.74-4.70 (m, 2H), 4.57 (s, 1H), 3.79-3.76 (m, 2H), 3.22-3.14 (m, 1H), 3.07-3.02 (m, 1H), 2.98 (s, 3H), 2.32 (bs, 3H), 2.08-2.04 (m, 1H), 1.85-1.77 (m, 3H). Molecular Formula: C$_{27}$H$_{30}$FN$_3$O$_2$; LC-MS purity: 98.5%; Expected: 447.5; Observed: 448.2 (M+1).

Example 39-B

Example 39-G

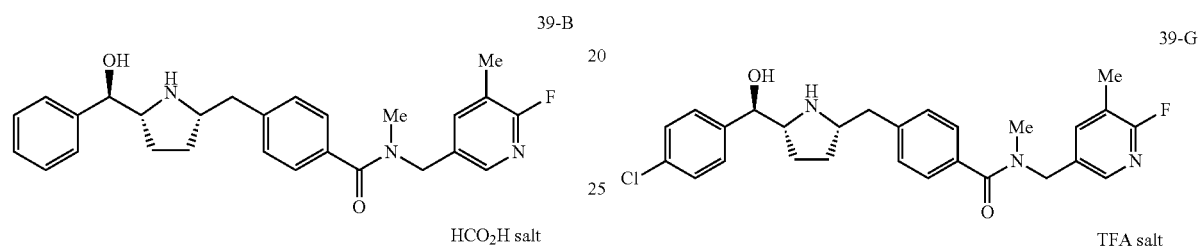

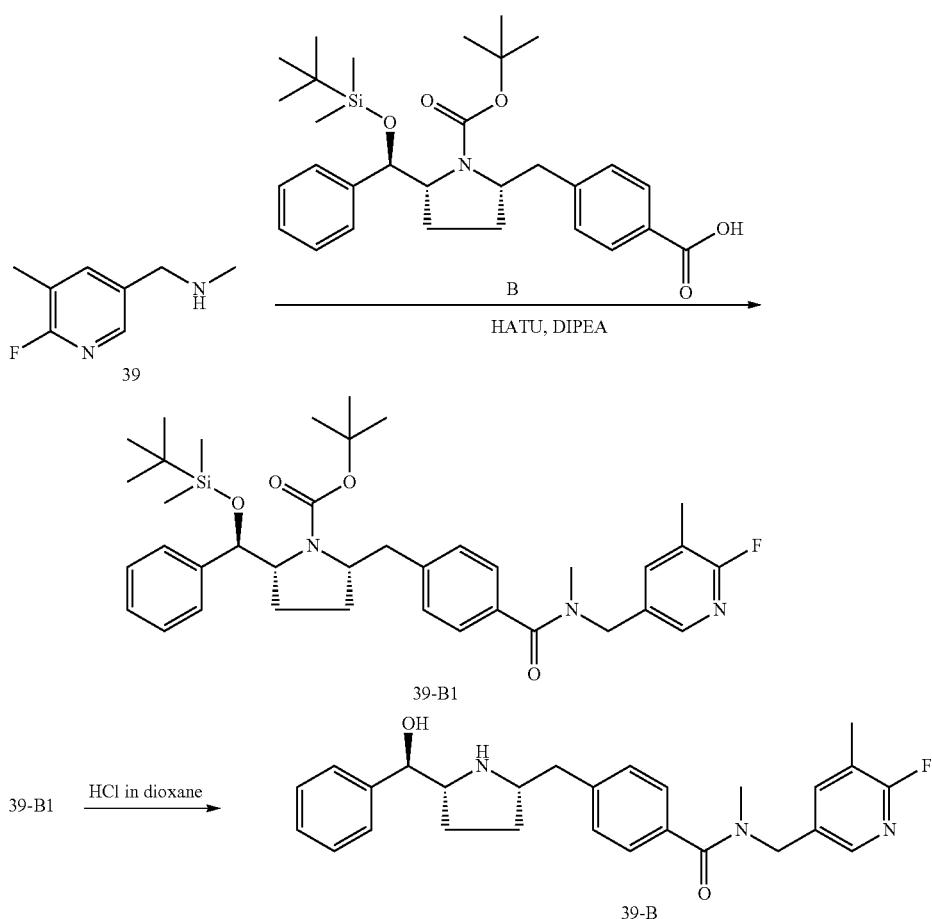

(R)-(4-chlorophenyl)((2R,5S)-5-(4-((((6-fluoro-5-methylpyridin-3-yl)methyl)(methyl)amino) methyl) benzyl)pyrrolidin-2-yl)methanol, triflic acid salt (39-G)

Compound 39-G was prepared in an analogous manner to the synthesis described in Example 4-E.

$^1$H NMR (400 MHz, CD$_3$OD): δ 8.03-8.00 (m, 1H), 7.48-7.40 (m, 9H), 4.75 (d, J=8.60 Hz, 2H), 3.91 (s, 3H), 3.81-3.76 (m, 2H), 3.24-3.20 (m, 1H), 3.12-3.07 (m, 4H), 2.70 (s, 1H), 2.31-2.28 (m, 1H), 2.10-2.06 (m, 1H), 1.85-1.82 (m, 3H). Molecular Formula: C$_{27}$H$_{29}$ClFN$_3$O$_2$; LC-MS purity: 94.8%; Expected: 482; Observed: 482 (M).

Example 39-H

(R)-((2R,5S)-5-(4-((((6-fluoro-5-methylpyridin-3-yl)methyl)(methyl)amino)methyl)benzyl) pyrrolidin-2-yl)(pyridin-3-yl)methanol, triflic acid salt (39-H)

Compound 39-H was prepared utilizing a analogous synthesis to that disclosed in Example 4-E.

$^1$H NMR (400 MHz, CD$_3$OD): δ 8.86 (s, 1H), 8.74 (d, J=4.00 Hz, 1H), 8.42 (bs, 1H), 8.04 (bs, 1H), 7.88-7.82 (m, 2H), 7.49-7.40 (m, 4H), 5.03 (d, J=7.20 Hz, 1H), 4.74 (bs, 1H), 4.58 (bs, 1H), 3.92-3.82 (m, 2H), 3.24 (dd, J=10.00 and 11.60 Hz, 1H), 3.14-3.05 (m, 1H), 2.97 (bs, 3H), 2.32 (bs, 3H), 2.16-2.12 (m, 1H), 1.99-1.88 (m, 3H). Molecular Formula: C$_{26}$H$_{29}$FN$_4$O$_2$; LC-MS purity: 99.8%; Expected: 448.6; Observed: 449.2 (M+1).

Example 40-A

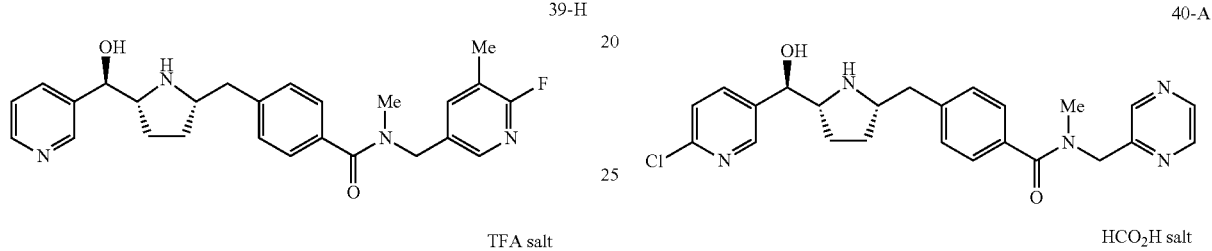

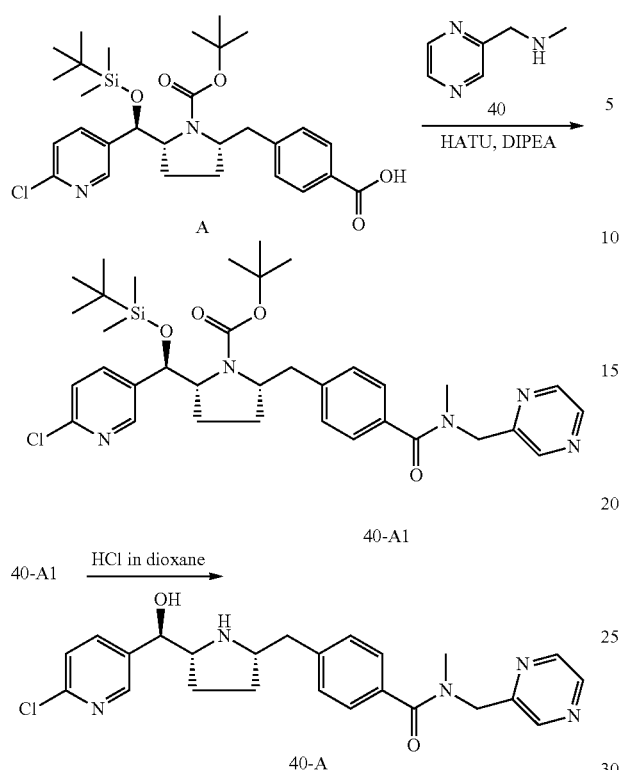

40-A1

4-(((2S,5R)-5-((R)-(6-chloropyridin-3-yl)(hydroxy)methyl)pyrrolidin-2-yl)methyl)-N-methyl-N-(pyrazin-2-ylmethyl)benzamide, formic acid salt (40-A)

Compound 40-A was prepared in an analogous manner to the synthesis route described in Example 4-A but without using HOAT.

$^1$H NMR (400 MHz, CD$_3$OD): δ 8.70 (bs, 1H), 8.65-8.63 (m, 1H), 8.55 (d, J=2.40 Hz, 1H), 8.46-8.44 (m, 2H), 7.92 (d, J=7.60 Hz, 1H), 7.52-7.48 (m, 3H), 7.42 (d, J=7.80 Hz, 1H), 7.34 (d, J=7.60 Hz, 1H), 4.85-4.83 (m, 1H), 4.71 (s, 1H), 3.81-3.78 (m, 2H), 3.21-3.00 (m, 5H), 2.12-2.07 (m, 1H), 1.86 (m, 3H). Molecular Formula: C$_{24}$H$_{26}$ClN$_5$O$_2$; LC-MS purity: 95.8%; Expected: 452; Observed: 452 (M).

Example 40-B

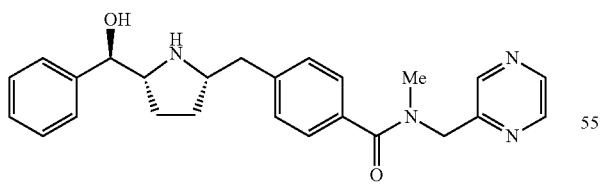

40-B 4-(((2S,5R)-5-((R)-hydroxy(phenyl)methyl)pyrrolidin-2-yl)methyl)-N-methyl-N-(pyrazin-2-ylmethyl)benzamide (40-B)

The compound 40-B was prepared following an analogous procedure as in the synthesis of 23-B.

Molecular Formula: C$_{25}$H$_{29}$N$_4$O$_2$; Expected: 417; Observed: 417 (M+1).

Example 40-D

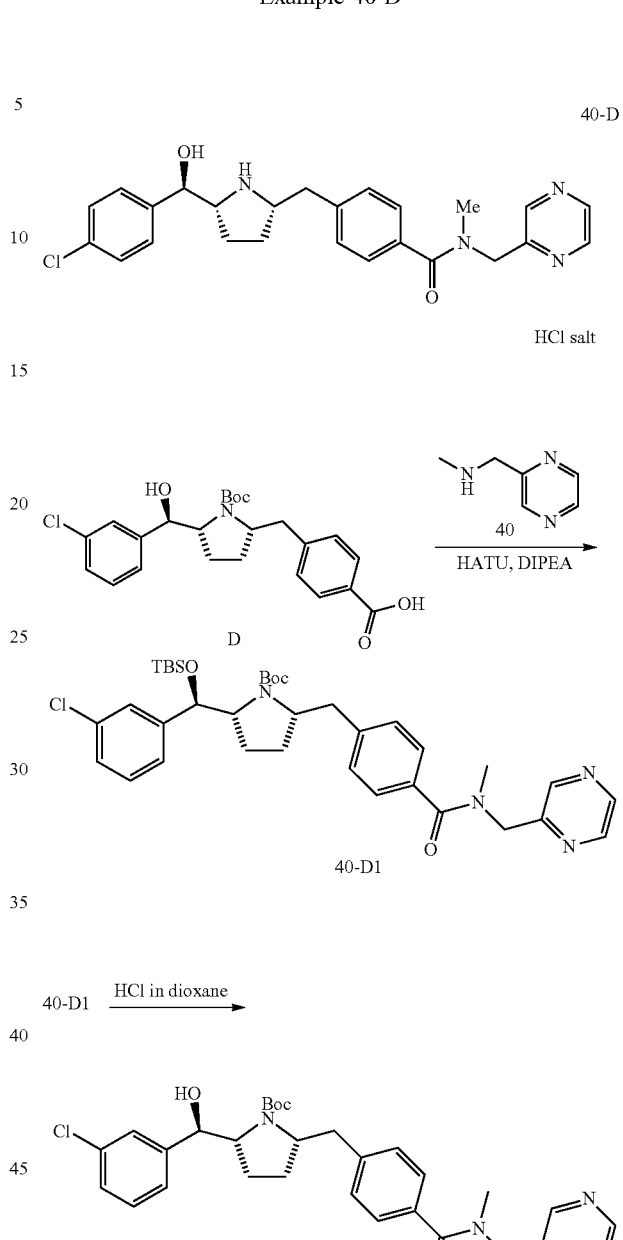

4-(((2S,5R)-5-((R)-(3-chlorophenyl)(hydroxy)methyl)pyrrolidin-2-yl)methyl)-N-methyl-N-(pyrazin-2-ylmethyl)benzamide, hydrochloride salt (40-D)

Compound 40-D was prepared in an analogous manner to that disclosed in Example 4-E $^1$H NMR (400 MHz, CD$_3$OD): δ 8.78-8.62 (m, 2H), 8.59-8.52 (m, 1H), 7.56-7.45 (m, 3H), 7.44-7.33 (m, 5H), 4.8-4.69 (m, 2H), 3.88-3.72 (m, 2H), 3.28-3.2 (m, 1H), 3.18-3.05 (m, 5H), 2.15-2.06 (m, 1H), 1.92-1.8 (m, 3H). Molecular Formula: C$_{25}$H$_{22}$ClN$_4$O$_2$; LC-MS purity: 97.4%; Expected: 450.2; Observed: 451.2 (M+1).

Example 40-G

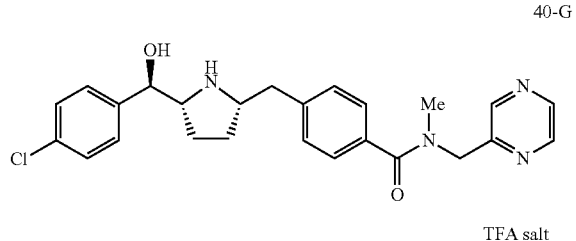 [SMILES: CN(Cc1cnccn1)C(=O)c1ccc(C[C@@H]2CC[C@H]([C@H](O)c3ccc(Cl)cc3)N2)cc1]

4-(((2S,5R)-5-((R)-(4-chlorophenyl)(hydroxy)methyl)pyrrolidin-2-yl)methyl)-N-methyl-N-(pyrazin-2-ylmethyl)benzamide, triflic acid salt (40-G)

Compound 40-G was prepared utilizing an analogous method to that of Example 4-E.

$^1$H NMR (400 MHz, CD$_3$OD): δ 8.69 (bs, 1H), 8.65 (bs, 1H), 8.54-8.44 (m, 1H), 7.51-7.33 (m, 8H), 4.76 (d, J=8.30 Hz, 2H), 4.72 (d, J=8.28 Hz, 2H), 3.81-3.76 (m, 2H), 3.32-3.30 (m, 1H), 3.22 (s, 3H), 3.12-3.07 (m, 1H), 2.11-2.06 (m, 1H), 1.85-1.80 (m, 3H). Molecular Formula: C$_{25}$H$_{27}$ClN$_4$O$_2$; LC-MS purity: 98.3%; Expected: 451; Observed: 451 (M).

Example 40-R

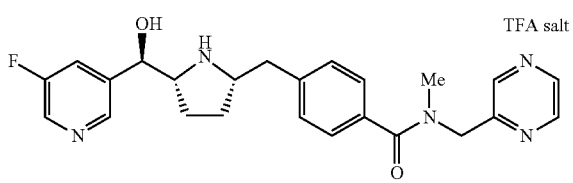

4-(((2S,5R)-5-((R)-(5-fluoropyridin-3-yl)(hydroxy)methyl)pyrrolidin-2-yl)methyl)-N-methyl-N-(pyrazin-2-ylmethyl)benzamide, triflic acid salt (40-R)

Compound 40-R was prepared in an analogous manner to that described in Example 4-E.

$^1$H NMR (400 MHz, CD$_3$OD): δ 8.63 (d, J=6.68 Hz, 1H), 8.54-8.44 (m, 4H), 7.81 (d, J=8.64 Hz, 1H), 7.51-7.47 (m, 2H), 7.43-7.33 (m, 2H), 4.90 (s, 2H), 4.71 (s, 2H), 3.87-3.81 (m, 2H), 3.32-3.30 (m, 2H), 3.21 (s, 3H), 3.12-3.07 (m, 1H), 2.12-2.08 (m, 1H), 1.91-1.83 (m, 3H). Molecular Formula: C$_{25}$H$_{27}$ClN$_4$O$_2$; LC-MS purity: 98.3%; Expected: 435.5; Observed: 436 (M+1).

Example 40-S

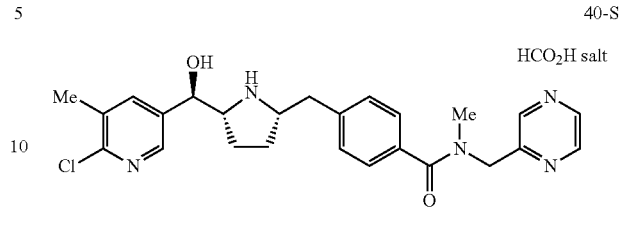

4-(((2S,5R)-5-((R)-(6-chloro-5-methylpyridin-3-yl)(hydroxy)methyl)pyrrolidin-2-yl)methyl)-N-methyl-N-(pyrazin-2-ylmethyl)benzamide, formic acid salt (40-S)

Compound 40-S was prepared in an analogous manner to that described in Example 4-E.

$^1$H NMR (400 MHz, CD$_3$OD): δ 8.69 (s, 1H), 8.63 (s, 1H), 8.54 (d, J=2.40 Hz, 1H), 8.26 (s, 1H), 7.83 (s, 1H), 7.50-7.40 (m, 4H), 4.90 (s, 2H), 4.75-4.71 (m, 2H), 3.70 (s, 2H), 3.12 (s, 3H), 3.08-3.06 (m, 2H), 2.41 (s, 3H), 2.06-2.04 (m, 1H), 1.79-1.77 (m, 3H). Molecular Formula: C$_{25}$H$_{28}$ClN$_5$O$_2$; LC-MS purity: 95.9%; Expected: 466; Observed: 466.2 (M+1).

Example 41-A

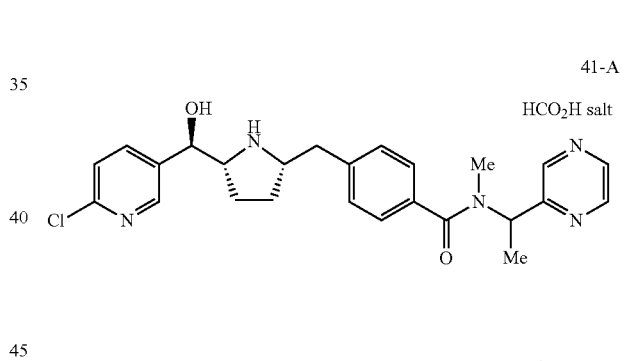

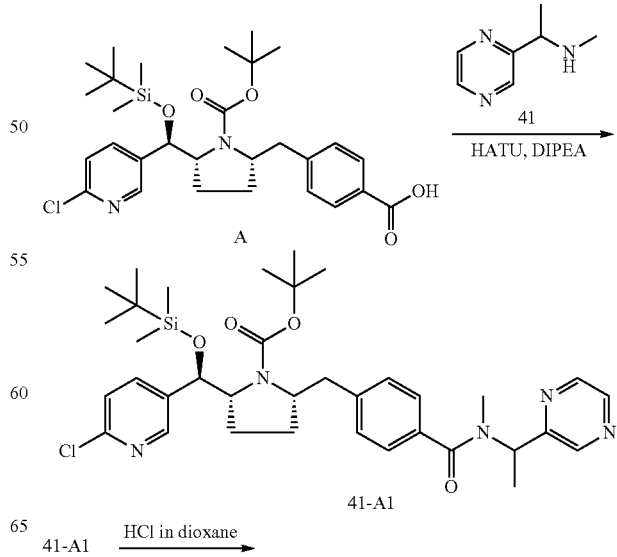

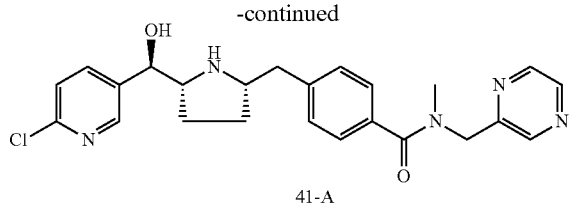

4-(((2S,5R)-5-((R)-(6-chloropyridin-3-yl)(hydroxy)methyl)pyrrolidin-2-yl)methyl)-N-methyl-N-(1-(pyrazin-2-yl)ethyl)benzamide, formic acid salt (41-A)

Compound 41-A was prepared in a similar manner to that described in Example 4-A without using HOAT.

$^1$H NMR (400 MHz, CD$_3$OD): δ 8.72 (bs, 1H), 8.64 (bs, 1H), 8.54 (d, J=2.40 Hz, 1H), 8.46-8.45 (m, 2H), 7.92 (dd, J=2.30 and J=8.20 Hz, 1H), 7.51 (d, J=8.40 Hz, 1H), 7.46 (bs, 1H), 7.41-7.39 (m, 2H), 4.83 (d, J=8.20 Hz, 1H), 3.80-3.76 (m, 2H), 3.18 (m, 1H), 3.04 (m, 1H), 2.91 (bs, 3H), 2.10 (m, 1H), 1.89-1.84 (m, 2H), 1.72 (m, 2H). Molecular Formula: C$_{25}$H$_{28}$ClN$_5$O$_2$; LC-MS purity: 97.6%; Expected: 466; Observed: 466.1 (M+1).

Example 41-B

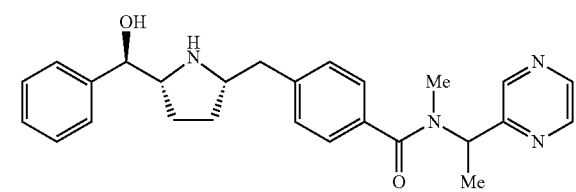

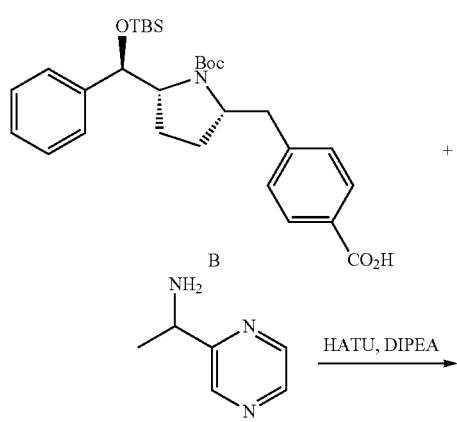

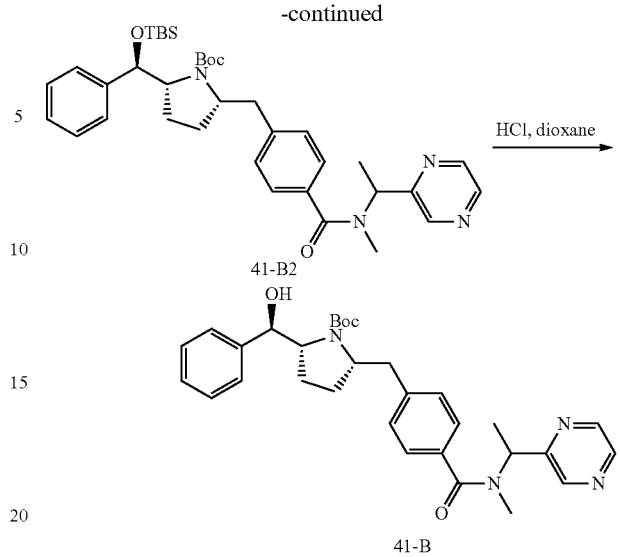

4-(((2S,5R)-5-((R)-hydroxy(phenyl)methyl)pyrrolidin-2-yl)methyl)-N-methyl-N-(1-(pyrazin-2-yl)ethyl)benzamide (41-B)

Compound 41-B was prepared using 1-(pyrazin-2-yl)ethanamine in the manner as in example 2-B.

$^1$H NMR (400 MHz, CD$_3$OD): δ 8.65-8.54 (m, 3H), 7.47-7.33 (m, 9H), 6.00-5.20 (m, 1H), 4.68 (d, J=8.00 Hz, 1H), 3.72-3.69 (m, 2H), 3.33-2.92 (m, 5H), 2.05-1.73 (m, 7H). Molecular Formula: C$_{26}$H$_{30}$N$_4$O$_2$; LCMS purity: 96.1%; Expected: 430.5; Observed: 431.1 (M+1).

Example 41-F

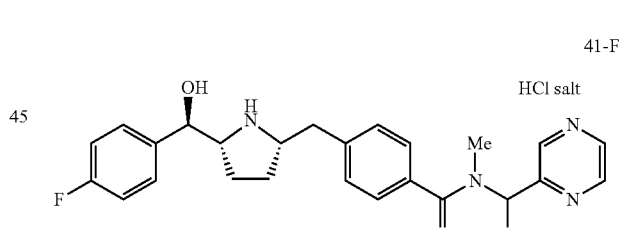

4-(((2S,5R)-5-((R)-(4-fluorophenyl)(hydroxy)methyl)pyrrolidin-2-yl)methyl)-N-methyl-N-(1-(pyrazin-2-yl)ethyl)benzamide, hydrochloride salt (41-F)

Compound 41-F was prepared in an analogous manner to that described in Example 4-E.

$^1$H NMR (400 MHz, CD$_3$OD): δ 8.73 (bs, 1H), 8.65 (s, 1H), 8.54 (d, J=2.36 Hz, 1H), 7.49-7.40 (m, 6H), 7.13 (t, J=8.72 Hz, 2H), 5.95 (bs, 1H), 5.18 (bs, 1H), 4.75 (d, J=8.68 Hz, 1H), 3.78-3.74 (m, 3H), 3.24-3.19 (m, 1H), 3.09-3.03 (m, 1H), 2.91 (s, 3H), 2.10-2.06 (1H), 1.89-1.83 (m, 6H). Molecular Formula: C$_{26}$H$_{29}$FN$_4$O$_2$; LC-MS purity: 96.2%; Expected: 448.5; Observed: 449.2 (M+1).

Example 42-A

Example 42-B

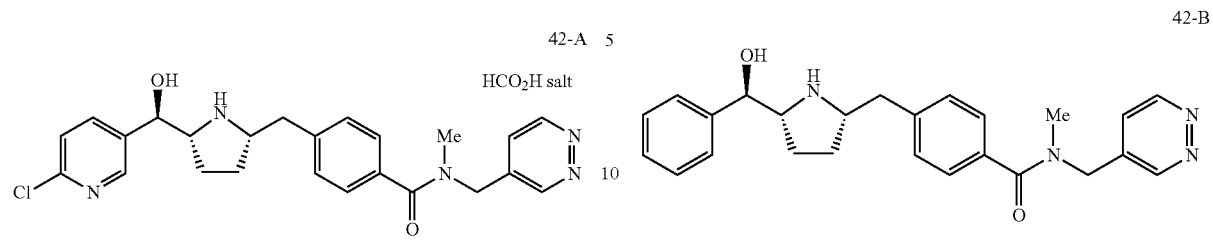

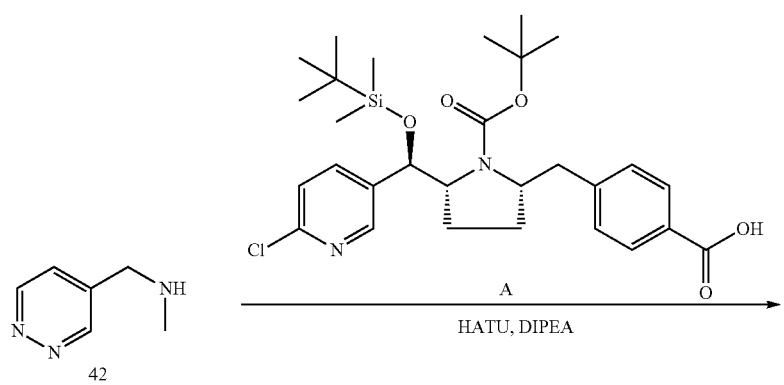

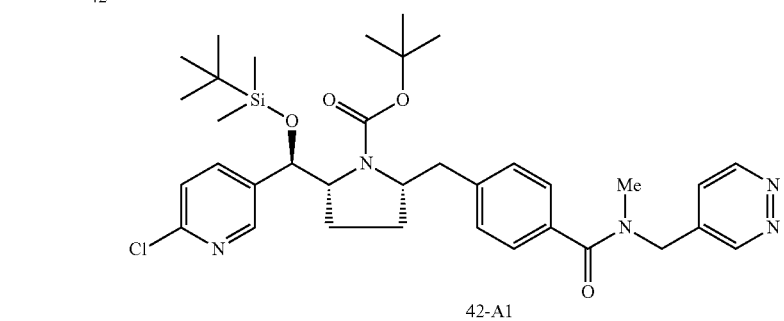

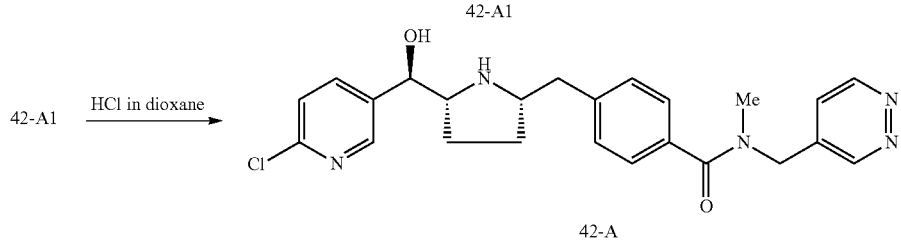

4-(((2S,5R)-5-((R)-(6-chloropyridin-3-yl)(hydroxy)
methyl)pyrrolidin-2-yl)methyl)-N-methyl-N-
(pyridazin-4-ylmethyl)benzamide, formic acid salt
(42-A)

Compound 42-A was prepared in an analogous manner to that as described in Example 4-E.

$^1$H NMR (400 MHz, CD$_3$OD): δ 9.18 (d, J=5.30 Hz, 1H), 8.49 (bs, 1H), 8.45 (d, J=1.90 Hz, 1H), 7.92 (dd, J=2.20 and 8.20 Hz, 1H), 7.72 (m, 1H), 7.55-7.50 (m, 2H), 7.44-7.39 (m, 3H), 4.83 (d, J=2.50 Hz, 1H), 4.81 (bs, 1H), 3.79-3.77 (m, 2H), 3.17 (m, 1H), 3.08 (s, 3H), 3.08-3.05 (m, 1H), 2.10 (m, 1H), 1.90-1.80 (m, 3H). Molecular Formula: C$_{24}$H$_{26}$ClN$_5$O$_2$; LC-MS purity: 97.5%; Expected: 451.9; Observed: 452.2 (M+1).

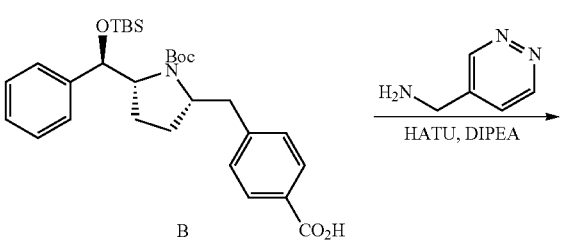

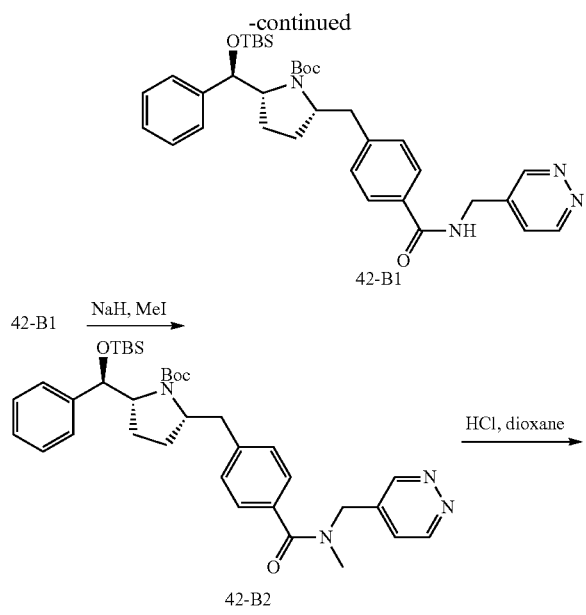
4-(((2S,5R)-5-((R)-hydroxy(phenyl)methyl)pyrrolidin-2-yl)methyl)-N-methyl-N-(pyridazin-4-ylmethyl)benzamide (42-B)
Compound 42-B was prepared in an analogous manner to that shown in Example 2-B.
$^{1}$H NMR (400 MHz, CD$_3$OD): δ 9.24-9.18 (m, 2H), 7.74-7.25 (m, 10H), 4.84-4.66 (m, 2H), 4.49-4.47 (m, 1H), 3.42-3.32 (m, 2H), 3.09 (s, 3H), 2.93-2.89 (m, 2H), 1.85 (m, 1H), 1.57-1.52 (m, 3H). Molecular Formula: C$_{25}$H$_{28}$N$_4$O$_2$; LCMS purity: 95%; Expected: 416.5; Observed: 417.1 (M+1).
Example 43-A
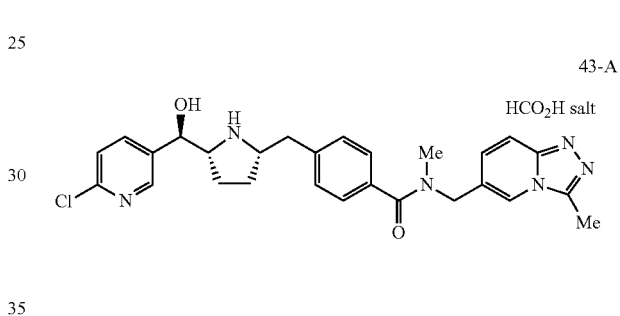
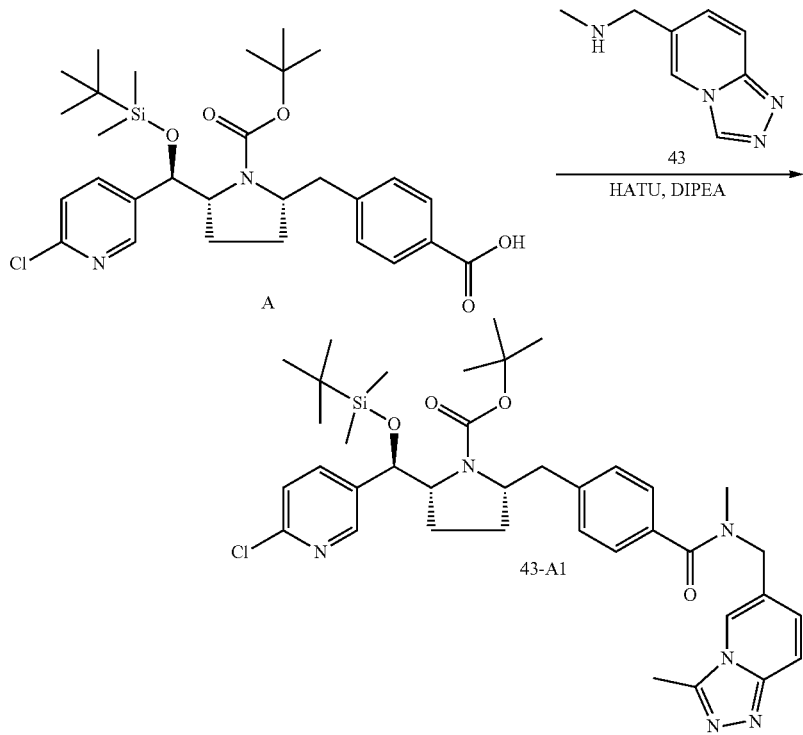

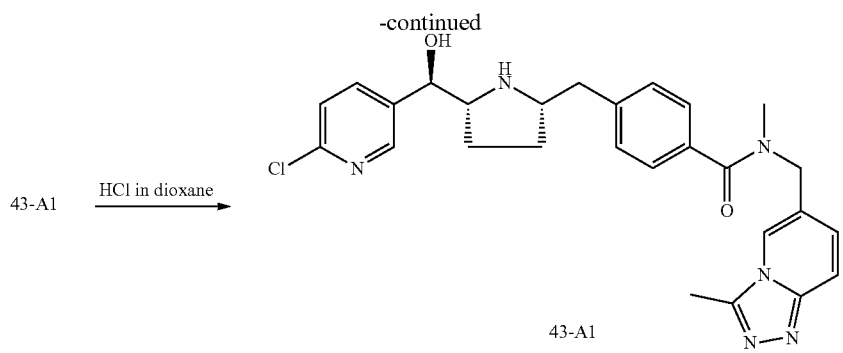

4-(((2S,5R)-5-((R)-(6-chloropyridin-3-yl)(hydroxy)methyl)pyrrolidin-2-yl)methyl)-N-methyl-N-((3-methyl-[1,2,4]triazolo[4,3-a]pyridin-6-yl)methyl)benzamide, formic acid salt (43-A)

Compound 43-A was prepared in an analogous manner as is described in Example 4-E.

$^1$H NMR (400 MHz, MeOD): δ 8.47 (d, J=2.00 Hz, 1H), 8.38-8.36 (m, 2H), 7.93 (dd, J=2.40 and 8.40 Hz, 1H), 7.74-7.72 (m, 1H), 7.54-7.52 (m, 3H), 7.43 (d, J=8.40 Hz, 2H), 4.85 (d, J=8.40 Hz, 1H), 4.81 (bs, 1H), 3.82-3.78 (m, 2H), 3.24-3.18 (m, 1H), 3.09-3.06 (m, 1H), 3.00 (bs, 3H), 2.78 (bs, 3H), 2.12-2.10 (m, 1H), 1.89-1.87 (m, 3H). Molecular Formula: $C_{27}H_{29}ClN_6O_2$; LCMS purity: 97.6%; Expected: 505; Observed: 506.2 (M+1).

Example 43-B

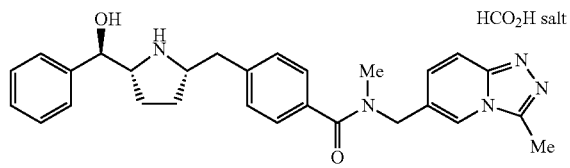

4-(((2S,5R)-5-((R)-hydroxy(phenyl)methyl)pyrrolidin-2-yl)methyl)-N-methyl-N-((3-methyl-[1,2,4]triazolo[4,3-a]pyridin-6-yl)methyl)benzamide, formic acid salt (43-B)

Compound 43-B was prepared in an analogous manner to that as shown in example 4-E.

$^1$H NMR (400 MHz, MeOD): δ 8.42 (bs, 1H), 8.36 (bs, 1H), 7.73 (d, J=8.00 Hz, 1H), 7.57-7.34 (m, 10H), 4.81 (s, 2H), 4.74 (d, J=8.40 Hz, 1H), 3.82-3.77 (m, 2H), 3.36 (s, 3H), 3.25-3.20 (m, 1H), 3.09-3.04 (m, 1H), 3.03 (s, 3H), 2.78 (s, 3H), 2.09-2.07 (m, 1H), 1.86-1.78 (m, 3H). Molecular Formula: $C_{28}H_{31}N_5O_2$; LCMS purity: 96.9%; Expected: 469.6; Observed: 470.2 (M+1).

Example 44-A

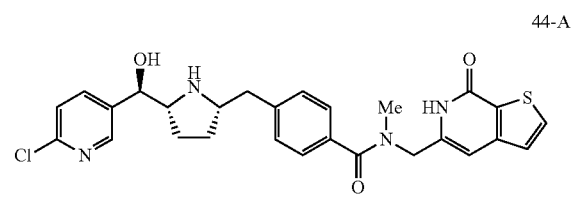 [SMILES: CN(Cc1cc2ccsc2c(=O)[nH]1)C(=O)c1ccc(C[C@@H]2CC[C@H]([C@H](O)c3ccc(Cl)nc3)N2)cc1]

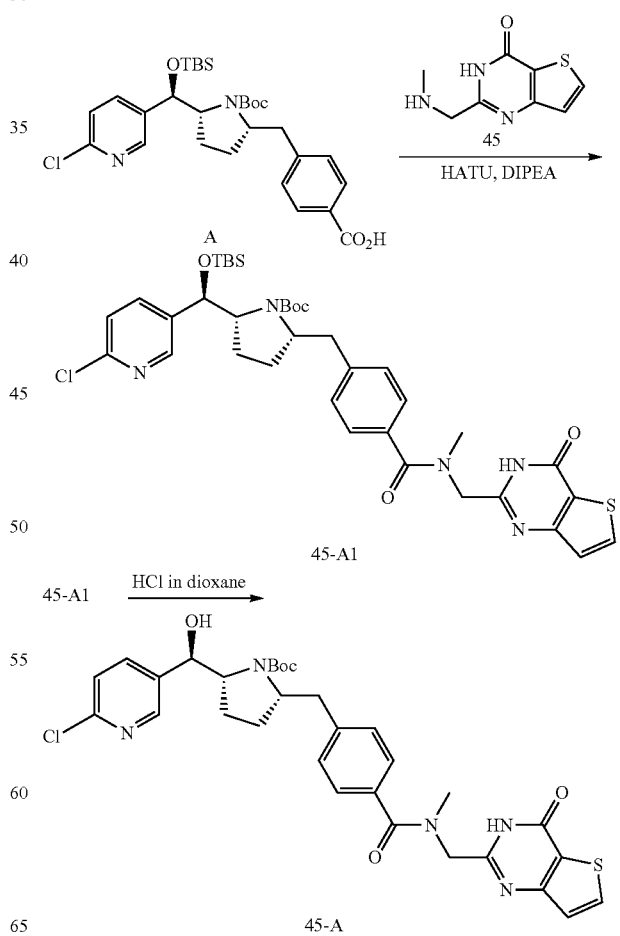

4-(((2S,5R)-5-((R)-(6-chloropyridin-3-yl)(hydroxy) methyl)pyrrolidin-2-yl)methyl)-N-methyl-N-((4-oxo-3,4-dihydrothieno[3,2-d]pyrimidin-2-yl)methyl) benzamide (44-A)

Compound 44-A was prepared in an analogous manner as shown in example 4-E.

$^1$H NMR (400 MHz, CD$_3$OD): δ8.40-7.28 (m, 9H), 4.74-4.52 (m, 3H), 3.54-3.48 (m, 2H), 3.19 (s, 3H), 3.03-2.95 (m, 2H), 1.93 (m, 1H), 1.72-1.64 (m, 3H). Molecular Formula: C$_{26}$H$_{26}$ClN$_5$O$_3$S; LCMS purity: >99%; Expected: 524; Observed: 524.2 (M+1).

Example 44-B

4-(((2S,5R)-5-((R)-hydroxy(phenyl)methyl)pyrrolidin-2-yl)methyl)-N-methyl-N-((4-oxo-3,4-dihydrothieno[3,2-d]pyrimidin-2-yl)methyl)benzamide (44-B)

Compound 44-B was prepared in a similar manner to that described in Example 4-E.

$^1$H NMR (400 MHz, CD$_3$OD): δ8.05-7.28 (m, 11H), 4.74-4.50 (m, 3H), 3.60-3.53 (m, 2H), 3.19 (s, 3H), 3.07-2.96 (m, 2H), 1.95-1.91 (m, 1H), 1.67-1.63 (m, 3H). Molecular Formula: C$_{27}$H$_{28}$N$_4$O$_3$S; LCMS purity: >99%; Expected: 488.6; Observed: 489.2 (M+1).

Example 45-A

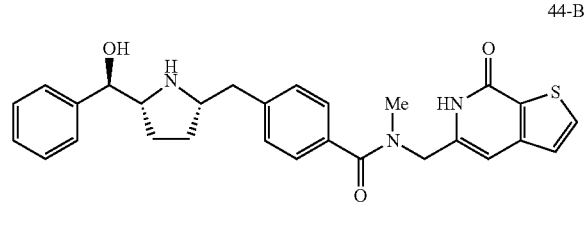 [SMILES: CN(Cc1cc2ccsc2c(=O)[nH]1)C(=O)c1ccc(C[C@@H]2CC[C@H]([C@H](O)c3ccccc3)N2)cc1]

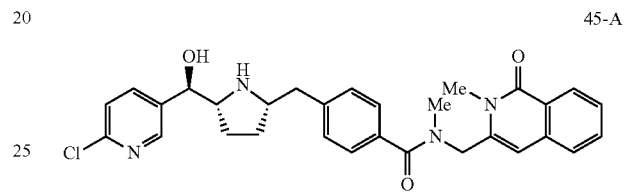

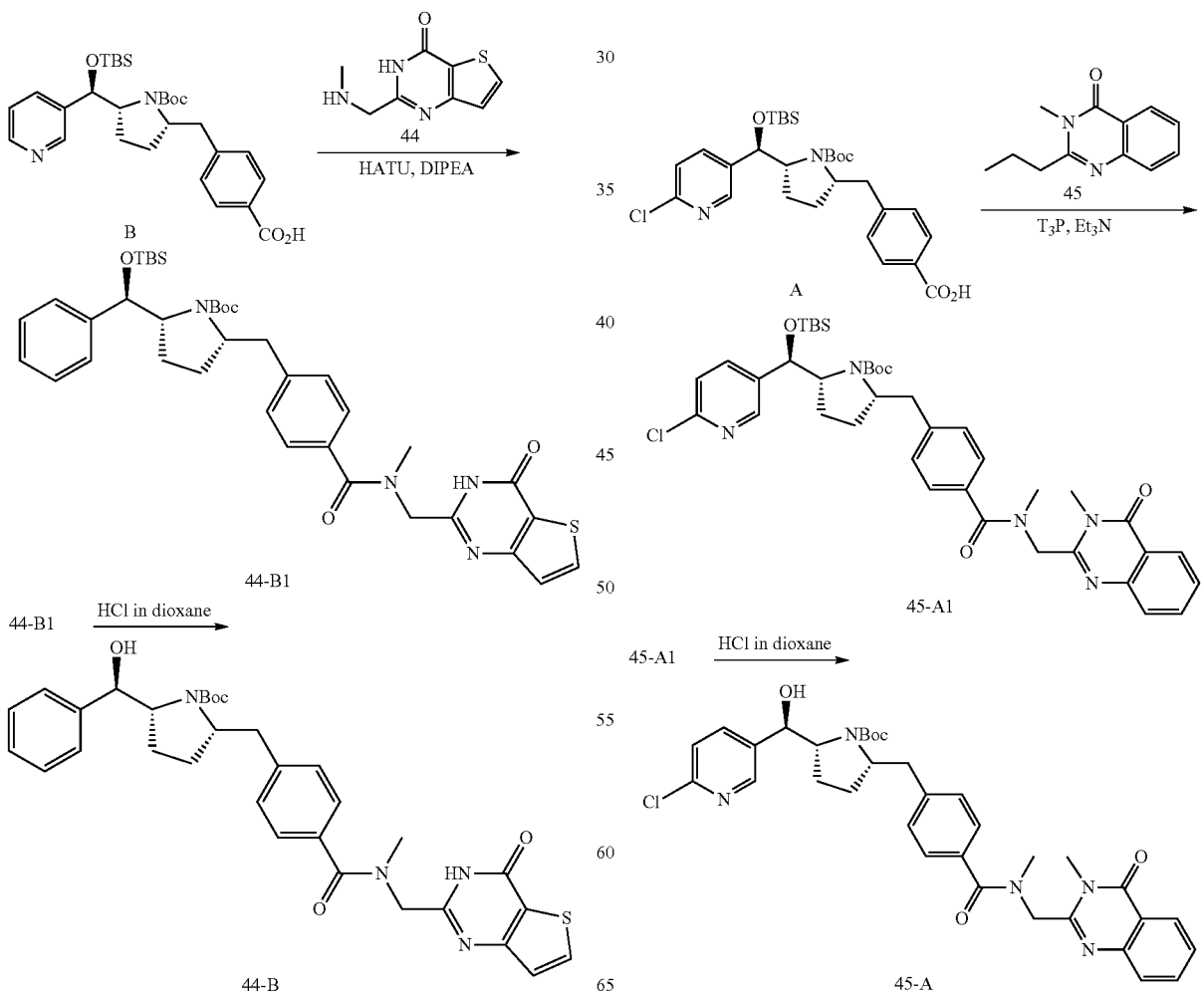

4-(((2S,5R)-5-((R)-(6-chloropyridin-3-yl)(hydroxy)methyl)pyrrolidin-2-yl)methyl)-N-methyl-N-((3-methyl-4-oxo-3,4-dihydroquinazolin-2-yl)methyl)benzamide (45-A)

Compound 45-A was prepared in an analogous manner to that described in example 5-A.

$^1$H NMR (400 MHz, DMSO-$d_6$): δ8.15-7.26 (m, 11H), 5.75 (m, 1H), 4.86 (s, 2H), 4.30 (m, 1H), 3.57 (s, 2H), 3.31-3.01 (m, 7H), 2.80-2.50 (m, 2H), 1.70-1.00 (m, 4H). Molecular Formula: $C_{29}H_{30}ClN_5O_3$; LCMS purity: >99%; Expected: 532; Observed: 532.3 (M+1).

Example 45-B

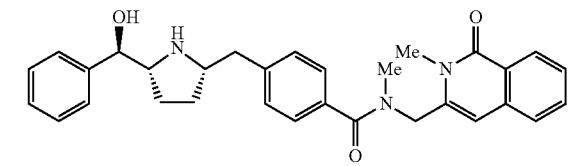

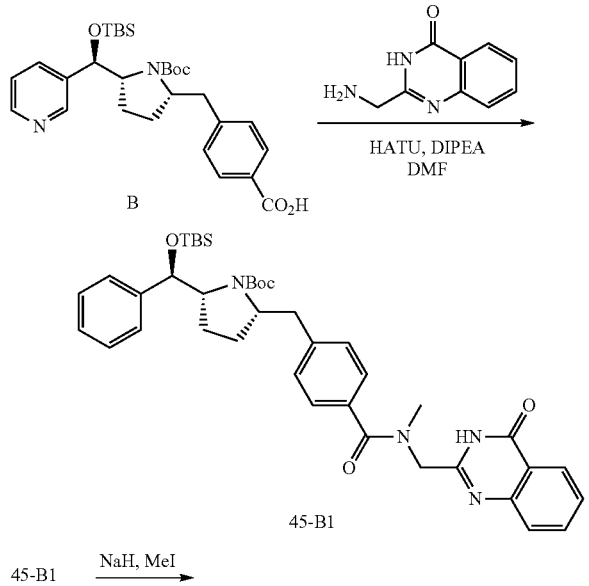

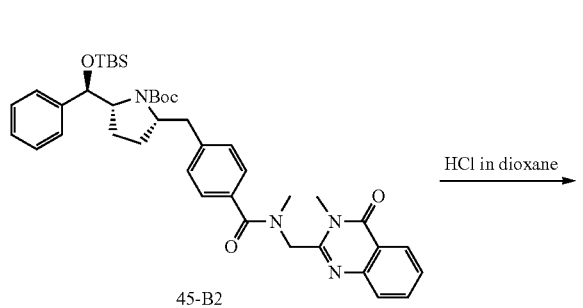

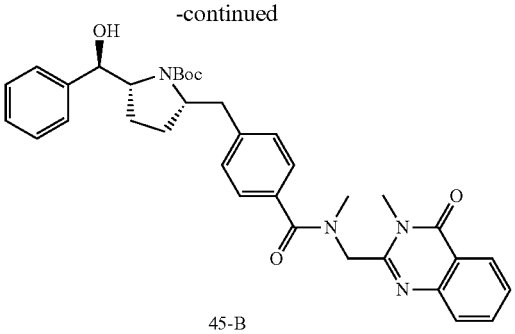

4-(((2S,5R)-5-((R)-hydroxy(phenyl)methyl)pyrrolidin-2-yl)methyl)-N-methyl-N-((3-methyl-4-oxo-3,4-dihydroquinazolin-2-yl)methyl)benzamide (45-B)

Compound 45-B was prepared in a manner analogous to the synthesis described in Example 2-B.

$^1$H NMR (400 MHz, CD$_3$OD): δ8.24-7.24 (m, 13H), 4.94-4.43 (m, 3H), 3.69 (s, 2H), 3.37-2.88 (m, 8H), 1.81-1.51 (m, 4H). Molecular Formula: $C_{30}H_{32}N_4O_3$; LCMS purity: 98.9%; Expected: 496.6; Observed: 497.2 (M+1).

Screening Methods

The ability of compounds to activate the human β3-AR receptor was measured using a CHO cell line stably expressing the cloned human β1-, β2-, and β3-adrenoceptors (β-AR). The cell line expressing β3-AR was at levels very similar to those observed in the human bladder detrusor muscle (unpublished observation). To quantify the amount of cAMP released following β3-AR activation, the LANCE cAMP kit (Perkin-Elmer), a time-resolved fluorescence resonance energy transfer immunoassay, was used. Compounds were serially diluted in DMSO and an aliquot added to either 384-well or 96-well micro titer plates in assay buffer (5 mM HEPES, 0.1% BSA in Hank's Balanced Salt Solution). The reaction was initiated by the addition of 6000 cells per well in assay buffer that also contained a cAMP specific antibody labeled with Alexa Fluor 647 and a phosphodiesterase inhibitor (IBMX). Following 30 min incubation at room temperature, the cells were lysed by the addition of LANCE detection buffer which contained a europium-labeled cAMP tracer. Fluorescence was measured following one hour incubation at room temperature using a Perkin-Elmer Envision plate reader, exciting at 340 nm and measuring emission at 615 nm and 665 nm. For each assay, a cAMP standard curve was included and used to convert fluorescence readings directly to cAMP amounts. The values were then normalized to isoproterenol, a known full agonist of β3-AR, which was titrated in every assay and the EC50 determined using a custom in-house data analysis package. Along with EC50, the percent maximum activation relative to isoproterenol is reported.

The following in vitro assays are suitable for screening compounds that have selective β3 agonist activity:

Functional Assay:

For compounds in examples 1-45, cAMP production in response to ligand is measured according to Barton, et al. (1991, Agonist-induced desensitization of D2 dopamine receptors in human Y-79 retinoblastoma cells. Mol. Pharmacol. v3229:650-658) modified as follows. The cAMP production is measured using a homogenous time-resolved fluorescence resonance energy transfer immunoassay (LANCE™, Perkin Elmer) according to the manufacture's instructions. Chinese hamster ovary (CHO) cells, stably transfected with the cloned β-adrenergic receptor (β1, β2 or β3) are harvested after 3 days of subculturing. Harvesting of cells is done with Enzyme-free Dissociation Media (Specialty Media). Cells are then counted and resuspended in assay buffer (Hank's Balanced salt solution supplemented with 5 mM HEPES, 01% BSA) containing a phosphodiesterase inhibitor (IBMX, 0.6 mM). The reaction is initiated by mixing 6,000 cells in 6 µL with 6 µL Alexa Fluor labeled cAMP antibody (LANCE™ kit) which is then added to an assay well containing 12 µL of compound (diluted in assay buffer to 2× final concentration). The reaction proceeds for 30 minutes at RT and is terminated by the addition of 24 ul detection buffer (LANCE™ kit). The assay plate is then incubated for 1 h at RT and time-resolved fluorescence measured on a Perkin Elmer Envision reader or equivalent. The unknown cAMP level is determined by comparing fluorescence levels to a cAMP standard curve.

The non-selective, full agonist β-adrenergic ligand isoproterenol is used at all three receptors to determine maximal stimulation. The human β3 adrenergic receptor (AR) selective ligand (S)—N-[4-[2-[[2-hydroxy-3-(4-hydroxyphenoxy)propyl]amino]ethyl]-phenyl]-4-iodobenzenesulfonamide is used as a control in all assays. Isoproterenol is titrated at a final concentration in the assay of 10-10 M to 10-5 and the selective ligand (S)—N-[4-[2-[[2-hydroxy-3-(4-hydroxyphenoxy)propyl]amino]ethyl]phenyl]-4-iodobenzenesulfonamide is titrated at the β3 receptor at concentration of 10-10 M to 10-5 M. Unknown ligands are titrated at all 3β-adrenergic receptor subtypes at a final concentration in the assay of 10-10 M to 10-5 M to determine the $EC_{50}$. The $EC_{50}$ is defined as the concentration of compound that gives 50% activation of its own maximum. Data are analyzed using Microsoft Excel and Graphpad Prism or an internally developed data analysis software package.

For compounds in examples 1-45, Isoproterenol is titrated at a final concentration in the assay of 10-12 M to 10-5 and the selective ligand (S)—N-[4-[2-[[2-hydroxy-3-(4-hydroxyphenoxy)propyl]amino]ethyl]phenyl]-4-iodobenzenesulfonamide is titrated at the β3 receptor at concentration of 10-12 M to 10-5 M. Unknown ligands are titrated at all 3β-adrenergic receptor subtypes at a final concentration in the assay of 10-12 M to 10-5 M to determine the $EC_{50}$. The $EC_{50}$ is defined as the concentration of compound that gives 50% activation of its own maximum. Functional antagonist assays are performed similar to described above; however, unknown ligands are titrated at β-adrenergic receptor subtypes 1 and 2 at a final concentration in the assay of 10-12 M to 10-5 M in the presence of 10-9 M full agonist β-adrenergic ligand isoproterenol. The $EC_{50}$ is defined as the concentration of compound that gives 50% inhibition of the full agonist response. Data are analyzed using Microsoft Excel and Graphpad Prism or an internally developed data analysis software package.

Binding Assay:

Compounds are also assayed at the β1 and β2 receptors to determine selectivity. All binding assays are run using membranes prepared from CHO cells recombinantly expressing β1 or β2 receptors. Cells are grown for 3-4 days post splitting; the attached cells are washed with PBS and then lysed in 1 mM Tris, pH 7.2 for 10 minutes on ice. The flasks are scraped to remove the cells and the cells then homogenized using a Teflon/glass homogenizer. Membranes are collected by centrifuging at 38,000×g for 15 minutes at 4° C. The pelleted membranes are resuspended in TME buffer (50 mM Tris, pH 7.4, 5 mM $MgCl_2$, 2 mM EDTA) at a concentration of 1 mg protein/mL. Large batches of membranes can be prepared, aliquoted and stored at −70° C. for up to a year without loss of potency. The binding assay is performed by incubating together membranes (2-5 µg of protein), the radiolabelled tracer $^{125}$I-cyanopindolol ($^{125}$I-CYP, 45 pM), 200 ug of WGA-PVT SPA beads (GE Healthcare) and the test compounds at final concentrations ranging from 10-10 M to 10-5 M in a final volume of 200 µL of TME buffer containing 0.1% BSA. The assay plate is incubated for 1 h with shaking at RT and then placed in a Perkin Elmer Trilux scintillation counter. The plates are allowed to rest in the Trilux counter for approximately 10 h in the dark prior to counting. Data are analyzed using a standard 4-parameter non-linear regression analysis using either Graphpad Prism software or an internally developed data analysis package. The $IC_{50}$ is defined as the concentration of the title compound capable of inhibiting 50% of the binding of the radiolabelled tracer ($^{125}$I-CYP). A compound's selectivity for the β3 receptor may be determined by calculating the ratio ($IC_{50}$ β1 AR, β2 AR)/($EC_{50}$ β3 AR).

Table 1 provides activity data ($EC_{50}$ and corresponding % agonism) for each of the examples of the invention. In nearly every case, the analog featuring the 2-chloropyridine moiety in the pharmacophore demonstrates superior agonist activity vs. comparator analogs containing alternative pharmacophore aryl rings.

The fold drop in potency of the comparative analog versus the inventive 2-chloropyridine compounds is found by dividing the $EC_{50}$ value of the comparative example by the $EC_{50}$ value of the corresponding 2-chloropyridine compound. For example, the fold drop in potency of comparative Example 1-B is (443/96)=4.6 and the fold drop in potency of comparative Example 2-B is (168/118)=1.4

TABLE 1

Claimed compounds N-A . vs. comparator compounds N-(B-S)

| Example | Human β3-AR Agonism $EC_{50}$ (nM) | Human β3-AR Agonist Activity (%) | Fold drop in potency vs. 2-chloropyridine analog |
|---|---|---|---|
| 1-A | 96 | 100 | — |
| 1-B | 443 | 93 | 4.6 |
| 2-A | 118 | 86 | — |
| 2-B | 168 | 94 | 1.4 |
| 3-A | 204 | 81 | — |
| 3-B | 410 | 101 | 2.0 |
| 4-A | 5 | 104 | — |
| 4-B | 14 | 108 | 2.6 |
| 4-E | 90 | 79 | 16.4 |
| 4-F | 19 | 105 | 3.5 |
| 4-G | 4 | 95 | 0.8 |
| 4-Q | 78 | 106 | 14.4 |
| 4-R | 45 | 101 | 8.3 |
| 5-A | 2 | 102 | — |
| 5-H | 3 | 106 | 1.6 |
| 6-A | 3 | 93 | — |
| 6-H | 7 | 92 | 2.4 |
| 7-A | 59 | 95 | — |
| 7-B | 188 | 110 | 3.2 |
| 8-A | 20 | 103 | — |
| 8-B | 39 | 103 | 2.0 |
| 9-A | 3 | 93 | — |
| 9-B | 15 | 102 | 5.5 |
| 9-E | 108 | 76 | 39.6 |
| 9-G | 4 | 97 | 1.6 |
| 9-H | 104 | 101 | 38.1 |
| 10-A | 2 | 96 | — |
| 10-B | 5 | 110 | 3.2 |
| 10-H | 22 | 98 | 13.9 |
| 11-A | 7 | 95 | — |
| 11-B | 26 | 116 | 4.0 |
| 12-A | 13 | 95 | — |

TABLE 1-continued

Claimed compounds N-A . vs. comparator compounds N-(B-S)

| Example | Human β3-AR Agonism EC$_{50}$ (nM) | Human β3-AR Agonist Activity (%) | Fold drop in potency vs. 2-chloropyridine analog |
|---|---|---|---|
| 12-B | 18 | 120 | 1.5 |
| 13-A | 2 | 99 | — |
| 13-B | 3 | 113 | 1.5 |
| 14-A | 3 | 108 | — |
| 14-H | 55 | 101 | 19.5 |
| 15-A | 1 | 94 | — |
| 15-B | 5 | 112 | 5.9 |
| 16-A | 2 | 102 | — |
| 16-B | 10 | 101 | 6.2 |
| 17-A | 4 | 94 | — |
| 17-B | 17 | 112 | 4.5 |
| 18-A | 8 | 101 | — |
| 18-B | 68 | 105 | 8.6 |
| 18-G | 13 | 101 | 1.7 |
| 19-A | 5 | 111 | — |
| 19-B | 32 | 115 | 5.8 |
| 20-A | 5 | 108 | — |
| 20-B | 9 | 103 | 2.1 |
| 20-E | 86 | 72 | 18.9 |
| 20-G | 6 | 99 | 4.5 |
| 21-A | 4 | 102 | — |
| 21-B | 41 | 86 | 9.7 |
| 21-C | 10 | 100 | 2.3 |
| 21-D | 120 | 97 | 28.2 |
| 21-F | 12 | 94 | 2.9 |
| 21-G | 6 | 88 | 1.3 |
| 21-H | 38 | 85 | 8.8 |
| 21-I | 19 | 71 | 4.4 |
| 21-J | 10000 | 38 | >2300 |
| 21-K | 112 | 87 | 26.3 |
| 21-L | 100003 | >2300 | |
| 21-M | 20 | 97 | 4.7 |
| 21-N | 10000 | 27 | >2300 |
| 21-O | 274 | 77 | 64.3 |
| 21-P | 24 | 93 | 5.7 |
| 21-R | 57 | 91 | 13.3 |
| 21-S | 307 | 84 | 72.1 |
| 22-A | 5 | 62 | — |
| 22-B | 10 | 103 | 2.0 |
| 23-A | 2 | 96 | — |
| 23-B | 3 | 93 | 1.5 |
| 24-A | 42 | 98 | — |
| 24-B | 229 | 106 | 5.4 |
| 25-A | 18 | 98 | — |
| 25-B | 109 | 96 | 6.0 |
| 26-A | 35 | 97 | — |
| 26-C | 143 | 98 | 4.1 |
| 26-F | 136 | 93 | 3.9 |
| 26-H | 397 | 96 | 11.3 |
| 27-A | 5 | 57 | — |
| 27-H | 1388 | 78 | 288.6 |
| 28-A | 175 | 87 | — |
| 28-C | 816 | 78 | 4.7 |
| 28-F | 732 | 88 | 4.2 |
| 29-A | 17 | 94 | — |
| 29-B | 86 | 99 | 5.1 |
| 30-A | 3 | 99 | — |
| 30-B | 28 | 100 | 8.9 |
| 30-F | 78 | 101 | 24.4 |
| 31-A | 7 | 96 | — |
| 31-B | 16 | 104 | 2.3 |
| 32-A | 13 | 94 | — |
| 32-B | 22 | 109 | 1.8 |
| 32-G | 16 | 98 | 1.2 |
| 33-A | 44 | 101 | — |
| 33-B | 87 | 111 | 87.0 |
| 33-G | 63 | 102 | 1.4 |
| 34-A | 6 | 90 | — |
| 34-B | 14 | 101 | 2.3 |
| 34-G | 18 | 90 | 2.9 |
| 35-A | 17 | 91 | — |
| 35-B | 62 | 102 | 3.6 |
| 36-A | 14 | 92 | — |
| 36-B | 59 | 101 | 4.3 |
| 37-A | 27 | 94 | — |
| 37-B | 63 | 101 | 2.4 |
| 38-A | 8 | 58 | — |
| 38-B | 7 | 100 | 0.9 |
| 39-A | 1 | 96 | — |
| 39-B | 2 | 104 | 3.8 |
| 39-G | 3 | 95 | 5.7 |
| 39-H | 7 | 103 | 14.1 |
| 40-A | 12 | 111 | — |
| 40-B | 17 | 99 | 1.5 |
| 40-D | 567 | 86 | 48.6 |
| 40-G | 19 | 100 | 1.6 |
| 40-R | 373 | 87 | 32.0 |
| 40-S | 3132 | 60 | 268.2 |
| 41-A | 2 | 98 | — |
| 41-B | 16 | 109 | 9.1 |
| 41-F | 6 | 83 | 3.5 |
| 42-A | 3 | 94 | — |
| 42-B | 55 | 111 | 16.1 |
| 43-A | >10000 | 45 | — |
| 43-B | 1625 | 79 | <0.12 |
| 44-A | 2 | 99 | — |
| 44-B | 4 | 97 | 1.7 |
| 45-A | 25 | 90 | — |
| 45-B | 65 | 81 | 2.6 |

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I, or a pharmaceutically acceptable salt thereof, or a stereoisomer thereof, or a pharmaceutically acceptable salt of the stereoisomer thereof:

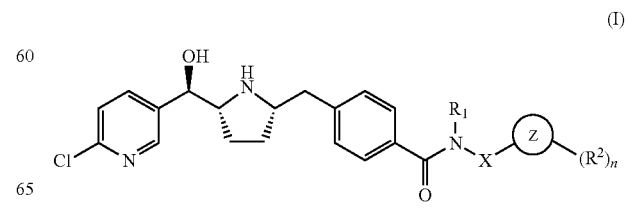

(I)

wherein:

n is 0, 1, 2, 3, or 4;

X is selected from:
(1) a bond, and
(2) $C_1$-$C_6$ alkanediyl optionally substituted with 1 to 5 groups independently selected from:
  (a) halogen,
  (b) —OR$^a$,
  (c) aryl, and
  (d) heteroaryl;

Z is selected from:
(1) a bond,
(2) 5 to 6-membered heterocyclic ring with from 1 to 4 heteroatoms selected from oxygen, sulfur and nitrogen,
(3) benzene ring fused to a $C_5$-$C_{10}$ carbocyclic ring,
(4) 5 or 6-membered heterocyclic ring with from 1 to 4 heteroatoms selected from oxygen, sulfur and nitrogen fused to a $C_5$-$C_{10}$ carbocyclic ring, and
(5) 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen;

$R^1$ is selected from:
(1) $C_1$-$C_6$ alkyl,
(2) —($C_{1-10}$ alkyl)OH,
(3) —($C_{1-10}$ alkyl)oxy($C_{1-10}$ alkyl),
(4) hydroxy, and
(5) —O($C_{1-10}$alkyl);

each occurrence of $R^2$ is independently selected from:
(1) $C_1$-$C_6$ alkyl optionally substituted with 1 to 5 halogen atoms,
(2) $C_3$-$C_6$ cycloalkyl, optionally substituted with 1 to 5 halogen atoms,
(3) oxo,
(4) halogen,
(5) cyano,
(6) —OH,
(7) —$C_0$-$C_6$ alkyloxy$C_1$-$C_6$ alkyl,
(8) —$CO_2R^a$,
(9) —(C=O) $C_1$-$C_6$ alkyl,
(10) 5 to 6-membered heterocyclic ring with from 1 to 4 heteroatoms selected from oxygen, sulfur and nitrogen, wherein the $C_1$-$C_6$ alkyl, $C_3$-$C_6$ cycloalkyl, —$C_0$-$C_6$ alkyloxy$C_1$-$C_6$ alkyl, and —(C=O) $C_1$-$C_6$ alkyl groups of $R^2$ are optionally substituted with 0, 1, 2, or 3 $R^3$ substituents selected from:
(1) $C_1$-$C_6$ alkyl optionally substituted with 1 to 5 halogens,
(2) halogen,
(3) —OH, and
(4) —$CO_2H$;

each occurrence of $R^a$ is independently selected from:
(1) hydrogen,
(2) $C_3$-$C_6$ cycloalkyl;
(3) $C_1$-$C_6$ alkyl optionally substituted with 1 to 5 groups independently selected from:
  (a) halogen,
  (b) hydroxy,
  (c) —CO($C_1$-$C_6$ alkyl),
  (d) —$CO_2$($C_1$-$C_6$ alkyl), and
  (e) —$CO_2H$, and provided that when n is 1, X is —$CH_2$—, $R^1$ is —$CH_3$, and $R^2$ is —$CH_3$ or F, then Z is other than pyridinyl, pyrazolyl, or [1,2,4]triazolo[4,3-a]pyridinyl.

2. The compound of claim 1, wherein n is 0, 1, 2, or 3.

3. The compound of claim 1, wherein X is a bond, —$CH_2$—, —$CH_2CH_2$—, —$CH(CH_3)$—, —CH(CH($CH_3$)$_2$)—, —$CH_2CHCH_3$—, —$CH(CH_2CH_3)$—, —$CH_2CHCH_3$—, —$CH_2CH(CH_3)_2$—, or —$CH(CH_3)CH_2$— and X is optionally substituted with one to three groups selected from —OR$^a$, and aryl.

4. The compound of claim 3, wherein X is optionally substituted with one to three groups selected from —$OCH_3$, —$OCHCH_3$, —$OCH(CH_3)_2$ and phenyl.

5. The compound of claim 4 wherein Z is thiazolyl, oxazolyl, pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, pyridinyl, dihydropyridinyl, dihydropyridazinyl, pyrrolidinyl, imidazolyl, pyrazolyl, 2,3-dihydro-1,3,4-oxadiazolyl, oxadiazolyl, dihydro-oxadiazolyl, 4,5-dihydro-1,3,4-oxadiazolyl, 1,2,4-oxadiazolyl, 1,2,5-oxadiazolyl,

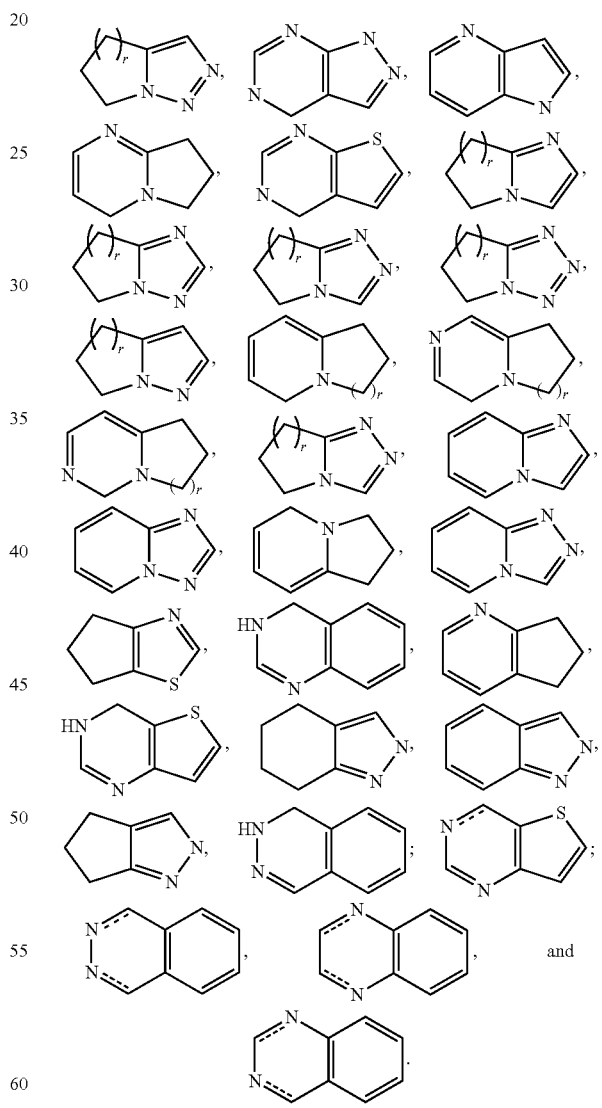

6. The compound of claim 5 wherein $R^1$ is selected from: $C_1$-$C_6$ alkyl, —($C_{1-10}$ alkyl)OH, —($C_{1-10}$ alkyl)oxy($C_{1-10}$ alkyl), hydroxy, and —O($C_{1-10}$alkyl).

7. The compound of claim 5 wherein Z is selected from dihydropyrazinyl, pyrazolyl,

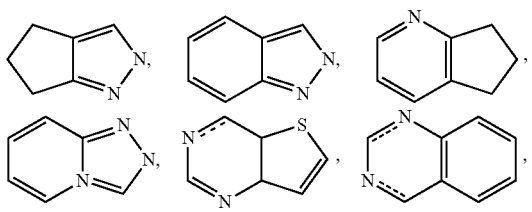

dihydro-oxadiazolyl, 4,5-dihydro-1,3,4-oxadiazolyl, dihydropyridinyl, pyridinyl, pyrazinyl, and pyridazinyl.

8. The compound of claim 7, wherein $R^1$ is selected from: —$C_1$-$C_4$ alkyl, —($C_{1-4}$ alkyl)OH, —($C_{1-4}$ alkyl)oxy($C_{1-4}$alkyl), hydroxy, and —O($C_{1-4}$ alkyl).

9. A compound of claim 1 or a pharmaceutically acceptable salt thereof, or a stereoisomer thereof, or a pharmaceutically acceptable salt of the stereoisomer thereof, selected from:

4-(((2S,5R)-5-((R)-(4-chlorophenyl)(hydroxy)methyl)pyrrolidin-2-yl)methyl)-N-(2-methoxyethyl)-N-methylbenzamide;

4-(((2S,5R)-5-((R)-(6-chloropyridin-3-yl)(hydroxy)methyl)pyrrolidin-2-yl)methyl)-N-(2-methoxypropyl)-N-methylbenzamide;

4-(((2S,5R)-5-((R)-(6-chloropyridin-3-yl)(hydroxy)methyl)pyrrolidin-2-yl)methyl)-N-(2-methoxy-2-(6-oxo-1,6-dihydropyridin-2-yl)ethyl)-N-methylbenzamide;

4-(((2S,5R)-5-((R)-(6-chloropyridin-3-yl)(hydroxy)methyl)pyrrolidin-2-yl)methyl)-N-methyl-N-(1-(5-methyl-1H-pyrazol-3-yl)propyl)benzamide;

4-(((2S,5R)-5-((R)-(6-chloropyridin-3-yl)(hydroxy)methyl)pyrrolidin-2-yl)methyl)-N-methyl-N-(1-(5-methyl-1H-pyrazol-3-yl)-2-phenylethyl)benzamide;

4-(((2S,5R)-5-((R)-(6-chloropyridin-3-yl)(hydroxy)methyl)pyrrolidin-2-yl)methyl)-N-((5-isopropyl-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-((5-cyclopropyl-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-((5-(methoxymethyl)-1H-pyrazol-3-yl)methyl)-N-methylbenzamide;

4-(((2 S,5R)-5-((R)-(6-chloropyridin-3-yl)(hydroxy)methyl)pyrrolidin-2-yl)methyl)-N-methyl-N-((5-(trifluoromethyl)-1H-pyrazol-3-yl)methyl)benzamide;

4-(((2S,5R)-5-((R)-(6-chloropyridin-3-yl)(hydroxy)methyl)pyrrolidin-2-yl)methyl)-N-((5-ethoxy-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-((5-ethyl-4-methyl-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-methyl-N-((1,4,5,6-tetrahydrocyclopenta[c]pyrazol-3-yl)methyl)benzamide;

4-(((2S,5R)-5-((R)-(6-chloropyridin-3-yl)(hydroxy)methyl)pyrrolidin-2-yl)methyl)-N-methyl-N-((4,5,6,7-tetrahydro-1H-indazol-3-yl)methyl)benzamide;

4-(((2 S,5R)-5-((R)-(6-chloropyridin-3-yl)(hydroxy)methyl)pyrrolidin-2-yl)methyl)-N-((4-hydroxy-5-methyl-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-((4-methoxy-5-methyl-1H-pyrazol-3-yl)methyl)-N-methylbenzamide;

N-((4-chloro-5-methyl-1H-pyrazol-3-yl)methyl)-4-(((2S,5R)-5-((R)-(6-chloropyridin-3-yl)(hydroxy)methyl)pyrrolidin-2-yl)methyl)-N-methylbenzamide;

4-(((2S,5R)-5-((R)-(6-chloropyridin-3-yl)(hydroxy)methyl)pyrrolidin-2-yl)methyl)-N-methyl-N—((R)-1-(4-methyl-5-oxo-4,5-dihydro-1,3,4-oxadiazol-2-yl)ethyl)benzamide;

4-(((2S,5R)-5-((R)-(6-chloropyridin-3-yl)(hydroxy)methyl)pyrrolidin-2-yl)methyl)-N-methyl-N-(-2-methyl-1-(4-methyl-5-oxo-4,5-dihydro-1,3,4-oxadiazol-2-yl)propyl) benzamide;

4-(((2S,5R)-5-((R)-(6-chloropyridin-3-yl)(hydroxy)methyl)pyrrolidin-2-yl)methyl)-N-methyl-N-((6-oxo-1,6-dihydropyridin-2-yl)methyl)benzamide;

4-(((2S,5R)-5-((R)-(6-chloropyridin-3-yl)(hydroxy)methyl)pyrrolidin-2-yl)methyl)-N-methyl-N-(pyridin-3-ylmethyl)benzamide, 4-(((2 S,5R)-5-((R)-(6-chloropyridin-3-yl)(hydroxy)methyl)pyrrolidin-2-yl)methyl)-N-ethyl-N-(pyridin-3-ylmethyl)benzamide;

4-(((2S,5R)-5-((R)-(6-chloropyridin-3-yl)(hydroxy)methyl)pyrrolidin-2-yl)methyl)-N-methyl-N-(1-(pyridin-3-yl)ethyl)benzamide;

4-(((2S,5R)-5-((R)-(6-chloropyridin-3-yl)(hydroxy)methyl)pyrrolidin-2-yl)methyl)-N-(6,7-dihydro-5H-cyclopenta[b]pyridin-5-yl)-N-methylbenzamide;

4-(((2S,5R)-5-((R)-(6-chloropyridin-3-yl)(hydroxy)methyl)pyrrolidin-2-yl)methyl)-N-((2-methoxypyridin-3-yl)methyl)-N-methylbenzamide;

4-(((2S,5R)-5-((R)-(6-chloropyridin-3-yl)(hydroxy)methyl)pyrrolidin-2-yl)methyl)-N-((2-fluoropyridin-3-yl)methyl)-N-methylbenzamide;

4-(((2S,5R)-5-((R)-(6-chloropyridin-3-yl)(hydroxy)methyl)pyrrolidin-2-yl)methyl)-N-((2-fluoropyridin-3-yl)methyl)-N-(2-hydroxyethyl)benzamide;

4-(((2S,5R)-5-((R)-(6-chloropyridin-3-yl)(hydroxy)methyl)pyrrolidin-2-yl)methyl)-N-methyl-N-((6-oxo-1,6-dihydropyridin-3-yl)methyl)benzamide, 4-(((2S,5R)-5-((R)-(6-chloropyridin-3-yl)(hydroxy)methyl)pyrrolidin-2-yl)methyl)-N-((6-methoxypyridin-3-yl)methyl)-N-methylbenzamide, 4-(((2S,5R)-5-((R)-(6-chloropyridin-3-yl)(hydroxy)methyl)pyrrolidin-2-yl)methyl)-N-((6-chloropyridin-3-yl)methyl)-N-methylbenzamide, (((2S,5R)-5-((R)-(6-chloropyridin-3-yl)(hydroxy)methyl)pyrrolidin-2-yl)methyl)-N-((5-(1-hydroxyethyl)pyridin-3-yl)methyl)-N-methylbenzamide;

4-(((2S,5R)-5-((R)-(6-chloropyridin-3-yl)(hydroxy)methyl)pyrrolidin-2-yl)methyl)-N-((5-(2-hydroxypropan-2-yl)pyridin-3-yl)methyl)-N-methylbenzamide;

5-((4-(((2S,5R)-5-((R)-(6-chloropyridin-3-yl)(hydroxy)methyl)pyrrolidin-2-yl)methyl)-N-methylbenzamido)methyl)nicotinic acid;

Methyl 5-((4-(((2S,5R)-5-((R)-(6-chloropyridin-3-yl)(hydroxy)methyl)pyrrolidin-2-yl) methyl)-N-methylbenzamido)methyl)nicotinate;

4-(((2S,5R)-5-((R)-(6-chloropyridin-3-yl)(hydroxy)methyl)pyrrolidin-2-yl)methyl)-N-((5-cyanopyridin-3-yl)methyl)-N-methylbenzamide;

4-(((2S,5R)-5-((R)-(6-chloropyridin-3-yl)(hydroxy)methyl)pyrrolidin-2-yl)methyl)-N-methyl-N-((5-(5-methyl-1,3,4-oxadiazol-2-yl)pyridin-3-yl)methyl)benzamide;

N-((5-(1H-tetrazol-5-yl)pyridin-3-yl)methyl)-4-(((2S,5R)-5-((R)-(6-chloropyridin-3-yl)(hydroxy)methyl)pyrrolidin-2-yl)methyl)-N-methylbenzamide;

4-(((2S,5R)-5-((R)-(6-chloropyridin-3-yl)(hydroxy)methyl)pyrrolidin-2-yl)methyl)-N-((6-fluoro-5-methylpyridin-3-yl)methyl)-N-methylbenzamide;

4-(((2S,5R)-5-((R)-(6-chloropyridin-3-yl)(hydroxy)methyl)pyrrolidin-2-yl)methyl)-N-methyl-N-(pyrazin-2-ylmethyl)benzamide;

4-(((2S,5R)-5-((R)-(6-chloropyridin-3-yl)(hydroxy)methyl)pyrrolidin-2-yl)methyl)-N-methyl-N-(1-(pyrazin-2-yl)ethyl)benzamide;

4-(((2S,5R)-5-((R)-(6-chloropyridin-3-yl)(hydroxy)methyl)pyrrolidin-2-yl)methyl)-N-methyl-N-(pyridazin-4-ylmethyl)benzamide;

4-(((2S,5R)-5-((R)-(6-chloropyridin-3-yl)(hydroxy)methyl)pyrrolidin-2-yl)methyl)-N-methyl-N-((4-oxo-3,4-dihydrothieno[3,2-d]pyrimidin-2-yl)methyl)benzamide; and 4-(((2S,5R)-5-((R)-(6-chloropyridin-3-yl)(hydroxy)methyl)pyrrolidin-2-yl)methyl)-N-methyl-N-((3-methyl-4-oxo-3,4-dihydroquinazolin-2-yl)methyl)benzamide.

10. A compound of claim 1 or a pharmaceutically acceptable salt thereof, or a stereoisomer thereof, or a pharmaceutically acceptable salt of the stereoisomer thereof, selected from:

4-(((2S,5R)-5-((R)-(6-chloropyridin-3-yl)(hydroxy)methyl) pyrrolidin-2-yl)methyl)-N-methyl-N-((5-methyl-1H-pyrazol-3-yl)methyl)benzamide;

4-(((2S,5R)-5-((R)-(6-chloropyridin-3-yl)(hydroxy)methyl)pyrrolidin-2-yl)methyl)-N-methyl-N-(1-(5-methyl-1H-pyrazol-3-yl)propyl)benzamide;

4-(((2S,5R)-5-((R)-(6-chloropyridin-3-yl)(hydroxy)methyl)pyrrolidin-2-yl)methyl)-N-methyl-N-(1-(5-methyl-1H-pyrazol-3-yl)-2-phenylethyl)benzamide;

4-(((2S,5R)-5-((R)-(6-chloropyridin-3-yl)(hydroxy)methyl)pyrrolidin-2-yl)methyl)-N-((5-isopropyl-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-((5-cyclopropyl-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-((5-(methoxymethyl)-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-methyl-N-((5-(trifluoromethyl)-1H-pyrazol-3-yl)methyl)benzamide;

4-(((2S,5R)-5-((R)-(6-chloropyridin-3-yl)(hydroxy)methyl)pyrrolidin-2-yl)methyl)-N-((5-ethoxy-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-((5-ethyl-4-methyl-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-((4-hydroxy-5-methyl-1H-pyrazol-3-yl)methyl)-N-methylbenzamide;

4-(((2S,5R)-5-((R)-(6-chloropyridin-3-yl)(hydroxy)methyl)pyrrolidin-2-yl)methyl)-N-((4-methoxy-5-methyl-1H-pyrazol-3-yl)methyl)-N-methylbenzamide; and N-((4-chloro-5-methyl-1H-pyrazol-3-yl)methyl)-4-(((2S,5R)-5-((R)-(6-chloropyridin-3-yl)(hydroxy)methyl)pyrrolidin-2-yl)methyl)-N-methylbenzamide.

11. A pharmaceutical composition comprising a compound of claim 1 and a pharmaceutically acceptable carrier.

12. A method for activation of β3-adrenoreceptor in subject comprising administering to said subject a compound of claim 1.

13. 4-(((2S,5R)-5-((R)-(6-chloropyridin-3-yl)(hydroxy)methyl)pyrrolidin-2-yl)methyl)-N-methyl-N—((R)-1-(4-methyl-5-oxo-4,5-dihydro-1,3,4-oxadiazol-2-yl)ethyl)benzamide, or a pharmaceutically acceptable salt thereof, or a stereoisomer thereof, or a pharmaceutically acceptable salt of the stereoisomer thereof.

14. 4-(((2S,5R)-5-((R)-(6-chloropyridin-3-yl)(hydroxy)methyl)pyrrolidin-2-yl)methyl)-N-methyl-N-(-2-methyl-1-(4-methyl-5-oxo-4,5-dihydro-1,3,4-oxadiazol-2-yl)propyl)benzamide or a pharmaceutically acceptable salt thereof, or a stereoisomer thereof, or a pharmaceutically acceptable salt of the stereoisomer thereof.

\* \* \* \* \*